(12) United States Patent
Nagai et al.

(10) Patent No.: US 9,512,119 B2
(45) Date of Patent: Dec. 6, 2016

(54) DIFLUOROMETHYLENE COMPOUND

(71) Applicant: SATO PHARMACEUTICAL CO., LTD., Tokyo (JP)

(72) Inventors: Keita Nagai, Matsudo (JP); Motoaki Baba, Tokyo (JP); Shinichi Fujioka, Tokyo (JP); Koh Nagasawa, Tokyo (JP); Hirobumi Takahashi, Ushiku (JP); Eri Kondoh, Yokohama (JP); Sachie Sogo, Fuchu (JP); Kenichi Tanaka, Ushiku (JP); Yoshiki Itoh, Tsukuba (JP)

(73) Assignee: SATO PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/417,488

(22) PCT Filed: Jul. 26, 2013

(86) PCT No.: PCT/JP2013/070359
§ 371 (c)(1),
(2) Date: Jan. 26, 2015

(87) PCT Pub. No.: WO2014/017643
PCT Pub. Date: Jan. 30, 2014

(65) Prior Publication Data
US 2015/0191463 A1    Jul. 9, 2015

(30) Foreign Application Priority Data
Jul. 27, 2012 (JP) .................... 2012-166658

(51) Int. Cl.
| | | |
|---|---|---|
| C07D 221/02 | (2006.01) |
| C07D 471/04 | (2006.01) |
| C07D 401/14 | (2006.01) |
| C07D 231/56 | (2006.01) |
| C07D 401/06 | (2006.01) |
| C07D 403/06 | (2006.01) |
| C07D 409/06 | (2006.01) |
| C07D 209/08 | (2006.01) |
| C07D 413/06 | (2006.01) |

(52) U.S. Cl.
CPC ........... *C07D 471/04* (2013.01); *C07D 209/08* (2013.01); *C07D 231/56* (2013.01); *C07D 401/06* (2013.01); *C07D 401/14* (2013.01); *C07D 403/06* (2013.01); *C07D 409/06* (2013.01); *C07D 413/06* (2013.01)

(58) Field of Classification Search
None
See application file for complete search history.

(56) References Cited

U.S. PATENT DOCUMENTS

| | | |
|---|---|---|
| 6,166,219 A | 12/2000 | Yamasaki et al. |
| 6,348,474 B1 | 2/2002 | Kayakiri et al. |
| 6,352,985 B1 | 3/2002 | Yamasaki et al. |
| 6,911,469 B2 | 6/2005 | Kayakiri et al. |
| 7,514,463 B2 | 4/2009 | Georg et al. |
| 7,772,271 B2 | 8/2010 | Karp et al. |
| 7,781,478 B2 | 8/2010 | Karp et al. |
| 7,855,225 B2 | 12/2010 | Niimi et al. |
| 7,868,037 B2 | 1/2011 | Karp et al. |
| 7,973,069 B2 | 7/2011 | Karp et al. |
| 8,003,647 B2 | 8/2011 | Shimizu et al. |
| 8,013,006 B2 | 9/2011 | Karp et al. |
| 8,263,619 B2 | 9/2012 | Xie et al. |
| 8,362,031 B2 | 1/2013 | Georg et al. |
| 8,377,958 B2 | 2/2013 | Georg et al. |

(Continued)

FOREIGN PATENT DOCUMENTS

| | | |
|---|---|---|
| EP | 1 932 833 A1 | 6/2008 |
| EP | 2 493 892 A1 | 9/2012 |

(Continued)

OTHER PUBLICATIONS

US 6,787,565, 09/2004, Kayakiri et al. (withdrawn)

(Continued)

*Primary Examiner* — Heidi Reese
(74) *Attorney, Agent, or Firm* — Sughrue Mion, PLLC

(57) ABSTRACT

The present invention relates to a compound having an URAT1 inhibitory activity, and to an URAT1 inhibitor, a blood uric acid level-reducing agent and a pharmaceutical composition containing the compound.

More specifically, the present invention relates to a compound represented by the formula (I):

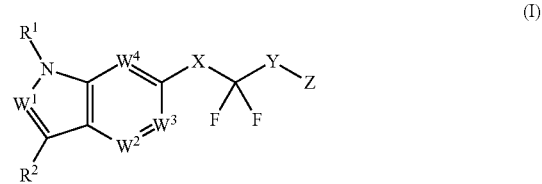

wherein
$R^1$ is $-Q^1-A^1$ or the like; $R^2$ is a hydrogen atom, a halogen atom, a lower alkyl group or the like; $W^1$, $W^2$, $W^3$ and $W^4$ are each independently a nitrogen atom or a methine group optionally having substituents, or the like; X and Y are each a single bond, an oxygen atom or the like; Z is a hydroxyl group or $COOR^3$ or the like.

40 Claims, No Drawings

(56) References Cited

U.S. PATENT DOCUMENTS

| | | |
|---|---|---|
| 8,466,152 B2 | 6/2013 | Shimizu et al. |
| 8,486,937 B2 | 7/2013 | Xie et al. |
| 8,691,841 B2 | 4/2014 | Xie et al. |
| 8,735,414 B2 | 5/2014 | Maccoss et al. |
| 8,829,040 B2 | 9/2014 | Shimizu et al. |
| 2002/0099212 A1 | 7/2002 | Kayakiri et al. |
| 2004/0180947 A1 | 9/2004 | Kayakiri et al. |
| 2005/0234095 A1 | 10/2005 | Xie et al. |
| 2006/0047126 A1 | 3/2006 | Georg et al. |
| 2006/0189606 A1 | 8/2006 | Karp et al. |
| 2006/0223863 A1 | 10/2006 | Karp et al. |
| 2007/0010670 A1 | 1/2007 | Hirata et al. |
| 2007/0197512 A1 | 8/2007 | Inoue et al. |
| 2007/0299068 A1 | 12/2007 | Karp et al. |
| 2007/0299069 A1 | 12/2007 | Karp et al. |
| 2009/0181960 A1 | 7/2009 | Niimi et al. |
| 2009/0197911 A1 | 8/2009 | Georg et al. |
| 2009/0306396 A1 | 12/2009 | Toyoshima et al. |
| 2010/0056521 A1 | 3/2010 | Shimizu et al. |
| 2010/0105677 A1 | 4/2010 | Xie et al. |
| 2010/0292187 A1 | 11/2010 | Karp et al. |
| 2010/0305100 A1 | 12/2010 | Karp et al. |
| 2011/0060003 A1 | 3/2011 | Georg et al. |
| 2011/0071146 A1 | 3/2011 | Niimi et al. |
| 2011/0230454 A1 | 9/2011 | Shimizu et al. |
| 2011/0268698 A1 | 11/2011 | Karp et al. |
| 2011/0319407 A1 | 12/2011 | Xie et al. |
| 2012/0009142 A1 | 1/2012 | Karp et al. |
| 2012/0184574 A1 | 7/2012 | Maccoss et al. |
| 2013/0123296 A1 | 5/2013 | Georg et al. |
| 2013/0217683 A1 | 8/2013 | Xie et al. |
| 2013/0252955 A1 | 9/2013 | Shimizu et al. |
| 2013/0259850 A1 | 10/2013 | O'Neil et al. |
| 2014/0005221 A1 | 1/2014 | Nagai et al. |
| 2014/0179932 A1 | 6/2014 | Shimizu et al. |

FOREIGN PATENT DOCUMENTS

| | | |
|---|---|---|
| WO | 98/15530 A1 | 4/1998 |
| WO | 99/00372 A1 | 1/1999 |
| WO | 2005/092890 A2 | 10/2005 |
| WO | 2006/019831 A1 | 2/2006 |
| WO | 2006/023704 A2 | 3/2006 |
| WO | 2006/057460 A1 | 6/2006 |
| WO | 2007/086504 A1 | 8/2007 |
| WO | 2007/100066 A1 | 9/2007 |
| WO | 2008/126898 A1 | 10/2008 |
| WO | 2009/151695 A1 | 12/2009 |
| WO | 2010/117932 A1 | 10/2010 |
| WO | 2011/053292 A1 | 5/2011 |
| WO | 2012/102405 A1 | 8/2012 |

OTHER PUBLICATIONS

John N. Loeb, "The Influence of Temperature on the Solubility of Monosodium Urate", Arthritis and Rheumatism, Mar.-Apr. 1972, pp. 189-192, vol. 15, No. 2.

Japanese Society of Gout and Nucleic Acid Metabolism, the 2nd Edition of Guideline of Hyperuricemia or Gout Treatment, 2010, pp. 30-31.

Hyon K. Choi, "Pathogenesis of Gout", Ann. Intern. Med., 2005, pp. 499-516, vol. 43.

Yuki Taniguchi et al., "Serum uric acid and the risk for hypertension and Type 2 diabetes in Japanese men: The Osaka Health Survey", J. Hypertension, 2001, pp. 1209-1215, vol. 19.

Johan Sundstrom et al., "Relations of Serum Uric Acid to Longitudinal Blood Pressure Tracking and Hypertension Incidence", American Heart Association Inc., 2005, pp. 28-33, vol. 45.

Hyon K. Choi et al., "Prevalence of the Metabolic Syndrome in Individuals with Hyperuricemia", The American Journal of Medicine, 2007, pp. 442-447, vol. 120.

Nobukazu Ishizaka et al., "Association Between Serum Uric Acid, Metabolic Syndrome, and Carotic Atherosclerosis in Japanese Individuals", Arterioscler Thromb Vasc. Biol., 2005, pp. 1038-1044, vol. 25.

Masako Tomita et al., "Gout and Nucleic Acid Metabolism", 2005, pp. 1-5, vol. 30.

Toru Nakamura et al., "Treatment of Hyperuricemia and Gout", Medical Review Co., Ltd., 2003, pp. 21-39.

Domenic A. Sica et al., "Renal Handling of Organic Anions and Cations: Excretion of Uric Acid", The Kidney, Saubder, Philadelphia PA, 1996, pp. 680-700.

Atsushi Enomoto et al., "Molecular identification of a renal urate-anion exchanger that regulates blood urate levels", Nature, 2002, pp. 447-452, vol. 417.

Kimiyoshi Ichida et al., Clinical and Molecular Analysis of Patients with Renal Hypouricemia in Japan-Influence of URAT1 Gene on Urinary Excretion:, J. Am Soc. Nephrol., 2004, pp. 164-173, vol. 15.

Iwao Ohno, "Uricosuric agent", Japan Clinics, 2008, pp. 743-747, vol. 66, No. 4.

Viktor O. Iaroshenko, "Synthesis of Some Fluorinated Heteroannulated Pyrimidines—Purine Isosteres—via Inverse-Electron-Demand Diels-Alder Protocol", Synthesis, 2009, pp. 3967-3974, No. 23.

Elisa M. Woolridge et al., "Synthesis and Reactivity of 6-(Fluoromethyl)Indole and 6-(Difluoromethyl)Indole", Tetrahedron Letters, 1989, pp. 6117-6120, vol. 30, No. 45.

International Search Report for PCT/JP2013/070359 dated Oct. 22, 2013.

Extended European Search Report dated Dec. 14, 2015 from the European Patent Office in corresponding European application No. 13823704.5.

DIFLUOROMETHYLENE COMPOUND

CROSS REFERENCE TO RELATED APPLICATIONS

This application is a National Stage of International Application No. PCT/JP2013/070359 filed Jul. 26, 2013, claiming priority based on Japanese Patent Application No. 2012-166658, filed Jul. 27, 2012, the contents of all of which are incorporated herein by reference in their entirety.

TECHNICAL FIELD

The present invention relates to a difluoromethylene compound that is useful in the field of medicine. More specifically, the present invention relates to a difluoromethylene compound that has an URAT1 inhibitory activity and is useful in the field of the treatment of diseases associated with blood uric acid, and an URAT1 inhibitor, a blood uric acid level-reducing agent and a pharmaceutical composition containing the compound.

BACKGROUND ART

Uric acid is a final product of a purine metabolism in humans. The purine nucleotide is generated by degradation of a nucleic acid in the cell, ATP that is an energy source in a living body, and the like, or is absorbed from a meal. The purine nucleotide is metabolized to uric acid via hypoxanthine and xanthine. Uric acid is a final product of the purine metabolism in the higher primates including human as urate oxidate (uricase) is genetically silenced in these species. In many other mammals, uric acid is oxidized by uricase and metabolized to allantoin.

About 98% of uric acid is present in the form of sodium urate in a body fluid (Non-Patent Literature 1).

Since the solubility of sodium urate at physiological pH conditions is 6.4 mg/dL (Non-Patent Literature 1), 7 mg/dL or more of the blood uric acid level beyond the solubility in the body fluid, is defined as hyperuricemia (Non-Patent Literature 2).

If the hyperuricemia persists, urate is crystallized and precipitated in the body fluid, which cause gout arthritis, gouty kidney, gouty node, urolithiasis, a renal function disorder and the like (Non-Patent Literature 3).

Furthermore, in recent years, the hyperuricemia is known to be complicated with lifestyle diseases such as hypertension, hyperlipidaemia, impaired glucose tolerance and obesity in high rate (Non-Patent Literatures 4, 5, 6 and 7), and such complications are known to increase the incidence rate of cardiovascular and cerebrovascular disorders.

Hyperuricemia is reported to be present in 20% or more of adult males in Japan, and tends to increase even now due to Westernalized lifestyle and the like (Non-Patent Literature 8). As for the classification of huperuricemia, the overproduction of uric acid is reported to be 12%, the decreased uric acid excretion to be 60% and the combined type to be 25% (Non-Patent Literature 9). Thus, the decreased uric acid excretion is seen in 85%, that is the sum of 60% of the decreased uric acid excretion and 25% of the combined type, which suggests the importance of the decreased uric acid excretion with respect to the cause of hyperuricemia.

Uric acid is mainly excreted from a kidney. In humans, about 70% is excreted from the kidney, and 30% is excreted from extra-renal pathway such as a bile or a saliva, a sweat and like. The uric acid is filtered by 100% in a renal glomerulus, and then most part of it is then re-absorbed in a proximal tubule, and about 10% is excreted in a terminal urine (Non-Patent Literatures 3 and 10). Thus, it is suggested that uric acid excretion is strictly regulated by the re-absorption.

Since uric acid is present as an organic acid at physiological pH conditions, it was expected that a transporter responsible for re-absorption of uric acid has similar structural characteristics with an organic anion transporter family proteins. In recent years, URAT1 was identified as a transporter responsible for re-absorption of uric acid, which is present in the proximal tuble (Non-Patent Literature 11). URAT1 is a 12-transmembrane transporter belonging to the SLC family. Northern blotting analysis showed that an expression of a URAT1 gene is localized in the kidney of an adult and fetus. It became clear from immunohistochemical analysis using anti-human URAT1 antibody that a URAT1 protein is present on a luminal surface of the proximal tubule. Furthermore, since uric acid is incorporated when URAT1 is expressed in a xenopus oocyte, it was confirmed that URAT1 can transport of uric acid (Non-Patent Literature 11).

Furthermore, it became clear that loss of function caused by mutations of the URAT1 gene lead renal hypouricemia, and thus the importance of URAT1 with respect to uric acid excretion came to the fore (Non-Patent Literatures 11 and 12).

Currently used uricosuric agents, benzbromarone and probenecid have been shown to inhibit uric acid-transport activity of URAT1, and importance in the uric acid excretion of URAT1 has been cleared pharmacologically as well (Non-Patent Literature 13).

From these, it is regarded that a drug inhibiting URAT1 can reduce the blood uric acid level by suppressing re-absorption of uric acid in the proximal tubule and by accelerating the uric acid excretion, and the drug inhibiting URAT1 is useful as an agent for treating or preventing a pathological condition associated with uric acid, specifically, hyperuricemia, gouty node, gout arthritis, gouty kidney, urolithiasis and renal function disorder. In addition, the drug inhibiting URAT1 is also useful as an agent for treating or preventing hypertension, hyperlipidemia, abnormal glucose tolerance, obesity, a coronary artery disease and cerebrovascular disorders, which are associated with hyperuricemia.

Incidentally, as a compound that has URAT1 inhibitory action, for example, Patent Literature 1 discloses a compound of the general formula described below.

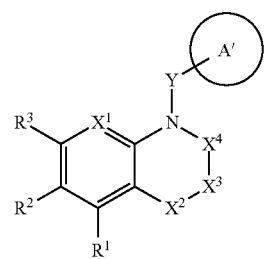

Patent Literature 2 discloses a compound of the general formula described below.

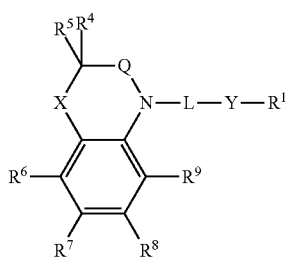

Patent Literature 3 discloses a compound of the general formula described below.

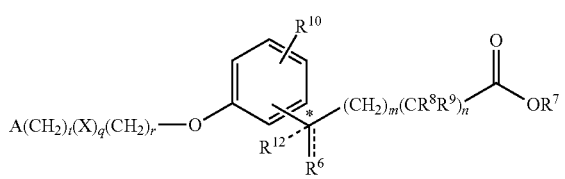

Patent Literature 4 discloses a compound of the general formula described below as a PDE5 (phosphodiesterase 5) inhibitor.

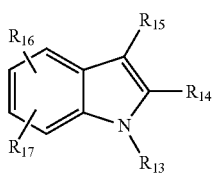

Patent Literature 5 discloses a compound of the general formula described below as a PDE5 inhibitor.

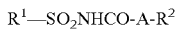

$R^1$—$SO_2NHCO$-A-$R^2$

Patent Literature 6 discloses a compound of the general formula described below as a 17βHSD (17β-hydroxysteroid dehydrogenase) type 5 inhibitor.

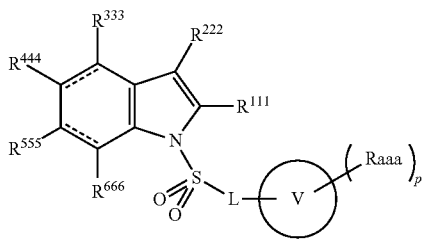

CITATION LIST

Patent Literatures

Patent Literature 1: WO 2006/057460 A
Patent Literature 2: WO 2007/086504 A
Patent Literature 3: WO 2009/151695 A
Patent Literature 4: WO 98/15530 A
Patent Literature 5: WO 99/00372 A
Patent Literature 6: WO 2007/100066 A Non-Patent Literatures Non-Patent Literature 1: Loeb J N., Arthritis Rhueum., 15, 189-192, 1972
Non-Patent Literature 2: Japanese Society of Gout and Nucleic Acid Metabolism, the $2^{nd}$ Edition of Guideline of Hyperuricemia or Gout Treatment, 30-31, 2010
Non-Patent Literature 3: Choi H K. et al. Ann. Intern. Med., 43, 499-516, 2005
Non-Patent Literature 4: Taniguchi Y. et al., J. Hypertension, 19, 1209-1215, 2001
Non-Patent Literature 5: Sunderstrom J. et al., Hypertension, 45, 28-33, 2005
Non-Patent Literature 6: Choi H K. et al., The Am. J. Med., 120, 442-447, 2007
Non-Patent Literature 7: Ishizaka N. et al., Arterioscler. Thromb. Vasc. Biol., 25, 1038-1044, 2005
Non-Patent Literature 8: Masako Tomita and Shoichi Mizuno, Gout and Nucleic Acid Metabolism, 30, 1-5, 2006
Non-Patent Literature 9: Toru Nakamura, Treatments of Hyperuricemia and Gout, Medical Review Co., Ltd., 21-39, 2003
Non-Patent Literature 10: Sica D A. and Schoolwerth A C., The Kidney, Saubder, Philadelphia Pa., 680-700, 1996
Non-Patent Literature 11: Enomoto A. et al., Nature, 417, 447-452, 2002
Non-Patent Literature 12: Ichida K. et al., J. Am. Soc. Nephrol. 15, 164-173, 2004
Non-Patent Literature 13: Iwao Ohno, Japan Clinics, 66, 743-747, 2008

SUMMARY OF INVENTION

Technical Problem

The above-mentioned benzbromarone and probenecid were shown to inhibit a uric acid-transport activity of URAT1, but the URAT1 inhibitory action thereof was not sufficient. Furthermore, benzbromarone is known to lead serious hepatic disorders and probenecid is known to lead gastrointestinal tract disorders, and the like. In addition, both of the compounds are also known to cause drug interaction with other drugs. Therefore, a uric acid excretion facilitator that is safer and highly effective, is required.

Accordingly, it became problems to provide a novel compound that has excellent URAT1 inhibitory action, and an agent for treating or preventing a disease associated with blood uric acid.

Solution to Problem

The present inventors have widely synthesized and examined difluoromethylene compounds so as to solve the above-mentioned problems, and consequently found that a compound represented by the general formula (I) has an excellent URAT1 inhibitory activity, and completed the present invention.

Specifically, the present invention relates to a compound represented by the formula (I) or a pharmaceutically acceptable salt or ester of the compound:

the formula (I):

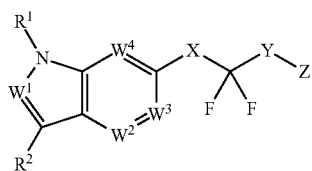

wherein

R¹ represents a lower alkyl group optionally substituted by a cycloalkyl group, a cycloalkyl group, a halo lower alkyl group, a hydroxy lower alkyl group, a lower alkoxy lower alkyl group, a lower alkoxy carbonyl group, a lower alkyl sulfonyl group or a group represented by the general formula: -Q¹-A¹;

Q¹ represents a single bond or a lower alkylene group (wherein the entirety of each of the 1 or 2 or more methylene group(s) that constitute(s) the lower alkylene group may be independently replaced with a carbonyl group, a sulfinyl group or a sulfonyl group, and/or the hydrogen(s) that constitute(s) the methylene group(s) may be substituted by lower alkyl group(s));

A¹ represents an aryl group or a heteroaryl group optionally substituted by 1 to 3 substituent(s) selected from the following <Substituent group L>(wherein the adjacent optional two substituents on the aryl group or heteroaryl group may be together to form a lower alkylenedioxy group);

R² represents a hydrogen atom, a substituent selected from the following <Substituent group M> or a group represented by the general formula: -Q²-A²;

Q² represents a single bond, a lower alkylene group or a lower alkenylene group (wherein the entirety of each of the 1 or 2 or more methylene group(s) that constitute(s) the lower alkylene group may be independently replaced with an oxygen atom, a nitrogen atom or a carbonyl group, and/or the hydrogen(s) that constitute(s) the methylene group(s) may be substituted by a halogen atom, a cyano group, a hydroxyl group or a lower alkyl group);

A² represents a cycloalkyl group, an aliphatic heterocycle group, an aryl group or a heteroaryl group optionally substituted by 1 to 3 substituent(s) selected from <Substituent group L>(wherein the adjacent optional two substituents on the aryl group or heteroaryl group may be together to form a lower alkylenedioxy group);

W¹, W², W³ and W⁴ are each independently a nitrogen atom, or a methine group optionally having substituent(s) selected from the group consisting of a halogen atom, a hydroxyl group, a cyano group, a lower alkyl group, a cycloalkyl group, a halo lower alkyl group, a lower alkoxy group and a halo lower alkoxy group; provided that 0 to 4 of W¹, W², W³ and W⁴ is/are nitrogen atom(s);

X and Y are each independently a single bond, a lower alkylene group, a lower alkenylene group or a lower alkynylene group (wherein the entirety of each of the 1 or 2 or more methylene group(s) that constitute(s) the lower alkylene group may be independently replaced with an oxygen atom, a sulfur atom, a sulfinyl group, a sulfonyl group, a carbonyl group or a group represented by the general formula: —N(RN)—, and/or the hydrogen(s) that constitute(s) the methylene group(s) may be substituted by a halogen atom, a cyano group, a hydroxyl group or a lower alkyl group;

R$^N$ represents a hydrogen atom, a lower alkyl group, a halo lower alkyl group or a lower alkanoyl group;

Z represents a hydroxyl group, COOR³, CONR⁴R⁵, SO₃R³, SO₃NR⁴R⁵, a 5-tetrazolyl group, a 5-oxo-1,2,4-oxadiazolyl group, a 2-oxo-1,3,4-oxadiazolyl group, a 5-imino-4,5-dihydro-1,3,4-oxadiazolyl group, a 2-thioxo-1,3,4-oxadiazolyl group or a 5-oxo-1,2,4-thiaziazolyl group;

wherein R³, R⁴ and R⁵ each independently represents a hydrogen atom or a lower alkyl group; and <Substituent group L> and <Substituent group M> are defined as follows.

<Substituent Group L>:

a halogen atom, a hydroxyl group, a nitro group, a cyano group, a formyl group, an amino group, a carboxyl group, a lower alkyl group, a halo lower alkyl group, a cycloalkyl group, a lower alkoxy group, a halo lower alkoxy group, a hydroxy lower alkyl group, a lower alkoxy lower alkyl group, a lower alkoxy carbonyl group, a lower alkanoyl group, a lower alkylthio group, a lower alkyl sulfonyl group, a lower alkylamino group, a di-lower alkylamino group, a carbamoyl group, a mono-lower alkyl carbamoyl group, a di-lower alkyl carbamoyl group, a lower alkanoyl amino group, a lower alkyl sulfonylamino group, a lower alkoxy carbonylamino group, an aralkyl group, an aryloxy group, a heteroaryloxy group, a lower alkenyl group, and a cyano lower alkyl group <Substituent Group M>:

a halogen atom, a hydroxyl group, a nitro group, a cyano group, a formyl group, an amino group, a carboxyl group, a lower alkyl group, a halo lower alkyl group, a cycloalkyl group, a lower alkoxy group, a halo lower alkoxy group, a hydroxy lower alkyl group, a lower alkoxy lower alkyl group, a lower alkoxy carbonyl group, a lower alkanoyl group, a lower alkylthio group, a lower alkyl sulfonyl group, a lower alkylamino group, a di-lower alkylamino group, a carbamoyl group, a mono-lower alkyl carbamoyl group, a di-lower alkyl carbamoyl group, a lower alkanoyl amino group, a lower alkyl sulfonylamino group, and a lower alkoxy carbonylamino group]

The above-mentioned compound represented by the formula (I) includes not only racemic mixture of the compound but also all enantiomers and diastereomers that can be present.

Furthermore, the present invention relates to a method for treating or preventing a pathological condition associated with blood uric acid selected from the group consisting of hyperuricemia, gouty node, acute gouty arthritis, chronic gouty arthritis, gouty kidney, urolithiasis, renal function disorder, coronary artery diseases and ischemic cardiac diseases in mammals (especially humans), including administering a therapeutically effective amount of the compound of the formula (I) to the mammals.

Furthermore, the present invention relates to a method for treating or preventing a pathological condition associated with blood uric acid selected from the group consisting of hyperuricemia, gouty node, acute gout arthritis, chronic gout arthritis, gouty kidney, urolithiasis, renal function disorder, coronary artery diseases and ischemic cardiac diseases in mammals (especially humans), comprising administering a therapeutically effective amount of an URAT1 inhibitor, a blood uric acid level-reducing agent or a pharmaceutical composition comprising the compound of the formula (I) to the mammals.

The present invention relates to an URAT1 inhibitor comprising the compound of the formula (I) as an active ingredient.

Furthermore, the present invention relates to a blood uric acid level-reducing agent comprising the compound of the formula (I) as an active ingredient.

Moreover, the present invention relates to a pharmaceutical composition for treating or preventing a pathological condition associated with blood uric acid selected from the group consisting of hyperuricemia, gouty node, acute gout arthritis, chronic gout arthritis, gouty kidney, urolithiasis, renal function disorder, coronary artery diseases and ischemic cardiac diseases, which comprises the compound of (I) as an active ingredient.

Effect of Invention

The compound represented by the formula (I) and the pharmaceutically acceptable salt and ester of the compound of the present invention have excellent URAT1 inhibitory action as shown in the following Examples, and thus promote uric acid excretion. Therefore, the compound represented by the formula (I) and the pharmaceutically acceptable salt and ester of the compound of the present invention can reduce the blood uric acid level, and thus are useful as a therapeutic drug or a prophylactic drug for a pathological condition associated with blood uric acid such as hyperuricemia, gouty node, acute gout arthritis, chronic gout arthritis, gouty kidney, urolithiasis, renal function disorder, coronary artery diseases or ischemic cardiac diseases.

DESCRIPTION OF EMBODIMENTS

The meanings of the terms used in the present invention will be described below, and the present invention will further be explained in detail.

Examples of the "halogen atom" in the above-mentioned formula (I) include a fluorine atom, a chlorine atom, a bromine atom and an iodine atom, and the like.

The "lower alkyl group" in the above-mentioned formula (I) means a linear or branched alkyl group having a carbon number of from 1 to 6, and for example, a methyl group, an ethyl group, a propyl group, an isopropyl group, a butyl group, an iso-butyl group, a sec-butyl group, a tert-butyl group, a pentyl group, an isopentyl group, an isoamyl group, a neopentyl group, a 1,1-dimethylpropyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,2,2-trimethylpropyl group and a 1-ethyl-3-methylpropyl group, etc. are mentioned.

The "cycloalkyl group" in the above-mentioned formula (I) means a 3- to 8-membered aliphatic cyclic group, and for example, a cyclopropyl group, a cyclobutyl group, a cyclopentyl group, a cyclohexyl group, a cycloheptyl group and a cyclooctyl group, etc. are mentioned.

The "halo lower alkyl group" in the above-mentioned formula (I) means the above-mentioned "lower alkyl group" in which the substitutable optional position(s) is/are substituted by 1 or 2 or more, preferably 1 to 3 of identical or different halogen atom(s) mentioned above, and for example, a fluoromethyl group, a difluoromethyl group, a trifluoromethyl group, a 2-fluoroethyl group, a 1,2-difluoroethyl group, a 2,2,2-trifluoroethyl group, a chloromethyl group, a 2-chloroethyl group, a 1,2-dichloroethyl group, a bromomethyl group and an iodomethyl group, etc. are mentioned.

The "lower alkoxy group" in the above-mentioned formula (I) means a group in which the hydrogen atom of a hydroxyl group is substituted by the above-mentioned "lower alkyl group", and for example, a methoxy group, an ethoxy group, a propoxy group, an isopropoxy group, a butoxy group, a sec-butoxy group, a tert-butoxy group, a pentyloxy group, an isopentyloxy group, a hexyloxy group and an isohexyloxy group, etc. are mentioned.

The "halo lower alkoxy group" in the above-mentioned formula (I) means the above-mentioned "lower alkoxy group" in which the substitutable optional position(s) is/are substituted by 1 or 2 or more, preferably 1 to 3 of identical or different halogen atom(s) mentioned above, and for example, a fluoromethoxy group, a difluoromethoxy group, a trifluoromethoxy group, a 2-fluoroethoxy group, a 1,2-difluoroethoxy group, a 2,2,2-trifluoroethoxy group, a chloromethoxy group, a 2-chloroethoxy group, a 1,2-dichloroethoxy group, a bromomethoxy group and an iodomethoxy group, etc. are mentioned.

The "hydroxy lower alkyl group" in the above-mentioned formula (I) means the above-mentioned "lower alkyl group" in which the substitutable optional position(s) is/are substituted by 1 or 2 or more, preferably 1 or 2 hydroxyl group(s), and for example, a hydroxymethyl group, a 1-hydroxyethyl group, a 1-hydroxypropyl group, a 2-hydroxyethyl group, a 2-hydroxypropyl group, a 2-hydroxy-1-methylethyl group, a 1-hydroxy-1-methylethyl group, a 1,2-dihydroxyethyl group and a 3-hydroxypropyl group, etc. are mentioned.

The "lower alkoxy lower alkyl group" in the above-mentioned formula (I) means the above-mentioned "lower alkyl group" in which the substitutable optional position(s) is/are substituted by 1 or 2 or more, preferably 1 or 2 of the identical or different "lower alkoxy group(s)" mentioned above, and for example, a methoxymethyl group, an ethoxymethyl group, a 2-methoxyethyl group, a 2-ethoxyethyl group, a 1-methoxy-1-methylethyl group, a 1,2-dimethoxyethyl group and a 3-methoxypropyl group, etc. are mentioned.

The "lower alkoxy carbonyl group" in the above-mentioned formula (I) means a group in which the above-mentioned "lower alkoxy group" and a carbonyl group are bonded, i.e., an alkoxycarbonyl group having a carbon number of from 2 to 7, and for example, a methoxycarbonyl group, an ethoxycarbonyl group, a propoxycarbonyl group, an isopropoxycarbonyl group, a butoxycarbonyl group, an isobutoxycarbonyl group, a tert-butoxycarbonyl group and a pentyloxycarbonyl group, etc. are mentioned.

The "lower alkanoyl group" in the above-mentioned formula (I) means a group in which the above-mentioned lower alkyl group and a carbonyl group are bonded, i.e., an alkanoyl group having a carbon number of from 2 to 7, and for example, an acetyl group, a propionyl group, a butyryl group, an isobutyryl group, a valeryl group, an isovaleryl group and a pivaloyl group, etc. are mentioned.

The "lower alkylthio group" in the above-mentioned formula (I) means a group in which the above-mentioned "lower alkyl group" and a sulfur atom are bonded, i.e., an alkylthio group having a carbon number of from 1 to 6, and for example, a methylthio group, an ethylthio group, a propylthio group, an isopropylthio group, a butylthio group, a sec-butylthio group, an isobutylthio group, a tert-butylthio group, a pentylthio group, an isopentylthio group, a hexylthio group and an isohexylthio group, etc. are mentioned.

The "lower alkyl sulfonyl group" in the above-mentioned formula (I) means a group in which the above-mentioned "lower alkyl group" and a sulfonyl group are bonded, and for example, a methylsulfonyl group, an ethylsulfonyl group, a propylsulfonyl group, an isopropylsulfonyl group, a butylsulfonyl group, a sec-butylsulfonyl group, an isobutylsulfonyl group, a tert-butylsulfonyl group, a pentylsulfonyl group, an isopentylsulfonyl group, a hexylsulfonyl group, an isohexylsulfonyl group, etc. are mentioned.

The "lower alkylamino group" in the above-mentioned formula (I) means an amino group that is N-mono-substituted by the above-mentioned "lower alkyl group", and for example, an N-methylamino group, an N-ethylamino group, an N-propylamino group, an N-isopropylamino group, an N-butylamino group, an N-sec-butylamino group and an N-tert-butylamino group, etc. are mentioned.

The "di-lower alkylamino group" in the above-mentioned formula (I) means an amino group that is N,N-di-substituted by the identical or different "lower alkyl groups" mentioned above, and for example, an N,N-dimethylamino group, an N,N-diethylamino group, an N,N-dipropylamino group, an N,N-diisopropylamino group, an N-methyl-N-ethylamino group, an N-methyl-N-propylamino group and an N-methyl-N-isopropylamino group, etc. are mentioned.

The "hydroxy lower alkylamino group" in the above-mentioned formula (I) means an amino group that is N-mono-substituted or N,N-di-substituted, preferably N-mono-substituted by the above-mentioned "hydroxy lower alkyl group(s)", and for example, a hydroxymethylamino group, a 2-hydroxyethylamino group, a 1-hydroxy-1-methylethylamino group, a 1,2-dihydroxyethylamino group and a 3-hydroxypropylamino group, etc. are mentioned.

The "mono-lower alkyl carbamoyl group" in the above-mentioned formula (I) means a group in which the nitrogen atom of a carbamoyl group is N-mono-substituted by the above-mentioned "lower alkyl group", and for example, an N-methylcarbamoyl group, an N-ethylcarbamoyl group, an N-propylcarbamoyl group, an N-isopropylcarbamoyl group, an N-butylcarbamoyl group, an N-sec-butylcarbamoyl group and an N-tert-butylcarbamoyl group, etc. are mentioned.

The "di-lower alkyl carbamoyl group" in the above-mentioned formula (I) means a group in which the nitrogen atoms of a carbamoyl group are N,N-di-substituted by the identical or different "lower alkyl groups" mentioned above, and for example, an N,N-dimethylcarbamoyl group, an N,N-diethylcarbamoyl group, an N-ethyl-N-methylcarbamoyl group, an N,N-dipropylcarbamoyl group, an N-methyl-N-propylcarbamoyl group and an N,N-diisopropylcarbamoyl group, etc. are mentioned.

Furthermore, the "di-lower alkyl carbamoyl group" also includes a 5-to 8-membered monocycle that is formed by the nitrogen atom that constitutes the carbamoyl group together with the identical or different "lower alkyl groups" mentioned above that are bonded to the nitrogen atom, or a bicycle that is formed by the condensation of the monocycle and a benzene ring or a pyridine ring, and for example, groups represented by the following formulas are mentioned.

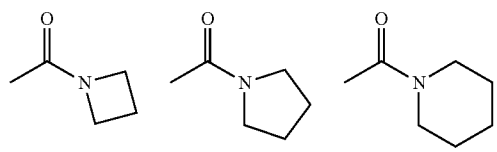

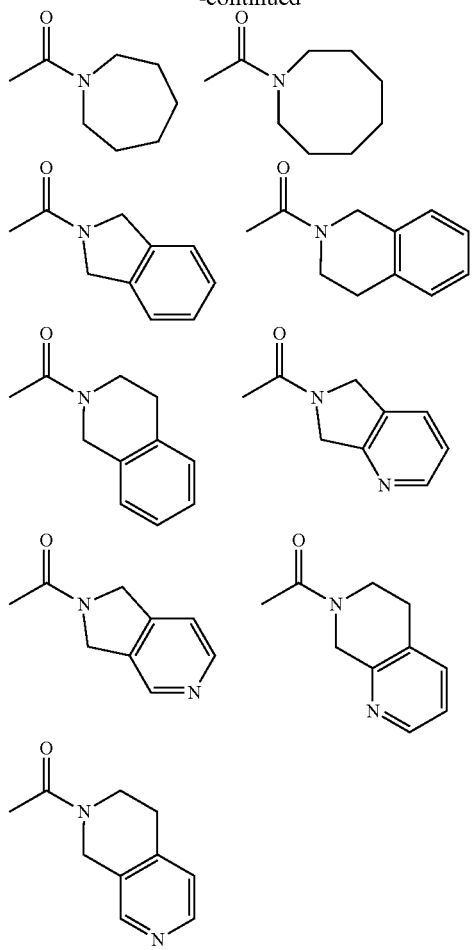

The "lower alkanoyl amino group" in the above-mentioned formula (I) means a group in which the above-mentioned "lower alkanoyl group" and an amino group or the above-mentioned "lower alkylamino group" are bonded, and for example, an N-acetylamino group, an N-propanoylamino group, an N-butanoylamino group, an N-pentanoylamino group, an N-pivaloylamino group, an N-methyl-N-acetylamino group, an N-methyl-N-propanoylamino group, an N-methyl-N-butanoylamino group, an N-methyl-N-pentanoylamino group, an N-ethyl-N-acetylamino group, an N-ethyl-N-propanoylamino group, an N-ethyl-N-butanoylamino group and an N-ethyl-N-pentanoylamino group, etc. are mentioned.

The "lower alkoxy carbonylamino group" in the above-mentioned formula (I) means a group in which the above-mentioned "lower alkoxy carbonyl group" and an amino group or the above-mentioned "lower alkylamino group" are bonded, and for example, a methoxycarbonylamino group, an ethoxycarbonylamino group, a propoxycarbonylamino group, an isopropoxycarbonylamino group, a butoxycarbonylamino group, an isobutoxycarbonylamino group, a sec-butoxycarbonylamino group, a tert-butoxycarbonylamino group, a pentyloxycarbonylamino group, a neopentyloxycarbonylamino group, a hexyloxycarbonylamino group, an isohexyloxycarbonylamino group, an N-methyl-methoxycarbonylamino group, an N-methyl-ethoxycarbonylamino group, etc. are mentioned.

The "lower alkyl sulfonylamino group" in the above-mentioned formula (I) means a group in which the above-mentioned "lower alkyl sulfonyl group" and an amino group or the above-mentioned "lower alkylamino group" are bonded, and for example, a methylsulfonylamino group, an ethylsulfonylamino group, a propylsulfonylamino group, an isopropylsulfonylamino group, a butylsulphonylamino group, a sec-butylsulphonylamino group, a tert-butylsulphonylamino group, an N-methyl-methylsulfonylamino group, an N-methyl-ethylsulfonylamino group, an N-methyl-propylsulfonylamino group, an N-methyl-isopropylsulfonylamino group, an N-methyl-butylsulphonylamino group, an N-methyl-sec-butylsulphonylamino group, an N-methyl-tert-butylsulphonylamino group, an N-ethyl-methylsulfonylamino group, an N-ethyl-ethylsulfonylamino group, an N-ethyl-propylsulfonylamino group, an N-ethyl-isopropylsulfonylamino group, an N-ethyl-butylsulphonylamino group, an N-ethyl-sec-butylsulphonylamino group and an N-ethyl-tert-butylsulphonylamino group, etc. are mentioned.

As the "aryl group" in the above-mentioned formula (I), for example, a phenyl group, a naphthyl group, a biphenyl group and an anthryl group, etc. are mentioned.

The "heteroaryl group" in the above-mentioned formula (I) means a 5- or 6- membered monocycle including 1 or 2 or more, preferably 1 to 4 heteroatom(s) that is/are identically or differently selected from the group consisting of an oxygen atom, a nitrogen atom and a sulfur atom, or a bicycle in which the monocycle and a benzene ring or a pyridine ring are condensed, and for example, a pyrrolyl group, a furyl group, a thienyl group, an imidazolyl group, a pyrazolyl group, a thiazolyl group, an isothiazolyl group, an oxazolyl group, an isoxazolyl group, a triazolyl group, a tetrazolyl group, a 1,2,3-oxadiazolyl group, a 1,2,4-oxadiazolyl group, a 1,3,4-oxadiazolyl group, a 1,2,5-oxadiazolyl group, a 1,2,3-thiadiazolyl group, a 1,2,4-thiadiazolyl group, a 1,3,4-thiadiazolyl group, a 1,2,5-thiadiazolyl group, a pyridyl group, a pyrazinyl group, a pyrimidinyl group, a pyridazinyl group, a 1,2,4-triazinyl group, a 1,3,5-triazinyl group, an indolyl group, an isoindolyl group, a benzofuranyl group, a benzothienyl group, a benzoimidazolyl group, a benzoxazolyl group, a benzoisoxazolyl group, a benzothiazolyl group, a benzoisothiazolyl group, an indazolyl group, an imidazo pyridyl group, a purinyl group, a quinolyl group, a quinolizinyl group, an isoquinolyl group, a phthalazinyl group, a naphthyridinyl group, a quinoxalinyl group, a quinazolinyl group, a cinnolinyl group, a pteridinyl group and a pyrid[3,2-b]pyridyl group, etc. are mentioned.

The "aliphatic heterocycle group" in the above-mentioned formula (I) means a 5- or 6-membered monocycle including 1 or 2 or more heteroatom(s) that is/are identically or differently selected from the group consisting of an oxygen atom, a nitrogen atom and a sulfur atom, or a saturated or unsaturated aliphatic heterocycle group that is a condensed ring formed of two or three rings including the above-mentioned heteroatom(s), and for example, an azetidyl group, a pyrrolidinyl group, a piperidinyl group, a pyrazinyl group, a morpholino group, a tetrahydrofuranyl group, an imidazolidinyl group, a thiomorpholino group, a tetrahydroquinolyl group and a tetrahydroisoquinolyl group, etc. are mentioned.

The "aryloxy group" in the above-mentioned formula (I) means a group in which an oxygen atom is bound to the above-mentioned "aryl group", and for example, a phenoxy group, a naphthalene-1-yloxy group and a naphthalene-2-yloxy group, etc. are mentioned.

The "heteroaryloxy group" in the above-mentioned formula (I) means a group in which an oxygen atom is bound to the above-mentioned "heteroaryl group", and for example, a furan-2-yloxy group, a furan-3-yloxy group, a thiophen-2-yloxy group, a thiophen-3-yloxy group, a 1H-pyrrol-2-yloxy group, a 1H-pyrrol-3-yloxy group, a 1H-imidazol-2-yloxy group, a 1H-imidazol-4-yloxy group, a 3H-imidazol-4-yloxy group, a 4H-[1,3,4]triazol-3-yloxy group, a 2H-[1,2,4]triazol-3-yloxy group, a 1H-[1,2,4]triazol-3-yloxy group, a thiazol-2-yloxy group, a thiazol-4-yloxy group, a thiazol-5-yloxy group, a pyridin-2-yloxy group, a pyridin-3-yloxy group, a pyridin-4-yloxy group, a pyrimidin-2-yloxy group, a pyrimidin-4-yloxy group, a pyrimidin-5-yloxy group, a pyridazin-3-yloxy group, a pyridazin-4-yloxy group, a 2H-pyrazol-3-yloxy group, a 1H-pyrazol-4-yloxy group, a 1H-pyrazol-3-yloxy group, a pyrazinyloxy group, a quinolin-2-yloxy group, a quinolin-3-yloxy group, a quinolin-4-yloxy group, an isoquinolin-1-yloxy group, an isoquinolin-3-yloxy group, an isoquinolin-4-yloxy group, a quinazolin-2-yloxy group, a quinazolin-3-yloxy group, a quinoxalin-2-yloxy group, a quinoxalin-3-yloxy group, a cinnolin-3-yloxy group, a cinnolin-4-yloxy group, a 1H-benzimidazol-2-yloxy group, a 1H-imidazo[4,5-b]pyridin-5-yloxy group, a 1H-imidazo[4,5-b]pyridin-6-yloxy group, a 1H-imidazo[4,5-b]pyridin-7-yloxy group, a benzo[d]isoxazol-4-yloxy group, a benzo[d]isoxazol-5-yloxy group, a benzo[d]isoxazol-6-yloxy group, a benzoxazol-4-yloxy group, a benzoxazol-5-yloxy group and a benzoxazol-6-yloxy group, etc. are mentioned.

The "lower alkylene group" in the above-mentioned formula (I) means a linear or branched alkylene group having a carbon number of from 1 to 6, and for example, a methylene group, an ethylene group, a trimethylene group, a tetramethylene group, a pentamethylene group and a hexamethylene group, etc. are mentioned.

The "lower alkenylene group" in the above-mentioned formula (I) means a divalent group that is formed by removing every hydrogen atom from the both chain terminals of above-mentioned "lower alkenyl group", and for example, a vinylene group and a propenylene group, etc. are mentioned.

The "lower alkynylene group" in the above-mentioned formula (I) means a divalent group that is formed by removing every hydrogen atom from the both chain terminals of the above-mentioned "lower alkynyl group", and for example, an ethynylene group and a propynylene group, etc. are mentioned.

The "lower alkylenedioxy group" in the above-mentioned formula (I) means a group that is formed by respectively bonding the both terminals of the above-mentioned "lower alkylene group" to oxygen atoms, and for example, a methylenedioxy group, an ethylenedioxy group and a propylenedioxy group, etc. are mentioned.

The "lower alkenyl group" in the above-mentioned formula (I) means a linear or branched alkenyl group having a carbon number of from 2 to 6, and for example, a vinyl group, a 1-propenyl group, an allyl group, an isopropenyl group, a 3-butenyl group, a 2-butenyl group, a 1-butenyl group, a 1-methyl-2-propenyl group, a 1-methyl-1-propenyl group, a 1-ethyl-1-ethenyl group, a 2-methyl-2-propenyl group, a 2-methyl-1-propenyl group, a 3-methyl-2-butenyl group and a 4-pentenyl group, etc. are mentioned.

The "lower alkynyl group" in the above-mentioned formula (I) means a linear or branched alkynyl group having a carbon number of from 2 to 6, and for example, an ethynyl group, a 1-propynyl group, a 2-propynyl group, a 3-butynyl group, a 2-butynyl group, a 1-butynyl group, a 1-methyl-2-propynyl group, a 1-ethyl-2-propynyl group, a 1-methyl-2-butynyl group and a 4-pentynyl group, etc. are mentioned.

The "aralkyl group" in the above-mentioned formula (I) means the above-mentioned "lower alkyl group" in which the substitutable optional position(s) is/are substituted by 1 or 2 or more, preferably 1 or 2 of the above-mentioned "aryl group(s)", and for example, a benzyl group, a 1-phenylethyl group, a 2-phenylethyl group and a 1-naphthylmethyl group, a 2-naphthylmethyl group, etc. are mentioned.

The "cyano lower alkyl group" in the above-mentioned formula (I) means the above-mentioned "lower alkyl group" in which the substitutable optional position(s) is/are substituted by 1 or 2 or more, preferably 1 or 2 cyano group(s), and for example, a cyanomethyl group, a 1-cyanoethyl group, a 1-cyanopropyl group, a 2-cyanoethyl group, a 2-cyanopropyl group, a 2-cyano-1-methylethyl group, a 2-cyano-1,1-dimethylethyl group, a 1-cyano-1-methylethyl group, a 1,2-dicyanodiethyl group and a 3-cyanopropyl group, etc. are mentioned.

The "substitutable optional position(s)" used in the present specification mean site(s) that is/are substitutable hydrogen atom(s) on a carbon atom, a nitrogen atom, an oxygen atom and/or a sulfur atom, where the substitution of the hydrogen atom(s) is/are chemically accepted, and consequently a stable compound is brought.

In order to further specifically disclose the compounds of the present invention, the respective symbols used in the formula (I) and the like will further be explained in detail with referring to their preferable specific examples.

In the above-mentioned formula (I), $R^1$ is a lower alkyl group optionally substituted by a cycloalkyl group, a cycloalkyl group, a halo lower alkyl group, a hydroxy lower alkyl group, a lower alkoxy lower alkyl group, a lower alkoxy carbonyl group, a lower alkyl sulfonyl group or a group represented by the general formula: $-Q^1-A^1$.

$R^1$ is preferably, for example, a lower alkyl group optionally substituted by a cycloalkyl group, a cycloalkyl group, a lower alkyl sulfonyl group, or a group represented by the general formula: $-Q^1-A^1$ or the like, and more preferably a group represented by the general formula: $-Q^1-A^1$ or the like.

The "lower alkyl group optionally substituted by a cycloalkyl group" for $R^1$ means an unsubstituted lower alkyl group, or a lower alkyl group in which the substitutable optional position(s) is/are substituted with the identical or different 1 or 2 or more, preferably 1 or 2 "cycloalkyl group(s)" mentioned above, and for example, a methyl group, an ethyl group, a propyl group, an isopropyl group, a butyl group, an iso-butyl group, a sec-butyl group, a tert-butyl group, a pentyl group, an isopentyl group, an isoamyl group, a neopentyl group, a 1,1-dimethylpropyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,2,2-trimethylpropyl group, a 1-ethyl-3-methylpropyl group, a cyclopropylmethyl group, a cyclobutylmethyl group, a cyclopentylmethyl group, a cyclohexylmethyl group, a cycloheptylmethyl group, a 1-cyclopropylethyl group, a 1-cyclobutylethyl group, a 1-cyclopentylethyl group, a 1-cyclohexylethyl group, a 1-cycloheptylethyl group, a 2-cyclopropylethyl group, a 2-cyclobutylethyl group, a 2-cyclopentylethyl group, a 2-cyclohexylethyl group, a 2-cycloheptylethyl group etc. are suitable and an isopropyl group, an iso-butyl group, a cyclopropylmethyl group, a cyclobutylmethyl group, a cyclopentylmethyl group and a cyclohexylmethyl group, etc. are more preferable.

As the cycloalkyl group for $R^1$, for example, a cyclopropyl group, a cyclobutyl group, a cyclopentyl group and a cyclohexyl group, etc. are preferable.

As the halo lower alkyl group for $R^1$, for example, a fluoromethyl group, a difluoromethyl group, a trifluoromethyl group and a 2,2,2-trifluoroethyl group, etc. are preferable.

As the hydroxy lower alkyl group for $R^1$, for example, a hydroxymethyl group and 2-hydroxyethyl group, etc. are preferable.

As the lower alkoxy lower alkyl group for $R^1$, for example, a methoxymethyl group and an ethoxymethyl group, etc. are preferable.

As the lower alkoxy carbonyl group for $R^1$, for example, a methoxycarbonyl group, an ethoxycarbonyl group, a propoxycarbonyl group, an isopropoxycarbonyl group, a butoxycarbonyl group, an isobutoxycarbonyl group, a tert-butoxycarbonyl group and a pentyloxycarbonyl group, etc. are preferable.

As the lower alkyl sulfonyl group for $R^1$, for example, a methanesulfonyl group and an ethanesulfonyl group, etc. are preferable.

$Q^1$ represents a single bond or a lower alkylene group (wherein the entirety of each of the 1 or 2 or more methylene group(s) that constititute(s) the lower alkylene group may be independently replaced with a carbonyl group, a sulfinyl group or a sulfonyl group, and/or the hydrogen(s) that constitute(s) the methylene group(s) may be substituted by lower alkyl group(s)).

As the lower alkylene group for $Q^1$, for example, a methylene group, an ethylene group and a trimethylene group, etc. are preferable.

The entirety of each of the 1 or 2 or more methylene group(s) that constitute(s) the lower alkylene group of $Q^1$ may be independently substituted by a carbonyl group, a sulfinyl group or a sulfonyl group, and/or the hydrogen (s) that constitute(s) the methylene group(s) may be substituted by lower alkyl group(s), and such replaced or substituted groups are, preferably, for example, groups selected from the following formulas.

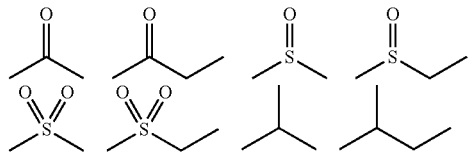

$A^1$ represents an aryl group or a heteroaryl group optionally substituted by 1 to 3 substituent(s) selected from <Substituent group L>(wherein the adjacent optional two substituents on the aryl group or heteroaryl group may be together to form a lower alkylenedioxy group).

Here, <Substituent group L> is a group consisting of a halogen atom, a hydroxyl group, a nitro group, a cyano group, a formyl group, an amino group, a carboxyl group, a lower alkyl group, a halo lower alkyl group, a cycloalkyl group, a lower alkoxy group, a halo lower alkoxy group, a hydroxy lower alkyl group, a lower alkoxy lower alkyl group, a lower alkoxy carbonyl group, a lower alkanoyl group, a lower alkylthio group, a lower alkyl sulfonyl group, a lower alkylamino group, a di-lower alkylamino group, a carbamoyl group, a mono-lower alkyl carbamoyl group, a di-lower alkylcarbamoyl group, a lower alkanoyl amino group, a lower alkyl sulfonylamino group, a lower alkoxy carbonylamino group, an aralkyl group, an aryloxy group, a heteroaryloxy group, a lower alkenyl group and a cyano lower alkyl group.

As the aryl group for $A^1$, for example, a phenyl group, a naphthyl group and a biphenyl group, etc. are preferable.

As the heteroaryl group for $A^1$, for example, an imidazolyl group, a furyl group, a thienyl group, a pyrazolyl group, a thiazolyl group, an isothiazolyl group, an oxazolyl group, an isoxazolyl group, a 1,2,4-oxadiazolyl group, a 1,3,4-oxadiazolyl group, a pyridyl group, a pyrazinyl group, a pyrimidinyl group, a benzofuranyl group, a quinolyl group, an isoquinolyl group, a benzothienyl group and the like, more preferably, a pyridyl group, a quinolyl group, an isoquinolyl group, a thienyl group, a pyrazolyl group, a thiazolyl group, an isoxazolyl group, a benzothienyl group, etc. are preferable.

The "adjacent optional two substituents on the aryl group or heteroaryl group may be together to form a lower alkylenedioxy group" for $A^1$ refers to a group in which the adjacent optional two substituents on the aryl group or heteroaryl group are together to form a lower alkylenedioxy group, and for example, a benzo[1,3]dioxolyl group and a 2,3-dihydro-benzo[1,4]dioxynyl group, etc. are preferable.

Therefore, $A^1$ is, for example a phenyl group, a 2-fluorophenyl group, a 3-fluorophenyl group, a 4-fluorophenyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2-chlorophenyl group, a 3-chlorophenyl group, a 4-chlorophenyl group, a 2,3-dichlorophenyl group, a 2,4-dichlorophenyl group, a 2,5-dichlorophenyl group, a 2,6-dichlorophenyl group, a 2-bromophenyl group, a 3-bromophenyl group, a 4-bromophenyl group, a 2-chloro-3-fluorophenyl group, a 2-chloro-4-fluorophenyl group, a 2-chloro-5-fluorophenyl group, a 2-chloro-6-fluorophenyl group, a 2-bromo-3-fluorophenyl group, a 2-bromo-4-fluorophenyl group, a 2-bromo-5-fluorophenyl group, a 2-bromo-6-fluorophenyl group, a 2-methylphenyl group, a 3-methylphenyl group, a 4-methylphenyl group, a 2-ethylphenyl group, a 3-ethylphenyl group, a 4-ethylphenyl group, a 2-cyclopropylphenyl group, a 3-cyclopropylphenyl group, a 4-cyclopropylphenyl group, a 2-trifluoromethylphenyl group, a 3-trifluoromethylphenyl group, a 4-trifluoromethylphenyl group, a 2-methoxyphenyl group, a 3-methoxyphenyl group, a 4-methoxyphenyl group, a 2-difluoromethoxyphenyl group, a 3-difluoromethoxyphenyl group, a 4-difluoromethoxyphenyl group, a 2-trifluoromethoxyphenyl group, a 3-trifluoromethoxyphenyl group, a 4-trifluoromethoxyphenyl group, a 2-hydroxyphenyl group, a 3-hydroxyphenyl group, a 4-hydroxyphenyl group, a 2-hydroxymethylphenyl group, a 3-hydroxymethylphenyl group, a 4-hydroxymethylphenyl group, a 2,3-dimethylphenyl group, a 2,4-dimethylphenyl group, a 2,5-dimethylphenyl group, a 2,6-dimethylphenyl group, a 2,4,6-trimethylphenyl group, a 2-fluoro-6-trifluoromethylphenyl group, a 4-fluoro-2-trifluoromethylphenyl group, a 2-chloro-6-methylphenyl group, a 2-chloro-6-cyclopropylphenyl group, a 2-chloro-6-cyanophenyl group, a 2-chloro-6-hydroxymethyl group, a 2,6-dicyclopropylphenyl group, a 2-cyano-5-methylphenyl group, a 2-cyano-6-methylphenyl group, a 2-cyclopropyl-6-fluorophenyl group, a 2-chloro-6-methoxyphenyl group, a 2-cyano-6-methoxyphenyl group, a 2-cyano-6-fluorophenyl group, a 2-cyano-6-hydroxymethyl group, a benzo[1,3]dioxo-5-yl group, a 6-chlorobenzo[1,3]dioxo-5-yl group, a 1-naphthyl group, a 2-naphthyl group, a 2-biphenyl group, a 3-biphenyl group, a 4-biphenyl group, a 2-imidazolyl group, a 2-furyl group, a 2-thienyl group, a 1,2,4-oxadiazol-5-yl group, a 1,3,4-oxadiazol-2-yl group, a 1,2,4-thiadiazol-5-yl group, a 1,3,4-thiadiazol-2-yl group, a 4-isoxazolyl group, a 3,5-dimethylisoxazolyl group, a 2-pyridyl group, a 3-pyridyl group, a 4-pyridyl group, a 2-fluoro-5-pyridyl group, a 3-fluoro-6-pyridyl group, a 2-chloro-3-pyridyl group, a 2-chloro-5-pyridyl group, a 2-methyl-3-pyridyl group, a 2-methyl-6-pyridyl group, a 2-pyrimidinyl group, a 4-benzo[b]furanyl group, a 7-benzo[b]furanyl group, a 2-quinolyl group, a 3-quinolyl group, a 4-quinolyl group, a 5-quinolyl group, a 6-quinolyl group, a 7-quinolyl group, an 8-quinolyl group, a 5-chlorothiophene-2-yl group, a 2-benzo[b]thiophenyl group, a 3-benzo[b]thiophenyl group, a 4-benzo[b]thiophenyl group, a 5-benzo[b]thiophenyl group, a 6-benzo[b]thiophenyl group, a 7-benzo[b]thiophenyl group, 5-chlorobenzo[b]thiophen-3-yl group, a 2-cyanophenyl group, a 3-cyanophenyl group, a 4-cyanophenyl group, a 2-carbamoylphenyl group, a 3-carbamoylphenyl group, a 4-carbamoylphenyl group, a 2-(N-methylcarbamoyl)phenyl group, a 3-(N-methylcarbamoyl)phenyl group, a 4-(N-methylcarbamoyl)phenyl group, a 2-methanesulfonylphenyl group, a 3-methanesulfonylphenyl group, a 4-methanesulfonylphenyl group, a 2-cyano-3-methylphenyl group, a 2-cyano-4-methylphenyl group, a 2-cyano-6-cyclopropylphenyl group, a 3-cyano-2-methylphenyl group, a 2,6-dicyanophenyl group, a 2-carbamoyl-3-methylphenyl group, a 2-carbamoyl-6-methylphenyl group, a 2-carbamoyl-6-ethylphenyl group, a 2-carbamoyl-6-cyclopropylphenyl group, a 2-carbamoyl-6-methoxyphenyl group, a 2-carbamoyl-6-chlorophenyl group, a 2-chloro-6-(N-methylcarbamoyl)phenyl group, a 2-chloro-6-methanesulfonylphenyl group, a 2-hydroxymethyl-6-methylphenyl group, a 2-cyanomethyl-6-methylphenyl group, a 2-carbamoylpyridin-3-yl group, a 2-cyanopyridin-3-yl group, a 2-chloro-4-cyanopyridin-3-yl group, a 1-isoquinolyl group, a 3-isoquinolyl group, a 4-isoquinolyl group, a 5-isoquinolyl group, a 6-isoquinolyl group, a 7-isoquinolyl group and an 8-isoquinolyl group, etc. are mentioned, and especially 2-fluorophenyl group, a 2-chlorophenyl group, a 2,3-dichlorophenyl group, a 2,6-dichlorophenyl group, a 2-chloro-6-fluorophenyl group, a 2-methylphenyl group, a 2-ethylphenyl group, a 2-cyclopropylphenyl group, a 2-trifluoromethylphenyl group, a 2-methoxyphenyl group, a 2-difluoromethoxyphenyl group, a 2-trifluoromethoxyphenyl group, a 2-hydroxyphenyl group, a 2-hydroxymethylphenyl group, a 2,5-dimethylphenyl group, a 2,6-dimethylphenyl group, a 2,4,6-trimethylphenyl group, a 2-fluoro-6-trifluoromethylphenyl group, a 2-chloro-6-methylphenyl group, a 2-chloro-6-cyclopropylphenyl group, a 2-chloro-6-cyanophenyl group, a 2-chloro-6-hydroxymethylphenyl group, a 2,6-dicyclopropylphenyl group, a 2-cyano-5-methylphenyl group, a 2-cyano-6-methylphenyl group, a 2-cyclopropyl-6-fluorophenyl group, a 2-chloro-6-methoxypheny group, a 2-cyano-6-methoxypheny group, a 2-cyano-6-fluorophenyl group, a 2-cyano-6-hydroxymethylphenyl group, a 1-naphthyl group, an 8-quinolyl group, a 5-chlorobenzo[b]thiophen-3-yl group, a phenyl group, a 2-chloro-5-fluorophenyl group, a 2-cyanophenyl group, a 3-cyanophenyl group, a 4-cyanophenyl group, a 2-carbamoylphenyl group, a 2-cyano-3-methylphenyl group, a 2-cyano-6-cyclopropylphenyl group, a 3-cyano-2-methylphenyl group, a 2,6-dicyanophenyl group, a 2-carbamoyl-3-methylphenyl group, a 2-carbamoyl-6-methylphenyl group, a 2-carbamoyl-6-ethylphenyl group, a 2-carbamoyl-6-cyclopropylphenyl group, a 2-carbamoyl-6-methoxyphenyl group, a 2-carbamoyl-6-chlorophenyl group, a 2-chloro-6-(N-methylcarbamoyl)phenyl group, a 2-chloro-6-methanesulfonylphenyl group, a 2-hydroxymethyl-6- methylphenyl group, a 2-cyanomethyl-6-methylphenyl group, a 3-pyridyl group, a 2-chloro-3-pyridyl group, a 2-carbamoylpyridin-3-yl group, a 2-cyanopyridin-3-yl group, a 2-chloro-4-cyanopyridin-3-yl group, a 5-quinolyl group, a 1-isoquinolyl group, a 5-isoquinolyl group and an 8-isoquinolyl group, etc. are suitable, and more preferably is a 2,3-dichlorophenyl group, a 2,6-dichlorophenyl group, a 2-chloro-6-fluorophenyl group, a 2,5-dimethylphenyl group, a 2,6-dimethylphenyl group, a 2,4,6-trimethylphenyl group, a 2-fluoro-6-trifluoromethylphenyl group, a 2-chloro-6-methylphenyl group, a 2-chloro-6-cyclopropylphenyl group, a 2-chloro-6-cyanophenyl group, a 2-cyano-6-methylphenyl group, a 2-cyclopropyl-6-fluorophenyl group, a 2-chloro-6-methoxyphenyl group, a 1-naphthyl group, a 5-chlorobenzo[b]thiophen-3-yl group, a phenyl group, a 2-fluorophenyl group, a 2-chlorophenyl group, a 2-methylphenyl group, a 2-trifluoromethylphenyl group, a 2-methoxyphenyl group, a 2-trifluoromethoxyphenyl group, a 2-cyanophenyl group, a 3-cyanophenyl group, a 2-cyano-3-methylphenyl group, a 2-cyano-6-cyclopropylphenyl group, a 2-cyano-6-fluorophenyl group, a 2-cyano-6-methoxyphenyl group, a 3-cyano-2-methylphenyl group, a 2-carbamoyl-6-methylphenyl group, a 2-carbamoyl-6-cyclopropylphenyl group, a 2-carbamoyl-6-chlorophenyl group, a 2-cyano-6-hydroxymethylphenyl group, a 2-hydroxymethyl-6-methylphenyl group, a 2-cyanomethyl-6-methylphenyl group, a 2-chloro-3-pyridyl group, a 2-chloro-4-cyanopyridin-3-yl group, a 5-quinolyl group, an 8-quinolyl group, a 1-isoquinolyl group, and a 5-isoquinolyl group, etc.

$R^2$ represents a hydrogen atom, a substituent selected from <Substituent group M> or a group represented by the general formula: $-Q^2-A^2$.

Here, <Substituent group M> is a group consisting of a halogen atom, a hydroxyl group, a nitro group, a cyano group, a formyl group, an amino group, a carboxyl group, a lower alkyl group, a halo lower alkyl group, a cycloalkyl group, a lower alkoxy group, a halo lower alkoxy group, a hydroxy lower alkyl group, a lower alkoxy lower alkyl group, a lower alkoxy carbonyl group, a lower alkanoyl group, a lower alkylthio group, a lower alkyl sulfonyl group, a lower alkylamino group, a di-lower alkylamino group, a carbamoyl group, a mono-lower alkyl carbamoyl group, a di-lower alkyl carbamoyl group, a lower alkanoyl amino group, a lower alkyl sulfonylamino group and a lower alkoxy carbonylamino group.

As $R^2$, for example a hydrogen atom, a halogen atom, a hydroxyl group, a cyano group, a formyl group, a carboxyl group, a lower alkyl group, a halo lower alkyl group, a cycloalkyl group, a hydroxy lower alkyl group, a lower alkoxy lower alkyl group, a lower alkoxy carbonyl group, a lower alkanoyl group, a group represented by general formula: $-Q^2-A^2$ are suitable, and a hydrogen atom, a halogen atom, a cyano group, a lower alkyl group, a halo lower alkyl group, a cycloalkyl group, a hydroxy lower alkyl group, and a group represented by general formula: $-Q^2-A^2$ etc. are more preferable.

For example a fluorine atom, a chlorine atom, a bromine atom, and an iodine atom are suitable for a halogen atom of $R^2$.

A lower alkyl group of $R^2$, for example a methyl group, an ethyl group, a propyl group, an isopropyl group, a butyl group, an iso-butyl group, a sec-butyl group, a tert-butyl group, a pentyl group, an isopentyl group, an isoamyl group, a neopentyl group, a 1,1-dimethylpropyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,2,2-trimethylpropyl group, a 1-ethyl-3-methylpropyl group, etc. are mentioned, and a methyl group, an ethyl group, a propyl group and an isopropyl group, etc. are especially suitable.

As the halo lower alkyl group for $R^2$, for example, a fluoromethyl group, a difluoromethyl group, a trifluoromethyl group and a 2,2,2-trifluoroethyl group and the like are mentioned, and among these, a difluoromethyl group and a trifluoromethyl group, etc. are preferable.

As the cycloalkyl group for $R^2$, for example, a cyclopropyl group, a cyclobutyl group, a cyclopentyl group and a cyclohexyl group and the like are mentioned, and among these, a cyclopropyl group, etc. are preferable.

As the hydroxy lower alkyl group for $R^2$, for example, a hydroxymethyl group, a 1-hydroxyethyl group, a 1-hydroxypropyl group, a 2-hydroxyethyl group, a 2-hydroxypropyl group, a 2-hydroxy-1-methylethyl group, a 1-hydroxy-1-methylethyl group, a 1,2-dihydroxyethyl group, a 3-hydroxypropyl group and the like are mentioned, and among these, a hydroxymethyl group is preferable.

$Q^2$ represents a single bond, a lower alkylene group or a lower alkenylene group wherein the entirety of each of the 1 or 2 or more methylene group(s) that constitute(s) the lower alkylene group may be independently replaced with an oxygen atom, a nitrogen atom or a carbonyl group, and/or the hydrogen(s) that constitute(s) the methylene group(s) may be substituted by a halogen atom, a cyano group, a hydroxyl group or a lower alkyl group.

As the lower alkylene group for $Q^2$, for example, a methylene group, an ethylene group and a trimethylene group, etc. are preferable.

The entirety of the 1 or 2 or more methylene group(s) that constitute(s) the lower alkylene group for $Q^2$ may be each independently substituted by an oxygen atom, a nitrogen atom or a carbonyl group, and/or the hydrogen(s) that constitute(s) the methylene group(s) may be substituted by a halogen atom, a cyano group, a hydroxyl group or a lower alkyl group. Such replaced or substituted groups are, preferably, for example, groups selected from the following formulas.

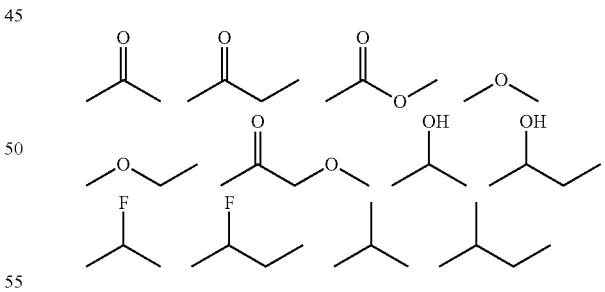

$Q^2$ is more preferably a single bond, a methylene group and a group selected from the following groups, etc.

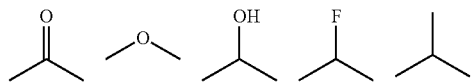

$A^2$ represents a cycloalkyl group, an aliphatic heterocycle group, an aryl group or a heteroaryl group, which is optionally substituted by 1 to 3 substituent(s) selected from <Substituent group L>(wherein the adjacent optional two substituents on the aryl group or heteroaryl group may be together to form a lower alkylenedioxy group).

As the aryl group for $A^2$, for example, a phenyl group, a naphthyl group and a biphenyl group, etc. are preferable.

As the heteroaryl group for $A^2$, for example, an imidazolyl group, a furyl group, a thienyl group, a pyrazolyl group, a thiazolyl group, an isothiazolyl group, an oxazolyl group, an isoxazolyl group, a 1,2,4-oxadiazolyl group, a 1,3,4-oxadiazolyl group, a pyridyl group, a pyrazinyl group, a pyrimidinyl group, a benzofuranyl group and a quinolyl group, etc. are preferable.

That "the adjacent optional two substituents on the aryl group or heteroaryl group may be together to form a lower alkylenedioxy group" for $A^2$ refers to that the adjacent optional two substituents on the aryl group or heteroaryl group come together to form a lower alkylenedioxy group. For example, a benzo[1,3]dioxolyl group and a 2,3-dihydrobenzo[1,4]dioxynyl group, etc. are preferable.

Therefore, $A^2$ is, for example, preferably a phenyl group, a 2-fluorophenyl group, a 3-fluorophenyl group, a 4-fluorophenyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2-chlorophenyl group, a 3-chlorophenyl group, a 4-chlorophenyl group, a 2-bromophenyl group, a 3-bromophenyl group, a 4-bromophenyl group, a 2-chloro-3-fluorophenyl group, a 2-chloro-4-fluorophenyl group, a 2-chloro-5-fluorophenyl group, a 2-chloro-6-fluorophenyl group, a 2-bromo-3-fluorophenyl group, a 2-bromo-4-fluorophenyl group, a 2-bromo-5-fluorophenyl group, a 2-bromo-6-fluorophenyl group, a 2-methylphenyl group, a 3-methylphenyl group, a 4-methylphenyl group, a 2-trifluoromethylphenyl group, a 3-trifluoromethylphenyl group, a 4-trifluoromethylphenyl group, a 2-methoxyphenyl group, a 3-methoxyphenyl group, a 4-methoxyphenyl group, a 2-difluoromethoxyphenyl group, a 3-difluoromethoxyphenyl group, a 4-difluoromethoxyphenyl group, a 2-trifluoromethoxyphenyl group, a 3-trifluoromethoxyphenyl group, a 4-trifluoromethoxyphenyl group, a 2-hydroxyphenyl group, a 3-hydroxyphenyl group, a 4-hydroxyphenyl group, a 2-hydroxymethylphenyl group, a 3-hydroxymethylphenyl group, a 4-hydroxymethylphenyl group, a 2,6-dimethylphenyl group, a 2,3-dichlorophenyl group, a 2,6-dichlorophenyl group, a 2-fluoro-6-trifluoromethylphenyl group, a 2-trifluoro-4-fluorophenyl group, a 2-imidazolyl group, a 2-furyl group, a 2-thienyl group, 1,2,4-oxadiazol-5-yl group, 1,3,4-oxadiazol-2-yl group, 1,2,4-thiadiazol-5-yl group, 1,3,4-thiadiazol-2-yl group, a 2-pyridyl group, a 3-pyridyl group, a 4-pyridyl group, a 2-fluoro-5-pyridyl group, a 3-fluoro-6-pyridyl group, a 2-pyrimidinyl group, a 4-benzo[b]furanyl group, a 7-benzo[b]furanyl group, a 2-quinolyl group, a 3-quinolyl group, a 4-quinolyl group, a 5-quinolyl group, a 6-quinolyl group, a 7-quinolyl group, an 8-quinolyl group, etc.

$W^1$, $W^2$, $W^3$ and $W^4$ each independently represents a nitrogen atom, or a methine group optionally having substituent(s) selected from the group consisting of a halogen atom, a hydroxyl group, a cyano group, a lower alkyl group, a cycloalkyl group, a halo lower alkyl group, a lower alkoxy group and a halo lower alkoxy group.

The "methine group optionally having substituent(s) selected from the group consisting of a halogen atom, a hydroxyl group, a cyano group, a lower alkyl group, a cycloalkyl group, a halo lower alkyl group, a lower alkoxy group and a halo lower alkoxy group" means an unsubstituted methine group or a methine group having substituent(s). The substituent(s) can be selected from the group consisting of a halogen atom, a hydroxyl group, a cyano group, a lower alkyl group, a cycloalkyl group, a halo lower alkyl group, a lower alkoxy group and a halo lower alkoxy group.

As the halogen atom for the substituent(s), for example, a fluorine atom, a chlorine atom, a bromine atom and an iodine atom are preferable.

As the lower alkyl group for the substituent(s), for example, a methyl group and an ethyl group, etc. are preferable.

As the cycloalkyl group for the substituent(s), for example, a cyclopropyl group, etc. are preferable.

As the halo lower alkyl group for the substituent(s), for example, a fluoromethyl group, a difluoromethyl group and a trifluoromethyl group, etc. are preferable.

As the lower alkoxy group for the substituent(s), for example, a methoxy group and an ethoxy group, etc. are preferable.

As the halo lower alkoxy group for the substituent(s), for example, a difluoromethoxy group and a trifluoromethoxy group, etc. are preferable.

In $W^1$, $W^2$, $W^3$ and $W^4$, 0 to 4, preferably 0 to 3, especially preferably 0 to 2 of $W^1$, $W^2$, $W^3$ and $W^4$ is/are nitrogen atom(s).

Accordingly, the combinations of $W^1$, $W^2$, $W^3$ and $W^4$ for the general formula (I) are exemplified as follows.

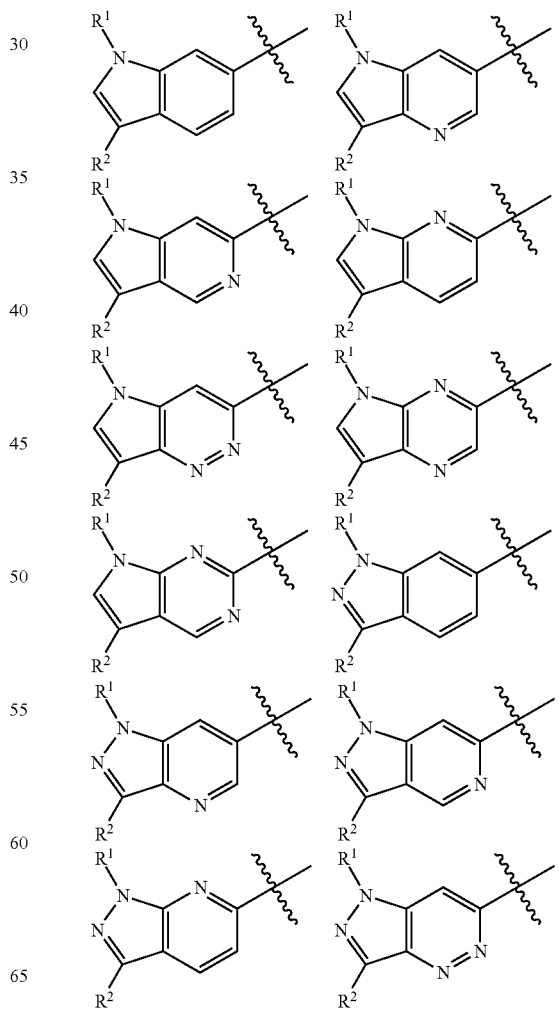

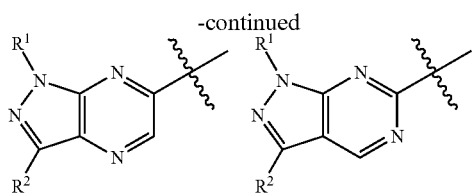

More preferably, the combination is selected from any of the followings.

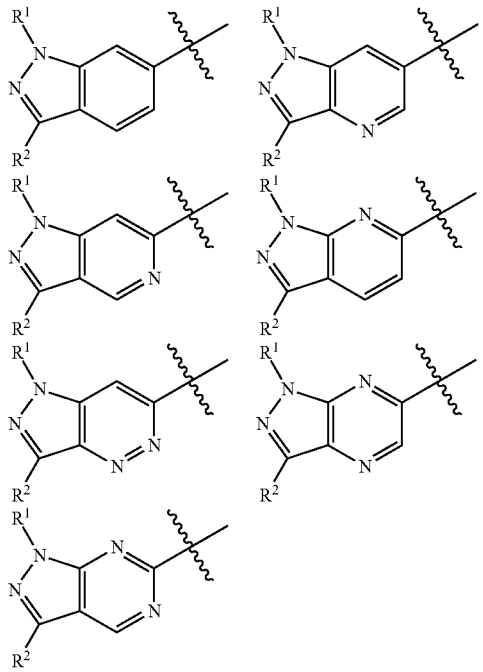

The following combinations are notably preferable.

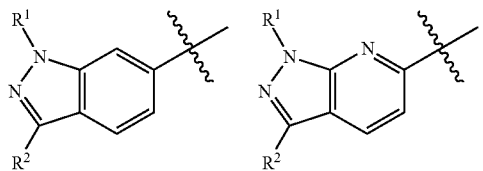

X and Y are each independently represents a single bond, a lower alkylene group, a lower alkenylene group or a lower alkynylene group (wherein the entirety of each of the 1 or 2 or more methylene group(s) that constitute(s) the lower alkylene group may be independently replaced with an oxygen atom, a sulfur atom, a sulfinyl group, a sulfonyl group, a carbonyl group or a group represented by the general formula: —N($R^N$)—, and/or the hydrogen (s) that constitute(s) the methylene group(s) may be substituted by a halogen atom, a cyano group, a hydroxyl group or a lower alkyl group).

As the lower alkylene group for X and Y, for example, a methylene group, an ethylene group and a triethylene group, etc. are preferable.

As the lower alkenylene group for X and Y, for example, a vinylene group, etc. are preferable.

As the lower alkynylene group for X and Y, for example, an ethynylene group, etc. are preferable.

The entirety of each of the 1 or 2 or more methylene group(s) that constitute(s) the lower alkylene group for X and Y may be independently replaced with an oxygen atom, a sulfur atom, a sulfinyl group, a sulfonyl group, a carbonyl group or a group represented by the general formula: —N($R^N$)—, and/or the hydrogen(s) that constitute(s) the methylene group(s) may be substituted with a halogen atom, a cyano group, a hydroxyl group or a lower alkyl group, and such replaced or substituted groups are preferably, for example, groups selected from the following formulas.

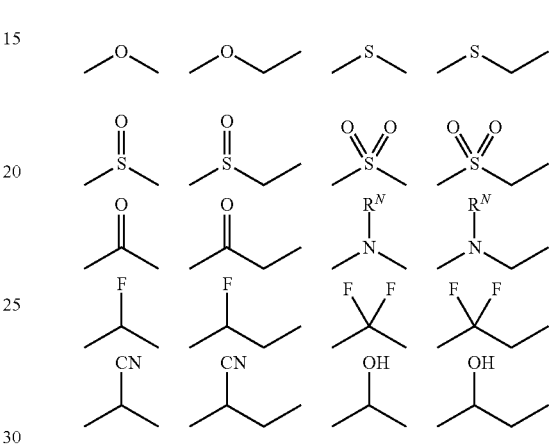

$R^N$ represents a hydrogen atom, a lower alkyl group, a halo lower alkyl group or a lower alkanoyl group.

As the lower alkyl group for $R^N$, for example, a methyl group, an ethyl group and a propyl group, etc. are preferable.

As the halo lower alkyl group for $R^N$, for example, a difluoromethyl group and a trifluoromethyl group, etc. are preferable.

As the lower alkanoyl group for $R^N$, for example, an acetyl group, a propionyl group, a valeryl group and a pivaloyl group, etc. are preferable.

Therefore, the combination of X and Y in the general formula (I) are exemplified as follows.

(1) When X is a single bond, and Y is a single bond, the combination of X and Y in the general formula (I) is represented as follows.

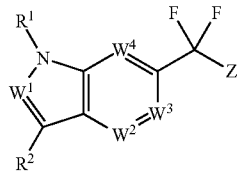

(2) When X is a single bond, and Y is a methylene group, the general formula (I) is represented as the following formula.

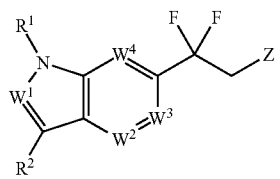

(3) When X is a single bond, and Y is an ethylene group, the general formula (I) is represented as the following formula.

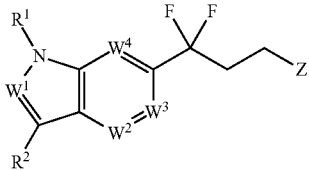

(4) When X is an oxygen atom, and Y is a single bond, the general formula (I) is represented as the following formula.

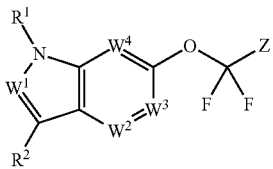

(5) When X is a methylene group, and Y is a single bond, the general formula (I) is represented as the following formula.

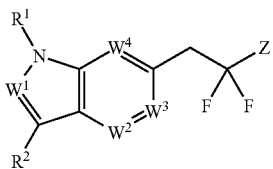

Z is a hydroxyl group, $COOR^3$, $CONR^4R^5$, $SO_3R^3$, $SO_3NR^4R^5$, a 5-tetrazolyl group, a 5-oxo-1,2,4-oxadiazolyl group, a 2-oxo-1,3,4-oxadiazolyl group, a 5-imino-4,5-dihydro-1,3,4-oxadiazolyl group, a 2-thioxo-1,3,4-oxadiazolyl group or a 5-oxo-1,2,4-thiadiazolyl group.

$R^3$, $R^4$ and $R^5$ are each independently a hydrogen atom or a lower alkyl group.

Preferable embodiments of the present invention can also be expressed as the following (1) to (9).

(1) The compound or a pharmaceutically acceptable salt or ester of the compound according to the above-mentioned formula (I), wherein $R^1$ is a group represented by the general formula: $-Q^1-A^1$, and $Q^1$ is a methylene group.

(2) The compound or a pharmaceutically acceptable salt or ester of the compound according to the above-mentioned formula (I) or the above-mentioned (1), wherein $R^2$ is a halogen atom, a cyano group, a lower alkyl group, a halo lower alkyl group, a cycloalkyl group or a hydroxy lower alkyl group.

(3) The compound or a pharmaceutically acceptable salt or ester of the compound according to the above-mentioned formula (I) or the above-mentioned (1) or (2), wherein X and Y are each a single bond.

(4) The compound or a pharmaceutically acceptable salt or ester of the compound according to the above-mentioned formula (I) or any one of the above-mentioned (1) to (3), wherein $A^1$ is an optionally substituted phenyl group, an optionally substituted naphthyl group, an optionally substituted quinolyl group, an optionally substituted isoquinolyl group, an optionally substituted isoindolyl group, an optionally substituted benzothienyl group or an optionally substituted pyridyl group.

(5) The compound or a pharmaceutically acceptable salt or ester of the compound according to the above-mentioned formula (I) or any one of the above-mentioned (1) to (4), wherein $R^2$ is a methyl group, an ethyl group, a trifluoromethyl group, a hydroxymethyl group or a chlorine atom.

(6) The compound or a pharmaceutically acceptable salt or ester of the compound according to the above-mentioned formula (I) or any one of the above-mentioned (1) to (5), wherein $W^1$ is a nitrogen atom.

(7) The compound or a pharmaceutically acceptable salt or ester of the compound according to the above-mentioned formula (I) or any one of the above-mentioned (1) to (6), wherein Z is COOH, a 5-tetrazolyl group or a 2-oxo-1,3,4-oxadiazolyl group.

(8) The compound or a pharmaceutically acceptable salt or ester of the compound according to the above-mentioned formula (I) or any one of the above-mentioned (1) to (7), wherein $W^2$, $W^3$ and $W^4$ are each a group represented by the general formula: =CH—.

(9) The compound or a pharmaceutically acceptable salt or ester of the compound according to the above-mentioned formula (I) or any one of the above-mentioned (1) to (7), wherein $W^2$ and $W^3$ are each a group represented by the general formula: =CH—, and $W^4$ is a nitrogen atom.

(10) The compound or a pharmaceutically acceptable salt or ester of the compound according to the above-mentioned formula (I) wherein $R^1$ is a group represented by the general formula: $-Q^1-A^1$, and $Q^1$ is a sulfonyl group.

Furthermore, as specific examples of the compound represented by the above-mentioned formula (I) or the pharmaceutically acceptable salt or ester, the compounds or pharmaceutically acceptable salts or esters of the compounds of Examples, etc. are mentioned, and specifically, the following compounds (a) to (k):

(a) [1-(2-chloro-6-fluorobenzyl)-3-methyl-1H-indazol-6-yl]difluoroacetic acid (example 9)
(b) [1-(2,3-dichlorobenzyl)-3-methyl-1H-indazol-6-yl]difluoroacetic acid (example 14)
(c) difluoro[1-(2-fluoro-6-trifluoromethylbenzyl)-3-methyl-1H-indazol-6-yl]acetic acid (example 22)
(d) [1-(2-cyano-6-methylbenzyl)-3-methyl-1H-indazol-6-yl]difluoroacetic acid (example 24)
(e) [1-(2-cyano-6-cyclopropylbenzyl)-3-methyl-1H-indazol-6-yl]difluoroacetic acid (example 32)
(f) [1-(2-cyano-6-hydroxymethylbenzyl)-3-methyl-1H-indazol-6-yl]difluoroacetic acid (example 53)
(g) 3-chloro-2-{6-[difluoro(1H-tetrazol-5-yl)methyl]-3-methyl-1H-indazol-1-ylmethyl}benzamide (example 67)
(h) 2-{6-[difluoro(1H-tetrazol-5-yl)methyl]-3-methyl-1H-indazol-1-ylmethyl}-3-(hydroxymethyl)benzonitrile (example 104)
(i) 2-{6-[difluoro(1H-tetrazol-5-yl)methyl]-3-methyl-H-pyrazolo[3,4-b]pyridin-1-ylmethyl}-3-methylbenzamide (example 110)
(j) 3-cyclopropyl-2-{6-[difluoro(1H-tetrazol-5-yl)methyl]-3-methyl-1H-pyrazolo[3,4-b]pyridin-1-ylmethyl}benzamide (example 116)
(k) [1-(2-cyano-6-methylbenzyl)-3-hydroxymethyl-1H-indazol-6-yl]difluoroacetic acid (example 121)
and pharmaceutically acceptable salts and esters of the above-mentioned compounds, etc. are more preferable.

The compound of the present invention may have an asymmetric center, a chiral axis, and a chiral plane.

The compound of the present invention may be generated as a racemate, as a racemic mixture, and as various diastereomers.

Furthermore, all of possible isomers including optical isomers, and mixtures thereof are covered by the present invention.

In addition, the compounds disclosed in the present specification may be present as tautomers, and it is intended that, even in the case when only one tautomer structure is depicted, both tautomer structure types are encompassed by the scope of the present invention.

In the present invention, the replacement of the methylene group(s) that constitute(s) the lower alkylene group with, for example, an oxygen atom, a sulfur atom, a sulfinyl group, a sulfonyl group, a carbonyl group or a group represented by the general formula: —N($R^N$)— is allowed in the case when such replacement is chemically allowed and a stable compound is consequently given.

The present invention further encompasses an N-oxide of the compound represented by the above-mentioned formula (I) in the scope thereof. In general, such N-oxide may be formed on an optionally available nitrogen atom. The N-oxide can be formed by a general means, for example, by reacting the compound of the formula (I) with an oxone in the presence of wet alumina.

Next, the above-mentioned "pharmaceutically acceptable salt or ester" will be explained.

The "salt" of the compound of the present invention means a conventional salt that can be allowed as a medicament. For example, in the case when a carboxyl group, a hydroxyl group or an acidic heteroaryl group such as a tetrazolyl group is possessed, a base addition salt at the carboxyl group, hydroxyl group or acidic heteroaryl group can be mentioned, and in the case when an amino group or a basic heteroaryl group is possessed, an acid addition salt at the amino group or basic heteroaryl group can be mentioned.

As the base addition salt, for example, alkali metal salts such as sodium salts and potassium salts; alkali earth metal salts such as calcium salts and magnesium salts; for example, ammonium salts; for example, organic amine salts such as trimethylamine salts, triethylamine salts, dicyclohexylamine salts, ethanol amine salts, diethanol amine salts, triethanol amine salts, procaine salts and N,N'-dibenzylethylenediamine salts, etc. are mentioned.

As the acid addition salt, for example, inorganic acid salts such as hydrochlorides, sulfates, nitrate, phosphate and perchlorates; organic acid salts such as maleate, fumarate, tartrate, citrate, ascorbate and trifluoroacetate; sulfonates such as methanesulfonate, isethionate, benzene sulfonate and p-toluene sulfonate etc. are mentioned.

The "ester" in the compound of the present invention means, for example, in the case when a carboxyl group is possessed, a conventional ester at the carboxyl group that can be allowed as a medicament. Examples of the ester include ester with lower alkyl group such as a methyl group, an ethyl group, a propyl group, an isopropyl group, a butyl group, a sec-butyl group, a tert-butyl group, a pentyl group, an isopentyl group, and a neopentyl group, ester with a cycloalkyl group such as a cyclopropyl group, a cyclobutyl group, and a cyclopentylic group, ester with an aralkyl group such as a benzyl group, and a phenethyl group, ester with a lower alkenyl group such as an allyl group, and a 2-butenyl group, ester with a lower alkoxy lower alkyl group such as a methoxymethyl group, a 2-methoxyethyl group, and a 2-ethoxyethyl group, ester with a lower alkanoloxy lower alkyl group such as an acetoxymethyl group, a pivaloyloxymethyl group, and a 1-pivaloyloxyethyl group, ester with a lower alkoxycarbonyl lower alkyl group such as a methoxycarbonylmethyl group, and an isopropoxycarbonylmethyl group, ester with a carboxy lower alkyl group such as a carboxymethyl group, ester with a lower alkoxycarbonyloxy lower alkyl group such as a 1-(ethoxycarbonyloxy) ethyl group, and a 1-(cyclohexyloxycarbonyloxy)ethyl group, ester with a carbamoyloxy lower alkyl group such as a carbamoyloxymethyl group, ester with a phthalidyl group and ester with a (5-substituted-2-oxo-1,3-dioxol-4-yl) methyl group such as a (5-methyl-2-oxo-1,3-dioxol-4-yl) methyl group, etc. are mentioned.

The method for producing the pharmaceutically acceptable salt of the compound according to the present invention can be conducted by appropriately combining methods that are generally used in the field of organic synthesis chemistry. Specifically, neutralization titration of a solution of a free form of the compound according to the present invention with an alkali solution or an acidic solution, etc. are mentioned.

The method for producing the ester of the compound according to the present invention can be conducted by suitably combining methods that are generally used in the field of organic synthesis chemistry. Specifically, the ester can be produced by esterification of the free carboxy group in accordance with a conventional method.

The "pharmaceutically acceptable salt" of the present invention also includes a solvate with water or a pharmaceutically acceptable solvent such as ethanol.

Next, the production methods of the present invention will be specifically explained. However, the present invention is not limited to these production methods. In producing the compound of the present invention, the order of the reactions can be appropriately modified. The reactions can be conducted from a step or site that is considered to be reasonable.

Furthermore, a step of converting substituents (conversion or further modification of substituents) between the respective steps may be appropriately inserted. In the case when a reactive functional group is present, protection or deprotection may be appropriately conducted. Furthermore, in order to promote the progress of the reaction, ragents other than the exemplified ragents can be appropriately used. For the heating in each reaction, microwave irradiation may be conducted as necessary. Furthermore, the raw material compounds not described for the production methods are commercially available compounds, or compounds that can be easily prepared by combining known synthesis reactions.

The compound obtained in each step can be isolated and purified by ordinal methods conventionally used such as crystallization, recrystallization, column chromatography and preparation HPLC, and in certain cases, the compound can proceed to the next process without isolation and purification.

In the following production methods, the "room temperature" means from 1 to 40° C.

The following Scheme 1 is a general synthesis method for a compound wherein Z is carboxylic acid in the compound of the formula (I) (formula (I-1)).

Scheme 1: A Method for Producing a Compound of the Formula (I-1) from a Compound of the Formula (II)

27

Scheme 1

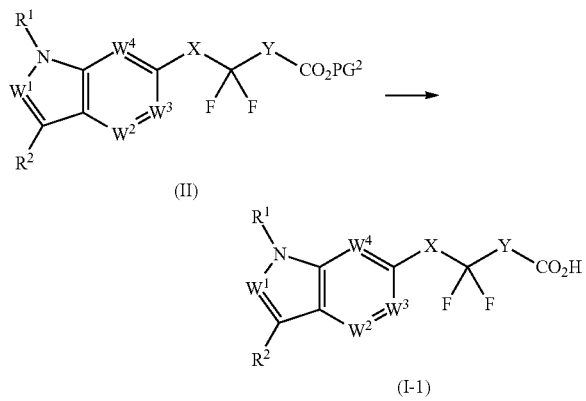

The compound of the above-mentioned formula (I-1) [wherein $R^1$, $R^2$, $W^1$, $W^2$, $W^3$, $W^4$, X and Y are as defined above] can be obtained by removing the protective group $PG^2$ of the compound represented by the above-mentioned formula (II) [wherein $R^1$, $R^2$, $W^1$, $W^2$, $W^3$, $W^4$, X and Y are as defined above, and $PG^2$ is a protective group].

The protective group $PG^2$ in the above-mentioned formula (II) is not especially limited as long as the group has its function, and for example, a lower alkyl group such as a methyl group, an ethyl group, a propyl group, an isopropyl group and a tert-butyl group; a halo lower alkyl group such as a 2,2,2-trichloroethyl group; a lower alkenyl group such as an allyl group; an aralkyl group such as a benzyl group, a p-methoxybenzyl group, a p-nitrobenzyl group, a benzhydryl group and a trityl group, etc. are mentioned, and a methyl group, an ethyl group, a tert-butyl group, an allyl group, a benzyl group, a p-methoxybenzyl group, a benzhydryl group, etc. are especially preferable.

The method for removing the protective group differs depending on the kind of the protective group and the stability of the intended compound (I-1), and the like, and is conducted by, for example, in accordance with a method described in a document [see Protective Groups in Organic Synthesis, third edition, authored by T. W. Greene, John Wiley & Sons (1999)] or a similar method, i.e., for example, solvolysis using an acid or a base, especially for example, a method of reacting 0.01 mol to a large excess amount of an acid, preferably trifluoroacetic acid, formic acid, hydrochloric acid and the like, or from an equal mol to a large excess amount of a base, preferably potassium hydroxide, calcium hydroxide and the like; chemical reduction using a hydrogenated metal complex and the like, or catalytic reduction using a palladium-carbon catalyst, a Raney nickel catalyst and the like; and the like.

The following Schemes 2 to 5 are general methods for synthesizing a compound wherein X is a single bond in the compound of the formula (II) (formula (II-1)).

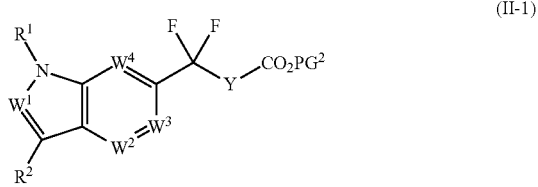

28

Scheme 2: A Method for Producing a Compound of the Formula (V) from the Compound of the Formula (III)

Scheme 2

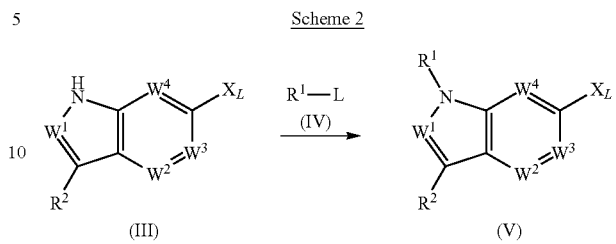

The compound of the above-mentioned formula (V) [wherein $R^1$, $R^2$, $W^1$, $W^2$, $W^3$ and $W^4$ are as defined above, and $X_L$ is a halogen atom or a trifluoromethanesulfonyloxy group, and the like] can be obtained by an alkylation reaction of the compound of the above-mentioned formula (III) [wherein $R^2$, $W^1$, $W^2$, $W^3$ and $W^4$ are as defined above, and $X_L$ is a halogen atom or a trifluoromethanesulfonyloxy group, and the like] with the compound of the above-mentioned formula (IV) [wherein $R^1$ are as defined above, and L represents a leaving group] in the presence of a base.

The leaving group L of the above-mentioned formula (IV) is not especially limited as long as it leaves by the reaction with the above-mentioned compound (III) to form the compound (V), and as the leaving group, a halogen atom (a chlorine atom, a bromine atom and the like), a p-toluenesulfonyloxy group, a benzenesulfonyloxy group, an ethanesulfonyloxy group, a methanesulfonyloxy group and the like is mentioned, and a bromine atom, a chlorine atom, a p-toluenesulfonyloxy group and the like are preferable.

In the reaction, ordinary 1 to 10 mol, and preferably 1 to 3 mol of the compound (IV) is used with respect to 1 mol of the compound (III).

Examples of the base include sodium carbonate, potassium carbonate, cesium carbonate, sodium hydrogen carbonate, cesium fluoride, sodium hydride, potassium tert-butoxide, potassium hydroxide, etc. are mentioned, and potassium carbonate, cesium carbonate, sodium hydride, potassium hydroxide, and the like are preferable.

In the reaction, ordinary 1 to 10 mol, and preferably 1 to 5 mol of the base is used with respect to 1 mol of the compound (III).

The reaction temperature is generally 0° C. to 160° C., preferably 25° C. to 100° C.

The reaction time is generally 1 hour to 24 hours, preferably 1 hour 15 to 12 hours.

The reaction solvent is not especially limited as long as it has no adverse effect on the reaction, and solvents such as N,N-dimethylformamide, N,N-dimethylacetamide, N-methyl-2-pyrrolidone, chloroform, dichloromethane, tetrahydrofuran, 1,4-dioxane, acetone, methylethylketone and acetonitrile are preferable.

As a compound of formula (III), for example, 6-bromoindole, 6-bromo-3-methylindole, 6-bromo-3-ethylindole, 6-bromoindazole, 6-bromo-3-methyl-1H-indazole, 6-bromo-3-ethyl-1H-indazole, 6-bromo-3-propyl-1H-indazole, 6-bromo-3-isopropyl-1H-indazole, 6-bromo-3-cyclopropyl-1H-indazole, 6-bromo-1H-indazole-3-carbonitrile, 6-bromo-3-chloro-1H-indazole, 6-bromo-3-iodo-1H-indazole, 6-bromo-3-trifluoromethyl-1H-indazole, 6-chloro-3-methyl-1H-pyrazolo[3,4-b]pyridine, 6-bromo-3-methyl-1H-pyrazolo[4,3-b]pyridine, 6-bromo-3-ethyl-1H-pyrazolo[4,3-b]pyridine, 6-bromo-3-propyl-1H-pyrazolo[4,3-b]pyridine, 6-bromo-3-cyclopropyl-1H-pyrazolo[4,3-b]pyridine, 6-bromo-3-chloro-1H-pyrazolo[4,3-b]pyridine, 6-bromo-3-iodo-1H-pyrazolo[4,3-b]pyridine, 6-bromo-3-trifluoromethyl-1H-pyrazolo[4,3-b]pyridine and 6-chloro-5-methoxy-3-methyl-1H-indazole or 6-bromo-3-methyl-1H-pyrazolo[3,4-b]pyridine etc. are mentioned. The compound of the formula (III) can be used a commercially available product, or can be obtained by a suitable combination of known methods or the methods described in Examples or similar methods as necessary.

Scheme 3: A Method for Producing a Compound of the Formula (VII) from the Formula (V)

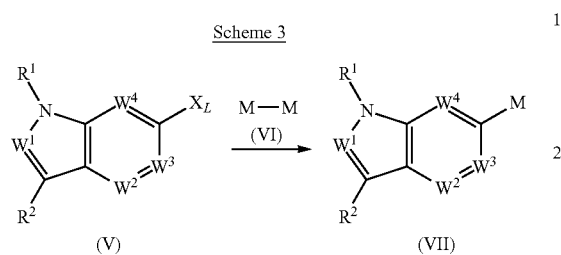

The compound of the above-mentioned formula (VII) [wherein $R^1$, $R^2$, $W^1$, $W^2$, $W^3$ and $W^4$ are as defined above, and M is boron, tin, and the like] can be obtained by a coupling reaction of a compound represented by the above-mentioned formula (V) [wherein $R^1$, $R^2$, $W^1$, $W^2$, $W^3$ and $W^4$ are as defined above, $X_L$ is a halogen atom or a trifluoromethanesulfonyloxy group, and the like] and the above-mentioned formula (VI) [wherein M is pinacolboran, a trialkyltin, and the like]. More specifically, the compound (VII) can be obtained by reacting the compound (V) and the compound (VI) in the presence of a palladium catalyst (furthermore, a phosphine ligand and a base as necessary).

In the reaction, ordinary 1 to 10 mol, and preferably 1 to 3 mol of the compound (VI) is used with respect to 1 mol of the compound (V).

As the compound (VI), for example, bis(trimethyltin), bis(triethyltin), bis(tributyltin), bispinacolatodiboron, etc. are mentioned.

As the base used, potassium acetate, triethylamine, etc. are mentioned as necessary.

In the reaction, ordinary 1 to 10 mol, and preferably 1 to 3 mol of the base is used with respect to 1 mol of the compound (V).

As the palladium catalyst used, for example, $Pd(PPh_3)_4$, $Pd(OAc)_2$, $Pd_2(dba)_3$, $PdCl_2(PPh_3)_2$, etc. are mentioned.

In the reaction, ordinary 0.01 to 0.5 mol, and preferably 0.05 to 0.2 mol of the palladium catalyst is used with respect to 1 mol of the compound (V).

As a phosphine ligand used, $PPh_3$, $P(o-tol)_3$, $P(tert-Bu)_3$, 2-[di(tert-butyl)phosphino]-1,1'-biphenyl, 2-[di(tert-butyl)phosphino]-2'-dimethylamino-1,1'-biphenyl, 2-[dicyclohexylphosphino]-1,1'-biphenyl, 2-[dicyclohexylphosphino]-2'-dimethylamino-1,1'-biphenyl, 1,1'-bis(diphenylphosphino)ferrocene, 1,1'-bis[(di-tert-butylphosphino)]ferrocene, etc. are mentioned.

The reaction temperature is generally 0° C. to 200° C., preferably 25° C. to 130° C.

The reaction solvent is not especially limited as long as it has no adverse effect on the reaction, and solvents such as dimethylformamide, tetrahydrofuran, dimethoxyethane, 1,4-dioxane, acetonitrile or toluene are preferable.

Scheme 4: A Method for Producing a Compound of the Formula (VIII) from the Formula (VII)

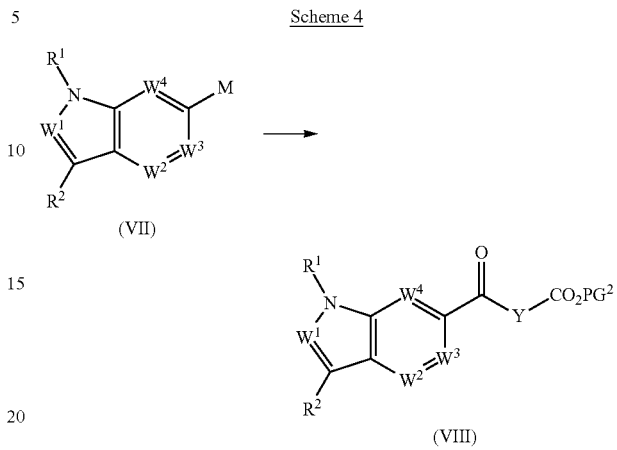

The compound of the above-mentioned formula (VIII) [wherein $R^1$, $R^2$, $W^1$, $W^2$, $W^3$, $W^4$ and Y are as defined above, and $PG^2$ represents a protective group] can be obtained by a coupling reaction of the compound of the above-mentioned formula (VII) [wherein $R^1$, $R^2$, $W^1$, $W^2$, $W^3$ and $W^4$ are as defined above, and M is boron, tin, and the like] with an acid chloride. More specifically, the compound (VIII) can be obtained by reacting the compound (VII) and the acid chloride in the presence of a palladium catalyst (further, a phosphine ligand and a base as necessary).

In the reaction, ordinary 1 to 10 mol, and preferably 1 to 3 mol of the acid chloride is used with respect to 1 mol of the compound (VII).

As the acid chloride, for example, succinic acid monomethylchloride, succinic acid monoethylchloride, ethyl chloroglyoxylate, etc. are mentioned.

The $PG^2$ in the formula (VIII) is a group derived from the acid chloride, and for example, a methyl group, an ethyl group, etc. are mentioned.

As the base used, triethylamine, diisopropylethylamine, etc. are mentioned.

In the reaction, ordinary 1 to 10 mol, and preferably 1 to 3 mol of the base is used with respect to 1 mol of the compound (VII).

As the palladium catalyst used, for example, $Pd(PPh_3)_4$, $Pd(OAc)_2$, $Pd(dba)_2$, $Pd_2(dba)_3$, $PdCl_2(PPh_3)_2$, etc. are mentioned.

In the reaction, ordinary 0.01 to 0.5 mol, and preferably 0.05 to 0.2 mol of the palladium catalyst is used with respect to 1 mol of the compound (VII).

As a phosphine ligand used, $PPh_3$, $P(o-tol)_3$, $P(tert-Bu)_3$, 2-[di(tert-butyl)phosphino]-1,1'-biphenyl, 2-[di(tert-butyl)phosphino]-2'-dimethylamino-1,1'-biphenyl, 2-[dicyclohexylphosphino]-1,1'-biphenyl, 2-[dicyclohexylphosphino]-2'-dimethylamino-1,1'-biphenyl, 1,1'-bis(diphenylphosphino)ferrocene, 1,1'-bis[di-tert-butylphosphino]ferrocene, etc. are mentioned.

The reaction temperature is generally 0° C. to 200° C., preferably 25° C. to 130° C.

The reaction solvent is not especially limited as long as it has no adverse effect on the reaction, and solvents such as N,N-dimethylformamide, tetrahydrofuran, 1,4-dioxane, acetonitrile and toluene are preferable.

Scheme 5: A Method for Producing a Compound of the Formula (II-1) from the Formula (VIII)

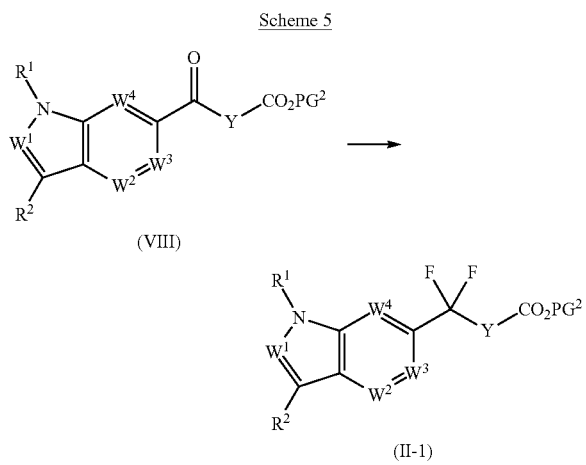

The compound of the above-mentioned formula (II-1) [wherein $R^1$, $R^2$, $W^1$, $W^2$, $W^3$, $W^4$ and Y are as defined above, and $PG^2$ is a protective group] can be obtained by fluorination of the compound represented by the above-mentioned formula (VIII) [wherein $R^1$, $R^2$, $W^1$, $W^2$, $W^3$, $W^4$ and Y are as defined above, and $PG^2$ is a protective group]. More specifically, the compound (II-1) can be obtained by reacting the compound (VIII) with a fluorinating agent such as diethylaminosulfur trifluoride (DAST).

In the reaction, ordinary 1 to 10 mol, and preferably 1 to 3 mol of the fluorinating agent is used with respect to 1 mol of the compound (VIII).

As a fluorinating agent, diethylaminosulfur trifluoride (DAST), bis(2-methoxyethyl)aminosulfur trifluoride, 1,1,2,2-tetrafluoroethyl-N,N-dimethylamine, diethylaminodifluorosulfinium tetrafluoroborate, morpholinodifluorosulfinium tetrafluoroborate, 4-tert-butyl-2,6-dimethylphenylsulfur trifluoride, etc. are mentioned.

The reaction temperature is generally 0° C. to 200° C., preferably 25° C. to 130° C.

The reaction solvent is not especially limited as long as it has no adverse effect on the reaction, and is preferably a solvent such as dichloromethane, tetrahydrofuran, 1,4-dioxane, 1,2-dimethoxyethane, acetonitrile or toluene.

The following Schemes 6 to 7 are general methods for the synthesis of a compound wherein X and Y are each a single bond in the compound of the formula (II) (formula (II-2)).

Scheme 6: A Method for Producing a Compound of the Formula (IX) from the Formula (V)

Scheme 6

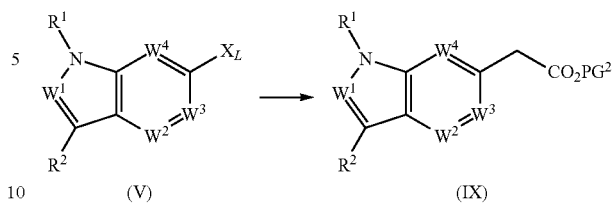

The compound of the above-mentioned formula (IX) [wherein $R^1$, $R^2$, $W^1$, $W^2$, $W^3$ and $W^4$ are as defined above, and $PG^2$ is a protective group] can be obtained by a coupling reaction of a compound represented by the above-mentioned formula (V) [wherein $R^1$, $R^2$, $W^1$, $W^2$, $W^3$ and $W^4$ are as defined above, and $X_L$ is a halogen atom, or a trifluoromethanesulfonyl group, and the like] and an organic zinc compound. More specifically, the compound (IX) can be obtained by reacting the compound (V) with an organic zinc compound such as a Reformatsky agent in the presence of a palladium catalyst (further, a phosphine ligand as necessary).

In the reaction, ordinary 1 to 10 mol, and preferably 1 to 3 mol of the organic zinc compound is used with respect to 1 mol of the compound (V).

As an organozinc compound, 2-tert-butoxy-2-oxoethylzinc chloride, a 2-tert-butoxy-2-oxoethylzinc bromide, 2-ethoxy-2-oxoethylzinc chloride, a 2-ethoxy-2-oxoethylzinc bromide, etc. are mentioned.

As the palladium catalyst used, for example, $Pd(PPh_3)_4$, $Pd(OAc)_2$, $Pd(dba)_2$, $Pd_2(dba)_3$, $PdCl_2(PPh_3)_2$, etc. are mentioned.

In the reaction, ordinary 0.01 to 0.5 mol, and preferably 0.05 to 0.2 mol of the palladium catalyst is used with respect to 1 mol of the compound (V).

As a phosphine ligand used, $PPh_3$, $P(o\text{-tol})_3$, $P(\text{tert-Bu})_3$, 2-[di(tert-butyl)phosphino]-1,1'-biphenyl, 2-[di(tert-butyl)phosphino]-2'-dimethylamino-1,1'-biphenyl, 2-[dicyclohexylphosphino]-1,1'-biphenyl, 2-[dicyclohexylphosphino]-2'-dimethylamino-1,1'-biphenyl, 1,1'-bis(diphenylphosphino)ferrocene, 1,1'-bis[di-tert-butylphosphino]ferrocene, pentaphenyl(di-tert-butylphosphino)ferrocene, etc. are mentioned.

The reaction temperature is generally 0° C. to 200° C., preferably 25° C. to 130° C.

The reaction solvent is not especially limited as long as it has no adverse effect on the reaction, and is preferably a solvent such as tetrahydrofuran, 1,4-dioxane, 1,2-dimethoxyethane, acetonitrile or toluene.

Furthermore, the compound of the above-mentioned formula (IX) can also be obtained by a coupling reaction of the compound of the above-mentioned formula (V) with an acetic acid ester. More specifically, the compound (IX) can be obtained by reacting the compound (V) with the acetic acid ester in the presence of a base and a palladium catalyst (further, a phosphine ligand as necessary).

In the reaction, ordinary 1 to 10 mol, and preferably 1 to 3 mol of the acetic acid ester is used with respect to 1 mol of the compound (V).

As the acetic acid ester, for example, methyl acetate, ethyl acetate, tert-butyl acetate, etc. are mentioned.

As a base used, lithium dicyclohexylamide, sodium dicyclohexylamide, lithium hexamethyldisilazide, sodium hexamethyldisilazide, potassium hexamethyldisilazide, lithium diisopropylamide, etc. are mentioned.

In the reaction, ordinary 1 to 10 mol, and preferably 1 to 3 mol of the base is used with respect to 1 mol of the compound (V).

As the palladium catalyst used, for example, Pd(PPh$_3$)$_4$, Pd(OAc)$_2$, Pd(dba)$_2$, Pd$_2$(dba)$_3$, PdCl$_2$(PPh$_3$)$_2$, etc. are mentioned.

In the reaction, ordinary 0.01 to 0.5 mol, and preferably 0.05 to 0.2 mol of the palladium catalyst is used with respect to 1 mol of the compound (V).

As a phosphine ligand used, PPh$_3$, P(o-tol)$_3$, P(tert-Bu)$_3$, 2-[di(tert-butyl)phosphino]-1,1'-biphenyl, 2-[di(tert-butyl)phosphino]-2'-dimethylamino-1,1'-biphenyl, 1,2,3,4,5-pentaphenyl-1'-[di(tert-butyl)phosphino]ferrocene, 2-[dicyclohexylphosphino]-1,1'-biphenyl, 2-[dicyclohexylphosphino]-2'-dimethylamino-1,1'-biphenyl, etc. are mentioned.

The reaction temperature is generally 0° C. to 80° C., preferably 0° C. to 25° C.

The reaction solvent is not especially limited as long as it has no adverse effect on the reaction, and is preferably a solvent such as N,N-dimethylformamide, tetrahydrofuran, 1,4-dioxane, cyclohexane, 1,3-dimethylbenzene, acetonitrile or toluene.

Scheme 7: A Method for Producing a Compound of the Formula (II-2) from the Formula (IX)

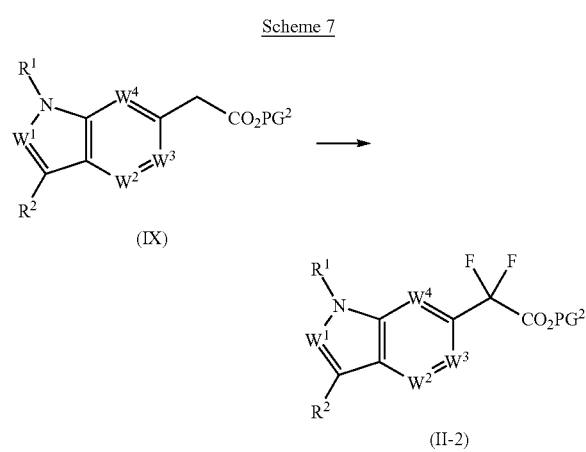

The compound of the above-mentioned formula (II-2) [wherein R$^1$, R$^2$, W$^1$, W$^2$, W$^3$ and W$^4$ are as defined above, and PG$^2$ is a protective group] can be obtained by a fluorination reaction of the compound represented by the above-mentioned formula (IX) [wherein R$^1$, R$^2$, W$^1$, W$^2$, W$^3$ and W$^4$ are as defined above, and PG$^2$ is a protective group]. More specifically, the compound (II-2) can be obtained by reacting the fluorinating agent with the compound (IX) in the presence of a base.

In the reaction, ordinary 1 to 10 mol, and preferably 1 to 3 mol of the fluorinating agent is used with respect to 1 mol of the compound (IX).

As the fluorinating agent used, N-fluorobenzenesulfoneimide (NFSI), 2-fluoro-3,3-dimethyl-2,3-dihydro-1,2-benzoisothiazole-1,1-dioxide, etc. are mentioned.

As a base used, lithium dicyclohexylamide, sodium dicyclohexylamide, lithium hexamethyldisilazide, sodium hexamethyldisilazide, potassium hexamethyldisilazide, lithium diisopropylamide, etc. are mentioned.

In the reaction, ordinary 1 to 10 mol, and preferably 1 to 3 mol of the base is used with respect to 1 mol of the compound (IX).

The reaction temperature is generally −100° C. to 0° C., preferably −90° C. to −60° C.

The reaction solvent is not especially limited as long as it has no adverse effect on the reaction, and is preferably a solvent such as tetrahydrofuran, 1,4-dioxane, 1,2-dimethoxyethane, acetonitrile or toluene.

The following Schemes 8 to 11 are other methods for the synthesis of a compound wherein X and Y are each a single bond in the compound of the formula (II) (formula (II-2)).

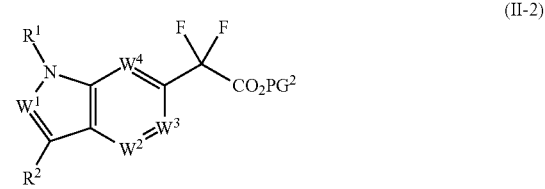

Scheme 8: A Method for Producing a Compound of the Formula (X) from the Formula (III)

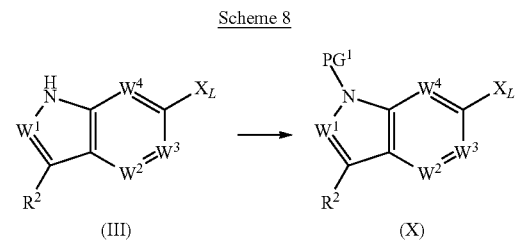

The compound of the above-mentioned formula (X) [wherein R$^2$, W$^1$, W$^2$, W$^3$ and W$^4$ are as defined above, PG$^1$ is a protective group, and X$_L$ is a halogen atom or a trifluoromethanesulfonyloxy group, and the like] can be obtained by protecting a compound of the above-mentioned formula (III) [wherein R$^2$, W$^1$, W$^2$, W$^3$ and W$^4$ are as defined above, X$_L$ is a halogen atom or a trifluoromethanesulfonyloxy group, and the like] with a protective group PG$^1$.

The protective group PG$^1$ in the above-mentioned formula (X) is not especially limited as long as the group has its function, and for example, an aralkyl group such as a benzyl group, a p-methoxybenzyl group, a 3,4-dimethoxybenzyl group, an o-nitrobenzyl group, a p-nitrobenzyl group, a benzhydryl group, a trityl group etc.; for example, a lower alkanoyl group such as a formyl group, an acetyl group, a propionyl group, a butyryl group, a pivaloyl group etc.; for example, a benzoyl group; for example, an aryl alkanoyl group such as a phenylacetyl group, a phenoxyacetyl group etc.; for example, a lower alkoxy carbonyl group such as a methoxycarbonyl group, an ethoxycarbonyl group, a propyloxycarbonyl group, a tert-butoxycarbonyl group etc.; for example, an aralkyloxycarbonyl group such as a benzyloxycarbonyl group, a p-nitrobenzyloxycarbonyl group, and a phenethyloxycarbonyl group etc.; for example, a lower alkyl silyl group such as a trimethylsilyl group, a tert-butyldimethylsilyl group etc.; for example, a tetrahydropyranyl group; for example, a trimethylsilylethoxymethyl group; for example, a lower alkyl sulfonyl group such as a methylsulfonyl group, an ethylsulfonyl group etc.; for example, a aryl sulfonyl group such as a benzenesulfonyl group, a p-toluenesulfonyl group, etc. are mentioned, and especially a tert-butoxycarbonyl group, a methylsulfonyl group, a p-toluenesulfonyl group, etc. are preferable.

The method for introducing the protective group differs depending on the kind of the protective group and the stability of the compound, etc., and the synthesis can be conducted in accordance with a method described in a document [see Protective Groups in Organic Synthesis, third edition, authored by T. W. Greene, John Wiley & Sons (1999)] or a similar method.

Scheme 9: A Method for Producing a Compound of the Formula (XI) from the Formula (X)

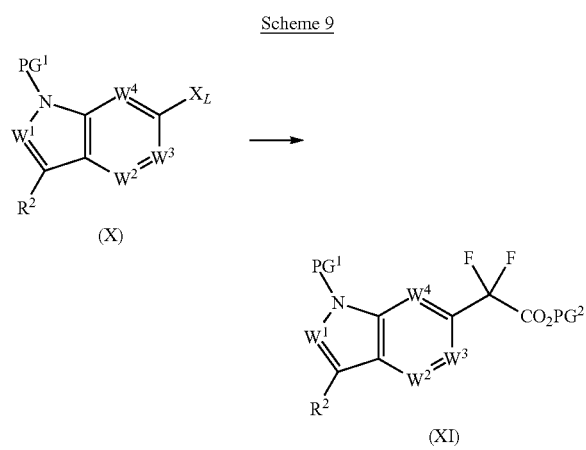

The compound of the above-mentioned formula (XI) [wherein $R^2$, $W^1$, $W^2$, $W^3$ and $W^4$ are as defined above, and $PG^1$ and $PG^2$ is a protective group] can be obtained from the compound represented by the above-mentioned formula (X) [wherein $R^2$, $W^1$, $W^2$, $W^3$ and $W^4$ are as defined above, and $PG^1$ is a protective group, $X_L$ is a halogen atom or a trifluoromethanesulfonyloxy group, and the like] by a similar method to that of the production methods described in Schemes 6 and 7.

Scheme 10: A Method for Producing a Compound of the Formula (XII) from the Formula (XI)

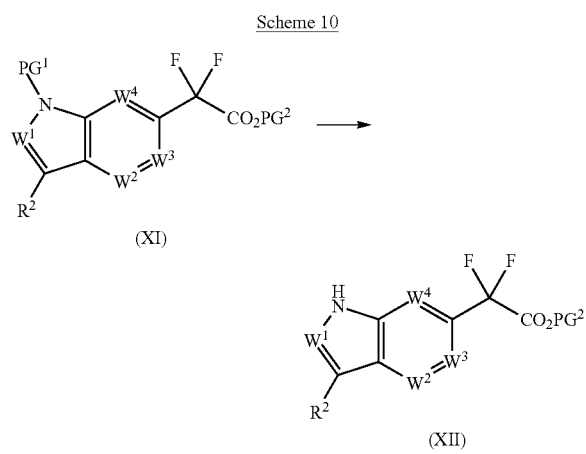

The compound of the above-mentioned formula (XII) [wherein $R^2$, $W^1$, $W^2$, $W^3$ and $W^4$ are as defined above, and $PG^2$ is a protective group] can be obtained by removing the protective group $PG^1$ of the compound represented by the above-mentioned formula (XI) [wherein $R^2$, $W^1$, $W^2$, $W^3$ and $W^4$ are as defined above, and $PG^1$ and $PG^2$ is a protective group].

The protective group $PG^1$ of the above-mentioned formula (XI) is not especially limited as long as the group has its function, and for example, an aralkyl group such as a benzyl group, a p-methoxybenzyl group, a 3,4-dimethoxybenzyl group, an o-nitrobenzyl group, a p-nitrobenzyl group, a benzhydryl group, a trityl group etc.; for example, a lower alkanoyl group such as a formyl group, an acetyl group, a propionyl group, a butyryl group, a pivaloyl group etc.; for example, a benzoyl group; for example, an aryl alkanoyl group such as a phenylacetyl group, a phenoxyacetyl group etc.; for example, a lower alkoxy carbonyl group such as a methoxycarbonyl group, an ethoxycarbonyl group, a propyloxycarbonyl group, a tert-butoxycarbonyl group etc.; for example, an aralkyloxy carbonyl group such as a benzyloxycarbonyl group, a p-nitrobenzyloxycarbonyl group, a phenethyloxycarbonyl group etc.; for example, a lower alkyl silyl group such as a trimethylsilyl group, a tert-butyldimethylsilyl group etc.; for example, tetrahydropyranyl group; for example, a trimethylsilylethoxymethyl group; for example, a lower alkyl sulfonyl group such as a methylsulfonyl group, an ethylsulfonyl group etc.; for example, a aryl sulfonyl group such as a benzenesulfonyl group, a p-toluenesulfonyl group, etc. are mentioned, and especially a tert-butoxycarbonyl group, a methylsulfonyl group, a p-toluenesulfonyl group, etc. are preferable.

The method for removing the protective group differs depending on the kind of the protective group and the stability of the intended compound (XII), and the like, and is conducted by, for example, solvolysis using, for example, an acid or a base, in accordance with a method described in a document [see Protective Groups in Organic Synthesis, third edition, authored by T. W. Greene, John Wiley & Sons (1999)] or a similar method, i.e., for example, a method including reacting from 0.01 mol to a large excess amount of an acid, preferably trifluoroacetic acid, formic acid, hydrochloric acid and the like, or from an equal amount mol to a large excess amount of a base, preferably potassium hydroxide, calcium hydroxide and the like; chemical reduction using a hydrogenated metal complex and the like, or catalytic reduction using a palladium-carbon catalyst, a Raney nickel catalyst and the like; and the like.

Depending on the reaction condition for the removal of the above-mentioned protective group $PG^1$, the protective group $PG^2$ is simultaneously removed in some cases. In such cases, the compound (XII) can be obtained by suitably protecting the carboxylic acid with the protective group $PG^2$.

Scheme 11: A Method for Producing a Compound of the Formula (II-2) from the Formula (XII)

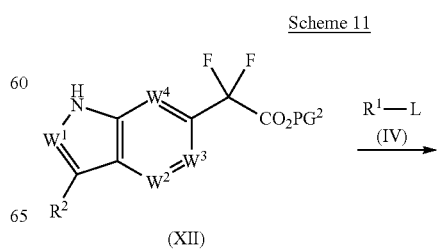

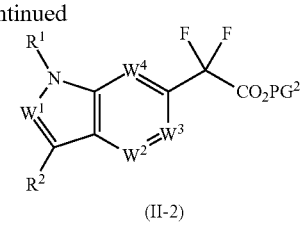

(II-2)

The compound of the above-mentioned formula (II-2) [wherein $R^1$, $R^2$, $W^1$, $W^2$, $W^3$ and $W^4$ are as defined above, and $PG^2$ is a protective group] can be obtained from the compound represented by the above-mentioned formula (XII) [wherein $R^2$, $W^1$, $W^2$, $W^3$ and $W^4$ are as defined above, and $PG^2$ is a protective group] by a similar method to the production method described in Scheme 2.

The following Schemes 12 to 14 show a general method for the synthesis of a compound wherein Z is a 5-tetrazolyl group in the compound of the formula (I) (formula (I-2)).

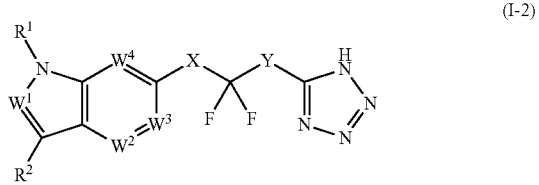

(I-2)

Scheme 12: A Method for Producing a Compound of the Formula (XIII) from the Compound of the Formula (I-1)

Scheme 12

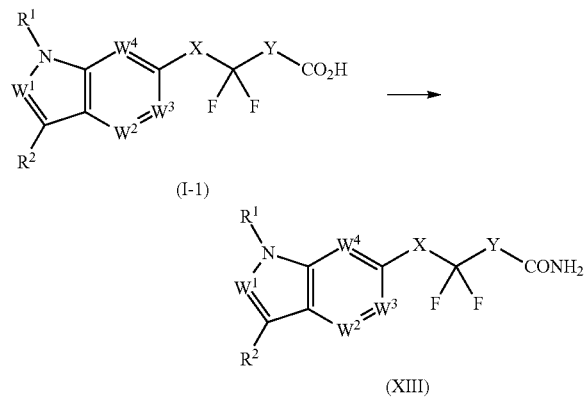

The compound of the above-mentioned formula (XIII) [wherein $R^1$, $R^2$, $W^1$, $W^2$, $W^3$, $W^4$, X and Y are as defined above] can be obtained by amidation of the compound represented by the above-mentioned formula (I-1) [wherein $R^1$, $R^2$, $W^1$, $W^2$, $W^3$, $W^4$, X and Y are as defined above].

More specifically, the compound (XIII) having an amide group can be prepared by reacting a corresponding acid chloride, which is obtained by reacting with a halogenating agent such as thionyl chloride or oxalyl chloride, with an aqueous ammonia.

In the reaction, ordinary 1 to 10 mol, and preferably 1 to 3 mol of the halogenating agent is used with respect to 1 mol of the compound (I-1).

As the halogenating agent, for example, thionyl chloride, oxalyl chloride, phosphorus trichloride, phosphorus pentachloride, sulfuryl chloride, etc. are mentioned.

The reaction temperature is generally 0° C. to 200° C., preferably 0° C. to 25° C.

The reaction solvent is not especially limited as long as it has no adverse effect on the reaction, and is preferably a solvent such as dichloromethane, chloroform, tetrahydrofuran, 1,3-dimethylbenzene, 1,4-dioxane or toluene.

Scheme 13: A Method for Producing a Compound of the Formula (XIV) from the Formula (XIII)

Scheme 13

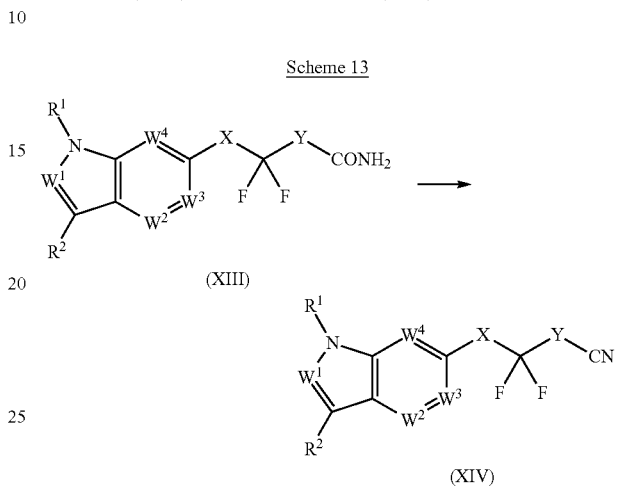

The compound of the above-mentioned formula (XIV) [wherein $R^1$, $R^2$, $W^1$, $W^2$, $W^3$, $W^4$, X and Y are as defined above] can be obtained by dehydration of the compound represented by the above-mentioned formula (XIII) [wherein $R^1$, $R^2$, $W^1$, $W^2$, $W^3$, $W^4$, X and Y are as defined above]. More specifically, the compound (XIV) can be obtained by reacting the compound having an amide group (XIII) in the presence of a dehydrating agent such as thionyl chloride.

In the reaction, ordinary 1 to 10 mol, and preferably 1 to 3 mol of the dehydrating agent is used with respect to 1 mol of the compound (XIII).

Regarding the dehydrating agent, for example, thionylchloride, oxalylchloride, cyanuricchloride, phosphoruspentaoxide, phosphoruspentachloride, acetic anhydride, phosphorusoxychloride, etc. are mentioned.

The reaction temperature is generally 0° C. to 200° C., preferably 0° C. to 25° C.

The reaction solvent is not especially limited as long as it has no adverse effect on the reaction, and is preferably a solvent such as dichloromethane, chloroform, tetrahydrofuran, 1,4-dioxane, acetonitrile or toluene.

Scheme 14: A Method for Producing the Compound of the Formula (I-2) from the Formula (XIV)

Scheme 14

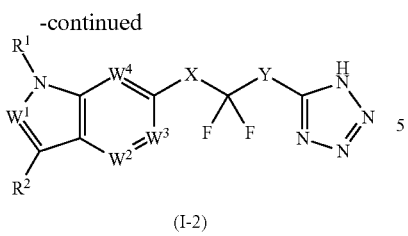

(I-2)

The compound of the above-mentioned formula (I-2) [wherein $R^1$, $R^2$, $W^1$, $W^2$, $W^3$, $W^4$, X and Y are as defined above] can be obtained by a reaction of the compound represented by the above-mentioned formula (XIV) [wherein $R^1$, $R^2$, $W^1$, $W^2$, $W^3$, $W^4$, X and Y are as defined above] and an azide. More specifically, the compound (I-2) can be obtained by reacting the compound having a cyano group (XIV) with an azide such as sodium azide (further, a salt or a Lewis acid as necessary).

In the reaction, ordinary 1 to 10 mol, and preferably 1 to 3 mol of the azide is used with respect to 1 mol of the compound (XIV).

As the azide, for example, alkali metal azides such as lithium azide, sodium azide and potassium azide; trialkyltin azides such as trioctyltin azide; or hydrogen azide, etc. are mentioned.

As the Lewis acid and salt used, ammonium chloride, zinc chloride, zinc bromide, aluminum chloride, etc. are mentioned.

In the reaction, ordinary 1 to 10 mol, and preferably 1 to 3 mol of the salt is used with respect to 1 mol of the compound (XIV).

The reaction temperature is generally 0° C. to 200° C., preferably 100° C. to 170° C.

The reaction solvent is not especially limited as long as it has no adverse effect on the reaction, and is preferably a solvent such as N,N-dimethylformamide, water, N,N-dimethylacetamide, N-methyl-2-pyrrolidone, tetrahydrofuran, 1,4-dioxane or toluene.

The following Schemes 15 to 22 are general methods for the synthesis of a compound wherein X and Y are each a single bond in the compound of the formula (I-2) (formula (I-3)).

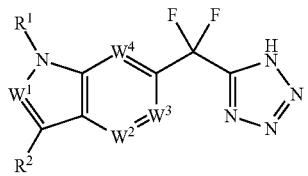

(I-3)

Scheme 15: A Method for Producing a Compound of the Formula (XVI) from the Compound of the Formula (X)

Scheme 15

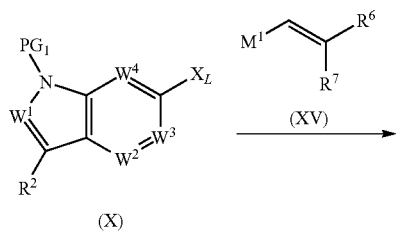

(X)  (XV)

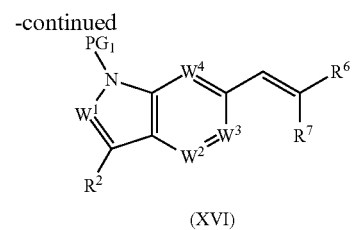

(XVI)

The compound of the above-mentioned formula (XVI) [wherein $R^2$, $W^1$, $W^2$, $W^3$ and $W^4$ are as defined above, and $PG^1$ represents a protective group, and $R^6$ and $R^7$ are each independently a hydrogen atom, a lower alkyl group or an aryl group, and the like] can be obtained by a coupling reaction of the compound represented by the above-mentioned formula (X) [wherein $R^2$, $W^1$, $W^2$, $W^3$ and $W^4$ are as defined above, and $PG^1$ represents a protective group, $X_L$ is a halogen atom or a trifluoromethanesulfonyloxy group, and the like] and the compound represented by the above-mentioned formula (XV) [wherein $R^6$ and $R^7$ are each independently a hydrogen atom, a lower alkyl group or an aryl group, and the like, and $M^1$ is boron, tin, and the like]. More specifically, the compound (XVI) can be obtained by reacting the compound (X), which has a halogen atom or a trifluoromethanesulfonyloxy group and the like, with the organic boron compound or organic tin compound and the like, represented by the above-mentioned formula (XV), in the presence of a base and a palladium catalyst (further, a phosphine ligand as necessary).

In the reaction, ordinary 1 to 10 mol, and preferably 1 to 3 mol of the compound (XV) is used with respect to 1 mol of the compound (X).

As the compound (XV), for example, potassium vinyltrifluoroborate, tributylvinyltin, etc. are mentioned.

As a base, triethylamine, tributylamine, diisopropylethylamine, 1,8-diazabicyclo[5.4.0]undec-7-ene, sodium carbonate, potassium carbonate, cesium carbonate, sodium fluoride, potassium fluoride, cesium fluoride, lithium chloride, etc. are mentioned.

In the reaction, ordinary 1 to 10 mol, and preferably 1 to 3 mol of the base is used with respect to 1 mol of the compound (X).

As a palladium catalyst, for example, $Pd(PPh_3)_4$, $Pd(OAc)_2$, $Pd(dba)_2$, $Pd_2(dba)_3$, $PdCl_2(PPh_3)_2$, $PdCl_2(dppf)$, etc. are mentioned.

In the reaction, ordinary 0.01 to 0.5 mol, and preferably 0.05 to 0.2 mol of the palladium catalyst is used with respect to 1 mol of the compound (X).

As a phosphine ligand, $PPh_3$, $P(o-tol)_3$, $P(tert-Bu)_3$, 2-[di(tert-butyl)phosphino]-1,1'-biphenyl, 2-[di(tert-butyl)phosphino]-2'-dimethylamino-1,1'-biphenyl, 2-[dicyclohexylphosphino]-1,1'-biphenyl, 2-dicyclohexylphosphino-2',6'-dimethoxybiphenyl, 2-dicyclohexylphosphino-2',4',6'-triisopropylbiphenyl, 2-[dicyclohexylphosphino]-2'-dimethylamino-1,1'-biphenyl, etc. are mentioned.

The reaction temperature is generally 0° C. to 200° C., preferably 25° C. to 130° C.

The reaction solvent is not especially limited as long as it has no adverse effect on the reaction, and is preferably a solvent such as N,N-dimethylformamide, methanol, ethanol, 1-propanol, 2-propanol, 1-butanol, 2-butanol, tert-butanol, tetrahydrofuran, 1,4-dioxane, dimethoxyethane, acetonitrile or toluene.

Scheme 16: A Method for Producing the Compound of the Formula (XVII) from the Compound of the Formula (XVI)

Scheme 16

(XVI) → (XVII)

The compound of the above-mentioned formula (XVII) [wherein $R^2$, $W^1$, $W^2$, $W^3$ and $W^4$ are as defined above, and $PG^1$ is a protective group] can be obtained by an oxidation reaction of the compound represented by the above-mentioned formula (XVI) [wherein $R^2$, $W^1$, $W^2$, $W^3$ and $W^4$ are as defined above, and $PG^1$ represents a protective group, $R^3$ and $R^4$ are each independently hydrogen atom, a lower alkyl group or an aryl group, and the like]. For example, it can be synthesized by reacting the compound (XVI) with osmium tetraoxide and sodium periodate in a mixed solvent of tert-butanol and water.

In the reaction, ordinary 0.0001 to 1 mol, and preferably 0.01 to 1 mol of the osmium tetraoxide is used with respect to 1 mol of the compound (XVI). In the reaction, ordinary 1 to 10 mol, and preferably 1 to 5 mol of the sodium periodate is used with respect to 1 mol of the compound (XVI).

The reaction temperature is generally 0° C. to 100° C., preferably 0° C. to 40° C.

The reaction solvent is not especially limited as long as it has no adverse effect on the reaction, and is preferably a mixed solvent of water and a water-soluble solvent such as tert-butanol, dioxane or acetone, and the like.

Scheme 17: A Method for Producing a Compound of the Formula (XIX) from the Compound of the Formula (XVII)

Scheme 17

(XVII) + (XVIII) →

(XIX)

The compound of the above-mentioned formula (XIX) [wherein $R^2$, $W^1$, $W^2$, $W^3$ and $W^4$ are as defined above, and $PG^1$ and $PG^3$ are each a protective group] can be obtained by reacting the compound represented by the above-mentioned formula (XVII) [wherein $R^2$, $W^1$, $W^2$, $W^3$ and $W^4$ are as defined above, and $PG^1$ is a protective group] with a nucleophilic agent prepared from a compound of the above-mentioned formula (XVIII) [wherein $PG^3$ is a protective group] and a base.

The protective group $PG^3$ in the above-mentioned formula (XVIII) and the above-mentioned formula (XIX) is not especially limited as long as the group has its function, and for example, a lower alkyl group such as a methyl group, an ethyl group, a propyl group, an isopropyl group and a tert-butyl group; for example, a halo lower alkyl group such as 2,2,2-trichloroethyl group; for example, a lower alkenyl group such as an allyl group etc.; for example, a aralkyl group such as a benzyl group, a p-methoxybenzyl group, a p-nitrobenzyl group, a benzhydryl group, trityl group etc. are mentioned, and a methyl group, an ethyl group, a tert-butyl group, an allyl group, a benzyl group, a p-methoxybenzyl group, a benzhydryl group, etc. are especially preferable.

In the reaction, ordinary 1 to 10 mol, and preferably 1 to 3 mol of the compound (XVIII) is used with respect to 1 mol of the compound (XVII).

As a base, n-butyl lithium, sec-butyl lithium, tert-butyl lithium, lithium diisopropylamide, lithium dicyclohexylamide, sodium dicyclohexylamide, lithium hexamethyldisilazide, sodium hexamethyldisilazide, and potassium hexamethyldisilazide, etc. are mentioned.

In the reaction, ordinary 1 to 10 mol, and preferably 1 to 3 mol of the base is used with respect to 1 mol of the compound (XVII).

The reaction temperature is generally −100° C. to 0° C., preferably −100° C. to −70° C.

The reaction solvent is not especially limited as long as it has no adverse effect on the reaction, and is preferably an aprotic solvent such as diethyl ether, tetrahydrofuran, 1,4-dioxane, 1,2-dimethoxyethane or toluene.

Scheme 18: A Method for Producing the Compound of the Formula (XX) from the Formula (XIX)

Scheme 18

(XIX) →

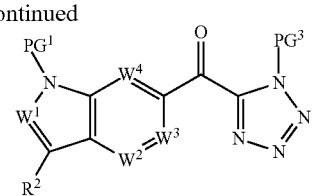

(XX)

The compound of the above-mentioned formula (XX) [wherein $R^2$, $W^1$, $W^2$, $W^3$ and $W^4$ are as defined above, and $PG^1$ and $PG^3$ are each a protective group] can be obtained by an oxidation reaction of the compound represented by the above-mentioned formula (XIX) [wherein $R^2$, $W^1$, $W^2$, $W^3$ and $W^4$ are as defined above, and $PG^1$ and $PG^3$ are each a protective group].

As an oxidizing agent, for example, 1,1,1-triacetoxy-1,1-dihydro-1,2-benziodoxol-3(1H)-one (Dess-Martin periodinane: DMP), 2-iodoxybenzoic acid (IBX), manganese dioxide, tetrapropylammonium perruthenate (TPAP), 2,2,6,6,-tetramethylpiperidine-1-oxyl (TEMPO), pyridinium dichromate (PDC), and pyridinium chlorochromate (PCC) are mentioned. Furthermore, an oxidant prepared from dimethylsulfoxide and oxalyl chloride or a sulfur trioxide-pyridine complex, and the like, can also be used in this reaction.

In the reaction, ordinary 1 to 10 mol, and preferably 1 to 3 mol of the oxidant is used with respect to 1 mol of the compound (XIX).

The reaction temperature is generally −100° C. to 100° C., preferably −80° C. to 80° C.

The reaction solvent is not especially limited as long as it has no adverse effect on the reaction, and is preferably a solvent such as N,N-dimethylformamide, N,N-dimethylacetamide, N-methyl-2-pyrrolidone, chloroform, dichloromethane, tetrahydrofuran, 1,4-dioxane, acetone, methyl ethyl ketone or acetonitrile.

Scheme 19: A Method for Producing the Compound of the Formula (XXI) from the Formula (XX)

Scheme 19

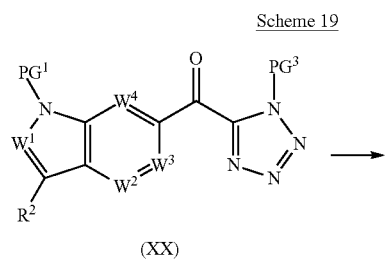

(XX)

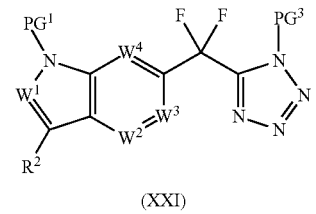

(XXI)

The compound of the above-mentioned formula (XXI) [wherein $R^2$, $W^1$, $W^2$, $W^3$ and $W^4$ are as defined above, and $PG^1$ and $PG^3$ are each a protective group] can be obtained from the compound represented by the above-mentioned formula (XX) [wherein $R^2$, $W^1$, $W^2$, $W^3$ and $W^4$ are as defined above, and $PG^1$ and $PG^3$ are each a protective group] by a similar method to the production method described in Scheme 5.

Scheme 20: A Method for Producing a Compound of the Formula (XXII) from the Compound of the Formula (XXI)

Scheme 20

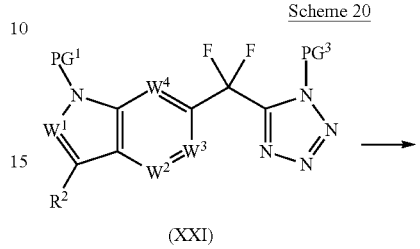

(XXI)

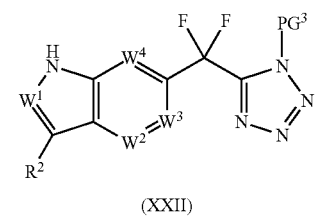

(XXII)

The compound of the above-mentioned formula (XXII) [wherein $R^2$, $W^1$, $W^2$, $W^3$ and $W^4$ are as defined above, and $PG^3$ is a protective group] can be obtained from the compound represented by the above-mentioned formula (XXI) [wherein $R^2$, $W^1$, $W^2$, $W^3$ and $W^4$ are as defined above, and $PG^1$ and $PG^3$ are each a protective group] by a similar method to the production method described in Scheme 10.

Scheme 21: A Method for Producing a Compound of the Formula (XXIII) from the Compound of the Formula (XXII)

Scheme 21

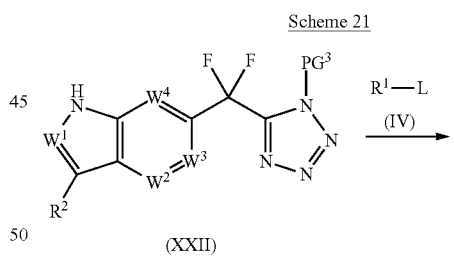

(XXII)

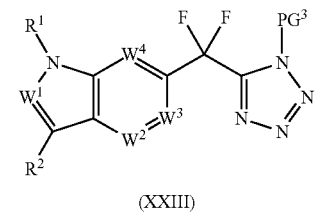

(XXIII)

The compound of the above-mentioned formula (XXIII) [wherein $R^1$, $R^2$, $W^1$, $W^2$, $W^3$ and $W^4$ are as defined above, and $PG^3$ is a protective group] can be obtained from the compound represented by the above-mentioned formula (XXII) [wherein $R^2$, $W^1$, $W^2$, $W^3$ and $W^4$ are as defined above, and $PG^3$ is a protective group] and the compound represented by the above-mentioned formula (IV) [wherein $R^1$ is as defined above, and L is a leaving group] by a similar method to the production method described in Scheme 2.

Scheme 22: A Method for Producing a Compound of the Formula (I-3) from the Compound of the Formula (XXIII)

Scheme 22

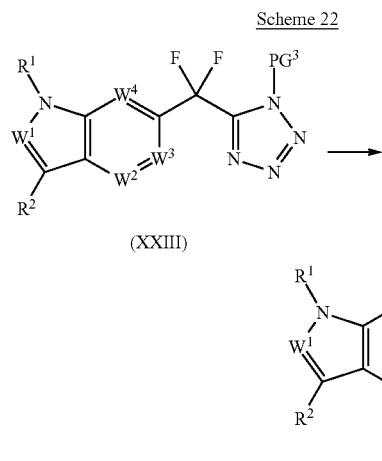

(XXIII)

(I-3)

The compound of the above-mentioned formula (I-3) [wherein $R^1$, $R^2$, $W^1$, $W^2$, $W^3$ and $W^4$ are as defined above] can be obtained by removing the protective group $PG^3$ of a compound of the above-mentioned formula (XXIII) [wherein $R^1$, $R^2$, $W^1$, $W^2$, $W^3$ and $W^4$ are as defined above, and $PG^3$ is a protective group].

The protective group $PG^3$ of the above-mentioned formula (XXIII) is not especially limited as long as the group has its function, and for example, a lower alkyl group such as a methyl group, an ethyl group, a propyl group, an isopropyl group, a tert-butyl group; for example, a halo lower alkyl group such as a 2,2,2-trichloroethyl group; for example, a lower alkenyl group such as an allyl group; for example, an aralkyl group such as a benzyl group, a p-methoxybenzyl group, a p-nitrobenzyl group, a benzhydryl group and a trityl group, etc. are mentioned, and a methyl group, an ethyl group, a tert-butyl group, an allyl group, a benzyl group, a p-methoxybenzyl group, a benzhydryl group, etc. are especially preferable.

The method for removing a protective group differs depending on the kind of the protective group and the stability of the intended compound (I-3), and the like, and is conducted by, for example, solvolysis using, for example, an acid or a base in accordance with a method described in a document [see Protective Groups in Organic Synthesis, third edition, authored by T. W. Greene, John Wiley & Sons (1999)] or a similar method, i.e., for example, a method including reacting from 0.01 mol to a large excess amount of an acid, preferably trifluoroacetic acid, formic acid, hydrochloric acid, and the like, or from an equivalent amount mol to a large excess amount of a base, preferably sodium hydroxide, potassium hydroxide, calcium hydroxide, and the like; chemical reduction using a hydrogenated metal complex, and the like, or catalytic reduction using a palladium-carbon catalyst, a Raney nickel catalyst and the like; and the like.

The following Schemes 23 to 25 are general methods for the synthesis of a compound wherein $W^4$ is a nitrogen atom, and X and Y are each a single bond in the compound of the formula (I-2) (formula (I-4)).

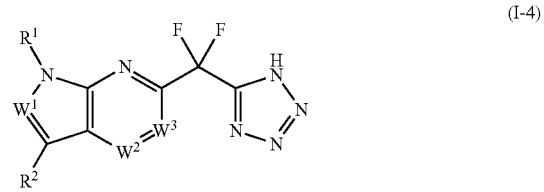

(I-4)

Scheme 23: A Method for Producing a Compound of the Formula (XXIV) from the Compound of the Formula (V-1)

Scheme 23

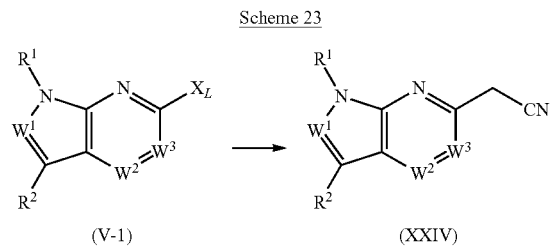

(V-1)                    (XXIV)

The compound of the above-mentioned formula (XXIV) [wherein $R^1$, $R^2$, $W^1$, $W^2$ and $W^3$ are as defined above] can be obtained by reacting the compound represented by the above-mentioned formula (V-1) [wherein $R^1$, $R^2$, $W^1$, $W^2$ and $W^3$ are as defined above, and $X_L$ is a halogen atom and the like] with a nucleophilic agent prepared from acetonitrile and a base.

In the reaction, ordinary 1 to 20 mol, and preferably 1 to 3 mol of the acetonitrile is used with respect to 1 mol of the compound (V-1). As a base, n-butyl lithium, sec-butyl lithium, tert-butyl lithium, lithium diisopropylamide, lithium dicyclohexylamide, sodium dicyclohexylamide, lithium hexamethyldisilazide, sodium hexamethyldisilazide, potassium hexamethyldisilazide, sodium hydride, potassium hydride, etc. are mentioned, and lithium hexamethyldisilazide, sodium hexamethyldisilazide, and potassium hexamethyldisilazide, etc. are preferable.

In the reaction, ordinary 1 to 20 mol, and preferably 1 to 6 mol of the base is used with respect to 1 mol of the compound (V-1).

The reaction temperature is generally −80° C. to 40° C., preferably 0° C. to 25° C.

The reaction solvent is not especially limited as long as it has no adverse effect on the reaction, and is preferably an aprotic solvent such as diethyl ether, tetrahydrofuran, 1,4-dioxane, 1,2-dimethoxyethane or toluene.

Scheme 24: A Method for Producing the Compound of the Formula (XVI-1) from the Compound of the Formula (XXIV)

Scheme 24

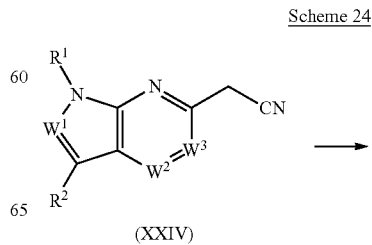

(XXIV)

-continued

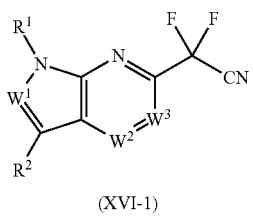

(XVI-1)

The compound of the above-mentioned formula (XVI-1) [wherein $R^1$, $R^2$, $W^1$, $W^2$ and $W^3$ are as defined above] can be obtained from the compound represented by the above-mentioned formula (XXIV) [wherein $R^1$, $R^2$, $W^1$, $W^2$ and $W^3$ are as defined above] by a similar method to the production method described in Scheme 7.

Scheme 25: A Method for Producing a Compound of the Formula (I-4) from the Compound of the Formula (XIV-1)

Scheme 25

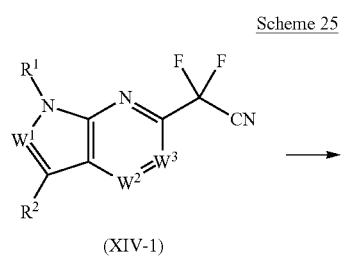

(XIV-1)

(I-4)

The compound of the above-mentioned formula (I-4) [wherein $R^1$, $R^2$, $W^1$, $W^2$ and $W^3$ are as defined above] can be obtained from the compound represented by the above-mentioned formula (XIV-1) [wherein $R^1$, $R^2$, $W^1$, $W^2$ and $W^3$ are as defined above] by a similar method to the production method described in Scheme 14.

The following Schemes 26 to 28 are general methods for the synthesis of a compound wherein Z is a 2-oxo-1,3,4-oxadiazolyl group in the compound of the formula (I) (formula (I-5)).

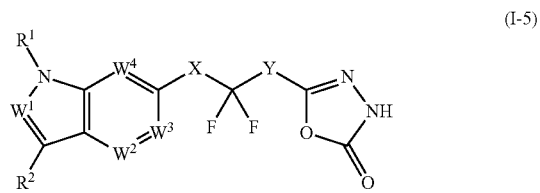

(I-5)

Scheme 26: A Method for Producing a Compound of the Formula (XXVI) from the Compound of the Formula (I-1)

Scheme 26

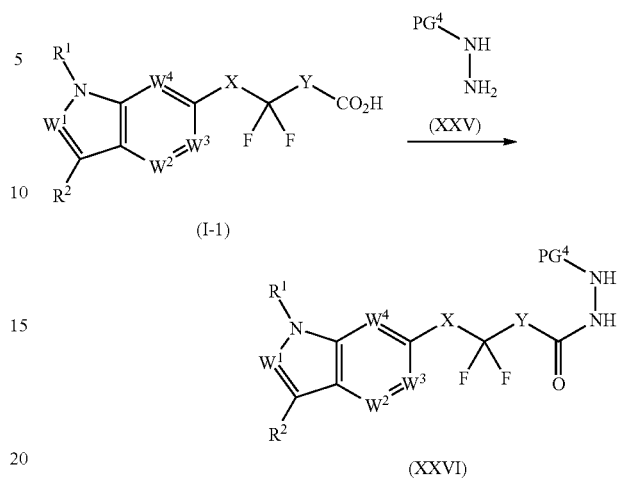

(I-1)

(XXVI)

The compound of the above-mentioned formula (XXVI) [wherein $R^1$, $R^2$, $W^1$, $W^2$, $W^3$, $W^4$, X and Y are as defined above, and $PG^4$ is a protective group] can be obtained by a condensation reaction of the compound represented by the above-mentioned formula (I-1) [wherein $R^1$, $R^2$, $W^1$, $W^2$, $W^3$, $W^4$, X and Y are as defined above] with the compound represented by the above-mentioned formula (XXV) [wherein $PG^4$ is a protective group]. More specifically, the compound (XXVI) can be obtained by reacting the compound (I-1), which has a carboxyl group, and the compound (XXV), which has a hydrazino group, in the presence of a condensing agent.

The protective group $PG^4$ in the above-mentioned formula (XXV) and the above-mentioned formula (XXVI) is not especially limited as long as the group has its function, and for example, a lower alkyl group such as a methyl group, an ethyl group, a propyl group, an isopropyl group, and a tert-butyl group etc.; for example, a halo lower alkyl group such as a 2,2,2-trichloroethyl group etc.; for example, a lower alkenyl group such as an allyl group etc.; for example, an aralkyl group such as a benzyl group, a p-methoxybenzyl group, p-nitrobenzyl group, a benzhydryl group, and a trityl group etc.; for example, a lower alkoxy carbonyl group such as a methoxycarbonyl group, an ethoxycarbonyl group, a propyloxycarbonyl group, and a tert-butoxycarbonyl group etc.; for example, an aralkyloxy carbonyl group such as a benzyloxycarbonyl group, p-nitrobenzyloxycarbonyl group, a phenethyloxycarbonyl group, etc. are mentioned, and a methyl group, an ethyl group, a tert-butyl group, an allyl group, a benzyl group, a p-methoxybenzyl group, a benzhydryl group, a methoxycarbonyl group, an ethoxycarbonyl group, a tert-butoxycarbonyl group, etc. are especially preferable.

As the condensing agent, for example, 1-(3-dimethylaminopropyl)-3-ethylcarbodiimide hydrochloride, N,N'-dicyclohexylcarbodiimide, N,N'-diisopropylcarbodiimide and the like, or combinations of those with 1-hydroxybenzotriazole, and the like are mentioned, and a combination of 1-(3-dimethylaminopropyl)-3-ethylcarbodiimide hydrochloride and 1-hydroxybenzotriazole, etc. are preferably mentioned.

In the reaction, ordinary 1 to 10 mol, and preferably 1 to 3 mol of the condensing agent is used with respect to 1 mol of the compound (I-1).

The reaction temperature is generally −30° C. to 100° C., preferably 0° C. to 60° C.

The reaction solvent is not especially limited as long as it has no adverse effect on the reaction, and is preferably a solvent such as N,N-dimethylformamide, N,N-dimethylacetamide, N-methyl-2-pyrrolidone, chloroform, dichloromethane, tetrahydrofuran, 1,4-dioxane, acetone, methyl ethyl ketone or acetonitrile.

Scheme 27: A Method for Producing a Compound of the Formula (XXVII) from the Compound of the Formula (XXVI)

a method including reacting from 0.01 mol to a large excess amount of an acid, preferably trifluoroacetic acid, formic acid, hydrochloric acid and the like, or from an equivalent amount mol to a large excess amount of a base, preferably sodium hydroxide, potassium hydroxide, calcium hydroxide and the like; chemical reduction using a hydrogenated metal complex and the like, or catalytic reduction using a palladium-carbon catalyst, a Raney nickel catalyst and the like; and the like.

Scheme 28: A Method for Producing a Compound of the Formula (I-5) from the Compound of the Formula (XXVII)

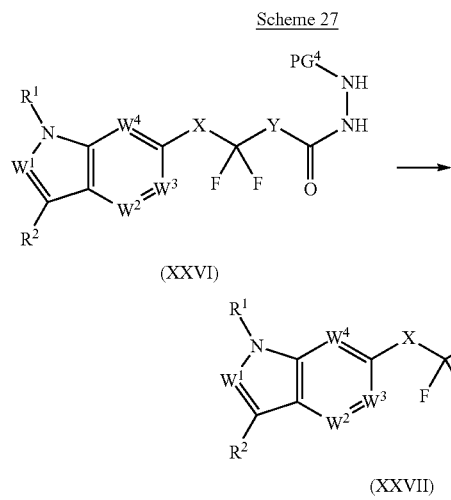

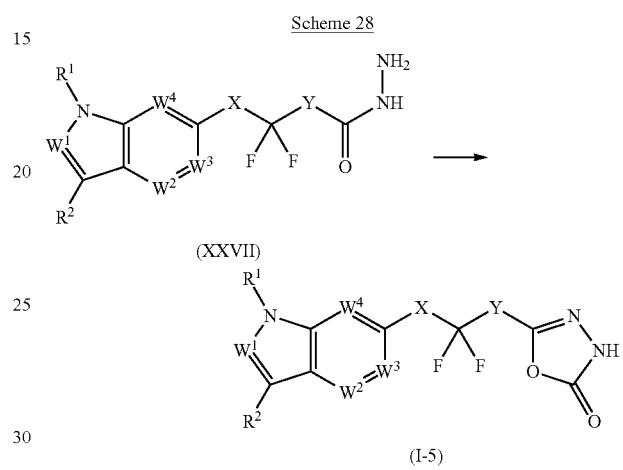

The compound of the above-mentioned formula (XXVII) [wherein $R^1$, $R^2$, $W^1$, $W^2$, $W^3$, $W^4$, X and Y are as defined above] can be obtained by removing the protective group $PG^4$ of the compound represented by the above-mentioned formula (XXVI) [wherein $R^1$, $R^2$, $W^1$, $W^2$, $W^3$, $W^4$, X and Y are as defined above, and $PG^4$ is a protective group].

The protective group $PG^4$ in the above-mentioned formula (XXVI) is not especially limited as long as the group has its function, and for example, a lower alkyl group such as a methyl group, an ethyl group, a propyl group, an isopropyl group, and a tert-butyl group etc.; for example, a halo lower alkyl group such as a 2,2,2-trichloroethyl group etc.; for example, a lower alkenyl group such as an allyl group etc.; for example, an aralkyl group such as a benzyl group, a p-methoxybenzyl group, a p-nitrobenzyl group, a benzhydryl group, and a trityl group etc.; for example, a lower alkoxy carbonyl group such as a methoxycarbonyl group, an ethoxycarbonyl group, a propyloxycarbonyl group, and a tert-butoxycarbonyl group etc.; for example, an aralkyloxy carbonyl group such as a benzyloxycarbonyl group, a p-nitrobenzyloxycarbonyl group and a phenethyloxycarbonyl group, etc. are mentioned, and a methyl group, an ethyl group, a tert-butyl group, an allyl group, a benzyl group, a p-methoxybenzyl group, a benzhydryl group, a methoxycarbonyl group, an ethoxycarbonyl group, and a tert-butoxycarbonyl group, etc. are especially preferable.

The method for removing a protective group differs depending on the kind of the protective group and the stability of the intended compound (XXVII), and the like, and is conducted by, for example, solvolysis using, for example, an acid or a base in accordance with a method described in a document [see Protective Groups in Organic Synthesis, third edition, authored by T. W. Greene, John Wiley & Sons (1999)] or a similar method, i.e., for example, The compound of the above-mentioned formula (I-5) [wherein $R^1$, $R^2$, $W^1$, $W^2$, $W^3$, $W^4$, X and Y are as defined above] can be obtained by reacting the compound represented by the above-mentioned formula (XXVII) [wherein $R^1$, $R^2$, $W^1$, $W^2$, $W^3$, $W^4$, X and Y are as defined above] with 1,1'-carbonyldiimidazole or triphosgene in the presence of a base.

For example, in the case of 1,1'-carbonyldiimidazole, ordinarily 1 to 10 mol, and preferably 1 to 3 mol of the reagent is used with respect to 1 mol of the compound (XXVII).

As a base, triethylamine, diisopropylethylamine, 1,8-diazabicyclo[5.4.0]undec-7-ene, sodium carbonate, potassium carbonate, cesium carbonate, etc. are mentioned.

In the reaction, ordinary 1 to 10 mol, and preferably 1 to 3 mol of the base is used with respect to 1 mol of the compound (XXVII).

The reaction temperature is generally 0° C. to 100° C., preferably 0° C. to 30° C.

The reaction solvent is not especially limited as long as it has no adverse effect on the reaction, and is preferably a solvent such as diethyl ether, tetrahydrofuran, 1,4-dioxane, chloroform or dichloromethane.

Next, the URAT1 inhibitor, the blood uric acid level-reducing agent, and the pharmaceutical composition for treating or preventing a pathological condition associated with the blood uric acid of the present invention will be explained.

The "URAT1" used in the present specification refers to uric acid transporter 1 (Uric acid transporter 1).

The "inhibiting URAT1" used in the present specification means inhibiting the function as uric acid transporter of URAT1 to thereby allow the disappearance or reduction of the activity thereof, and for example, means specifically inhibiting the function of URAT1 based on the condition of Example 122 mentioned below.

The "URAT1 inhibitor" used in the present specification means a drug containing the compound of the formula (I) (the cases in the form of a pharmaceutically acceptable salt or an ester of the compound are included), which inhibits the function as uric acid transporter of URAT1 to thereby allow the disappearance or reduction of the activity thereof.

The "blood uric acid level-reducing agent" used in the present specification means a drug containing the compound of the formula (I) (the cases in the form of a pharmaceutically acceptable salt or an ester of the compound are included), which inhibits URAT1 to thereby reduce a blood uric acid level.

The "reducing a blood uric acid level" used in the present specification means inhibiting the function as uric acid transporter of URAT1 to thereby reduce uric acid (including urates) in blood (including in blood serum or in blood plasma), preferably means reducing a high uric acid level in blood serum, more preferably means reducing an uric acid level in blood serum to less than 8 mg/dL (preferably to less than 7 mg/dL, more preferably to less than 6 mg/dL as an uric acid level in blood serum).

The "high blood uric acid level" used in the present specification means that the uric acid level in blood serum is 6 mg/dL or more, preferably 7 mg/dL or more, more preferably 8 mg/dL or more.

The "pharmaceutical composition for treating or preventing of a pathological condition associated with blood uric acid" used in the present specification means a pharmaceutical composition that contains the compound of the formula (I) (including the cases in the form of a pharmaceutically acceptable salt or an ester of the compound), and inhibits URAT1 to thereby treat or prevent a pathological condition associated with blood uric acid.

The "pathological condition associated with blood uric acid" used in the present specification refers to a pathological condition associated with the above-mentioned "high blood uric acid level", and for example, hyperuricemia, gouty node, acute gout arthritis, chronic gout arthritis, gouty kidney, urolithiasis, renal function disorder, coronary artery diseases and ischemic cardiac diseases, etc. are mentioned.

Either of the URAT1 inhibitor, the blood uric acid level-reducing agent and the pharmaceutical composition for treating or preventing a pathological condition associated with blood uric acid can be provided as a formulation.

The "formulation" includes oral formulations and parenteral formulations. The oral formulations are, for example, tablets, capsule agents, powder agents, granular agents and the like, whereas the parenteral formulations are, for example, sterilized liquid formulations such as solutions or suspension liquids, specifically injection agents and infusion agents and the like, preferably intravenous injection agents and intravenous infusion agents.

The "formulation" of the present invention may generally contain a therapeutically effective dose of the compound according to the present invention together with a pharmaceutically acceptable carrier or diluent. This formulation technology is regarded as a technique of common knowledge to one of ordinarily skilled in the art, and is well-known. Preferably, the compound can be formulated into an oral formulation, an intravenous infusion or an injectable formulation with a pharmaceutically acceptable carrier or a diluent by many methods that are well-known to one of ordinarily skilled in the art.

As the "pharmaceutically acceptable carrier or diluent", excipients (for example, fat, beeswax, semi-solid and liquid polyols, natural or hardened oils and the like); waters (for example, distilled water, especially distilled water for injection and the like), physiological saline, alcohols (for example, ethanol), glycerol, polyols, aqueous glucose solution, mannitol, vegetable oils and the like; additives (for example, fillers, disintegrant, binders, lubricants, wetting agents, stabilizers, emulsifiers, dispersants, preservatives, sweeteners, colorants, seasonings or aromatic substances, thickeners, diluents, buffering substances, solvents or solubilizers, agents for accomplishing the storage effect, salts for changing osmotic pressure, coating agents or antioxidants) and the like are mentioned.

Various forms can be selected for the formulation according to the present invention. For example, oral formulations such as tablets, capsule agents, powder agents, granular agents or liquid agents, sterilized liquid parenteral formulations such as solutions or suspension liquids, suppositories, ointments, etc. are mentioned.

The formulation according to the present invention may be either a solid formulation or a liquid formulation.

The solid formulation can be manufactured as it is as a form of a tablet, a capsule, a granule or a powder, or may be manufactured by using a suitable carrier (additive). As such carrier (additive), for example, saccharides such as lactose or glucose; for example, the starch such as a corn, wheat or rice etc.; for example, the fatty acid such as stearic acid etc.; for example, the inorganic salt such as magnesium aluminometasilicate or phosphoric anhydride calcium etc.; the synthetic polymers such as polyvinyl pyrrolidone, or polyalkylene glycol etc.; the fatty acid salt such as calcium stearate or magnesium stearate etc.; for example alcohols such as, stearyl alcohol or benzyl alcohol etc.; for example, synthetic cellulose derivatives such as methyl cellulose, carboxymethylcellulose, ethyl cellulose, or hydroxypropylmethylcellulose etc.; in addition to this, additives which are usually used, gelatin, talc, vegetable oil, and gum arabic, etc. are mentioned.

These solid formulations such as a tablet, a capsule agent, a granular agent and a powder may contain the compound represented by the above-mentioned formula (I) as an active ingredient, for example, by generally from 0.1 to 100 mass %, preferably from 5 to 98 mass % based on the total mass of the formulation.

The liquid formulation is produced as a form such as a suspension, a syrup agent, an injection or an infusion agent (intravenous infusion) by using suitable additives that are generally used in liquid formulations such as water, alcohols, and oils derived from plants such as soybean oil, peanut oil and sesame oil.

Especially, as a suitable solvent or diluting agent in the case of parenteral administration in the form of intramuscular injection, intravenous injection or subcutaneous injection, for example, injectable distilled water, an aqueous lidocaine hydrochloride solution (for intramuscular injection), physiological saline, an aqueous glucose solution, ethanol, polyethylene glycol, propylene glycol, intravenous injectable liquids (for example, aqueous solutions of citric acid and sodium citrate), electrolyte solutions (intravenous infusion and intravenous injection), etc., and mixed solutions thereof are mentioned.

These injection agents may be in a form that is dissolved at the time of use as a powder of the active ingredient as it is or a powder of the active ingredient added with a proper carrier (additive), in addition to a form in which the active gradient is preliminarily dissolved. These injection liquids may contain, for example, from 0.1 to 10 mass % of the active ingredient based on the total mass of the formulation.

Furthermore, a solution for oral administration such as a suspension and a syrup may contain, respectively, from 0.1 to 10 mass % of the active ingredient based on the total mass of the formulation.

The compound of the present invention, the URAT1 inhibitor, the blood uric acid level-reducing agent and the pharmaceutical composition for treating or preventing a pathological condition associated with uric acid of the present invention can be used in combination with another pharmaceutical composition or drug (hereinafter also referred to as the combination drug).

The "combination" means combination use of multiple drugs as an active ingredient. For example, use as a combination drug, use as a kit, and use in combination in which drugs are separately administered by identical or different administration routes, etc. are mentioned.

The timings of the administration of the compound of the present invention, and the URAT1 inhibitor, the blood uric acid level-reducing agent and the pharmaceutical composition for treating or preventing a pathological condition associated with blood uric acid and the combination drug are not limited, and these may be simultaneously administered or administered at a time interval to a subject for administration. The dose of the combination drug may be in accordance with a clinically-used dose, and can be suitably selected depending on a subject for administration, and the age and body weight of the subject for administration, the symptom, the administration time, the dosage form, the administration method, the combination, etc. The dosage form of the combination drug is not specifically limited, and it is sufficient that the URAT1 inhibitor, the blood uric acid level-reducing agent or the pharmaceutical composition for treating a pathological condition associated with blood uric acid of the present invention is combined with the combination drug at the time of administration.

As the combination drug, for example, "therapeutic drug and/or prophylactic drug for hyperuricemia", "therapeutic drug and/or prophylactic drug for gout arthritis", "therapeutic drug and/or prophylactic drug for gouty kidney", "therapeutic drug and/or prophylactic drug for urolithiasis", "therapeutic drug and/or prophylactic drug for hypertension or hypertension complication", "therapeutic drug and/or prophylactic drug for hyperlipidemia or hyperlipidemia complication", "therapeutic drug and/or prophylactic drug for diabetes or diabetic complication", "therapeutic drug and/or prophylactic drug for obesity or obesity complication", "therapeutic drug and/or prophylactic drug for a primary disease that causes secondary hyperuricemia", "therapeutic drug and/or prophylactic drug for kidney failure, a cardiovascular disorder or a cerebrovascular disorder caused by hyperuricemia" and "nucleic acid antimetabolite" are mentioned. One to three of these combination drugs can be used in combination with the URAT1 inhibitor, the blood uric acid level-reducing agent and the pharmaceutical composition for treating or preventing a pathological condition associated with blood uric acid of the present invention.

As the "therapeutic drug and/or a prophylactic drug for hyperuricemia", for example, drugs for suppressing production of uric acid such as xanthine oxidase inhibitors, a drug for promoting uric acid excretion, etc. are mentioned. Specifically, allopurinol, probenecid, bucolome, febuxostat, FYX-051 (4-(5-pyridin-4-yl-1H-[1,2,4]triazol-3-yl)pyridine-2-carbonitrile), benzbromarone, oxipurinol, etc. are mentioned.

As the "therapeutic drug and/or a prophylactic drug for gout arthritis", for example, non-steroidal anti-inflammatory drugs such as indomethacin, naproxen, fenbufen, pranoprofen and oxaprozin, colchicine, corticosteroids, etc. are mentioned.

As the "therapeutic drug and/or a prophylactic drug for gouty kidney", for example, drugs for suppressing production of uric acid such as xanthine oxidase inhibitors, drugs for promoting excretion of uric acid, citric acid formulations, urine alkalinization agents such as sodium bicarbonate, etc. are mentioned. Specifically, allopurinol, probenecid, bucolome, febuxostat, FYX-051 (4-(5-pyridin-4-yl-1H-[1,2,4]triazol-3-yl)pyridine-2-carbonitrile), benzbromarone, oxipurinol, etc. are mentioned.

As the "therapeutic drug and/or a prophylactic drug for urolithiasis", for example, citric acid formulations, urine alkalinization agents such as sodium bicarbonate, etc. are mentioned.

As the "therapeutic drug and/or a prophylactic drug for hypertension or hypertension complication", for example, loop diuretics, angiotensin-converting enzyme inhibitors, angiotensin II receptor antagonist, Ca antagonist, β-blockers, α,β-blockers, α-blockers, etc. are mentioned. More specifically, for example a furosemide sustained release drug, captopril, a captopril sustained release drug, enalapril maleate, alacepril, delapril hydrochloride, cilazapril, lisinopril, benazepril hydrochloride, imidapril hydrochloride, temocapril hydrochloride, quinapril hydrochloride, trandolapril, perindopril erbumine, losartan potassium, candesartan cilexetil, nicardipine hydrochloride, a nicardipine hydrochloride sustained release drug, nilvadipine, nifedipine, a nifedipine sustained release drug, benidipine hydrochloride, diltiazem hydrochloride, a diltiazem hydrochloride sustained release drug, nisoldipine, nitrendipine, manidipine hydrochloride, barnidipine hydrochloride, efonidipine hydrochloride, amlodipine besylate, felodipine, cilnidipine, aranidipine, propranolol hydrochloride, a propranolol hydrochloride sustained release drug, pindolol, a pindolol sustained release drug, indenolol hydrochloride, carteolol hydrochloride, a carteolol hydrochloride sustained release drug, bunitrolol hydrochloride, a bunitrolol hydrochloride sustained release drug, atenolol, acebutolol hydrochloride, metoprolol tartrate, a metoprolol tartrate sustained release drug, nipradilol, penbutolol sulfate, tilisolol hydrochloride, carvedilol, bisoprolol fumarate, betaxolol hydrochloride, celiprolol hydrochloride, bopindolol malonate, bevantolol hydrochloride, labetalol hydrochloride, arotinolol hydrochloride, amosulalol hydrochloride, prazosin hydrochloride, terazosin hydrochloride, doxazosin mesilate, bunazosin hydrochloride, a bunazosin hydrochloride sustained release drug, urapidil, and phentolamine mesilate, etc. are mentioned.

As the "therapeutic drug and/or a prophylactic drug for hyperlipidemia or hyperlipidemia complication", for example, HMG-CoA reductase inhibitors, anion exchange resin, probucol, nicotinic acid formulation, fibrates drug, eicosapentaenoic acid formulation, etc. are mentioned. More specifically, for example lovastatin, simvastatin, pravastatin, fluvastatin, atrovastatin, cerivastatin, colestimide, colestyramine, niceritrol, nicomol, fenofibrate, bezafibrate, clinofibrate, clofibrate, ethyl icosapentate, etc. are mentioned.

As the "therapeutic drug and/or a prophylactic drug for diabetes or diabetic complication", for example, insulin formulation, sulfonylurea agent, insulin secretion facilitator, sulfonamide agent, biguanide agent, alpha-glucosidase inhibitor, an insulin resistance-improving agent, dipeptidyl-peptidase-IV inhibitor, an angiotensin converting enzyme inhibitor, aldose reductase inhibitor, an antiarrhythmic drug, etc. are mentioned. More specifically, for example insulin, chlorpropamide, glibenclamide, glipizide, tolbutamide, glyclopyramide, acetohexamide, glimepiride, tolazamide, gliclazide, nateglinide, glybuzole, metformin hydrochloride, buformin hydrochloride, voglibose, acarbose, pioglitazone hydrochloride, sitagliptin phosphate, vldagliptin, benzoic acid alogliptin mexiletine, and epalrestat, etc. are mentioned.

As the "therapeutic drug and/or a prophylactic drug for obesity or complicating diseases of obesity", for example, mazindol, acarbose, voglibose, epalrestat, etc. are mentioned.

As the "therapeutic drug and/or a prophylactic drug for a primary disease that causes uric acid excretion reductiontype secondary hyperuricemia", for example, therapeutic agents or prophylactic agents for chronic kidney diseases, polycystic kidney, pregnancy toxemia, lead nephropathy, hyperlacticacidemia, Down's syndrome, sarcoidosis, type I glycogenesis (via hyperlacticacidemia), dehydration and the like, etc. are mentioned.

As the "therapeutic drug and/or a prophylactic drug for kidney failure, a cardiovascular disease or a cerebrovascular disorder caused by hyperuricemia", for example, loop diuretics (for example, furocemide), citric acid formulations, sodium bicarbonate, cation exchange resins, aluminum hydroxide, α-calcidol, β-blockers (for example, propranolol hydrochloride), angiotensin transferase inhibitors (for example, captopril), cardiotonic agents (for example, digoxin), agents for treating angina pectoris (for example, isosorbide nitrate), Ca antagonist (for example, diltiazem hydrochloride), drugs for suppressing generation of uric acid (for example, allopurinol), amino acid formulations, drugs for ameliorating hyperammonemia, antiarrhythmic treatment drugs (for example, mexiletine), drug for treating anemia (for example, mepitiostane, erythropoietin), and the "therapeutic drug and/or a prophylactic drug for hypertension or complicating diseases of hypertension", the "therapeutic drug and/or a prophylactic drug for hyperlipidemia or complicating diseases of hyperlipidemia", the "therapeutic drug and/or a prophylactic drug for diabetes mellitus or complicating diseases of diabetes mellitus", the "therapeutic drug and/or a prophylactic drug for obesity or complicating diseases of obesity", etc. are mentioned.

As the "nucleic acid antimetabolite", for example, azathiopurine, mizoribine, mycophenolic acid, etc. are mentioned.

Furthermore, either of the compound of the present invention, the URAT1 inhibitor, the blood uric acid level-reducing agent, and the pharmaceutical composition for treating or preventing a pathological condition associated with uric acid of the present invention can reduce a blood uric acid level by using in combination with a drug that increases a blood uric acid level.

As the "drug that increases a blood uric acid level", nucleic acid antimetabolites, hypotensive diuretics (for example, furocemide, thiazide-based diuretics), antitubercular drugs (for example, pyrazinamide, ethambutol), antiinflammatory analgesics (for example, salicylic acid), hyperlipidemia drugs (for example, nicotinic acid), drugs for treating asthma (for example, theophylline), immunosuppressive drugs (for example, cyclosporine), drugs for treating hepatitis C (for example, ribavirin), ethanol, etc. are mentioned.

EXAMPLES

The present invention will further be specifically described with Examples below, but the present invention is not limited to these Examples. For various reagents used in Examples, commercial products were used unless otherwise stated. In the Examples, a Silica gel$_{60}$F$_{254}$ manufactured by MERCK KGaA was used as a plate, and a UV detector was used as a detection method for the thin layer chromatography.

For the silica gel column chromatography, a Biotage (registered trademark) SNAP Cartridge KP-Sil silica gel prepacked column manufactured by Biotage, or a Chromatorex (registered trademark) Q-PACK SO$_3$H silica gel prepacked column manufactured by Fuji Silysia Chemical Ltd. was used. For the reverse phase preparation liquid chromatography, a CombiPrep Pro C18 manufactured by YMC Co., LTD. was used as a column, and 0.1% trifluoroacetic acid in water and 0.1% trifluoroacetic acid in acetonitrile were used as the mobile phase.

For $^1$H-NMR, AL400 (400 MHz) manufactured by JEOL Ltd. was used, and $^1$H-NMR was measured using tetramethylsilane as a standard substance. The mass spectrum was measured by electrospray ionization (ESI) using ACQUITY (registered trademark) SQD manufactured by Waters Corporation. The microwave reaction was performed using Initiator (registered trademark) manufactured by Biotage.

The meanings of the abbreviations are shown below.
s: Singlet
d: Doublet
t: Triplet
q: Quartet
dd: Double Doublet
dt: Double Triplet
td: Triple Doublet
tt: Triple Triplet
ddd: Double Double Doublet
ddt: Double Double Triplet
dtd: Double Triple Doublet
tdd: Triple Double Doublet
tq: Triple Quartet
m: Multiplet
br: Broad
DMSO-d$_6$: Deuterated dimethyl sulfoxide
CDCl$_3$: Deuterated chloroform
CD$_3$OD: Deuterated methanol
tBu: tert-butyl group Example 1

Synthesis of [1-(2,6-dichlorobenzyl)-3-methyl-1H-indazol-6-yl]difluoroacetic acid [1] (hereinafter referred to as a compound [1])

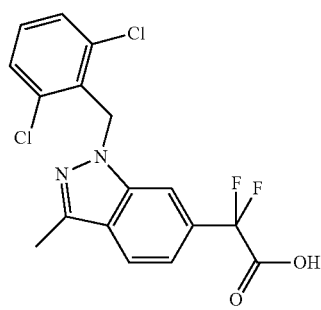

(1) Synthesis of 6-bromo-1-(2,6-dichlorobenzyl)-3-methyl-1H-indazole [1-1] (hereinafter referred to as a compound [1-1])

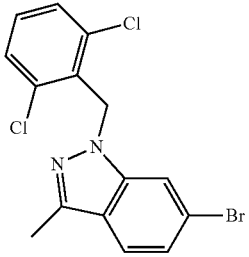 [SMILES: Cc1nn(Cc2c(Cl)cccc2Cl)c2cc(Br)ccc12]

To a solution of 6-bromo-3-methyl-1H-indazole (9.57 g), which was obtained by the method described in the document (JP 2009-528363 W), in N,N-dimethylformamide (100 mL), were added potassium carbonate (12.6 g) and 2,6-dichlorobenzyl chloride (9.79 g) and the mixture was stirred at room temperature for 20 hours. The reaction mixture was quenched with water, and the mixture was extracted with ethyl acetate.

The obtained organic layer was dried over anhydrous sodium sulfate, filtered, and the filtrate was concentrated under reduced pressure. The obtained residue was purified by silica gel column chromatography to give the titled compound (10.4 g) as a white solid.

$^1$H-NMR (400 MHz, CDCl$_3$) δ: 7.55 (1H, s), 7.47 (1H, d, J=8.5 Hz), 7.38 (2H, d, J=8.1 Hz), 7.25 (1H, d, J=5.9 Hz), 7.22-7.20 (1H, m), 5.66 (2H, s), 2.50 (3H, s).

(2) Synthesis of 6-tributylstannyl-1-(2,6-dichlorobenzyl)-3-methyl-1H-indazole [1-2] (hereinafter referred to as a compound [1-2])

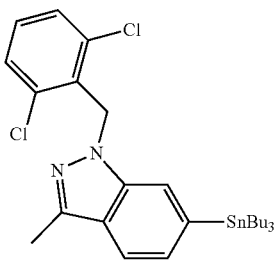

To a solution of the compound [1-1] (1.12 g) in toluene (30 mL) were added bis(tributyltin) (1.8 mL) and tetrakis(triphenylphosphine)palladium(0) (177 mg) at room temperature, and the mixture was heated at reflux for 2 hours. The reaction mixture was quenched with water, and the mixture was extracted with ethyl acetate. The obtained organic layer was dried over anhydrous sodium sulfate, filtered, and the filtrate was concentrated under reduced pressure. The obtained residue was purified by silica gel column chromatography to give the titled compound (774 mg) as a colorless oil.

$^1$H-NMR (400 MHz, CDCl$_3$) δ: 7.59 (1H, d, J=7.8 Hz), 7.37-7.36 (3H, m), 7.23-7.21 (1H, m), 7.16 (1H, d, J=7.8 Hz), 5.77 (2H, s), 2.53 (3H, s), 1.54-1.48 (6H, m), 1.39-1.28 (12H, m), 0.95-0.87 (9H, m).

(3) Synthesis of ethyl [1-(2,6-dichlorobenzyl)-3-methyl-1H-indazol-6-yl]oxoacetate [1-3] (hereinafter referred to as a compound [1-3])

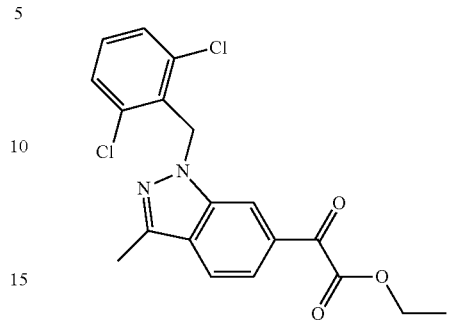

To a solution of the compound [1-2] (1.47 g) in tetrahydrofuran (15 mL) were added Diisopropylethylamine (0.56 mL), tris(dibenzylideneacetone)dipalladium(0) (118 mg) and ethyl chloroglyoxylate (0.42 mL) at 0° C., and the mixture was stirred at room temperature for 24 hours. The reaction mixture was quenched with water, and the mixture was extracted with ethyl acetate. The obtained organic layer was dried over anhydrous sodium sulfate, filtered, and the filtrate was concentrated under reduced pressure. The obtained residue was purified by silica gel column chromatography to give the titled compound (218 mg) as a yellow solid.

$^1$H-NMR (400 MHz, CDCl$_3$) δ: 8.10 (1H, s), 7.72 (2H, s), 7.38 (2H, d, J=8.1 Hz), 7.27-7.25 (1H, m), 5.81 (2H, s), 4.48 (2H, q, J=7.2 Hz), 2.56 (3H, s), 1.45 (3H, t, J=7.1 Hz).

(4) Synthesis of ethyl [1-(2,6-dichlorobenzyl)-3-methyl-1H-indazol-6-yl]difluoroacetate [1-4] (hereinafter referred to as a compound [1-4])

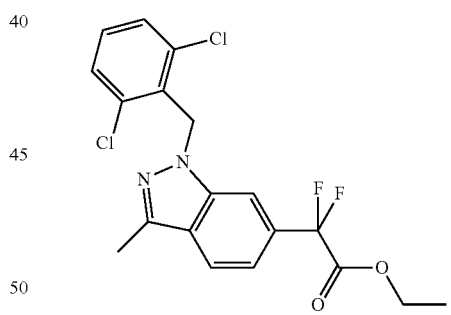

To a solution of the compound [1-1] (102 mg) in dichloromethane (1 mL) was added N,N-diethylaminosulfur trifluoride (0.35 mL), and the mixture was stirred at room temperature for 24 hours. The reaction mixture was quenched with water and a saturated aqueous solution of sodium hydrogen carbonate, and the mixture was extracted with chloroform. The obtained organic layer was dried over anhydrous sodium sulfate, filtered, and the filtrate was concentrated under reduced pressure. The obtained residue was purified by silica gel column chromatography to give the titled compound (100 mg) as a white solid.

$^1$H-NMR (400 MHz, CDCl$_3$) δ: 7.70-7.68 (2H, m), 7.38 (2H, d, J=8.1 Hz), 7.32 (1H, d, J=9.0 Hz), 7.25-7.23 (1H, m), 5.75 (2H, s), 4.29 (2H, q, J=7.2 Hz), 2.53 (3H, s), 1.29 (3H, t, J=7.1 Hz).

(5) Synthesis of [1-(2,6-dichlorobenzyl)-3-methyl-1H-indazol-6-yl]difluoroacetic acid[1]

To a solution of the compound [1-4] (96 mg) in ethanol (2 mL) was added an aqueous solution of 1N-sodium hydroxide (2 mL) at room temperature, and the mixture was stirred at 60° C. for 1 hour. To the reaction mixture was added 1N-hydrochloric acid, and the precipitated solid was filtered to give the titled compound (89 mg) as a white solid.

$^1$H-NMR (400 MHz, CD$_3$OD) δ: 7.81-7.79 (2H, m), 7.45 (2H, d, J=8.1 Hz), 7.36-7.34 (2H, m), 5.81 (2H, s), 2.50 (3H, s).

ESI-MS found: 385 [M+H]$^+$

Example 2

Synthesis of potassium [1-(2,6-dichlorobenzyl)-3-methyl-1H-indazol-6-yl]difluoroacetate [2] (hereinafter referred to as a compound [2])

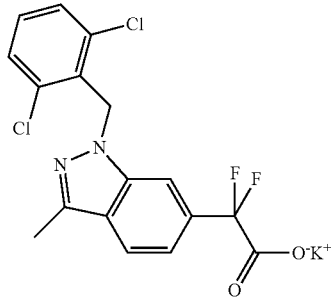

To a solution of the compound [1] (89 mg) in ethanol (2 mL) was added an aqueous solution of 1N-potassium hydroxide (233 μL) at room temperature, and the solution was concentrated under reduced pressure to give the titled compound (98 mg) as a white solid.

$^1$H-NMR (400 MHz, CD$_3$OD) δ: 7.88 (1H, s), 7.71 (1H, d, J=8.5 Hz), 7.44-7.42 (3H, m), 7.35-7.33 (1H, m), 5.77 (2H, s), 2.48 (3H, s).

ESI-MS found: 385 [M−K+2H]$^+$

Example 3

Synthesis of [1-(2-chloro-6-methylbenzyl)-3-methyl-1H-indazol-6-yl]difluoroacetic acid [3] (hereinafter referred to as a compound [3])

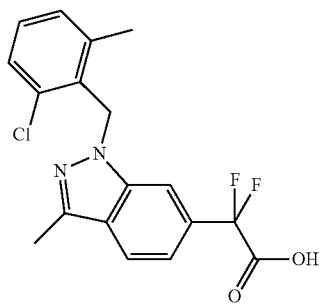 [SMILES: Cc1cccc(Cl)c1Cn1nc(C)c2ccc(C(F)(F)C(=O)O)cc21]

(1) Synthesis of 2-chloro-6-methylbenzyl alcohol [3-1] (hereinafter referred to as a compound [3-1])

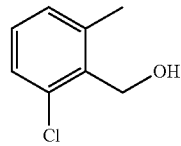

To a solution of 2-chloro-6-methylbenzaldehyde (2.08 g) in methanol (26 mL) was added sodium borohydride (508.6 mg) at 0° C., and the mixture was stirred at 0° C. for 10 minutes. The reaction mixture was quenched with a saturated aqueous solution of ammonium chloride, and the mixture was extracted with chloroform.

The obtained organic layer was dried over anhydrous sodium sulfate, filtered, and the filtrate was concentrated under reduced pressure. The obtained residue was purified by silica gel column chromatography to give the titled compound (2.00 g) as a white solid.

$^1$H-NMR (400 MHz, CDCl$_3$) δ: 7.24 (1H, d, J=7.3 Hz), 7.16-7.10 (2H, m), 4.85 (2H, d, J=6.3 Hz), 2.47 (3H, s), 1.77 (1H, t, J=6.5 Hz).

(2) Synthesis of 2-chloro-6-methylbenzyl chloride [3-2] (hereinafter referred to as a compound [3-2])

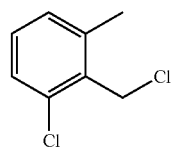

To a solution of the compound [3-1] (2.00 g) in dimethyl sulfoxide (25 mL) was added cyanuric chloride (2.83 g) at 0° C., and the mixture was stirred at room temperature for 45 minutes. The reaction mixture was quenched with water, and the mixture was extracted with hexane. The obtained organic layer was dried over anhydrous sodium sulfate, filtered, and the filtrate was concentrated under reduced pressure to give the titled compound (2.09 g) as a colorless oil.

$^1$H-NMR (400 MHz, CDCl$_3$) δ: 7.27-7.25 (1H, m), 7.18-7.10 (2H, m), 4.79 (2H, s), 2.47 (3H, s).

(3) Synthesis of 6-bromo-1-(2-chloro-6-methylbenzyl)-3-methyl-1H-indazole [3-3] (hereinafter referred to as a compound [3-3])

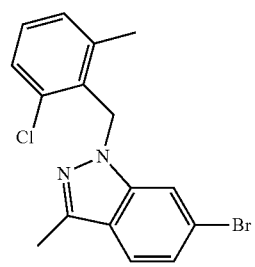

The titled compound (1.6 g) as a white solid was prepared from 6-bromo-3-methyl-1H-indazole (1.94 g), which was obtained by the method described in the document (JP 2009-528363 W), and the compound [3-2] (2.09 g) according to the method of the process (1) in Example 1.

$^1$H-NMR (400 MHz, CDCl$_3$) δ: 7.46 (2H, d, J=8.1 Hz), 7.31 (1H, d, J=8.1 Hz), 7.20-7.18 (2H, m), 7.12 (1H, d, J=7.3 Hz), 5.59 (2H, s), 2.50 (3H, s), 2.37 (3H, s).

(4) Synthesis of tert-butyl [1-(2-chloro-6-methylbenzyl)-3-methyl-1H-indazol-6-yl]acetate [3-4] (hereinafter referred to as a compound [3-4])

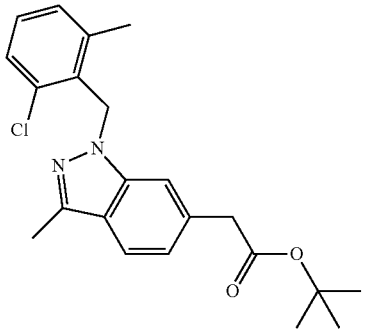 [SMILES: Cc1cccc(Cl)c1Cn1nc(C)c2ccc(CC(=O)OC(C)(C)C)cc21]

To a mixture of the compound [3-3] (46.5 mg), bis(dibenzylideneacetone)palladium(0) (3.8 mg) and 1,2,3,4,5-pentaphenyl-1'-(di-tert-butylphosphino)ferrocene (4.7 mg) in tetrahydrofuran (0.3 mL) was added 0.5M diethyl ether solution of 2-tert-butoxy-2-oxoethyl zinc chloride (0.6 mL) at room temperature, and the mixture was stirred at room temperature for 1 hour. The reaction mixture was concentrated under reduced pressure, and the obtained residue was then purified by silica gel column chromatography to give the titled compound (47.6 mg) as a white solid.

$^1$H-NMR (400 MHz, CDCl$_3$) δ: 7.55 (1H, d, J=8.3 Hz), 7.29 (1H, d, J=7.8 Hz), 7.18-7.16 (2H, m), 7.10 (1H, d, J=7.6 Hz), 7.01 (1H, d, J=8.1 Hz), 5.61 (2H, s), 3.59 (2H, s), 2.51 (3H, s), 2.36 (3H, s), 1.42 (9H, s).

(5) Synthesis of tert-butyl [1-(2-chloro-6-methylbenzyl)-3-methyl-1H-indazol-6-yl]difluoroacetate [3-3] (hereinafter referred to as a compound [3-5])

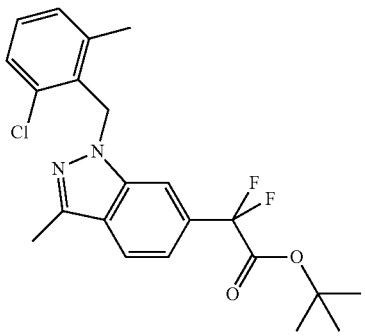 [SMILES: Cc1cccc(Cl)c1Cn1nc(C)c2ccc(C(F)(F)C(=O)OC(C)(C)C)cc21]

To a solution of the compound [3-4] (206.0 mg) in tetrahydrofuran (2.7 mL) was added 1.0M tetrahydrofuran solution of lithium bis(trimethylsilyl)amide (1.3 mL) at −78° C., and the mixture was stirred for 10 minutes. N-fluorobenzenesulfonimide (506.1 mg) was then added at −78° C., and the mixture was stirred at 0° C. for 1 hour. A saturated aqueous solution of ammonium chloride was added to the mixture, and the mixture was extracted with chloroform. The obtained organic layer was dried over anhydrous sodium sulfate, filtered, and the filtrate was concentrated under reduced pressure. The obtained residue was purified by silica gel column chromatography to give the titled compound (149.9 mg) as a white solid.

$^1$H-NMR (400 MHz, CDCl$_3$) δ: 7.67 (1H, d, J=8.3 Hz), 7.61 (1H, s), 7.29-7.27 (2H, m), 7.19 (1H, t, J=7.8 Hz), 7.13 (1H, d, J=7.6 Hz), 5.66 (2H, s), 2.54 (3H, s), 2.41 (3H, s), 1.44 (9H, s).

(6) Synthesis of [1-(2-chloro-6-methylbenzyl)-3-methyl-1H-indazol-6-yl]difluoroacetic acid [3]

Water (100 μL) and trifluoroacetic acid (600 μL) were added to the compound [3-3] (27.9 mg) at room temperature, and the mixture was then stirred at room temperature for 2 hours. Water was added to the reaction mixture, and the mixture was extracted with chloroform. The obtained organic layer was dried over anhydrous sodium sulfate, filtered, and the filtrate was concentrated under reduced pressure to give the titled compound (24.1 mg) as a white solid.

$^1$H-NMR (400 MHz, CD$_3$OD) δ: 7.78 (1H, d, J=8.3 Hz), 7.73 (1H, s), 7.32-7.30 (2H, m), 7.24 (1H, t, J=7.7 Hz), 7.19 (1H, d, J=7.1 Hz), 5.71 (2H, s), 2.51 (3H, s), 2.36 (3H, s).

ESI-MS found: 365 [M+H]$^+$

Example 4

Synthesis of potassium [1-(2-chloro-6-methylbenzyl)-3-methyl-1H-indazol-6-yl]difluoroacetate [4] (hereinafter referred to as a compound [4])

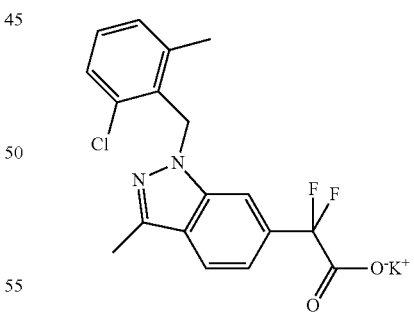

To a solution of the compound [3] (24.1 mg) in ethanol (3 mL) was added an aqueous solution of 1N-potassium hydroxide (76 μL) at room temperature, and the solution was concentrated under reduced pressure to give the titled compound (29.6 mg) as a white solid.

$^1$H-NMR (400 MHz, CD$_3$OD) δ: 7.83 (1H, s), 7.71 (1H, d, J=8.5 Hz), 7.40 (1H, d, J=8.5 Hz), 7.30 (1H, d, J=7.8 Hz), 7.24-7.17 (2H, m), 5.67 (2H, s), 2.48 (3H, s), 2.34 (3H, s).

ESI-MS found: 365 [M−K+2H]$^+$

Example 5

Synthesis of [1-(2-chloro-6-cyanobenzyl)-3-methyl-1H-indazol-6-yl]difluoroacetic acid [5] (hereinafter referred to as a compound [5])

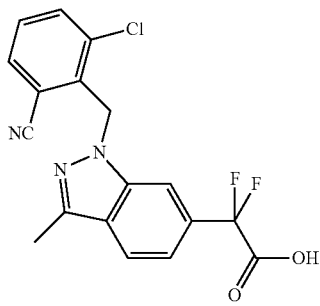

(1) Synthesis of 3-methyl-6-(4,4,5,5-tetramethyl[1,3,2]dioxaborolan-2-yl)-1H-indazole [5-1] (hereinafter referred to as a compound [5-1])

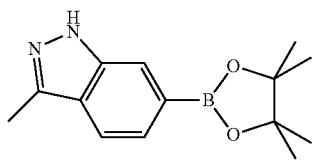

To a solution of 6-bromo-3-methyl-1H-indazole (647 mg), which was obtained by the method described in the document (JP 2009-528363 W), in 1,4-dioxane (10 mL) were added bis(pinacolato)diboron (1.15 g), potassium acetate (899 mg) and [1,1'-bis(diphenylphosphino)ferrocene]dichloropalladium(II) dichloromethane complex (126 mg), and the mixture was subjected to microwave irradiation at 150° C. for 30 min. The reaction mixture was quenched with water, and the mixture was extracted with ethyl acetate. The obtained organic layer was dried over anhydrous sodium sulfate, filtered, and the filtrate was concentrated under reduced pressure. The obtained residue was purified by silica gel column chromatography to give the titled compound (618 mg) as a yellow solid.

$^1$H-NMR (400 MHz, CDCl$_3$) δ: 7.93 (1H, s), 7.67 (1H, dd, J=8.1, 0.7 Hz), 7.55 (1H, d, J=8.3 Hz), 2.60 (3H, s), 1.37 (12H, s).

(2) Synthesis of 2-bromo-6-chlorobenzyl bromide [5-2] (hereinafter referred to as a compound [5-2])

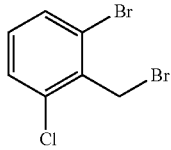

To a solution of 2-bromo-6-chlorotoluene (1.58 g) in carbon tetrachloride (15 mL) were added N-bromosuccinimide (1.63 g) and 2,2'-azobis(isobutyronitrile) (125 mg), and the mixture was heated at reflux for 24 hours. The reaction mixture was quenched with water, and the mixture was extracted with chloroform. The obtained organic layer was dried over anhydrous sodium sulfate, filtered, and the filtrate was concentrated under reduced pressure. The obtained residue was purified by silica gel column chromatography to give the titled compound (2.16 g) as a white solid.

$^1$H-NMR (400 MHz, CDCl$_3$) δ: 7.51 (1H, d, J=8.1 Hz), 7.37 (1H, d, J=8.1 Hz), 7.11 (1H, d, J=8.1 Hz), 4.80 (2H, s).

(3) Synthesis of 1-(2-bromo-6-chlorobenzyl)-3-methyl-6-(4,4,5,5-tetramethyl[1,3,2]dioxaborolan-2-yl)-1H-indazole [5-5] (hereinafter referred to as a compound [5-3])

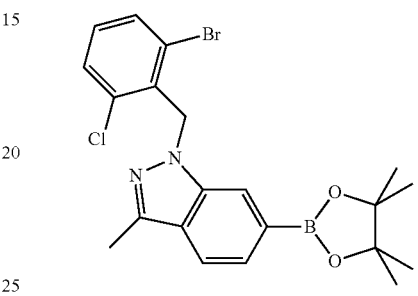

To a solution of the compound [5-1] (618 mg) in N,N-dimethylformamide (10 mL) were added potassium carbonate (678 mg) and the compound [5-2] (1.09 g) at room temperature, and the mixture was stirred at room temperature for 24 hours. The reaction mixture was quenched with water, and the mixture was extracted with ethyl acetate.

The obtained organic layer was dried over anhydrous sodium sulfate, filtered, and the filtrate was concentrated under reduced pressure. The obtained residue was purified by silica gel column chromatography to give the titled compound (413 mg) as yellow foam.

$^1$H-NMR (400 MHz, CDCl$_3$) δ: 7.98 (1H, s), 7.62 (1H, d, J=8.1 Hz), 7.55-7.53 (2H, m), 7.40 (1H, d, J=8.1 Hz), 7.16-7.14 (1H, m), 5.72 (2H, s), 2.50 (3H, s), 1.39 (12H, s).

(4) Synthesis of ethyl [1-(2-bromo-6-chlorobenzyl)-3-methyl-1H-indazol-6-yl]oxoacetate [5-4] (hereinafter referred to as a compound [5-4])

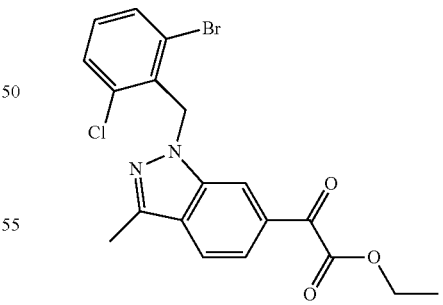

To a solution of the compound [5-3] (405 mg) in 1,4-dioxane (3 mL) were added ethyl cyanoformate (86 µL), boric acid (112 mg) and hydroxy(cyclooctadiene)rhodium(I) dimer (14 mg) at room temperature, and the mixture was stirred at 60° C. for 24 hours. The reaction mixture was quenched with water, and extracted with chloroform. The obtained organic layer was dried over anhydrous sodium sulfate, filtered, and the filtrate was concentrated under reduced pressure. The obtained residue was purified by silica gel column chromatography to give the titled compound (43 mg) as a white solid.

¹H-NMR (400 MHz, CDCl₃) δ: 8.07 (1H, s), 7.72 (2H, s), 7.58 (1H, d, J=8.1 Hz), 7.42 (1H, d, J=8.1 Hz), 7.20-7.18 (1H, m), 5.82 (2H, s), 4.48 (2H, q, J=7.2 Hz), 2.56 (3H, s), 1.44 (3H, t, J=7.1 Hz).

(5) Synthesis of ethyl [1-(2-chloro-6-cyanobenzyl)-3-methyl-1H-indazol-6-yl]oxoacetate [5-5] (hereinafter referred to as a compound [5-5])

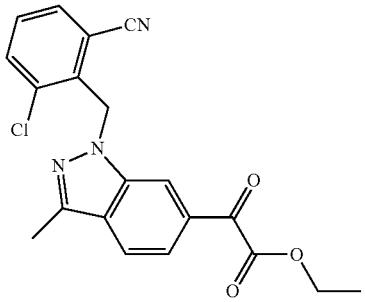 [SMILES: CCOC(=O)C(=O)c1ccc2c(C)nn(Cc3c(Cl)cccc3C#N)c2c1]

To a solution of the compound [5-4] (75 mg) in N,N-dimethylformamide (1 mL) were added zinc cyanide (28 mg) and tetrakis(triphenylphosphine)palladium(0) (10 mg), and the mixture was subjected to microwave irradiation at 150° C. for 20 minutes. The reaction mixture was quenched with water and a saturated aqueous solution of sodium hydeogen carbonate, and the mixture was extracted with ethyl acetate. The obtained organic layer was dried over anhydrous sodium sulfate, filtered, and the filtrate was concentrated under reduced pressure. The obtained residue was purified by silica gel column chromatography to give the titled compound (42 mg) as white foam.

¹H-NMR (400 MHz, CDCl₃) δ: 8.27 (1H, s), 7.81-7.78 (2H, m), 7.74-7.70 (2H, m), 7.49-7.47 (1H, m), 5.84 (2H, s), 4.54 (2H, q, J=7.2 Hz), 2.59 (3H, s), 1.50 (3H, t, J=7.2 Hz).

(6) Synthesis of ethyl [1-(2-chloro-6-cyanobenzyl)-3-methyl-1H-indazol-6-yl]difluoroacetate [5-6] (hereinafter referred to as a compound [5-6])

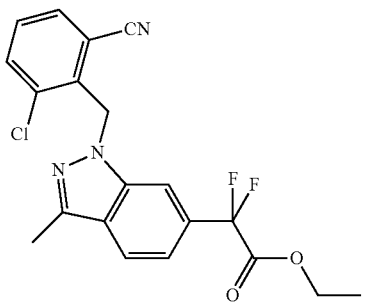 [SMILES: CCOC(=O)C(F)(F)c1ccc2c(C)nn(Cc3c(Cl)cccc3C#N)c2c1]

The titled compound (39 mg) as a white foam was prepared from the compound [5-5] (42 mg) according to the method of the process (4) in Example 1.

¹H-NMR (400 MHz, CDCl₃) δ: 7.77 (1H, s), 7.71-7.69 (2H, m), 7.65 (1H, d, J=7.8 Hz), 7.44-7.42 (1H, m), 7.36 (1H, d, J=8.3 Hz), 5.75 (2H, s), 4.31 (2H, q, J=7.1 Hz), 2.52 (3H, s), 1.31 (3H, t, J=7.2 Hz).

(7) Synthesis of [1-(2-chloro-6-cyanobenzyl)-3-methyl-1H-indazol-6-yl]difluoroacetic acid [5]

To a solution of the compound [5-5] (39 mg) in ethanol (1 mL) was added an aqueous solution of 1N-sodium hydrogen carbonate (1 mL) at room temperature, and the mixture was stirred at 80° C. for 24 hours. The reaction mixture was quenched with 1N-hydrochloric acid, and the precipitated solid was filtered to give the titled compound (29 mg) as a white solid.

¹H-NMR (400 MHz, CD₃OD) δ: 7.93 (1H, s), 7.80-7.73 (3H, m), 7.54-7.52 (1H, m), 7.36 (1H, d, J=8.5 Hz), 5.81 (2H, s), 2.49 (3H, s).

ESI-MS found: 376 [M+H]⁺

Example 6

Synthesis of potassium [1-(2-chloro-6-cyanobenzyl)-3-methyl-1H-indazol-6-yl]difluoroacetate [6] (hereinafter referred to as a compound [6])

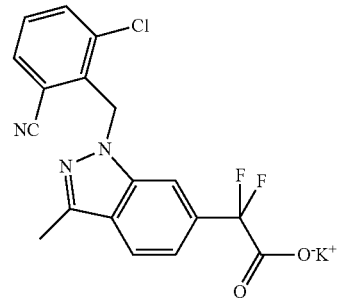

To a solution of the compound [5] (24 mg) in ethanol (1 mL) was added an aqueous solution of 1N-potassium hydroxide (65 μL) at room temperature, and the solution was concentrated under reduced pressure to give the titled compound (27 mg) as a white solid.

¹H-NMR (400 MHz, CD₃OD) δ: 7.93 (1H, s), 7.79 (1H, d, J=7.6 Hz), 7.74-7.73 (2H, m), 7.54-7.52 (1H, m), 7.44 (1H, d, J=8.3 Hz), 5.79 (2H, s), 2.48 (3H, s).

ESI-MS found: 376 [M−K+2H]⁺

Example 7

Synthesis of difluoro[1(2,6-dimethylbenzyl)-3-methyl-1H-indazol-6yl]acetic acid [7](hereinafter referred to as a compound [7])

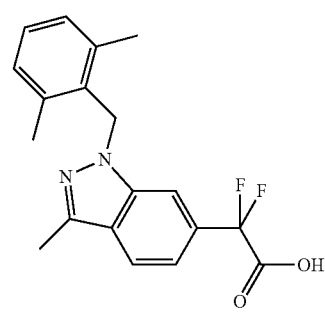 [SMILES: Cc1cccc(C)c1Cn1nc(C)c2ccc(C(F)(F)C(=O)O)cc21]

(1) Synthesis of 6-bromo-3-methyl-1-tosyl-1H-indazole [7-1] (hereinafter referred to as a compound [7-1])

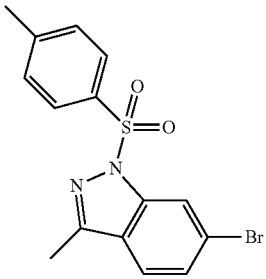 [SMILES: Cc1ccc(S(=O)(=O)n2nc(C)c3ccc(Br)cc32)cc1]

To a solution of 6-bromo-3-methyl-1H-indazole (1.00 g), which was obtained by the method described in the document (JP 2009-528363 W), in tetrahydrofuran (24 mL) was added 1.0M tetrahydrofuran solution of potassium tert-butoxide (7.1 mL) at 0° C., and the mixture was stirred at 0° C. for 5 minutes. 4-Toluenesulfonylchloride (1.17 g) was then added at 0° C., and the mixture was stirred at 0° C. for 2 hours. A saturated aqueous solution of ammonium chloride was added to the reaction mixture, and the mixture was extracted with ethyl acetate. The obtained organic layer was dried over anhydrous sodium sulfate, filtered, and the filtrate was concentrated under reduced pressure. The obtained residue was purified by silica gel column chromatography to give the titled compound (1.18 g) as a white solid.

$^1$H-NMR (400 MHz, CDCl$_3$) δ: 8.37 (1H, d, J=1.2 Hz), 7.85 (2H, d, J=8.4 Hz), 7.44-7.43 (2H, m), 7.25 (2H, d, J=8.4 Hz), 2.50 (3H, s), 2.37 (3H, s).

(2) Synthesis of tert-butyl (3-methyl-1-tosyl-1H-indazol-6-yl)acetate [7-2] (hereinafter referred to as a compound [7-2])

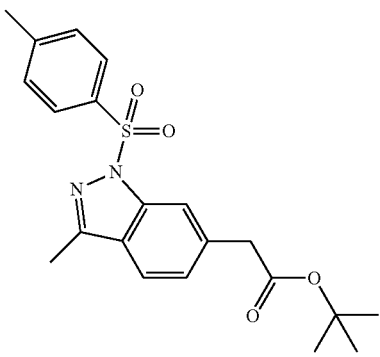 [SMILES: Cc1ccc(S(=O)(=O)n2nc(C)c3ccc(CC(=O)OC(C)(C)C)cc32)cc1]

The titled compound (908.1 mg) as a white solid was prepared from the compound [7-1] (1.26 g) according to the method of the process (4) in Example 3.

$^1$H-NMR (400 MHz, CDCl$_3$) δ: 8.07 (1H, s), 7.83 (2H, d, J=8.3 Hz), 7.53 (1H, d, J=8.1 Hz), 7.25-7.20 (3H, m), 3.71 (2H, s), 2.50 (3H, s), 2.35 (3H, s), 1.46 (9H, s).

(3) Synthesis of tert-butyl difluoro(3-methyl-1-tosyl-1H-indazol-6-yl)acetate [7-3] (hereinafter referred to as a compound [7-3])

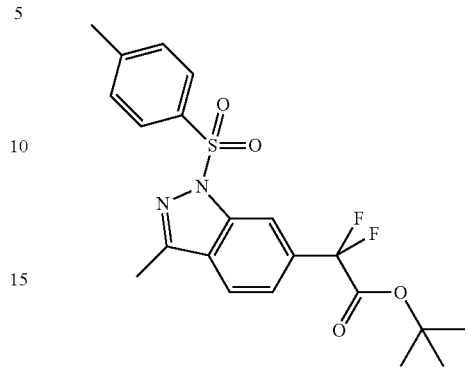

The titled compound (937.8 mg) as a colorless oil was prepared from the compound [7-2] (908.1 mg) according to the method of the process (5) in Example 3.

$^1$H-NMR (400 MHz, CDCl$_3$) δ: 8.44 (1H, s), 7.86 (2H, d, J=8.3 Hz), 7.67 (1H, d, J=8.3 Hz), 7.55-7.52 (1H, m), 7.25 (2H, d, J=8.1 Hz), 2.55 (3H, s), 2.36 (3H, s), 1.51 (9H, s).

(4) Synthesis of difluoro(3-methyl-1H-indazol-6-yl)acetic acid [7-4] (hereinafter referred to as a compound [7-4])

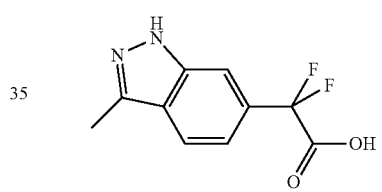

The compound [7-7] (647.6 mg) was dissolved in tetrahydrofuran (10 mL) and water (10 mL), and the solution was added potassium hydroxide (499.6 mg) at room temperature, and the mixture was then heated at reflux for 1 hour. After cooling to room temperature, 3N-hydrochloric acid was added to the reaction mixture for acidification, and the reaction mixture was extracted with ethyl acetate. The obtained organic layer was dried over anhydrous sodium sulfate, filtered, and the filtrate was concentrated under reduced pressure to give the titled compound (335.6 mg) as a yellow solid.

$^1$H-NMR (400 MHz, CD$_3$OD) δ: 7.83 (1H, d, J=8.3 Hz), 7.73 (1H, s), 7.33 (1H, d, J=8.5 Hz), 2.58 (3H, s).

(5) Synthesis of methyl difluoro(3-methyl-1H-indazol-6-yl)acetate [7-5] (hereinafter referred to as a compound [7-5])

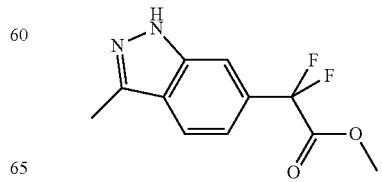

To a solution of the compound [7-4] (335.6 mg) in methanol (8 mL) was added 0.6M cyclohexane solution of trimethylsilyldiazomethane (10 mL) at room temperature, and the mixture was stirred for 15 minutes. The reaction mixture was concentrated under reduced pressure, and the obtained residue was purified by silica gel column chromatography to give the titled compound (165.9 mg) as a white solid.

$^1$H-NMR (400 MHz, CDCl$_3$) δ: 7.77 (1H, d, J=8.5 Hz), 7.73 (1H, s), 7.37 (1H, d, J=8.5 Hz), 3.85 (3H, s), 2.62 (3H, s).

(6) Synthesis of methyl difluoro[1-(2,6-dimethylbenzyl)-3methyl-1H-indazol-6-yl]acetate [7-6] (hereinafter referred to as a compound [7-6])

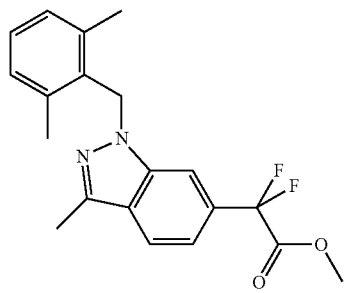 [SMILES: COC(=O)C(F)(F)c1ccc2c(C)nn(Cc3c(C)cccc3C)c2c1]

The titled compound (29.1 mg) as a white solid was prepared from the compound [7-5] (28.3 mg) and 2,6-dimethylbenzyl chloride (27.4 mg) according to the method of the process (1) in Example 1.

$^1$H-NMR (400 MHz, CDCl$_3$) δ: 7.68 (1H, d, J=8.8 Hz), 7.28-7.26 (2H, m), 7.19 (1H, t, J=7.4 Hz), 7.10 (2H, d, J=7.6 Hz), 5.53 (2H, s), 3.81 (3H, s), 2.54 (3H, s), 2.34 (6H, s).

(7) Synthesis of difluoro[2,6-dimethylbenzyl)-3-methyl-1H-indazol-6-yl]acetic acid [7]

The compound [7-6] (29.1 mg) was dissolved in a mixed solvent (0.8 mL) of tetrahydrofuran/methanol (volume ratio 1/1), and added an aqueous solution of 1N-sodium hydroxide (0.4 mL), and the mixture was stirred at room temperature for 1 hour. 1N-hydrochloric acid was added for acidification, and the reaction mixture was extracted with chloroform. The obtained organic layer was dried over anhydrous sodium sulfate, filtered, and the filtrate was concentrated under reduced pressure to give the titled compound (28.4 mg) as a white solid.

$^1$H-NMR (400 MHz, CD$_3$OD) δ: 7.78 (1H, d, J=8.3 Hz), 7.51 (1H, s), 7.30 (1H, d, J=8.5 Hz), 7.15 (1H, t, J=7.4 Hz), 7.07 (2H, d, J=7.6 Hz), 5.58 (2H, s), 2.52 (3H, s), 2.28 (6H, s).

ESI-MS found: 345 [M+H]$^+$

Example 8

Synthesis of potassium difluoro[1-(2,6-dimethylbenzyl)-3-methyl-1H-indazol-6-yl]acetate [8] (hereinafter referred to as a compound [8])

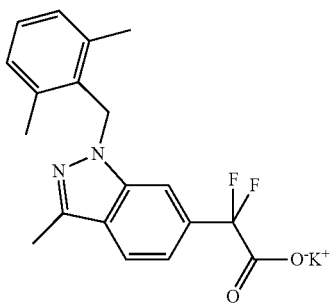

To a solution of the compound [7] (22.8 mg) in ethanol (2 mL) was added an aqueous solution of 1N-potassium hydroxide (66 μL) at room temperature, and the solution was concentrated under reduced pressure to give the titled compound (26.5 mg) as a white solid.

$^1$H-NMR (400 MHz, CD$_3$OD) δ: 7.72-7.71 (2H, m), 7.39 (1H, d, J=8.8 Hz), 7.13 (1H, t, J=7.4 Hz), 7.06 (2H, d, J=7.6 Hz), 5.54 (2H, s), 2.49 (3H, s), 2.28 (6H, s).

ESI-MS found: 345 [M−K+2H]$^+$

Example 9

Synthesis of [1-(2-chloro-6-fluorobenzyl)-3-methyl-1H-indazol-6-yl]difluoroacetic acid [9] (hereinafter referred to as a compound [9])

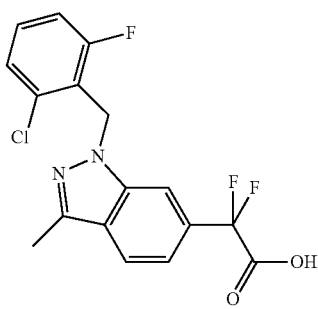 [SMILES: Cc1nn(Cc2c(F)cccc2Cl)c2cc(C(F)(F)C(=O)O)ccc12]

(1) Synthesis of 6-bromo-1-(2-chloro-6-fluorobenzyl)-3-methyl-1H-indazole [9-1] (hereinafter referred to as a compound [9-1])

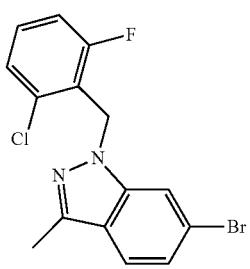 [SMILES: Cc1nn(Cc2c(F)cccc2Cl)c2cc(Br)ccc12]

The titled compound (829 mg) as a white solid was prepared from 6-bromo-3-methyl-1H-indazole (614 mg), which was obtained by the method described in the document (JP 2009-528363 W), and 2-chloro-6-fluorobenzyl chloride (677 mg) according to the method of the process (1) in Example 1.

$^1$H-NMR (400 MHz, CDCl$_3$) δ: 7.64 (1H, s), 7.47 (1H, dd, J=8.4, 0.6 Hz), 7.30-7.19 (3H, m), 7.07-7.02 (1H, m), 5.57 (2H, s), 2.51 (3H, s).

(2) Synthesis of tert-butyl [1-(2-chloro-6-fluorobenzyl)-3-methyl-1H-indazol-6-yl]difluoroacetate [9-2] (hereinafter referred to as a compound [9-2])

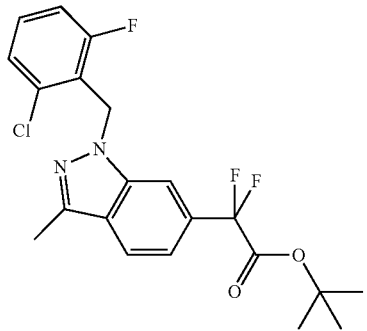 [SMILES: Cc1nn(Cc2c(F)cccc2Cl)c2cc(C(F)(F)C(=O)OC(C)(C)C)ccc12]

The titled compound (439 mg) as a white solid was prepared from the compound [9-1] (826 mg) according to the methods of the processes (4) to (5) in Example 3.

$^1$H-NMR (400 MHz, CDCl$_3$) δ: 7.77 (1H, s), 7.68 (1H, d, J=8.3 Hz), 7.32-7.21 (3H, m), 7.06-7.02 (1H, m), 5.66 (2H, s), 2.54 (3H, s), 1.46 (9H, s).

(3) Synthesis of [1-(2-chloro-6-fluorobenzyl)-3-methyl-1H-indazol-6-yl]difluoroacetic acid [9]

The titled compound (132 mg) as a white solid was prepared from the compound [9-2] (155 mg) according to the method of the process (6) in Example 3.

$^1$H-NMR (400 MHz, CD$_3$OD) δ: 7.88 (1H, s), 7.78 (1H, d, J=8.3 Hz), 7.39-7.33 (2H, m), 7.28 (1H, d, J=8.1 Hz), 7.14 (1H, t, J=8.8 Hz), 5.70 (2H, s), 2.51 (3H, s).
ESI-MS found: 369 [M+H]$^+$ Example 10

Synthesis of potassium [1-(2-chloro-6-fluorobenzyl)-3-methyl-1H-indazol-6-yl]difluoroacetate [10] (hereinafter referred to as a compound [10])

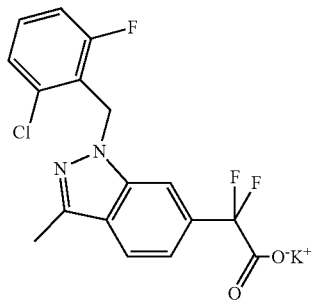

To a solution of the compound [9] (11 mg) in ethanol (2 mL) was added an aqueous solution of 1N-potassium hydroxide (29 μL) at room temperature, and the solution was concentrated under reduced pressure to give the titled compound (12 mg) as a yellow white solid.

$^1$H-NMR (400 MHz, CD$_3$OD) δ: 7.92 (1H, s), 7.71 (1H, d, J=8.5 Hz), 7.41 (1H, t, J=7.0 Hz), 7.35 (1H, dd, J=8.2, 6.0 Hz), 7.28 (1H, d, J=8.1 Hz), 7.14 (1H, t, J=8.8 Hz), 5.68 (2H, s), 2.49 (3H, s).
ESI-MS found: 369 [M−K+2H]$^+$ Example 11

Synthesis of [1-(2-chloro-5-fluorobenzyl)-3-methyl-1H-indazol-6-yl]difluoroacetic acid [11] (hereinafter referred to as a compound [11])

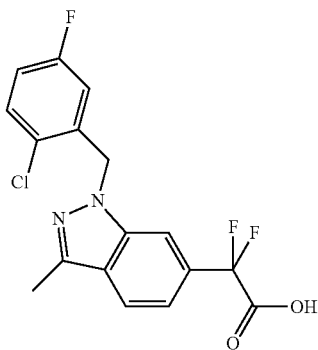 [SMILES: Cc1nn(Cc2cc(F)ccc2Cl)c2cc(C(F)(F)C(=O)O)ccc12]

The titled compound (18 mg) as a white solid was prepared from the compound [7-5] (30 mg) and 2-chloro-5-fluorobenzyl bromide (36 mg) according to the methods of the processes (6) to (7) in Example 7.

$^1$H-NMR (400 MHz, CD$_3$OD) δ: 7.87 (1H, d, J=8.5 Hz), 7.77 (1H, s), 7.46 (1H, dd, J=8.9, 5.0 Hz), 7.39 (1H, d, J=8.3 Hz), 7.05 (1H, td, J=8.4, 2.9 Hz), 6.55-6.48 (1H, m), 5.69 (2H, s), 2.59 (3H, s).
ESI-MS found: 369 [M+H]$^+$ Example 12

Synthesis of [1-(2-chloro-6-cyclopropylbenzyl)-3-methyl-1H-indazol-6-yl]difluoroacetic acid [12] (hereinafter referred to as a compound [12])

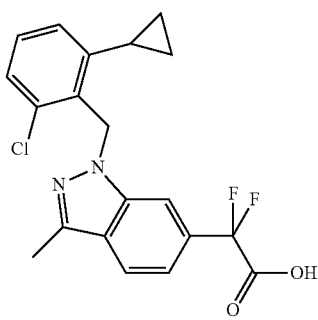 [SMILES: Cc1nn(Cc2c(Cl)cccc2C2CC2)c2cc(C(F)(F)C(=O)O)ccc12]

(1) Synthesis of 2-chloro-6-cyclopropylbenzaldehyde[12-1] (hereinafter referred to as a compound [12-1])

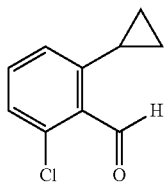 [SMILES: O=Cc1c(Cl)cccc1C1CC1]

2,6-Dichlorobenzaldehyde (500 mg), cyclopropylboronic acid monohydrate (445 mg), tetrakis(triphenylphosphine)palladium(0) (165 mg) and cesium carbonate (2.8 g) were suspended in a mixed solvent (14 mL) of 1,4-dioxane/water (volume ratio 2/1), and the suspension was subjected to microwave irradiation at 130° C. for 30 minutes. After cooling, water was then added to the reaction mixture, and the mixture was extracted with ethyl acetate. The obtained organic layer was sequentially washed with water and brine, dried over anhydrous sodium sulfate, filtered, and the filtrate was concentrated under reduced pressure. The obtained residue was purified by silica gel column chromatography to give the titled compound (292 mg) as a pale yellow oil.

$^1$H-NMR (400 MHz, CDCl$_3$) δ: 10.70 (1H, s), 7.34 (1H, t, J=7.9 Hz), 7.26-7.25 (1H, m), 6.97 (1H, d, J=7.8 Hz), 2.75-2.69 (1H, m), 1.07-1.01 (2H, m), 0.71-0.67 (2H, m).

(2) Synthesis of 2-chloro-6-cyclopropylbenzyl chloride [12-2] (hereinafter referred to as a compound [12-2])

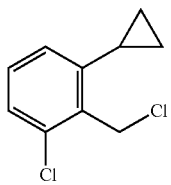 [SMILES: ClCc1c(Cl)cccc1C1CC1]

The titled compound (105 mg) as a colorless oil was prepared from the compound [12-1] (602 mg) according to the methods of the processes (1) to (2) in Example 3.

$^1$H-NMR (400 MHz, CDCl$_3$) δ: 7.26-7.25 (1H, m), 7.18 (1H, t, J=7.9 Hz), 6.98 (1H, d, J=7.6 Hz), 5.01 (2H, s), 2.16-2.09 (1H, m), 1.06-1.01 (2H, m), 0.79-0.71 (2H, m).

(3) Synthesis of [1-(2-chloro-6-cyclopropylbenzyl)-3-methyl-1H-indazol-6-yl]difluoroacetic acid [12]

The titled compound (30 mg) as a white solid was prepared from the compound [12-2] (36 mg) and the compound [7-7] (30 mg) according to the methods of the processes (6) to (7) in Example 7.

$^1$H-NMR (400 MHz, CD$_3$OD) δ: 7.78 (1H, d, J=8.3 Hz), 7.71 (1H, s), 7.32-7.24 (3H, m), 7.06 (1H, d, J=7.6 Hz), 5.91 (2H, s), 2.51 (3H, s), 2.03-1.97 (1H, m), 0.84-0.79 (2H, m), 0.63-0.59 (2H, m).

ESI-MS found: 391 [M+H]$^+$

Example 13

Synthesis of potassium [1-(2-chloro-6-cyclopropylbenzyl)-3-methyl-1H-indazol-6-yl]difluoroacetate [13] (hereinafter referred to as a compound [13])

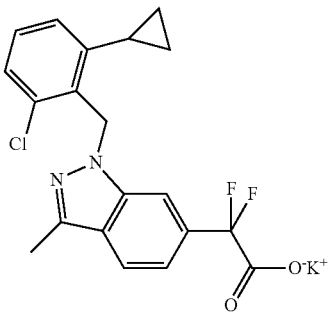

To a solution of the compound [12] (23 mg) in ethanol (2 mL) was added an aqueous solution of 1N-potassium hydroxide (58 μL) at room temperature, and the solution was concentrated under reduced pressure to give the titled compound (24 mg) as a yellow white solid.

$^1$H-NMR (400 MHz, CD$_3$OD) δ: 7.84 (1H, s), 7.71 (1H, d, J=8.5 Hz), 7.40 (1H, d, J=8.5 Hz), 7.31 (1H, d, J=7.3 Hz), 7.25 (1H, t, J=7.8 Hz), 7.07 (1H, d, J=7.6 Hz), 5.87 (2H, s), 2.48 (3H, s), 2.02-1.95 (1H, m), 0.84-0.79 (2H, m), 0.63-0.59 (2H, m).

ESI-MS found: 391 [M−K+2H]$^+$

Example 14

Synthesis of [1-(2,3-dichlorobenzyl)-3-methyl-1H-indazol-6-yl]difluoroacetic acid [14] (hereinafter referred to as a compound [14])

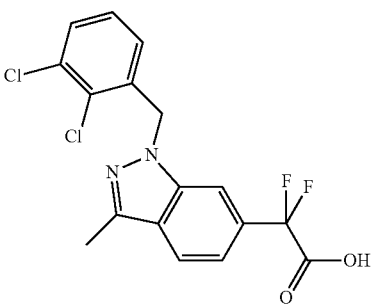 [SMILES: Cc1nn(Cc2cccc(Cl)c2Cl)c2cc(C(F)(F)C(=O)O)ccc12]

The titled compound (16 mg) as a white solid was prepared from the compound [7-7] (30 mg) and 2,3-dichlorobenzyl chloride (43 mg) according to the methods of the processes (6) to (7) in Example 7.

$^1$H-NMR (400 MHz, CD$_3$OD) δ: 7.77 (1H, d, J=8.3 Hz), 7.66 (1H, s), 7.37 (1H, d, J=7.3 Hz), 7.28 (1H, d, J=7.8 Hz), 7.08-7.06 (1H, m), 6.59 (1H, d, J=7.6 Hz), 5.64 (2H, s), 2.48 (3H, s).

ESI-MS found: 385 [M+H]$^+$

Example 15

Synthesis of potassium [1-(2,3-dichlorobenzyl)-3-methyl-1H-indazol-6-yl]difluoroacetate [15] (hereinafter referred to as a compound [15])

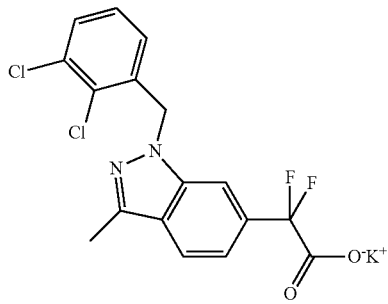

To a solution of the compound [14] (16 mg) in ethanol (1 mL) was added an aqueous solution of 1N-potassium hydroxide (42 μL) at room temperature, and the solution was concentrated under reduced pressure to give the titled compound (18 mg) as a white solid.

$^1$H-NMR (400 MHz, CD$_3$OD) δ: 7.79-7.76 (2H, m), 7.47-7.45 (2H, m), 7.15-7.13 (1H, m), 6.54 (1H, d, J=7.6 Hz), 5.73 (2H, s), 2.58 (3H, s).

ESI-MS found: 385 [M−K+2H]$^+$

Example 16

Synthesis of difluoro[3-methyl-1-(naphthalen-1-yl)methyl-1H-indazol-6-yl]acetic acid [16] (hereinafter referred to as a compound [16])

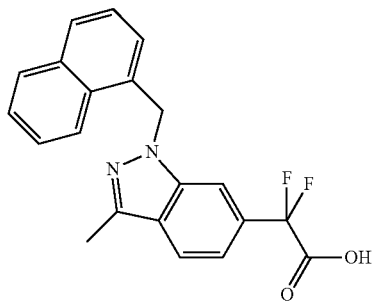 [SMILES: Cc1nn(Cc2cccc3ccccc23)c2cc(C(F)(F)C(=O)O)ccc12]

The titled compound (6 mg) as a white solid was prepared from the compound [7-5] (29 mg) and 1-(chloromethyl)naphthalene (32 mg) according to the methods of the processes (6) to (7) in Example 7.

$^1$H-NMR (400 MHz, CD$_3$OD) δ: 8.07 (1H, d, J=7.1 Hz), 7.80-7.79 (1H, m), 7.75-7.73 (2H, m), 7.61 (1H, s), 7.43-7.40 (2H, m), 7.29-7.25 (2H, m), 6.90 (1H, d, J=6.8 Hz), 6.00 (2H, s), 2.50 (3H, s).

ESI-MS found: 367 [M+H]$^+$

Example 17

Synthesis of difluoro[1-(2,5-dimethylbenzyl)-3-methyl-1H-indazol-6-yl]acetic acid [17] (hereinafter referred to as a compound [17])

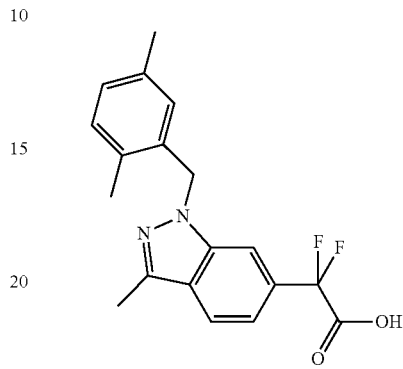

The titled compound (12 mg) as a white solid was prepared from the compound [7-7] (32 mg) and 2,5-dimethylbenzyl chloride (32 mg) according to the methods of the processes (6) to (7) in Example 7.

$^1$H-NMR (400 MHz, CD$_3$OD) δ: 7.74 (1H, d, J=8.5 Hz), 7.54 (1H, s), 7.24 (1H, d, J=8.3 Hz), 6.96 (1H, d, J=7.6 Hz), 6.89 (1H, d, J=7.8 Hz), 6.56 (1H, s), 5.46 (2H, s), 2.48 (3H, s), 2.15 (3H, s), 2.08 (3H, s).

ESI-MS found: 345 [M+H]$^+$

Example 18

Synthesis of [1-(5-chlorobenzo[b]thiophen-3-yl)methyl-3-methyl-1H-indazol-6-yl]difluoroacetic acid [18] (hereinafter referred to as a compound [18])

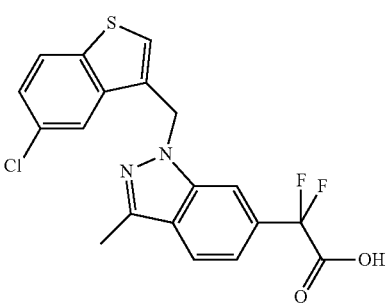 [SMILES: Cc1nn(Cc2csc3ccc(Cl)cc23)c2cc(C(F)(F)C(=O)O)ccc12]

The titled compound (45.3 mg) as a white solid was prepared from the compound [7-5] (30.8 mg) and 3-bromomethyl-5-chlorobenzo[b]thiophene (50.2 mg) according to the methods of the processes (6) to (7) in Example 7.

$^1$H-NMR (400 MHz, CD$_3$OD) δ: 7.90-7.82 (4H, m), 7.50 (1H, s), 7.34-7.31 (2H, m), 5.83 (2H, s), 2.59 (3H, s).

ESI-MS found: 407 [M+H]$^+$

Example 19

Synthesis of potassium [1-(5-chlorobenzo[b]thiophen-3-yl)methyl-3-methyl-1H-indazol-6-yl]difluoroacetate [19] (hereinafter referred to as a compound [19])

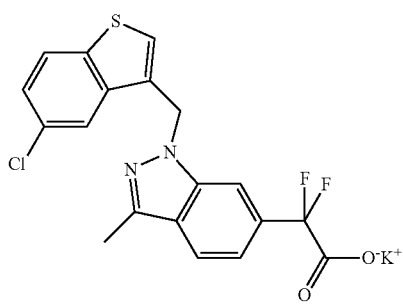

To a solution of the compound [18] (35.2 mg) in ethanol (3 mL) was added an aqueous solution of 1N-potassium hydroxide (87 μL) at room temperature, and the solution was concentrated under reduced pressure to give the titled compound (30.5 mg) as a yellow solid.

$^1$H-NMR (400 MHz, CD$_3$OD) δ: 7.94 (1H, s), 7.84-7.82 (2H, m), 7.75 (1H, d, J=8.5 Hz), 7.42-7.41 (2H, m), 7.32 (1H, dd, J=8.5, 1.7 Hz), 5.81 (2H, s), 2.58 (3H, s).

ESI-MS found: 407 [M−K+2H]$^+$

Example 20

Synthesis of difluoro[3-methyl-1-(2,4,6-trimethylbenzyl)-1H-indazol-6-yl]acetic acid [20] (hereinafter referred to as a compound [20])

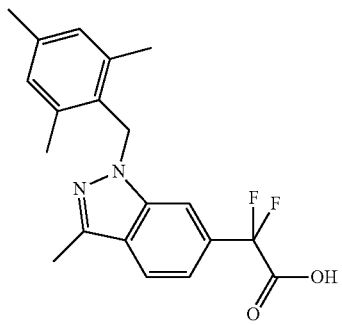 [SMILES: Cc1cc(C)c(Cn2nc(C)c3ccc(C(F)(F)C(=O)O)cc32)c(C)c1]

The titled compound (23.9 mg) as a white solid was prepared from the compound [7-7] (38.6 mg) and 2,4,6-trimethylbenzyl chloride (40.7 mg) according to the methods of the processes (6) to (7) in Example 7.

$^1$H-NMR (400 MHz, CD$_3$OD) δ: 7.77 (1H, d, J=8.5 Hz), 7.48 (1H, s), 7.30 (1H, d, J=8.5 Hz), 6.90 (2H, s), 5.54 (2H, s), 2.52 (3H, s), 2.27 (3H, s), 2.24 (6H, s).

ESI-MS found: 359 [M+H1]$^+$

Example 21

Synthesis of difluoro [3-methyl-1-(quinolin-8-yl)methyl-1H-indazol-6-yl]acetic acid [21] (hereinafter referred to as a compound [21])

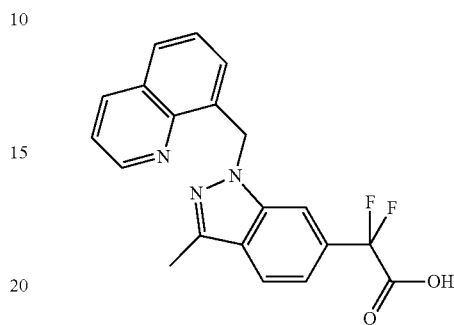

The titled compound (9 mg) as a brown solid was prepared from the compound [7-7] (19.1 mg) and 8-(bromomethyl)quinoline (21.3 mg) according to the methods of the processes (6) to (7) in Example 7.

$^1$H-NMR (400 MHz, CDCl$_3$) δ: 8.99 (1H, d, J=2.7 Hz), 8.33 (1H, d, J=7.1 Hz), 8.00 (1H, s), 7.86 (1H, t, J=8.1 Hz), 7.81 (1H, t, J=8.3 Hz), 7.56 (1H, dd, J=8.2, 4.3 Hz), 7.47 (1H, t, J=7.7 Hz), 7.34 (1H, d, J=8.3 Hz), 7.28 (1H, d, J=7.1 Hz), 6.26 (2H, s), 2.58 (3H, s).

ESI-MS found: 368 [M+H]$^+$

Example 22

Synthesis of difluoro[1-(2-fluoro-6-trifluoromethylbenzyl)-3-methyl-1H-indazol-6-yl]acetic acid [22] (hereinafter referred to as a compound [22])

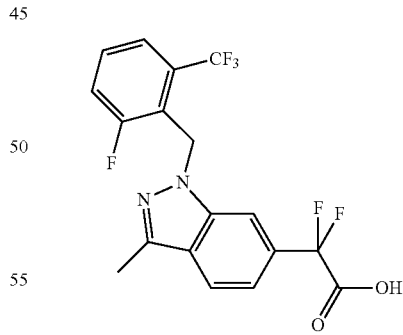

The titled compound (27.0 mg) as a white solid was prepared from the compound [7-5] (20.9 mg) and 2-fluoro-6-trifluoromethylbenzylbromide (29.9 mg) according to the methods of the processes (6) to (7) in Example 7.

$^1$H-NMR (400 MHz, CD$_3$OD) δ: 7.80-7.77 (2H, m), 7.65-7.59 (2H, m), 7.42 (1H, t, J=8.9 Hz), 7.36 (1H, d, J=8.5 Hz), 5.72 (2H, s), 2.48 (3H, s).

ESI-MS found: 403 [M+H]$^+$

Example 23

Synthesis of potassium difluoro[1-(2-fluoro-6-trifluoromethylbenzyl)-3-methyl-1H-indazol-6-yl]acetate [23] (hereinafter referred to as a compound [23])

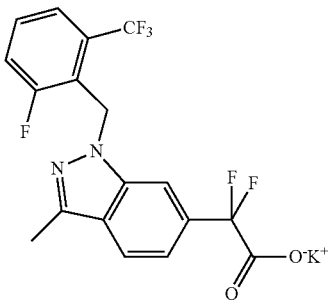

To a solution of the compound [22] (19.7 mg) in ethanol (2 mL) was added an aqueous solution of 1N-potassium hydroxide (49 μL) at room temperature, and the solution was concentrated under reduced pressure to give the titled compound (19.0 mg) as a white solid.

$^1$H-NMR (400 MHz, CD$_3$OD) δ: 7.84 (1H, s), 7.71 (1H, d, J=7.8 Hz), 7.64-7.56 (2H, m), 7.43-7.40 (2H, m), 5.69 (2H, s), 2.46 (3H, s).

ESI-MS found: 403 [M−K+2H]$^+$

Example 24

Synthesis of [1-(2-cyano-6-methylbenzyl)-3-methyl-1H-indazol-6-yl]difluoroacetic acid [24] (hereinafter referred to as a compound [24])

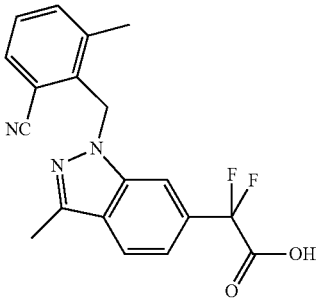

(1) Synthesis of tert-butyl [1-(2-cyano-6-methylbenzyl)-3-methyl-1H-indazol-6-yl]acetate [24-1] (hereinafter referred to as a compound [24-1])

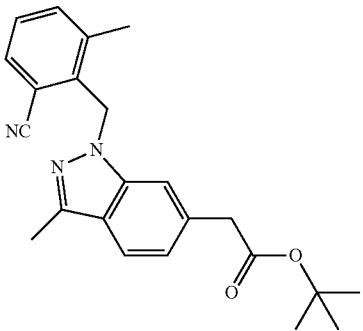 [SMILES: Cc1cccc(C#N)c1Cn1nc(C)c2ccc(CC(=O)OC(C)(C)C)cc21]

To a solution of the compound [3-4] (225.6 mg) in N,N-dimethylformamide (2.9 mL) were added zinc cyanide (48.2 mg), tris(dibenzylideneacetone)dipalladium(0) (53.7 mg) and 2-dicyclohexylphosphino-2',4',6'-triisopropylbiphenyl (55.9 mg) at room temperature, and the mixture was subjected to microwave irradiation at 160° C. for 1 hour. After cooling to room temperature, a saturated aqueous solution of ammonium chloride was added, and the mixture was extracted with ethyl acetate. The obtained organic layer was dried over anhydrous sodium sulfate, filtered, and the filtrate was concentrated under reduced pressure. The obtained residue was purified by silica gel column chromatography to give the titled compound (175.8 mg) as a yellow oil.

$^1$H-NMR (400 MHz, CDCl$_3$) δ: 7.59 (1H, d, J=7.6 Hz), 7.57 (1H, d, J=8.3 Hz), 7.40 (1H, d, J=7.8 Hz), 7.34 (1H, t, J=7.7 Hz), 7.24 (1H, s), 7.04 (1H, d, J=8.3 Hz), 5.65 (2H, s), 3.62 (2H, s), 2.50 (3H, s), 2.27 (3H, s), 1.42 (9H, s).

(2) Synthesis of tert-butyl [1-(2-cyano-6-methylbenzyl)-3-methyl-1H-indazol-6-yl]difluoroacetate [24-2] (hereinafter referred to as a compound [24-2])

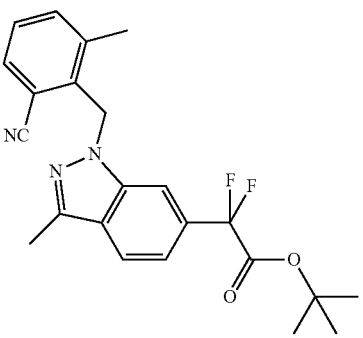 [SMILES: Cc1cccc(C#N)c1Cn1nc(C)c2ccc(C(F)(F)C(=O)OC(C)(C)C)cc21]

The titled compound (19.6 mg) as a yellow oil was prepared from the compound [24-1] (37.1 mg) according to the method of the process (5) in Example 3.

$^1$H-NMR (400 MHz, CDCl$_3$) δ: 7.70 (1H, d, J=8.3 Hz), 7.62-7.61 (2H, m), 7.42 (1H, d, J=7.3 Hz), 7.36 (1H, t, J=7.7 Hz), 7.32 (1H, d, J=8.3 Hz), 5.69 (2H, s), 2.53 (3H, s), 2.26 (3H, s), 1.46 (9H, s).

(3) Synthesis of [1-(2-cyano-6-methylbenzyl)-3-methyl-1H-indazol-6-yl]difluoroacetic acid [24]

Water (120 μL) and trifluoroacetic acid (1.2 mL) were added to the compound [24-2] (51.6 mg) at room temperature, and the mixture was stirred at room temperature for 16 hours. Water was added to the reaction mixture, and the mixture was extracted with chloroform. The obtained organic layer was dried over anhydrous sodium sulfate, filtered, and the filtrate was concentrated under reduced pressure to give the titled compound (44.4 mg) as a white solid.

$^1$H-NMR (400 MHz, CD$_3$OD) δ: 7.74 (1H, s), 7.71 (1H, d, J=8.5 Hz), 7.55 (1H, d, J=7.6 Hz), 7.40 (1H, d, J=7.3 Hz), 7.32 (1H, t, J=7.7 Hz), 7.25 (1H, d, J=8.5 Hz), 5.65 (2H, s), 2.40 (3H, s), 2.13 (3H, s).

ESI-MS found: 356 [M+H]$^+$

Example 25

Synthesis of potassium [1-(2-cyano-6-methylbenzyl)-3-methyl-1H-indazol-6-yl]difluoroacetate [25] (hereinafter referred to as a compound [25])

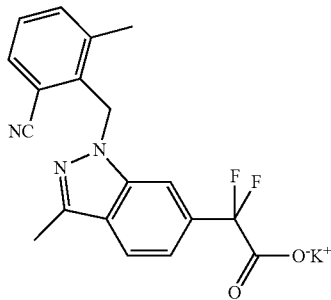

To a solution of the compound [24] (46.7 mg) in ethanol (4.5 mL) was added an aqueous solution of 1N-potassium hydroxide (131 μL) at room temperature, and the solution was concentrated under reduced pressure to give the titled compound (48.1 mg) as a yellow solid.

$^1$H-NMR (400 MHz, CD$_3$OD) δ: 7.86 (1H, s), 7.74 (1H, d, J=8.5 Hz), 7.65 (1H, d, J=7.6 Hz), 7.50 (1H, d, J=7.3 Hz), 7.45-7.43 (2H, m), 5.74 (2H, s), 2.49 (3H, s), 2.17 (3H, s).

ESI-MS found: 356 [M−K+2H]$^+$

Example 26

Synthesis of [1-(2-cyano-6-fluorobenzyl)-3-methyl-1H-indazol-6-yl]difluoroacetic acid [26] (hereinafter referred to as a compound [26])

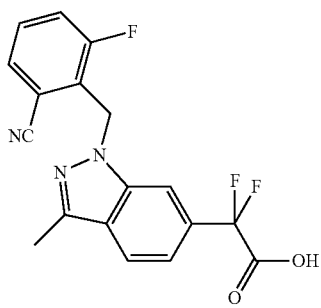

To a solution of the compound [9] (51.1 mg) in N,N-dimethylformamide (0.6 mL) were added zinc cyanide (9.9 mg), tris(dibenzylideneacetone)dipalladium(0) (11.0 mg) and 2-dicyclohexylphosphino-2',4',6'-triisopropylbiphenyl (11.4 mg) at room temperature, and the mixture was subjected to microwave irradiation at 160° C. for 1 hour. After cooling to room temperature, 1N-hydrochloric acid was added for acidification, and the mixture was extracted with ethyl acetate. The obtained organic layer was dried over anhydrous sodium sulfate, filtered, and the filtrate was concentrated under reduced pressure. The obtained residue was purified by reverse phase preparative liquid chromatography to give the titled compound (7.3 mg) as a white solid.

$^1$H-NMR (400 MHz, CD$_3$OD) δ: 7.94 (1H, s), 7.80 (1H, dd, J=8.5 Hz, 0.7 Hz), 7.64 (1H, dd, J=7.6 Hz, 0.7 Hz), 7.56-7.54 (1H, m), 7.48-7.43 (1H, m), 7.36 (1H, dd, J=8.4 Hz, 1.3 Hz), 5.77 (2H, d, J=1.2 Hz), 2.51 (3H, s).

ESI-MS found: 360 [M+H]$^+$

Example 27

Synthesis of [1-(2-cyclopropyl-6-fluorobenzyl)-3-methyl-1H-indazol-6-yl]difluoroacetic acid [27] (hereinafter referred to as a compound [27])

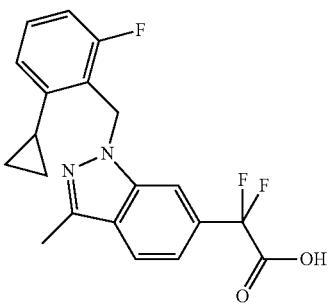 [SMILES: Cc1nn(Cc2c(F)cccc2C2CC2)c2cc(C(F)(F)C(=O)O)ccc12]

The compound [9] (30 mg), cyclopropylboronic acid monohydrate (17 mg), tetrakis(triphenylphosphine)palladium(0) (4.7 mg) and cesium carbonate (80 mg) were suspended in a mixed solvent (1.2 mL) of 1,4-dioxane/water (volume ratio 2/1), and the suspension was subjected sequentially to microwave irradiation at 160° C. for 1 hour and at 180° C. for 30 minutes. Water was added to the reaction mixture, and the mixture was extracted with ethyl acetate. The obtained organic layer was washed sequentially with water and brine, dried over anhydrous sodium sulfate, filtered, and the filtrate was concentrated under reduced pressure. The obtained residue was purified by reverse phase preparative liquid chromatography to give the titled compound (6.6 mg) as a white solid.

$^1$H-NMR (400 MHz, CD$_3$OD) δ: 7.79-7.77 (2H, m), 7.32-7.23 (2H, m), 6.98 (1H, t, J=8.8 Hz), 6.86 (1H, d, J=7.8 Hz), 5.79 (2H, s), 2.52 (3H, s), 2.09-2.01 (1H, m), 0.86-0.81 (2H, m), 0.62-0.58 (2H, m).

ESI-MS found: 375 [M+H]$^+$

Example 28

Synthesis of [1-(2-chloro-6-methoxybenzyl)-3-methyl-1H-indazol-6-yl]difluoroacetic acid [28] (hereinafter referred to as a compound [28])

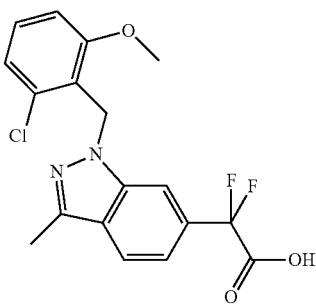 [SMILES: COc1cccc(Cl)c1Cn1nc(C)c2ccc(C(F)(F)C(=O)O)cc21]

(1) Synthesis of 2-chloro-6-methoxybenzyl bromide [28-1] (hereinafter referred to as a compound [28-1])

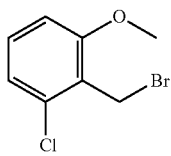

The titled compound (419 mg) as a white solid was prepared from 2-chloro-6-methoxytoluene (313 mg) according to the method of the process (2) in Example 5.

$^1$H-NMR (400 MHz, CDCl$_3$) δ: 7.21 (1H, t, J=8.5 Hz), 7.00 (1H, d, J=8.1 Hz), 6.80 (1H, d, J=8.3 Hz), 4.71 (2H, s), 3.91 (3H, s).

(2) Synthesis of 6-bromo-1-(2-chloro-6-methoxybenzyl)-3-methyl-1H-indazole [28-2] (hereinafter referred to as a compound [28-2])

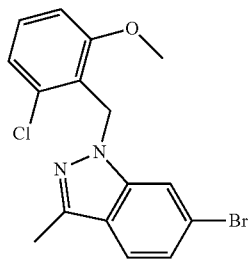 [SMILES: COc1cccc(Cl)c1Cn1nc(C)c2ccc(Br)cc21]

The titled compound (218 mg) as a yellow white solid was prepared from 6-bromo-3-methyl-1H-indazole, which was obtained by the method described in the document (JP 2009-528363 W) (164 mg), and the compound [28-1] (237 mg), according to the method of the process (1) in Example 1.

$^1$H-NMR (400 MHz, CDCl$_3$) δ: 7.65 (1H, t, J=0.7 Hz), 7.44 (1H, d, J=8.5 Hz), 7.22 (1H, t, J=8.8 Hz), 7.17-7.15 (1H, m), 7.04 (1H, d, J=8.1 Hz), 6.81 (1H, d, J=8.3 Hz), 5.60 (2H, s), 3.81 (3H, s), 2.50 (3H, s).

(3) Synthesis of tert-butyl [1-(2-chloro-6-methoxybenzyl)-3-methyl-1H-indazol-6-yl]acetate [28-3] (hereinafter referred to as a compound [28-3])

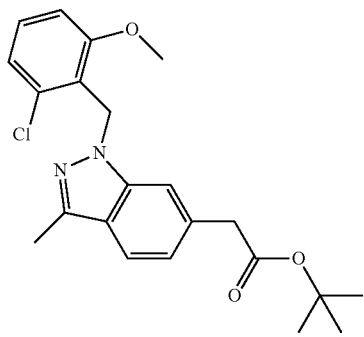 [SMILES: COc1cccc(Cl)c1Cn1nc(C)c2ccc(CC(=O)OC(C)(C)C)cc21]

The titled compound (220 mg) as a white pink solid was prepared from the compound [28-2] (218 mg) according to the method of the process (4) in Example 3.

$^1$H-NMR (400 MHz, CDCl$_3$) δ: 7.53 (1H, d, J=8.3 Hz), 7.37 (1H, s), 7.20 (1H, t, J=8.2 Hz), 7.03 (1H, d, J=8.1 Hz), 6.99 (1H, d, J=8.8 Hz), 6.79 (1H, d, J=8.3 Hz), 5.62 (2H, s), 3.77 (3H, s), 3.63 (2H, s), 2.51 (3H, s), 1.43 (9H, s).

(4) Synthesis of [1-(2-chloro-6-methoxybenzyl)-3-methyl-1H-indazol-6-yl]difluoroacetic acid [28]

The titled compound (67 mg) as a white solid was prepared from the compound [28-3] (85 mg) according to the methods of the processes (5) to (6) in Example 3.

$^1$H-NMR (400 MHz, CD$_3$OD) δ: 7.87 (1H, s), 7.73 (1H, d, J=7.8 Hz), 7.33 (1H, dd, J=8.4, 1.3 Hz), 7.28 (1H, t, J=8.2 Hz), 7.04 (1H, dd, J=8.1, 1.0 Hz), 6.95 (1H, d, J=8.3 Hz), 5.69 (2H, s), 3.78 (3H, s), 2.50 (3H, s).

ESI-MS found: 381 [M+H]$^+$

Example 29

Synthesis of potassium [1-(2-chloro-6-methoxybenzyl)-3-methyl-1H-indazol-6-yl]difluoroacetate [29] (hereinafter referred to as a compound [29])

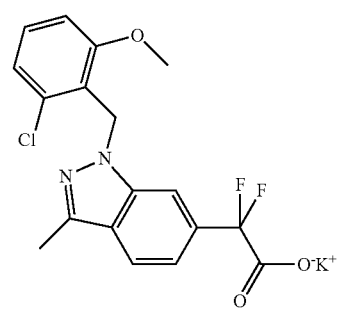

To a solution of the compound [28] (59 mg) in ethanol (3 mL) was added an aqueous solution of 1N-potassium hydroxide (154 μL) at room temperature, and the solution was concentrated under reduced pressure to give the titled compound (62 mg) as a yellow white solid.

$^1$H-NMR (400 MHz, CD$_3$OD) δ: 7.92 (1H, s), 7.67 (1H, d, J=8.5 Hz), 7.39 (1H, dd, J=8.4, 1.1 Hz), 7.27 (1H, t, J=8.2 Hz), 7.02 (1H, dd, J=8.2, 0.9 Hz), 6.93 (1H, d, J=8.3 Hz), 5.67 (2H, s), 3.78 (3H, s), 2.48 (3H, s).

ESI-MS found: 381 [M−K+2H]$^+$

Example 30

Synthesis of [1-(2-cyano-6-methoxybenzyl)-3-methyl-1H-indazol-6-yl]difluoroacetic acid [30] (hereinafter referred to as a compound [30])

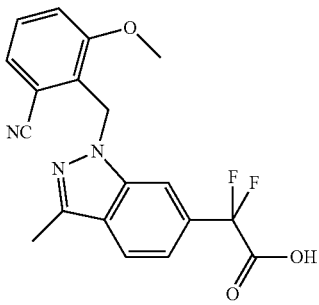 [SMILES: COc1cccc(C#N)c1Cn1nc(C)c2ccc(C(F)(F)C(=O)O)cc21]

(1) Synthesis of tert-butyl [1-(2-cyano-6-methoxybenzyl)-3-methyl-1H-indazol-6-yl]acetate [30-1] (hereinafter referred to as a compound [30-1])

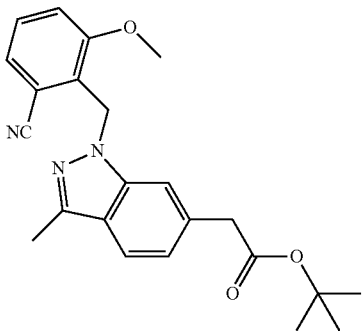 [SMILES: COc1cccc(C#N)c1Cn1nc(C)c2ccc(CC(=O)OC(C)(C)C)cc21]

The titled compound (84 mg) as a yellow white solid was prepared from the compound [28-3] (130 mg) according to the method of the process (1) in Example 24.

$^1$H-NMR (400 MHz, CDCl$_3$) δ: 7.54 (1H, d, J=8.1 Hz), 7.40 (1H, s), 7.36 (1H, t, J=8.1 Hz), 7.30 (1H, dd, J=7.8, 1.0 Hz), 7.06 (1H, d, J=8.3 Hz), 7.02 (1H, dd, J=8.3, 1.2 Hz), 5.62 (2H, s), 3.75 (3H, s), 3.66 (2H, s), 2.50 (3H, s), 1.44 (9H, s).

(2) Synthesis of [1-(2-cyano-6-methoxybenzyl)-3-methyl-1H-indazol-6-yl]difluoroacetic acid [30]

The titled compound (26 mg) was obtained as a white solid from the compound [30-1] (76 mg) according to the method of the steps (5) to (6) in Example 3.

$^1$H-NMR (400 MHz, CD$_3$OD) δ: 7.94 (1H, s), 7.75 (1H, d, J=7.8 Hz), 7.46 (1H, t, J=7.8 Hz), 7.36-7.33 (2H, m), 7.25 (1H, d, J=8.3 Hz), 5.71 (2H, s), 3.72 (3H, s), 2.49 (3H, s).

ESI-MS found: 372 [M+H]$^+$

Example 31

Synthesis of [1-(2-cyano-5-methylbenzyl)-3-methyl-1H-indazol-6-yl]difluoroacetic acid [31] (hereinafter referred to as a compound [31])

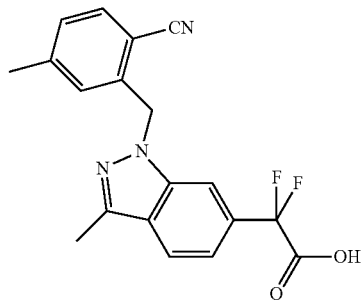 [SMILES: Cc1ccc(C#N)c(Cn2nc(C)c3ccc(C(F)(F)C(=O)O)cc32)c1]

(1) Synthesis of 2-chloro-5-methylbenzyl alcohol [31-1] (hereinafter referred to as a compound [31-1])

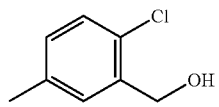

To a solution of 2-chloro-5-methylbenzoic acid (1.0 g) in tetrahydrofuran (59 mL) was added lithium aluminum hydride (445 mg) at 0° C., and the mixture was stirred at 0° C. for 20 minutes. The reaction mixture was quenched with saturated aqueous solution of sodium sulfate, and the mixture was stirred at room temperature for 2 hours. The obtained white gel was filtered, and the filtrate was concentrated under reduced pressure. The obtained residue was purified by silica gel column chromatography to give the titled compound (390 mg) as a yellow solid. $^1$H-NMR (400 MHz, CDCl$_3$) δ: 7.29 (1H, s), 7.24 (1H, d, J=8.4 Hz), 7.05 (1H, d, J=7.6 Hz), 4.75 (2H, d, J=6.3 Hz), 2.34 (3H, s), 1.91 (1H, t, J=6.3 Hz).

(2) Synthesis of 2-chloro-5-methylbenzyl chloride [31-2] (hereinafter referred to as a compound [31-2])

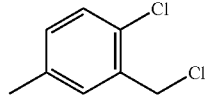

The titled compound (205 mg) as a colorless oil was prepared from the compound [31-1] (374 mg) according to the method of the process (2) in Example 3.

$^1$H-NMR (400 MHz, CDCl$_3$) δ: 7.28-7.26 (2H, m), 7.08 (1H, d, J=7.3 Hz), 4.67 (2H, s), 2.33 (3H, s).

(3) Synthesis of [1-(2-cyano-5-methylbenzyl)-3-methyl-1H-indazol-6-yl]difluoroacetic acid [31]

The titled compound (7.0 mg) as a white solid was prepared from 6-bromo-3-methyl-1H-indazole (140 mg),

Example 32

Synthesis of [1-(2-cyano-6-cyclopropylbenzyl)-3-methyl-1H-indazol-6-yl]difluoroacetic acid [32] (hereinafter referred to as a compound [32])

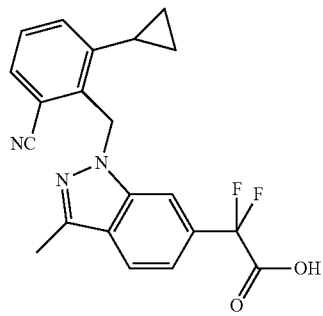 [SMILES: Cc1nn(Cc2c(C#N)cccc2C2CC2)c2cc(C(F)(F)C(=O)O)ccc12]

(1) 3-bromo-2-methylbenzonitrile [32-1] (hereinafter referred to as a compound [32-1])

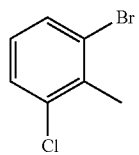

To a solution of 3-bromo-2-methylbenzoic acid (2.06 g) in thionyl chloride (10 mL) was added N,N-dimethylformamide (0.1 mL), and the mixture was stirred at room temperature for 2 hours. The reaction mixture was concentrated under reduced pressure, the obtained residue was dissolved in tetrahydrofuran (10 mL), 28% ammonia solution (10 mL) was added to the mixture at 0° C., and the mixture was stirred at 0° C. for 10 minutes. Water was added to the reaction mixture, and the mixture was extracted with ethyl acetate. The obtained organic layer was dried over anhydrous sodium sulfate, filtered, and the filtrate was concentrated under reduced pressure. Thionyl chloride (10 mL) was added to a solution of the above obtained residue in benzene (20 mL), and the mixture was stirred at 75° C. for 2 hours. Ice water was added to the reaction mixture, and the mixture was neutralized by adding sodium hydrogen carbonate and then extracted with ethyl acetate. The obtained organic layer was dried over anhydrous sodium sulfate, filtered, and the filtrate was concentrated under reduced pressure to give the titled compound (1.76 g) as a white solid.

$^1$H-NMR (400 MHz, CDCl$_3$) δ: 7.77 (1H, d, J=8.1 Hz), 7.57 (1H, d, J=7.6 Hz), 7.15 (1H, d, J=7.9 Hz), 2.63 (3H, s).

(2) 3-bromo-2-bromomethylbenzonitrile [32-2] (hereinafter referred to as a compound [32-2])

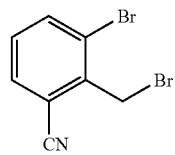 [SMILES: N#Cc1cccc(Br)c1CBr]

The titled compound (1.50 g) as a white solid was prepared from the compound [32-1] (1.76 g) according to the method of the process (2) in Example 5.

$^1$H-NMR (400 MHz, CDCl$_3$) δ: 7.83 (1H, d, J=8.1 Hz), 7.65 (1H, d, J=7.6 Hz), 7.29 (1H, d, J=7.9 Hz), 4.79 (2H, s).

(3) Synthesis of tert-butyl (3-methyl-1H-indazol-6-yl)acetate [32-3] (hereinafter referred to as a compound [32-3])

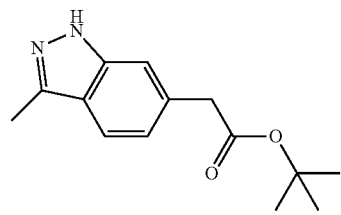 [SMILES: Cc1n[nH]c2cc(CC(=O)OC(C)(C)C)ccc12]

The titled compound (272 mg) as a yellow solid was prepared from 6-bromo-3-methyl-1H-indazole (700 mg), which was obtained by the method described in the document (JP 2009-528363 W), according to the method of the process (4) in Example 3.

$^1$H-NMR (400 MHz, CDCl$_3$) δ: 9.67 (1H, brs), 7.61 (1H, d, J=8.3 Hz), 7.32 (1H, s), 7.07 (1H, dd, J=8.3, 1.0 Hz), 3.65 (2H, s), 2.57 (3H, s), 1.44 (9H, s).

(4) Synthesis of tert-butyl [1-(2-bromo-6-cyanobenzyl)-3-methyl-1H-indazol-6-yl]acetate [32-4] (hereinafter referred to as a compound [32-4])

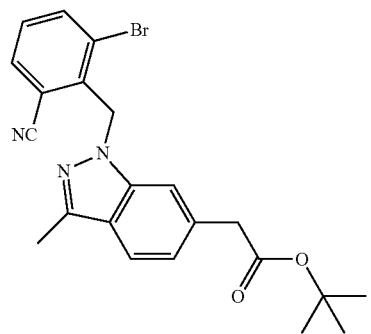 [SMILES: Cc1nn(Cc2c(Br)cccc2C#N)c2cc(CC(=O)OC(C)(C)C)ccc12]

The titled compound (119 mg) as a white solid was prepared from the compound [32-2] (127 mg) and the compound [32-3] (98 mg) according to the method of the process (1) in Example 1.

¹H-NMR (400 MHz, CDCl₃) δ: 7.82 (1H, dd, J=8.1, 1.0 Hz), 7.71 (1H, dd, J=7.7, 1.1 Hz), 7.57 (1H, dJ=8.1 Hz), 7.35 (1H, s), 7.34-7.30 (1H, m), 7.06 (1H, dd, J=8.3, 1.0 Hz), 5.67 (2H, s), 3.66 (2H, s), 2.49 (3H, s), 1.43 (9H, s).

(5) Synthesis of tert-butyl [1-(2-cyano-6-cyclopropylbenzyl)-3-methyl-1H-indazol-6-yl]acetate [32-5] (hereinafter referred to as a compound [32-5])

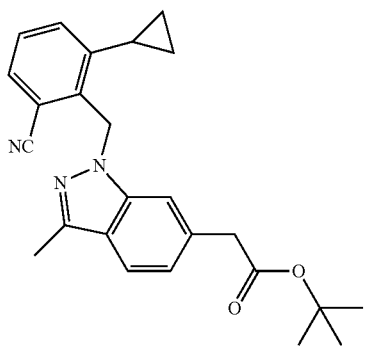 [SMILES: Cc1nn(Cc2c(C#N)cccc2C2CC2)c2cc(CC(=O)OC(C)(C)C)ccc12]

The titled compound (39 mg) as a white solid was prepared from the compound [32-4] (119 mg) according to the method of the process (1) in Example 12.

¹H-NMR (400 MHz, CDCl₃) δ: 7.58-7.56 (2H, m), 7.37-7.33 (1H, m), 7.27-7.26 (2H, m), 7.03 (1H, dd, J=8.3, 1.0 Hz), 5.81 (2H, s), 3.62 (2H, s), 2.49 (3H, s), 1.98-1.96 (1H, m), 1.42 (9H, s), 0.86-0.84 (2H, m), 0.59-0.58 (2H, m).

(6) Synthesis of [1-(2-cyano-6-cyclopropylbenzyl)-3-methyl-1H-indazol-6-yl]difluoroacetic acid [32]

The titled compound (22 mg) as a white solid was prepared from the compound [32-5] (39 mg) according to the methods of the processes (5) to (6) in Example 3.

¹H-NMR (400 MHz, CD₃OD) δ: 7.82-7.79 (2H, m), 7.64 (1H, d, J=7.6 Hz), 7.46-7.42 (1H, m), 7.36-7.32 (2H, m), 5.93 (2H, s), 2.50 (3H, s), 1.83-1.76 (1H, m), 0.79-0.72 (2H, m), 0.60-0.56 (2H, m).

ESI-MS found: 382 [M+H]⁺

Example 33

Synthesis of potassium [1-(2-cyano-6-cyclopropylbenzyl)-3-methyl-1H-indazol-6-yl]difluoroacetate [33] (hereinafter referred to as a compound [33])

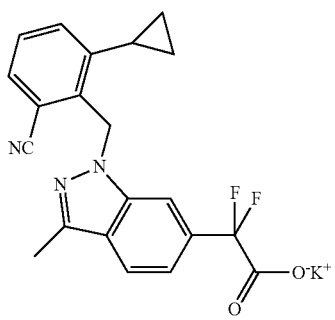

To a solution of the compound [32] (18 mg) in ethanol (1 mL) was added an aqueous solution of 1N-potassium hydroxide (48 μL) at room temperature, and the solution was concentrated under reduced pressure to give the titled compound (20 mg) as a yellow white solid.

¹H-NMR (400 MHz, CD₃OD) δ: 7.88 (1H, s), 7.73 (1H, d, J=8.5 Hz), 7.65 (1H, t, J=4.6 Hz), 7.44 (2H, t, J=7.8 Hz), 7.37 (1H, d, J=7.8 Hz), 5.90 (2H, s), 2.49 (3H, s), 1.72-1.71 (1H, m), 0.75-0.73 (2H, m), 0.55-0.54 (2H, m).

ESI-MS found: 382 [M−K+2H]⁺

Example 34

Synthesis of [3-chloro-1-(2,6-dichlorobenzyl)-1H-indazol-6-yl]difluoroacetic acid [34] (hereinafter referred to as a compound [34])

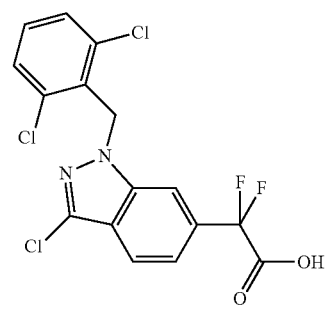

(1) Synthesis of 6-bromo-3-chloro-1H-indazole [34-1] (hereinafter referred to as a compound [34-1])

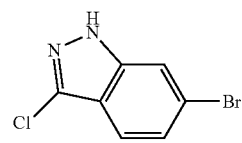 [SMILES: Clc1n[nH]c2cc(Br)ccc12]

6-Bromo-1H-indazole (1.0 g) and N-chlorosuccinimide (746 mg) were dissolved in N,N-dimethylformamide (17 mL), and the solution was stirred at room temperature for 1 hour.

The reaction mixture was quenched with water, and the mixture was extracted with ethyl acetate. The obtained organic layer was dried over anhydrous sodium sulfate, filtered, and the filtrate was concentrated under reduced pressure. The obtained residue was purified by silica gel column chromatography to give the titled compound (640 mg) as a white solid.

¹H-NMR (400 MHz, CDCl₃) δ: 9.99 (1H, s), 7.66 (1H, s), 7.57 (1H, d, J=8.3 Hz), 7.35 (1H, dd, J=8.5, 1.2 Hz).

(2) Synthesis of 6-bromo-3-chloro-1-(2,6-dichlorobenzyl)-1H-indazole [34-2] (hereinafter referred to as a compound [34-2])

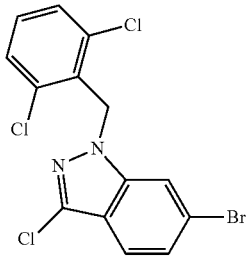 [SMILES: Clc1cccc(Cl)c1Cn1nc(Cl)c2ccc(Br)cc21]

The titled compound (299 mg) as a white solid was prepared from the compound [34-1] (201 mg) and 2,6-dichlorobenzyl chloride (228 mg) according to the method of the process (1) in Example 1.

$^1$H-NMR (400 MHz, CDCl$_3$) δ: 7.64 (1H, s), 7.51 (1H, d, J=8.8 Hz), 7.39 (2H, d, J=8.1 Hz), 7.31-7.26 (2H, m), 5.68 (2H, s).

(3) Synthesis of tert-butyl [3-chloro-1-(2,6-dichlorobenzyl)-1H-indazol-6-yl]acetate [34-3] (hereinafter referred to as a compound [34-3])

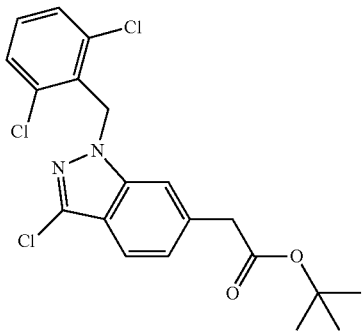 [SMILES: CC(C)(C)OC(=O)Cc1ccc2c(Cl)nn(Cc3c(Cl)cccc3Cl)c2c1]

The titled compound (175 mg) as a white pink solid was prepared from the compound [34-2] (197 mg) according to the method of the process (4) in Example 3.

$^1$H-NMR (400 MHz, CDCl$_3$) δ: 7.59 (1H, d, J=8.3 Hz), 7.38-7.36 (3H, m), 7.27-7.23 (1H, m), 7.12 (1H, d, J=8.3 Hz), 5.70 (2H, s), 3.66 (2H, s), 1.44 (9H, s).

(4) Synthesis of [3-chloro-1-(2,6-dichlorobenzyl)-1H-indazol-6-yl]difluoroacetic acid [34]

The titled compound (28 mg) as a white solid was prepared from the compound [34-3] (118 mg) according to the methods of the processes (5) to (6) in Example 3.

$^1$H-NMR (400 MHz, CD$_3$OD) δ: 7.99 (1H, s), 7.76 (1H, d, J=8.5 Hz), 7.48-7.44 (3H, m), 7.37 (1H, dd, J=9.0, 7.3 Hz), 5.86 (2H, s).

ESI-MS found: 405 [M+H]$^+$

Example 35

Synthesis of [3-chloro-1-(2-chloro-6-methylbenzyl)-1H-indazol-6-yl]difluoroacetic acid [35] (hereinafter referred to as a compound [35])

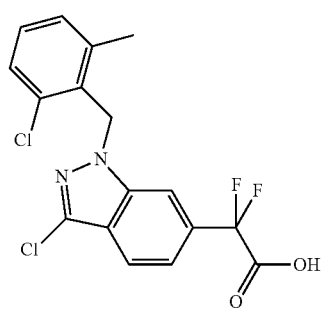

(1) Synthesis of 6-bromo-3-chloro-1-(2-chloro-6-methylbenzyl)-1H-indazole [35-1] (hereinafter referred to as a compound [35-1])

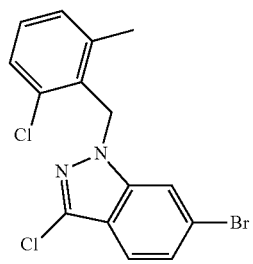

The titled compound (79 mg) as a white solid was prepared from the compound [34-1] (50.0 mg) and the compound [3-2] (45.4 mg) according to the method of the process (1) in Example 1.

$^1$H-NMR (400 MHz, CDCl$_3$) δ: 7.57 (1H, s), 7.50 (1H, d, J=8.5 Hz), 7.31-7.29 (2H, m), 7.21 (1H, t, J=7.8 Hz), 7.15 (1H, d, J=7.3 Hz), 5.60 (2H, s), 2.42 (3H, s)

(2) Synthesis of [3-chloro-1-(2-chloro-6-methylbenzyl)-1H-indazol-6-yl]difluoroacetic acid [35]

The titled compound (56.7 mg) as a white solid was prepared from the compound [35-1] (77.7 mg) according to the methods of the processes (4) to (6) in Example 3.

$^1$H-NMR (400 MHz, CD$_3$OD) δ: 7.91 (1H, s), 7.76 (1H, d, J=8.5 Hz), 7.44 (1H, d, J=8.5 Hz), 7.31 (1H, d, J=7.6 Hz), 7.27-7.21 (2H, m), 5.75 (2H, s), 2.44 (3H, s).

ESI-MS found: 385 [M+H]$^+$

Example 36

Synthesis of [1-(2,6-dichlorobenzyl)-3-trifluoromethyl-1H-indazol-6-yl]difluoroacetic acid [36] (hereinafter referred to as a compound [36])

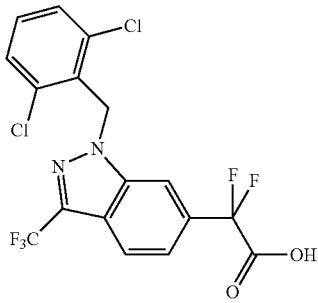 [SMILES: O=C(O)C(F)(F)c1ccc2c(C(F)(F)F)nn(Cc3c(Cl)cccc3Cl)c2c1]

(1) Synthesis of 6-bromo-3-iodo-1H-indazole [36-1] (hereinafter referred to as a compound [36-1])

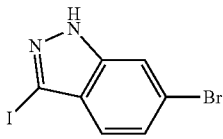

To a solution of 6-bromo-1H-indazole (1.11 g) in N,N-dimethylformamide (10 mL) were added iodine (2.17 g) and potassium hydroxide (1.14 g), and the mixture was stirred at room temperature for 1 hour. The reaction mixture was quenched with water, and extracted with chloroform. The obtained organic layer was dried over anhydrous sodium sulfate, filtered, and the filtrate was concentrated under reduced pressure. The obtained residue was purified by silica gel column chromatography to give the titled compound (1.45 g) as a yellow solid.

$^1$H-NMR (400 MHz, CDCl$_3$) δ: 11.22 (1H, s), 7.71 (1H, s), 7.39-7.31 (2H, m).

(2) Synthesis of 6-bromo-1-(2,6-dichlorobenzyl)-3-iodo-1H-indazole [36-2] (hereinafter referred to as a compound [36-2])

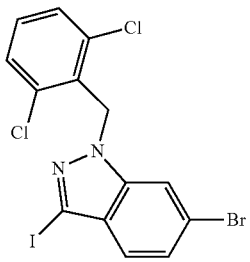

The titled compound (374 mg) as a white solid was prepared from the compound [36-1] (314 mg) and 2,6-dichlorobenzyl chloride (309 mg) according to the method of the process (1) in Example 1.

$^1$H-NMR (400 MHz, CDCl$_3$) δ: 7.59 (1H, s), 7.39 (2H, d, J=8.1 Hz), 7.32-7.27 (3H, m), 5.76 (2H, s).

(3) Synthesis of 6-bromo-1-(2,6-dichlorobenzyl)-3-trifluoromethyl-1H-indazole [36-3] (hereinafter referred to as a compound [36-3])

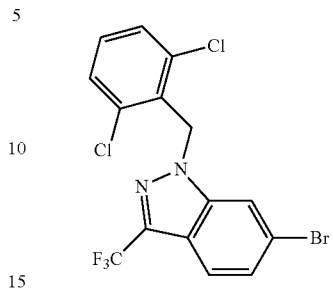

To a solution of the compound [36-2] (374 mg) in N,N-dimethylformamide (3 mL) were added hexamethylphosphoric triamide (0.58 mL), copper(I) iodide (72 mg) and methyl difluoro(fluorosulfonyl)acetate (0.1 mL), and the mixture was stirred at 100° C. for 24 hours. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (286 mg) as a white solid.

$^1$H-NMR (400 MHz, CDCl$_3$) δ: 7.68 (1H, s), 7.41-7.37 (3H, m), 7.31-7.26 (2H, m), 5.80 (2H, s).

(4) Synthesis of tert-butyl [1-(2,6-dichlorobenzyl)-3-trifluoromethyl-1H-indazol-6-yl]acetate [36-4] (hereinafter referred to as a compound [36-4])

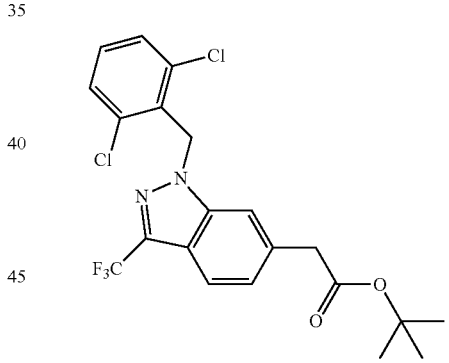

The titled compound (80 mg) as a brown solid was prepared from the compound [36-3] (124 mg) according to the method of the process (4) in Example 3.

$^1$H-NMR (400 MHz, CDCl$_3$) δ: 7.76 (1H, d, J=8.3 Hz), 7.43 (1H, s), 7.39-7.38 (2H, m), 7.27-7.25 (1H, m), 7.21-7.19 (1H, m), 5.83 (2H, s), 3.66 (2H, s), 1.44 (9H, s).

(5) Synthesis of [1-(2,6-dichlorobenzyl)-3-trifluoromethyl-1H-indazol-6-yl]difluoroacetic acid [36]

The titled compound (29 mg) as a white solid was prepared from the compound [36-4] (102 mg) according to the methods of the processes (5) to (6) in Example 3.

$^1$H-NMR (400 MHz, CD$_3$OD) δ: 8.11 (1H, s), 7.83 (1H, d, J=8.3 Hz), 7.61 (1H, d, J=8.5 Hz), 7.46-7.44 (2H, m), 7.36-7.34 (1H, m), 5.92 (2H, s).

ESI-MS found: 439 [M+H]$^+$

Example 37

Synthesis of [1-(2,6-dichlorobenzyl)-3-methyl-1H-pyrazolo[4,3-b]pyridin-6-yl]difluoroacetic acid [37] (hereinafter referred to as a compound [37])

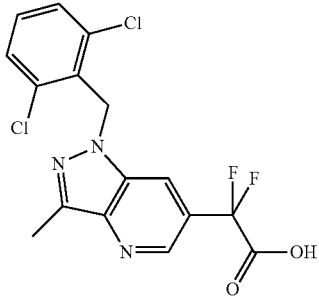 [SMILES: Cc1nn(Cc2c(Cl)cccc2Cl)c2cc(C(F)(F)C(=O)O)cnc12]

(1) Synthesis of 1-(5-bromo-3-fluoropyridin-2-yl)ethanone [37-1] (hereinafter referred to as a compound [37-1])

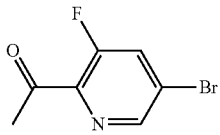

To a solution of 5-bromo-3-fluoropyridine-2-carbonitrile (2.2 g), which was obtained by the method described in the document (Journal of Organic Chemistry, 2009, Vol. 74, 4547), in toluene (22 mL) was added 3.0M tetrahydrofuran solution of methylmagnesium chloride (5.4 mL) at room temperature, and the mixture was stirred for 20 minutes. The reaction mixture was quenched with water, and extracted with chloroform. The obtained organic layer was dried over anhydrous sodium sulfate, filtered, and the filtrate was concentrated under reduced pressure. The obtained residue was purified by silica gel column chromatography to give the titled compound (793 mg) as a pale yellow oil.

$^1$H-NMR (400 MHz, CDCl$_3$) δ: 8.56 (1H, s), 7.74 (1H, d, J=9.6 Hz), 2.68 (3H, s).

(2) Synthesis of 6-bromo-3-methyl-1H-pyrazolo[4,3-b]pyridine [37-2] (hereinafter referred to as a compound [37-2])

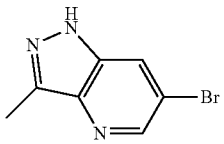

The compound [37-1] (1.2 g) was dissolved in ethylene glycol (11 mL), hydrazine monohydrate (11 mL) was added to the mixture at room temperature, and the mixture was then stirred at 140° C. for 17 hours. After cooling to room temperature, water was then added to the reaction mixture, and the precipitated solid was collected by filtration to give the titled compound (788 mg) as a yellow crystal.

$^1$H-NMR (400 MHz, CD$_3$OD) δ: 8.51 (1H, d, J=1.7 Hz), 8.16 (1H, d, J=2.0 Hz), 2.59 (3H, s).
ESI-MS found: 212 [M+H]$^+$

(3) Synthesis of 6-bromo-1-(2,6-dichlorobenzyl)-3-methyl-1H-pyrazolo[4,3-b]pyridine [37-3] (hereinafter referred to as a compound [37-3])

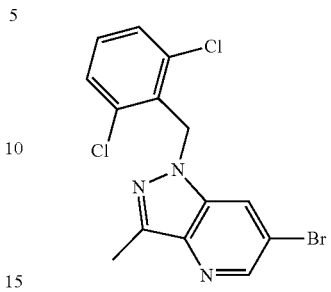

The titled compound (274 mg) as a white solid was prepared from the compound [37-2] (196 mg) and 2,6-dichlorobenzyl chloride (361 mg) according to the method of the process (1) in Example 1.

$^1$H-NMR (400 MHz, CDCl$_3$) δ: 8.51 (1H, d, J=1.7 Hz), 7.80 (1H, d, J=1.7 Hz), 7.39 (2H, d, J=7.8 Hz), 7.29-7.26 (1H, m), 5.69 (2H, s), 2.60 (3H, s).
ESI-MS found: 370 [M+H]$^+$

(4) Synthesis of tert-butyl [1-(2,6-dichlorobenzyl)-3-methyl-1H-pyrazolo[4,3-b]pyridin-6-yl]acetate [37-4] (hereinafter referred to as a compound [37-4])

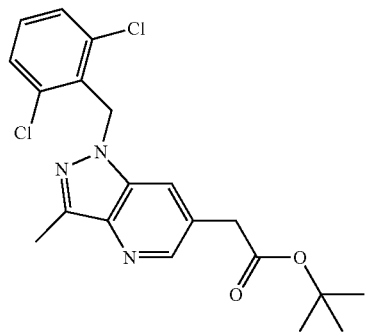 [SMILES: Cc1nn(Cc2c(Cl)cccc2Cl)c2cc(CC(=O)OC(C)(C)C)cnc12]

To a solution of dicyclohexylamine (339 μL) in toluene (5 mL) was added 1.65M hexane solution of n-butyllithium (1.0 mL) at 0° C., and the mixture was stirred at 0° C. for 30 minutes. tert-butyl acetate (200 μL) was then added to the mixture at 0° C., and the mixture was stirred at 0° C. for 30 minutes. The obtained solution was added to the compound [37-3] (371 mg), bis(dibenzylideneacetone)palladium(0) (173 mg) and tri-tertbutylphosphonium tetrafluoroborate (87 mg) at room temperature, and the mixture was stirred at room temperature for 2 days. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (163 mg) as a yellow oil.

$^1$H-NMR (400 MHz, CDCl$_3$) δ: 8.41 (1H, s), 7.62 (1H, s), 7.38 (2H, d, J=8.1 Hz), 7.26-7.24 (1H, m), 5.72 (2H, s), 3.66 (2H, s), 2.62 (3H, s), 1.43 (9H, s).

(5) Synthesis of [1-(2,6-dichlorobenzyl)-3-methyl-1H-pyrazolo[4,3-b]pyridin-6-yl]difluoroacetic acid [37]

The titled compound (92 mg) as a white solid was prepared from the compound [37-4] (154 mg) according to the methods of the processes (5) to (6) in Example 3.

$^1$H-NMR (400 MHz, CD$_3$OD) δ: 8.68 (1H, s), 8.35 (1H, s), 7.46 (2H, d, J=7.8 Hz), 7.37 (1H, t, J=8.1 Hz), 5.88 (2H, s), 2.56 (3H, s).

ESI-MS found: 386 [M+H]$^+$

Example 38

Synthesis of [1-(2-chloro-6-cyclopropylbenzyl)-3-methyl-1H-pyrazolo[4,3-b]pyridin-6-yl]difluoroacetic acid [38] (hereinafter referred to as a compound [38])

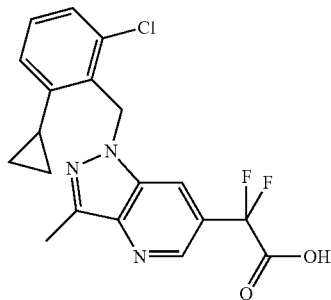

The titled compound (5.5 mg) as a yellow white solid was prepared from the compound [37] (30 mg) according to the method of Example 27.

$^1$H-NMR (400 MHz, CD$_3$OD) δ: 8.65 (1H, s), 8.15 (1H, s), 7.33-7.27 (2H, m), 7.10 (1H, d, J=7.1 Hz), 5.98 (2H, s), 2.58 (3H, s), 2.15-2.08 (1H, m), 0.89-0.84 (2H, m), 0.67-0.63 (2H, m).

ESI-MS found: 392 [M+H]$^+$

Example 39

Synthesis of potassium [1-(2-chloro-6-cyclopropylbenzyl)-3-methyl-1H-pyrazolo[4,3-b]pyridin-6-yl]difluoroacetate [39] (hereinafter referred to as a compound [39])

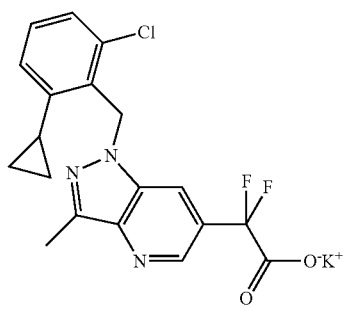

To a solution of the compound [38] (38 mg) in ethanol (2 mL) was added an aqueous solution of 1N-potassium hydroxide (97 μL) at room temperature, and the solution was concentrated under reduced pressure to give the titled compound (40 mg) as a white solid.

$^1$H-NMR (400 MHz, CD$_3$OD) δ: 8.72 (1H, d, J=1.7 Hz), 8.22 (1H, d, J=1.2 Hz), 7.32-7.25 (2H, m), 7.10 (1H, dd, J=7.4, 1.1 Hz), 5.94 (2H, s), 2.56 (3H, s), 2.14-2.07 (1H, m), 0.89-0.84 (2H, m), 0.67-0.63 (2H, m).

ESI-MS found: 392 [M−K+2H]$^+$

Example 40

Synthesis of [1-(2-chloro-6-methylbenzyl)-3-methyl-1H-pyrazolo[4,3-b]pyridin-6-yl]difluoroacetic acid [40] (hereinafter referred to as a compound [40])

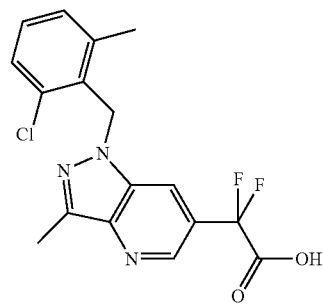

(1) Synthesis of 6-bromo-1-(2-chloro-6-methylbenzyl)-3-methyl-1H-pyrazolo[4,3-b]pyridine [40-1] (hereinafter referred to as a compound [40-1])

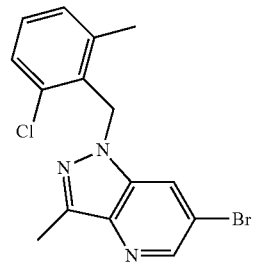 [SMILES: Cc1cccc(Cl)c1Cn1nc(C)c2ncc(Br)cc21]

The titled compound (204.1 mg) as a white solid was prepared from the compound [37-2] (194 mg) and the compound [3-2] (191.8 mg) according to the method of the process (1) in Example 1.

$^1$H-NMR (400 MHz, CDCl$_3$) δ: 8.49 (1H, s), 7.68 (1H, s), 7.32 (1H, d, J=7.8 Hz), 7.23 (1H, t, J=7.8 Hz), 7.15 (1H, d, J=7.3 Hz), 5.62 (2H, s), 2.61 (3H, s), 2.40 (3H, s).

(2) Synthesis of [1-(2-chloro-6-methylbenzyl)-3-methyl-1H-pyrazolo[4,3-b]pyridin-6-yl]difluoroacetic acid [40]

The titled compound (45.2 mg) as a white solid was prepared from the compound [40-1] (169.4 mg) according to the methods of the processes (4) to (6) in Example 3.

$^1$H-NMR (400 MHz, CD$_3$OD) δ: 8.66 (1H, d, J=2.0 Hz), 8.21 (1H, d, J=1.7 Hz), 7.31 (1H, dd, J=7.7 Hz, 1.6 Hz), 7.26 (1H, t, J=7.6 Hz), 7.23-7.22 (1H, m), 5.76 (2H, s), 2.58 (3H, s), 2.44 (3H, s).

ESI-MS found: 366 [M+H]$^+$

Example 41

Synthesis of potassium [1-(2-chloro-6-methylbenzyl)-3-methyl-1H-pyrazolo[4,3-b]pyridin-6-yl]difluoroacetate [41] (hereinafter referred to as a compound [41])

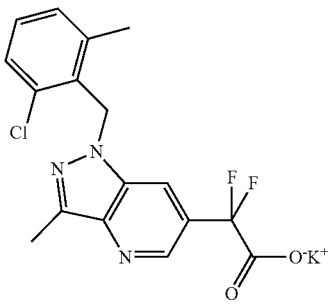

To a solution of the compound [40] (38.4 mg) in ethanol (4 mL) was added an aqueous solution of 1N-potassium hydroxide (105 μL) at room temperature, and the solution was concentrated under reduced pressure to give the titled compound (42.4 mg) as a white solid.

$^1$H-NMR (400 MHz, CD$_3$OD) δ: 8.72 (1H, d, J=1.7 Hz), 8.24 (1H, s), 7.30 (1H, d, J=7.6 Hz), 7.26-7.20 (2H, m), 5.73 (2H, s), 2.55 (3H, s), 2.44 (3H, s).

ESI-MS found: 366 [M−K+2H]$^+$

Example 42

Synthesis of [1-(2-chloro-6-fluorobenzyl)-3-methyl-1H-pyrazolo[4,3-b]pyridin-6-yl]difluoroacetic acid [42] (hereinafter referred to as a compound [42])

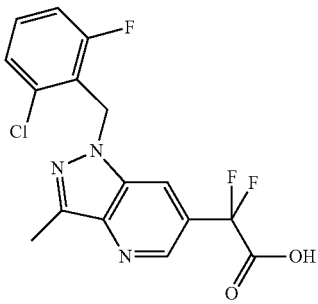

(1) Synthesis of 6-bromo-3-methyl-1-tosyl-1H-pyrazolo[4,3-b]pyridine [42-1] (hereinafter referred to as a compound [42-1])

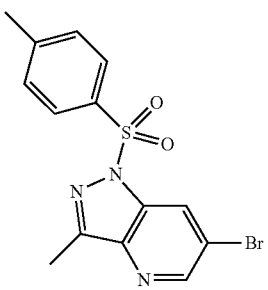 [SMILES: Cc1ccc(S(=O)(=O)n2nc(C)c3ncc(Br)cc32)cc1]

The titled compound (970.2 mg) as a white solid was prepared from the compound [37-2] (649.0 mg) according to the method of the process (1) in Example 7.

$^1$H-NMR (400 MHz, CDCl$_3$) δ: 8.68 (1H, d, J=1.7 Hz), 8.63 (1H, d, J=1.7 Hz), 7.87 (2H, d, J=8.5 Hz), 7.30 (2H, d, J=8.5 Hz), 2.60 (3H, s), 2.40 (3H, s).

(2) Synthesis of tert-butyl (3-methyl-1-tosyl-1H-pyrazolo[4,3-b]pyridin-6-yl) acetate [42-2] (hereinafter referred to as a compound [42-2])

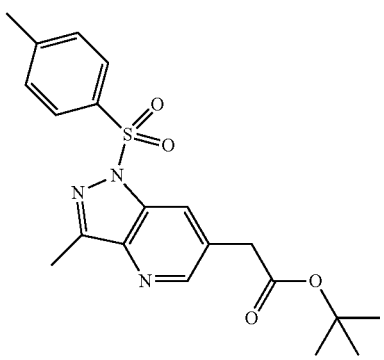 [SMILES: Cc1ccc(S(=O)(=O)n2nc(C)c3ncc(CC(=O)OC(C)(C)C)cc32)cc1]

The titled compound (995.6 mg) as a red oil was prepared from the compound [42-1] (970.2 mg) according to the method of the process (4) in Example 3.

$^1$H-NMR (400 MHz, CDCl$_3$) δ: 8.54 (1H, d, J=1.5 Hz), 8.36 (1H, d, J=1.2 Hz), 7.83 (2H, d, J=8.3 Hz), 7.24 (2H, d, J=8.8 Hz), 3.73 (2H, s), 2.58 (3H, s), 2.35 (3H, s), 1.45 (9H, s).

(3) Synthesis of tert-butyl difluoro(3-methyl-1-tosyl-1H-pyrazolo[4,3-b]pyridin-6-yl) acetate [42-3] (hereinafter referred to as a compound [42-3])

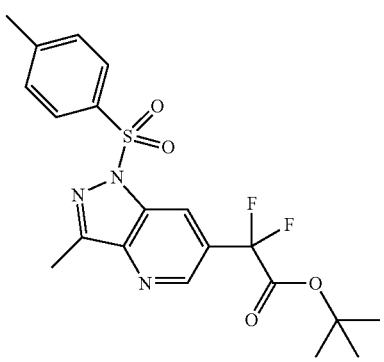 [SMILES: Cc1ccc(S(=O)(=O)n2nc(C)c3ncc(C(F)(F)C(=O)OC(C)(C)C)cc32)cc1]

The titled compound (900.5 mg) as a white solid was prepared from the compound [42-2] (995.6 mg) according to the method of the process (5) in Example 3.

$^1$H-NMR (400 MHz, CDCl$_3$) δ: 8.86 (1H, d, J=1.7 Hz), 8.69 (1H, d, J=1.2 Hz), 7.88 (2H, d, J=8.3 Hz), 7.29 (2H, d, J=8.5 Hz), 2.65 (3H, s), 2.39 (3H, s), 1.52 (9H, s).

(4) Synthesis of methyl difluoro(3-methyl-1H-pyrazolo[4,3-b]pyridin-6-yl) acetate [42-4] (hereinafter referred to as a compound [42-4])

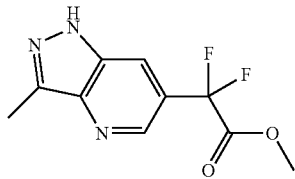

The titled compound (259.1 mg) as a white solid was prepared from the compound [42-3] (721.8 mg) according to the methods of the processes (4) to (5) in Example 7.

$^1$H-NMR (400 MHz, CD$_3$OD) δ: 8.66 (1H, d, J=2.0 Hz), 8.19 (1H, s), 3.89 (3H, s), 2.65 (3H, s).

(5) Synthesis of [1-(2-chloro-6-fluorobenzyl)-3-methyl-1H-pyrazolo[4,3-b]pyridin-6-yl]difluoroacetic acid [42]

The titled compound (5.8 mg) as a white solid was prepared from the compound [42-4] (18.9 mg) and 2-chloro-6-fluorobenzyl chloride (12.3 µL) according to the methods of the processes (6) to (7) in Example 7.

$^1$H-NMR (400 MHz, CD$_3$OD) δ: 8.68 (1H, d, J=1.7 Hz), 8.40 (1H, s), 7.40-7.36 (1H, m), 7.31-7.30 (1H, m), 7.17-7.14 (1H, m), 5.78 (2H, d, J=1.5 Hz), 2.57 (3H, s).

ESI-MS found: 370 [M+H]$^+$

Example 43

Synthesis of [1-(2,3-dichlorobenzyl)-3-methyl-1H-pyrazolo[4,3-b]pyridin-6-yl]difluoroacetic acid [43] (hereinafter referred to as a compound [43])

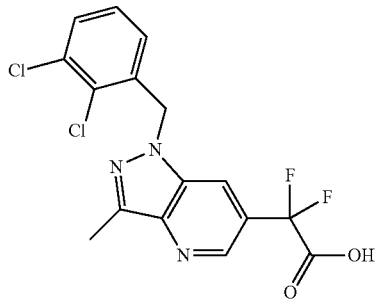 [SMILES: Cc1nn(Cc2cccc(Cl)c2Cl)c2cc(C(F)(F)C(=O)O)cnc12]

The titled compound (4.8 mg) as a white solid was prepared from the compound [42-4] (25.0 mg) and 2,3-dichlorobenzyl chloride (17.0 µL) according to the methods of the processes (6) to (7) in Example 7.

$^1$H-NMR (400 MHz, CD$_3$OD) δ: 8.71 (1H, s), 8.33 (1H, s), 7.50 (1H, d, J=8.1 Hz), 7.23 (1H, t, J=7.9 Hz), 6.90 (1H, d, J=7.8 Hz), 5.79 (2H, s), 2.63 (3H, s).

ESI-MS found: 386 [M+H]$^+$

Example 44

Synthesis of difluoro[1-(2-fluoro-6-trifluoromethylbenzyl)-3-methyl-1H-pyrazolo[4,3-b]pyridin-6-yl]acetic acid [44] (hereinafter referred to as a compound [44])

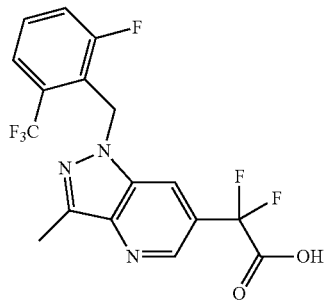 [SMILES: Cc1nn(Cc2c(F)cccc2C(F)(F)F)c2cc(C(F)(F)C(=O)O)cnc12]

The titled compound (16.6 mg) as a white solid was prepared from the compound [42-4] (32.7 mg) and 2-fluoro-6-trifluoromethylbenzyl bromide (41.9 mg) according to the methods of the processes (6) to (7) in Example 7.

$^1$H-NMR (400 MHz, CD$_3$OD) δ: 8.69 (1H, d, J=1.7 Hz), 8.35 (1H, s), 7.64-7.61 (1H, m), 7.54-7.53 (1H, m), 7.44-7.42 (1H, m), 5.79 (2H, s), 2.55 (3H, s).

ESI-MS found: 404 [M+H]

Example 45

Synthesis of [1-(2-chloro-6-fluorobenzyl)-3-ethyl-1H-pyrazolo[4,3-b]pyridin-6-yl]difluoroacetic acid [45] (hereinafter referred to as a compound [45])

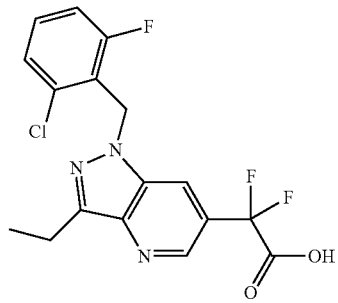 [SMILES: CCc1nn(Cc2c(F)cccc2Cl)c2cc(C(F)(F)C(=O)O)cnc12]

(1) Synthesis of 6-bromo-3-ethyl-1H-pyrazolo[4,3-b]pyridine [45-1] (hereinafter referred to as a compound [45-1])

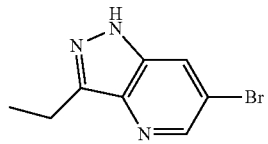

The titled compound (225 mg) as a white solid was prepared from 5-bromo-3-fluoropyridine-2-carbonitrile (201 mg), which was obtained by the method described in the document (Journal of Organic Chemistry, 2009, Vol. 74, 4547), and ethyl magnesium chloride according to the methods of the processes (1) and (2) in Example 37.

$^1$H-NMR (400 MHz, CDCl$_3$) δ: 9.87 (1H, s), 8.58 (1H, d, J=1.7 Hz), 7.95 (1H, d, J=1.7 Hz), 3.12 (2H, q, J=7.6 Hz), 1.45 (3H, t, J=7.6 Hz).

(2) Synthesis of [1-(2-chloro-6-fluorobenzyl)-3-ethyl-1H-pyrazolo[4,3-b]pyridin-6-yl]difluoroacetic acid [45]

The titled compound (132 mg) as a white solid was prepared from the compound [45-1] (429 mg) and 2-chloro-6-fluorobenzyl chloride (441 mg) according to the methods of the process (1) in Example 1 and the processes (4) to (6) in Example 3.

$^1$H-NMR (400 MHz, CD$_3$OD) δ: 8.67 (1H, d, J=2.0 Hz), 8.38 (1H, d, J=1.2 Hz), 7.41-7.36 (1H, m), 7.32-7.29 (1H, m), 7.18-7.14 (1H, m), 5.78 (2H, d, J=1.7 Hz), 3.03 (2H, q, J=7.6 Hz), 1.35 (3H, t, J=7.6 Hz).

ESI-MS found: 384 [M+H]$^+$

Example 46

Synthesis of [1-(2-cyclopropyl-6-fluorobenzyl)-3-ethyl-1H-pyrazolo[4,3-b]pyridin-6-yl]difluoroacetic acid [46] (hereinafter referred to as a compound [46])

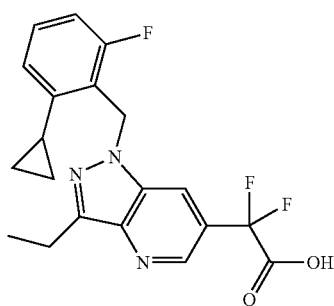 [SMILES: CCc1nn(Cc2c(F)cccc2C2CC2)c2cc(C(F)(F)C(=O)O)cnc12]

The titled compound (17 mg) as a yellow white solid was prepared from the compound [45] (50 mg) according to the method of Example 27.

$^1$H-NMR (400 MHz, CD$_3$OD) δ: 8.64 (1H, d, J=1.7 Hz), 8.22 (1H, s), 7.31-7.25 (1H, m), 6.99 (1H, t, J=8.8 Hz), 6.88 (1H, d, J=7.8 Hz), 5.87 (2H, d, J=1.5 Hz), 3.05 (2H, q, J=7.6 Hz), 2.23-2.16 (1H, m), 1.37 (3H, t, J=7.6 Hz), 0.91-0.86 (2H, m), 0.65-0.61 (2H, m).

ESI-MS found: 390 [M+H]$^+$

Example 47

Synthesis of [3-chloro-1-(2-chloro-6-cyclopropylbenzyl)-1H-pyrazolo[4,3-b]pyridin-6-yl]difluoroacetic acid [47] (hereinafter referred to as a compound [47])

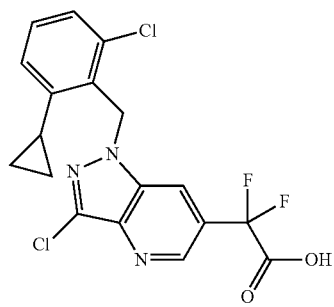 [SMILES: O=C(O)C(F)(F)c1cnc2c(Cl)nn(Cc3c(Cl)cccc3C3CC3)c2c1]

(1) Synthesis of 5-bromo-3-fluoropyridine-2-carboaldehyde [47-1] (hereinafter referred to as a compound [47-1])

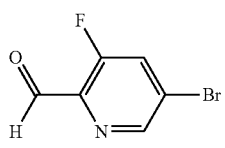

5-Bromo-3-fluoropyridine-2-carbonitrile (4.5 g), which was obtained by the method described in the document (Journal of Organic Chemistry, 2009, Vol. 74, 4547), was dissolved in dichloromethane (140 mL), and the solution was cooled to −78° C. 1.0M toluene solution of diisobutylaluminum hydride (33 mL) was added to the mixture at −78° C., and the solution was warmed to 0° C. and the solution was stirred for 5 minutes. The reaction mixture was cooled again to −78° C., 3N-hydrochloric acid was added to the reaction mixture, and the mixture was extracted with chloroform. The obtained organic layer was dried over anhydrous sodium sulfate, filtered, and the filtrate was concentrated under reduced pressure. The obtained residue was purified by silica gel column chromatography to give the titled compound (848 mg) as a yellow solid.

$^1$H-NMR (400 MHz, CDCl$_3$) δ: 10.17 (1H, s), 8.69 (1H, s), 7.80 (1H, dd, J=9.1, 1.3 Hz).

(2) Synthesis of 6-bromo-1H-pyrazolo[4,3-b]pyridine [47-2] (hereinafter referred to as a compound [47-2])

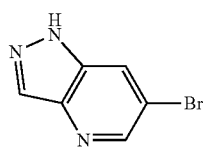

To a solution of the compound [47-1] (426 mg) in ethylene glycol (2.1 mL) was added hydrazine monohydrate (197 μL) at room temperature, and the mixture was stirred at 140° C. for 23 hours. After cooling to room temperature, water was added to the reaction mixture, and the mixture was extracted with a mixed solution of chloroform/isopropanol (volume ratio 10/1). The obtained organic layer was dried over anhydrous sodium sulfate, filtered, and the filtrate was concentrated under reduced pressure. The obtained residue was purified by silica gel column chromatography to give the titled compound (275 mg) as a yellow solid.

$^1$H-NMR (400 MHz, CDCl$_3$) δ: 10.17 (1H, br), 8.65 (1H, d, J=1.7 Hz), 8.31 (1H, s), 8.04 (1H, s).

ESI-MS found: 198 [M+H]$^+$ (3) Synthesis of 6-bromo-3-chloro-1H-pyrazolo[4,3-b]pyridine [47-3] (hereinafter referred to as a compound [47-3])

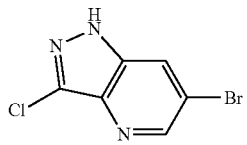

To a solution of the compound [47-2] (123 mg) in acetonitrile (4.1 mL) was added N-chlorosuccinimide (91 mg) at room temperature, and the mixture was stirred at 60° C. for 3 hours. N-Chlorosuccinimide (91 mg) was added again to the reaction mixture at 60° C., and stirred at 60° C. for 2 hours. After cooling, an aqueous solution of 1N-sodium hydroxide was added, and the mixture was extracted with ethyl acetate. The obtained organic layer was dried over anhydrous sodium sulfate, filtered, and the filtrate was concentrated under reduced pressure to give the titled compound (140 mg) as a pale yellow solid.

$^1$H-NMR (400 MHz, CDCl$_3$) δ: 9.99 (1H, br), 8.69 (1H, d, J=2.0 Hz), 8.02 (1H, d, J=2.0 Hz).

ESI-MS found: 232 [M+H]$^+$ (4) Synthesis of 6-bromo-3-chloro-1-(2-chloro-6-cyclopropylbenzyl)-1H-pyrazolo[4,3-b]pyridine [47-4] (hereinafter referred to as a compound [47-4])

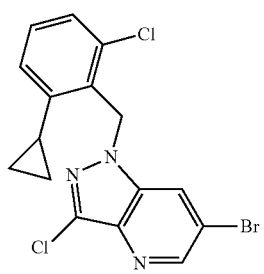 [SMILES: Clc1cccc(C2CC2)c1Cn1nc(Cl)c2ncc(Br)cc21]

The titled compound (160 mg) as a white solid was prepared from the compound [47-3] (119 mg) and the compound [12-2] (134 mg) according to the method of the process (1) in Example 1.

$^1$H-NMR (400 MHz, CDCl$_3$) δ: 8.59 (1H, d, J=1.5 Hz), 7.80 (1H, d, J=1.5 Hz), 7.33-7.25 (2H, m), 7.05 (1H, d, J=7.3 Hz), 5.86 (2H, s), 2.16-2.09 (1H, m), 0.98-0.92 (2H, m), 0.68-0.64 (2H, m).

(5) Synthesis of [3-chloro-1-(2-chloro-6-cyclopropylbenzyl)-1H-pyrazolo[4,3-b]pyridin-6-yl]difluoroacetic acid [47]

The titled compound (30 mg) as a white solid was prepared from the compound [47-4] (88 mg) according to the methods of the processes (4) to (6) in Example 3.

$^1$H-NMR (400 MHz, CD$_3$OD) δ: 8.75 (1H, d, J=1.7 Hz), 8.35 (1H, d, J=1.5 Hz), 7.34-7.28 (2H, m), 7.13 (1H, dd, J=6.6, 2.0 Hz), 6.03 (2H, s), 2.19-2.12 (1H, m), 0.92-0.87 (2H, m), 0.69-0.65 (2H, m).

ESI-MS found: 412 [M+H]$^+$

Example 48

Synthesis of [1-(2-chloro-6-cyclopropylbenzyl)-3-trifluoromethyl-1H-pyrazolo[4,3-b]pyridin-6-yl] difluoroacetic acid [48] (hereinafter referred to as a compound [48])

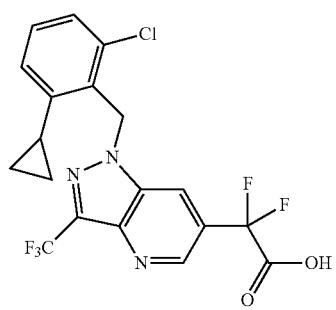 [SMILES: O=C(O)C(F)(F)c1cnc2c(C(F)(F)F)nn(Cc3c(Cl)cccc3C3CC3)c2c1]

(1) Synthesis of 6-bromo-3-iodo-1H-pyrazolo[4,3-b]pyridine [48-1] (hereinafter referred to as a compound [48-1])

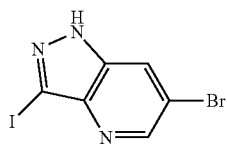 [SMILES: Brc1cnc2c(I)n[nH]c2c1]

The titled compound (1.02 g) as a yellow solid was prepared from the compound [47-2] (482 mg) according to the method of the process (1) in Example 36.

$^1$H-NMR (400 MHz, CD$_3$OD) δ: 8.57 (1H, d, J=1.7 Hz), 8.25 (1H, d, J=2.0 Hz).

(2) Synthesis of 6-bromo-1-(2-chloro-6-cyclopropylbenzyl)-3-iodo-1H-pyrazolo[4,3-b]pyridine [48-2] (hereinafter referred to as a compound [48-2])

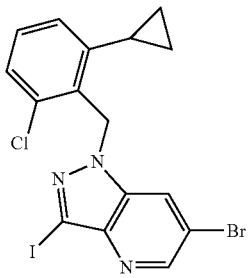 [SMILES: Clc1cccc(C2CC2)c1Cn1nc(I)c2ncc(Br)cc21]

The titled compound (395 mg) as a yellow solid was prepared from the compound [48-1] (510 mg) and the compound [12-2] (277 mg) according to the method of the process (1) in Example 1.

$^1$H-NMR (400 MHz, CDCl$_3$) δ: 8.58 (1H, d, J=1.7 Hz), 7.73 (1H, d, J=1.7 Hz), 7.33-7.25 (2H, m), 7.03 (1H, d, J=7.8 Hz), 5.94 (2H, s), 2.14-2.07 (1H, m), 0.96-0.91 (2H, m), 0.65-0.61 (2H, m).

(3) 6-bromo-1-(2-chloro-6-cyclopropylbenzyl)-3-trifluoromethyl-1H-pyrazolo[4,3-b]pyridine [48-3] (hereinafter referred to as a compound [48-3])

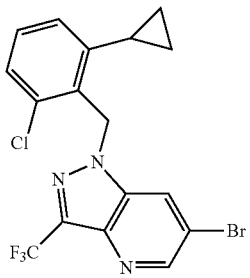 [SMILES: FC(F)(F)c1nn(Cc2c(Cl)cccc2C2CC2)c2cc(Br)cnc12]

The titled compound (243 mg) as a white solid was prepared from the compound [48-2] (394 mg) according to the method of the process (3) in Example 36.

$^1$H-NMR (400 MHz, CDCl$_3$) δ: 8.69 (1H, d, J=1.7 Hz), 7.87 (1H, d, J=2.0 Hz), 7.34-7.29 (2H, m), 7.05 (1H, d, J=8.1 Hz), 5.98 (2H, s), 2.11-2.05 (1H, m), 0.96-0.91 (2H, m), 0.66-0.62 (2H, m).

(4) [1-(2-chloro-6-cyclopropylbenzyl)-3-trifluoromethyl-1H-pyrazolo[4,3-b]pyridin-6-yl]difluoroacetic acid [48]

The titled compound (61 mg) as a white solid was prepared from the compound [48-3] (186 mg) according to the methods of the processes (4) to (6) in Example 3.

$^1$H-NMR (400 MHz, CD$_3$OD) δ: 8.90 (1H, s), 8.45 (1H, s), 7.30-7.28 (2H, m), 7.12-7.10 (1H, m), 6.09 (2H, s), 2.16-2.12 (1H, m), 0.89-0.86 (2H, m), 0.66-0.64 (2H, m).
ESI-MS found: 446 [M+H]$^+$ Example 49

Synthesis of [1-(2,6-dichlorobenzyl)-3-methyl-1H-indol-6-yl]difluoroacetic acid [49] (hereinafter referred to as a compound [49])

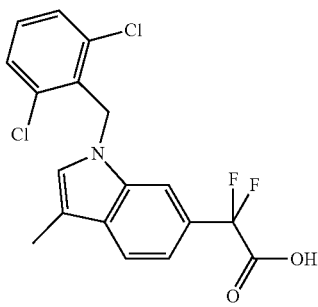 [SMILES: Cc1cn(Cc2c(Cl)cccc2Cl)c2cc(C(F)(F)C(=O)O)ccc12]

(1) Synthesis of (3-methyl-1-tosyl-1H-indol-6-yl)methanol [49-1] (hereinafter referred to as a compound [49-1])

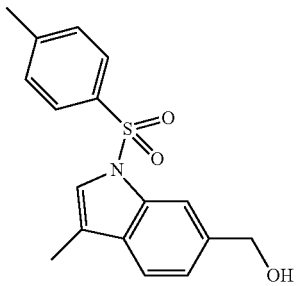 [SMILES: Cc1ccc(S(=O)(=O)n2cc(C)c3ccc(CC#N)cc32)cc1]

To a solution of methyl 3-methyl-1H-indole-6-carboxylate (1.3 g), which was obtained by the method described in the document (WO 1998/15530 A), in 2-pentanone (40 mL) were added 4-toluenesulfonyl chloride (2.0 g) and potassium carbonate (2.9 g) at room temperature, and the mixture was heated at reflux for 8 hours. After cooling to room temperature, water was added to the reaction mixture, and the mixture was extracted with ethyl acetate. The obtained organic layer was dried over anhydrous sodium sulfate, filtered, and the filtrate was concentrated under reduced pressure. The obtained residue was dissolved in tetrahydrofuran (20 mL), and to the solution was added a solution of lithium aluminum hydride (518 mg) in tetrahydrofuran (20 mL) at 0° C., and the mixture was stirred for 10 minutes. The reaction mixture was quenched with water and 1N-hydrochloric acid, and the mixture was extracted with chloroform. The obtained organic layer was dried over anhydrous sodium sulfate, filtered, and the filtrate was concentrated under reduced pressure. The obtained residue was purified by silica gel column chromatography to give the titled compound (1.6 g) as a white solid.

$^1$H-NMR (400 MHz, CDCl$_3$) δ: 7.98 (1H, s), 7.75 (2H, d, J=8.3 Hz), 7.44 (1H, d, J=8.1 Hz), 7.31-7.26 (2H, m), 7.21 (2H, d, J=8.1 Hz), 4.81 (2H, d, J=5.1 Hz), 2.34 (3H, s), 2.24 (3H, s), 1.77 (1H, t, J=5.4 Hz).

(2) Synthesis of (3-methyl-1-tosyl-1H-indol-6-yl)acetonitrile [49-2] (hereinafter referred to as a compound [49-2])

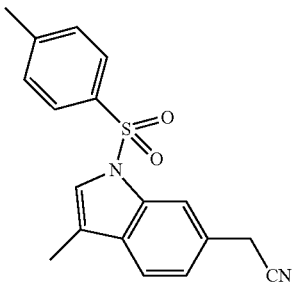

A solution of the compound [49-1] (1.6 g) in chloroform (12 mL) was cooled to 0° C., triethylamine (0.97 mL) and methanesulfonyl chloride (0.54 mL) were added at 0° C., and the mixture was stirred at 0° C. for 30 minutes and then stirred at room temperature for 16 hours. The reaction mixture was quenched with a saturated aqueous solution of ammonium chloride, and extracted with chloroform. The obtained organic layer was dried over anhydrous sodium sulfate, filtered, and the filtrate was concentrated under reduced pressure. The obtained residue was dissolved in dimethylsulfoxide (20 mL), and to the mixture was added sodium cyanide (516 mg) at room temperature, and the mixture was stirred at room temperature for 20 hours. The reaction mixture was quenched with water, and extracted with chloroform. The obtained organic layer was dried over anhydrous sodium sulfate, filtered, and the filtrate was concentrated under reduced pressure. The obtained residue was purified by silica gel column chromatography to give the titled compound (1.3 g) as a white solid.

$^1$H-NMR (400 MHz, CDCl$_3$) δ: 7.93 (1H, s), 7.74 (2H, d, J=8.5 Hz), 7.45 (1H, d, J=8.1 Hz), 7.32 (1H, s), 7.23-7.21 (3H, m), 3.86 (2H, s), 2.34 (3H, s), 2.24 (3H, s).

(3) Synthesis of methyl (3-methyl-1H-indol-6-yl)acetate [49-3] (hereinafter referred to as a compound [49-3])

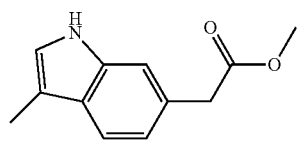

To a solution of the compound [49-2] (1.3 g) in ethanol (10 mL) was added an aqueous solution of 3N-sodium hydroxide (10 mL) at room temperature, and the mixture was then heated at reflux for 20 hours. After cooling to room temperature, 1N-hydrochloric acid was added for acidification, and the mixture was then extracted with chloroform. The obtained organic layer was dried over anhydrous sodium sulfate, filtered, and the filtrate was concentrated under reduced pressure. The obtained residue was dissolved in N,N-dimethylformamide (15 mL). To the solution were added potassium carbonate (846 mg) and methyl iodide (0.5 mL) at 0° C., and the mixture was stirred at room temperature for 10 minutes. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (677 mg) as a yellow solid.

$^1$H-NMR (400 MHz, CDCl$_3$) δ: 7.89 (1H, s), 7.53 (1H, d, J=7.8 Hz), 7.28 (1H, s), 7.05 (1H, d, J=8.1 Hz), 6.96 (1H, s), 3.74 (2H, s), 3.69 (3H, s), 2.33 (3H, s).

(4) Synthesis of methyl [1-(2,6-dichlorobenzyl)-3-methyl-1H-indol-6-yl]acetate [49-4] (hereinafter referred to as a compound [49-4])

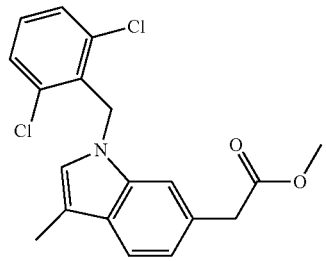 [SMILES: COC(=O)Cc1ccc2c(C)cn(Cc3c(Cl)cccc3Cl)c2c1]

To a solution of the compound [49-3] (272 mg) in N-methyl-2-pyrrolidone (4 mL) were added potassium carbonate (555 mg) and 2,6-dichlorobenzyl chloride (516 mg) at room temperature, and the mixture was subjected to microwave irradiation at 130° C. for 40 minutes. Water was added to the reaction mixture, and the mixture was extracted with ethyl acetate. The obtained organic layer was dried over anhydrous sodium sulfate, filtered, and the filtrate was concentrated under reduced pressure. The obtained residue was purified by silica gel column chromatography to give the titled compound (206 mg) as a yellow solid.

$^1$H-NMR (400 MHz, CDCl$_3$) δ: 7.49 (1H, d, J=8.1 Hz), 7.44-7.36 (3H, m), 7.28-7.22 (1H, m), 7.04 (1H, d, J=8.1 Hz), 6.65 (1H, s), 5.45 (2H, s), 3.78 (2H, s), 3.69 (3H, s), 2.24 (3H, s).

(5) Synthesis of methyl [1-(2,6-dichlorobenzyl)-3-methyl-1H-indol-6-yl]difluoroacetate [49-5] (hereinafter referred to as a compound [49-5])

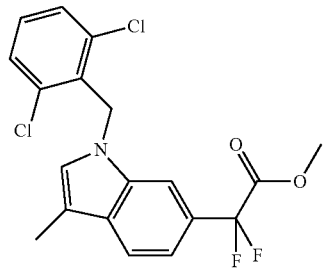 [SMILES: COC(=O)C(F)(F)c1ccc2c(C)cn(Cc3c(Cl)cccc3Cl)c2c1]

The titled compound (26 mg) as a yellow solid was prepared from the compound [49-4] (77 mg) according to the method of the process (5) in Example 3.

$^1$H-NMR (400 MHz, CDCl$_3$) δ: 7.78 (1H, s), 7.59 (1H, d, J=7.8 Hz), 7.45-7.20 (4H, m), 6.81 (1H, s), 5.51 (2H, s), 3.84 (3H, s), 2.26 (3H, s).

(6) Synthesis of [1-(2,6-dichlorobenzyl)-3-methyl-1H-indol-6-yl]difluoroacetic acid [49]

To a solution of the compound [49-5] (26 mg) in methanol (1 mL) were added an aqueous solution of 1N-sodium hydroxide (0.14 mL), and the mixture was stirred at room temperature for 4 hours. 2N-hydrochloric acid was added to the reaction mixture, and the mixture was extracted with ethyl acetate. The obtained organic layer was dried over anhydrous sodium sulfate, filtered, and the filtrate was concentrated under reduced pressure. The obtained residue was purified by SO₃H silica gel column chromatography to give the titled compound (15 mg) as a yellow solid.

$^1$H-NMR (400 MHz, CD$_3$OD) δ: 7.78 (1H, s), 7.57 (1H, d, J=8.3 Hz), 7.49 (1H, s), 7.47 (1H, s), 7.37 (1H, dd, J=8.8, 7.3 Hz), 7.27 (1H, dd, J=8.3, 1.5 Hz), 6.85 (1H, s), 5.58 (2H, s), 2.25 (3H, s).

ESI-MS found: 384 [M+H]$^+$

Example 50

Synthesis of 1-(2,6-dichlorobenzyl)-6-[difluoro(1H-tetrazol-5-yl)methyl]-3-methyl-1H-indazole [50] (hereinafter referred to as a compound [50])

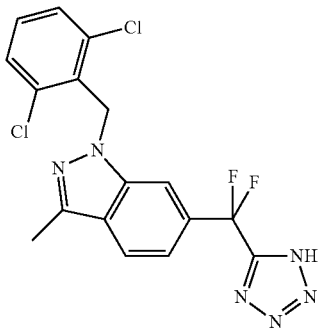 [SMILES: Cc1nn(Cc2c(Cl)cccc2Cl)c2cc(C(F)(F)c3nnn[nH]3)ccc12]

(1) Synthesis of [1-(2,6-dichlorobenzyl)-3-methyl-1H-indazol-6-yl]difluoroacetamide [50-1] (hereinafter referred to as a compound [50-1])

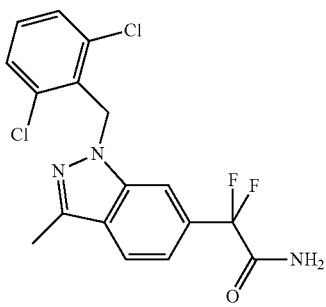 [SMILES: Cc1nn(Cc2c(Cl)cccc2Cl)c2cc(C(F)(F)C(N)=O)ccc12]

To a solution of the compound [1] (192 mg) in tetrahydrofuran (5 mL) were added thionyl chloride (180 μL) and N,N-dimethylformamide (18 μL) at room temperature, and the mixture was stirred at 60° C. for 1 hour. The reaction mixture was concentrated under reduced pressure. The obtained residue was then dissolved in tetrahydrofuran (3 mL), and the solution was added to a solution of 28% ammonia (500 μL) in tetrahydrofuran (2 mL) at 0° C., and the mixture was stirred at 0° C. for 1 hour. An aqueous solution of 3N-sodium hydroxide was added to the reaction mixture, and the mixture was extracted with ethyl acetate. The obtained organic layer was dried over anhydrous sodium sulfate, filtered, and the filtrate was concentrated under reduced pressure to give the titled compound (125 mg) as a white solid.

$^1$H-NMR (400 MHz, CD$_3$OD) δ: 7.86 (1H, s), 7.79 (1H, d, J=7.8 Hz), 7.45 (2H, d, J=7.6 Hz), 7.38-7.33 (2H, m), 5.80 (2H, s), 2.50 (3H, s).

(2) Synthesis of [1-(2,6-dichlorobenzyl)-3-methyl-1H-indazol-6-yl]difluoroacetonitrile[50-2] (hereinafter referred to as a compound [50-2])

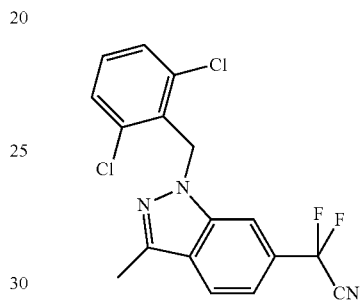

To a solution of the compound [50-1] (65 mg) in 1,4-dioxane (1.7 mL) were sequentially added triethylamine (187 μL) and trifluoroacetic anhydride (93 μL) at 0° C., and the mixture was stirred at 0° C. for 5 minutes. The reaction mixture was quenched with water, and extracted with ethyl acetate. The obtained organic layer was dried over anhydrous sodium sulfate, filtered, and the filtrate was concentrated under reduced pressure to give the titled compound (61 mg) as a yellow solid.

$^1$H-NMR (400 MHz, CDCl$_3$) δ: 7.78 (1H, d, J=8.3 Hz), 7.70 (1H, s), 7.40 (2H, d, J=7.8 Hz), 7.35 (1H, d, J=8.3 Hz), 7.29-7.25 (1H, m), 5.80 (2H, s), 2.56 (3H, s).

(3) Synthesis of 1-(2,6-dichlorobenzyl)-6-[difluoro (1H-tetrazol-5-yl)methyl]-3-methyl-1H-indazole [50]

To a solution of the compound [50-2] (61 mg) in N,N-dimethylformamide (3.3 mL) was added sodium azide (16 mg), and the mixture was subjected microwave irradiation at 110° C. for 30 minutes. After cooling, 3N-hydrochloric acid was then added to the reaction mixture, and the mixture was extracted with ethyl acetate. The obtained organic layer was dried over anhydrous sodium sulfate, filtered, and the filtrate was concentrated under reduced pressure. The obtained residue was purified by silica gel column chromatography to give the titled compound (57 mg) as a white solid.

$^1$H-NMR (400 MHz, CD$_3$OD) δ: 7.75 (1H, d, J=8.3 Hz), 7.67 (1H, s), 7.43-7.41 (2H, m), 7.35-7.31 (2H, m), 5.77 (2H, s), 2.49 (3H, s).

ESI-MS found: 409 [M+H]$^+$

Example 51

Synthesis of potassium 5-[1-(2,6-dichlorobenzyl)-3-methyl-1H-indazol-6-yl]difluoromethyl-1H-tetrazol-1-ide [51] (hereinafter referred to as a compound [51])

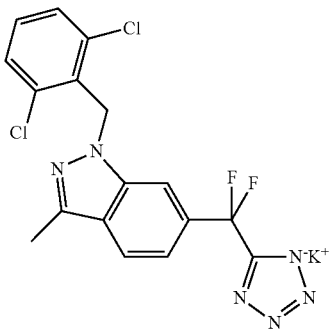

To a solution of the compound [50] (48 mg) in ethanol (2 mL) was added an aqueous solution of 1N-potassium hydroxide (117 μL) at room temperature, and the solution was concentrated under reduced pressure to give the titled compound (51 mg) as a yellow solid.
$^1$H-NMR (400 MHz, CD$_3$OD) δ: 7.75 (1H, d, J=8.5 Hz), 7.67 (1H, s), 7.43-7.41 (2H, m), 7.35-7.31 (2H, m), 5.77 (2H, s), 2.49 (3H, s).
ESI-MS found: 409 [M−K+2H]$^+$

Example 52

Synthesis of [1-(2-cyano-6-methylbenzyl)-3-methyl-1H-indol-6-yl]difluoroacetic acid [52] (hereinafter referred to as a compound [52])

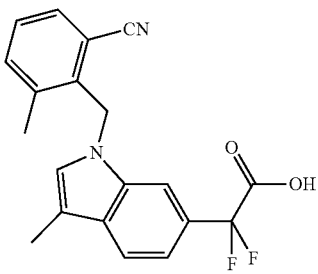 [SMILES: Cc1cccc(C#N)c1Cn1cc(C)c2ccc(C(F)(F)C(=O)O)cc21]

(1) Synthesis of difluoro(3-methyl-1-tosyl-1H-indol-6-yl)acetonitrile [52-1] (hereinafter referred to as a compound [52-1])

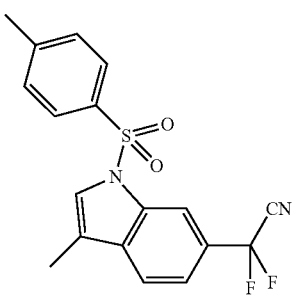 [SMILES: Cc1ccc(S(=O)(=O)n2cc(C)c3ccc(C(F)(F)C#N)cc32)cc1]

The titled compound (180 mg) as a yellow solid was prepared from the compound [49-2] (1.16 g) according to the method of the process (5) in Example 3.
$^1$H-NMR (400 MHz, CDCl$_3$) δ: 8.30 (1H, d, J=0.7 Hz), 7.77 (2H, d, J=8.5 Hz), 7.60 (1H, d, J=8.3 Hz), 7.52-7.50 (2H, m), 7.27-7.25 (2H, m), 2.36 (3H, s), 2.28 (3H, s).

(2) Synthesis of difluoro(3-methyl-1H-indol-6-yl)acetic acid [52-2] (hereinafter referred to as a compound [52-2])

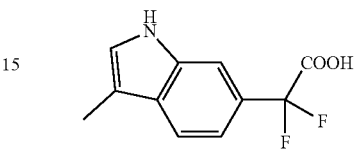

To a solution of the compound [52-1] (180 mg) in ethanol (5 mL) was added an aqueous solution of 3N-sodium hydroxide (3 mL) at room temperature, and the mixture was stirred at 80° C. for 8 hours. 2N-hydrochloric acid was added to the reaction mixture, and the mixture was extracted with chloroform. The obtained organic layer was dried over anhydrous sodium sulfate, filtered, and the filtrate was concentrated under reduced pressure. The obtained residue was purified by silica gel column chromatography to give the titled compound (69 mg) as a white solid.
$^1$H-NMR (400 MHz, CD$_3$OD) δ: 8.06 (1H, t, J=0.7 Hz), 7.67 (1H, dd, J=8.5, 1.5 Hz), 7.61 (1H, dd, J=8.5, 0.7 Hz), 7.32 (1H, d, J=1.0 Hz), 2.33 (3H, d, J=1.0 Hz).

(3) Synthesis of 2-iodo-6-methylbenzyl difluoro[1-(2-iodo-6-methylbenzyl)-3-methyl-1H-indol-6-yl]acetate [52-3] (hereinafter referred to as a compound [52-3])

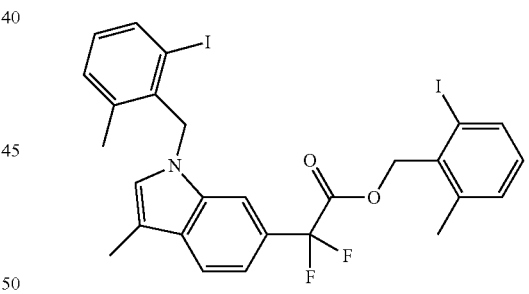

The titled compound (92 mg) as a yellow solid was prepared from the compound [52-2] (69 mg) according to the method of the process (1) in Example 1.
$^1$H-NMR (400 MHz, CDCl$_3$) δ: 8.17 (1H, d, J=1.2 Hz), 7.83 (1H, d, J=8.5 Hz), 7.79 (1H, dd, J=8.5, 1.5 Hz), 7.73 (1H, d, J=7.6 Hz), 7.61 (1H, d, J=8.5 Hz), 7.26-7.18 (2H, m), 7.01 (1H, t, J=7.8 Hz), 6.93 (1H, t, J=7.8 Hz), 6.66 (1H, d, J=1.0 Hz), 5.66 (2H, s), 5.39 (2H, s), 2.53 (3H, s), 2.24 (3H, d, J=0.7 Hz), 2.21 (3H, s).

(4) Synthesis of [1-(2-cyano-6-methylbenzyl)-3-methyl-1H-indol-6-yl]difluoroacetic acid [52] (hereinafter referred to as a compound [52])

To a solution of the compound [52-3] (90 mg) in tetrahydrofuran (2 mL) were added methanol (2 mL) and an aqueous solution of 1N-sodium hydrogen carbonate (2 mL) at room temperature, and the mixture was stirred at 80° C. for 2 days. 1N-hydrochloric acid was added to the reaction mixture, and the mixture was extracted with chloroform. The obtained organic layer was dried over anhydrous sodium sulfate, filtered, and the filtrate was concentrated under reduced pressure. The titled compound (5 mg) was obtained as a yellow solid from the obtained residue according to the method of the process (5) in the following Example 55.

$^1$H-NMR (400 MHz, DMSO-d$_6$) δ: 8.04 (1H, s), 7.94 (1H, s), 7.84-7.79 (1H, m), 7.61-7.49 (3H, m), 6.87 (1H, s), 5.50 (2H, s), 2.19 (3H, s), 2.15 (3H, s).

Example 53

Synthesis of [1-(2-cyano-6-hydroxymethylbenzyl)-3-methyl-1H-indazol-6-yl]difluoroacetic acid [53] (hereinafter referred to as a compound [53])

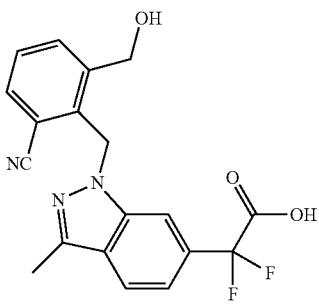 [SMILES: Cc1nn(Cc2c(C#N)cccc2CO)c2cc(C(F)(F)C(=O)O)ccc12]

(1) Synthesis of 3-bromo-2-methylbenzyl acetate [53-1] (hereinafter referred to as a compound [53-1])

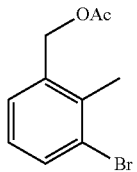

To a solution of 3-bromo-2-methylbenzoic acid (490 mg) in tetrahydrofuran (10 mL) were added sodium borohydride (519 mg) and iodine (878 mg), and the mixture was stirred at room temperature for 20 hours. 1N-hydrochloric acid was added to the reaction mixture, and the mixture was extracted with chloroform. The obtained organic layer was dried over anhydrous sodium sulfate, filtered, and the filtrate was concentrated under reduced pressure. The obtained residue was dissolved in tetrahydrofuran (10 mL). To the solution were added triethylamine (1.2 mL) and acetic anhydride (0.82 mL), and the mixture was heated at reflux for 20 hours. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (664 mg) as a colorless oil.

$^1$H-NMR (400 MHz, CDCl$_3$) δ: 7.55 (1H, d, J=8.1 Hz), 7.28 (1H, d, J=7.6 Hz), 7.05 (1H, t, J=7.8 Hz), 5.14 (2H, s), 2.42 (3H, s), 2.11 (3H, s).

(2) Synthesis of 3-bromo-2-bromomethylbenzaldehyde [53-2] (hereinafter referred to as a compound [53-2])

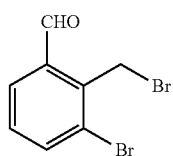 [SMILES: O=Cc1cccc(Br)c1CBr]

The titled compound (168 mg) as a white solid was prepared from the compound [53-1] (232 mg), N-bromosuccinimide (381 mg) and α,α'-azobis(isobutyronitrile) (22 mg) according to the method of the process (2) in Example 5.

$^1$H-NMR (400 MHz, CDCl$_3$) δ: 10.19 (1H, s), 7.85-7.80 (2H, m), 7.42-7.38 (1H, m), 5.14 (2H, s).

(3) Synthesis of 2-trimethylsilylethyl 6-bromo-3-methylindazole-1-carboxylate [53-3] (hereinafter referred to as a compound [53-3])

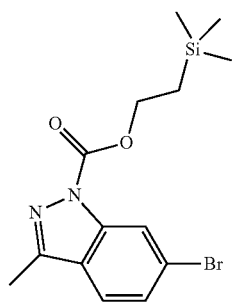

To a solution of 6-bromo-3-methyl-1H-indazole (1.0 g), which was obtained by the method described in the document (JP 2009-528363 W), in 1,4-dioxane (24 mL) were added sodium hydride (227 mg) and N-[2-(trimethylsilyl)ethoxycarbonyloxy]succinimide (1.84 g) at room temperature, and the mixture was stirred at room temperature for 2 hours. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (1.44 g) as a colorless oil.

ESI-MS found: 355 [M+H]

(4) Synthesis of 2-trimethylsilylethyl 6-tert-butoxycarbonylmethyl-3-methylindazole-1-carboxylate [53-4] (hereinafter referred to as a compound [53-4])

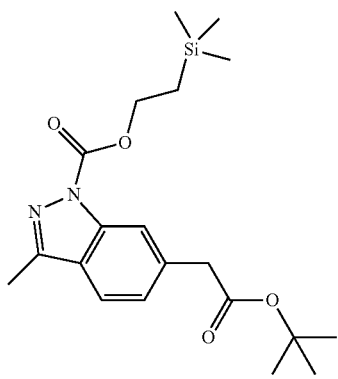 [SMILES: Cc1nn(C(=O)OCC[Si](C)(C)C)c2cc(CC(=O)OC(C)(C)C)ccc12]

The titled compound (756 mg) as a red oil was prepared from the compound [53-3] (1.44 g), bis(dibenzylideneacetone)palladium(0) (47 mg), 1,2,3,4,5-pentaphenyl-1'-(di-tert-butylphosphino)ferrocene (58 mg) and 0.5M diethyl ether solution of 2-tert-butoxy-2-oxoethylzinc chloride (18 mL) according to the method of the process (4) in Example 3.

ESI-MS found: 391 [M+H]$^+$

(5) Synthesis of 2-trimethylsilylethyl 6-(tert-butoxycarbonyldifluoromethyl)-3-methyl-indazole-1-carboxylate[53-5] (hereinafter referred to as a compound [53-5])

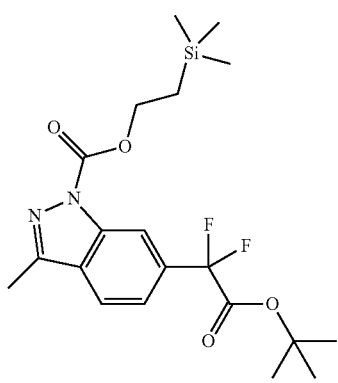 [SMILES: Cc1nn(C(=O)OCC[Si](C)(C)C)c2cc(C(F)(F)C(=O)OC(C)(C)C)ccc12]

The titled compound (424 mg) as a colorless oil was prepared from the compound [53-4] (583 mg) according to the method of the process (5) in Example 3.

ESI-MS found: 427 [M+H]$^+$

(6) Synthesis of tert-butyl difluoro(3-methyl-1H-indazol-6-yl)acetate [53-6] (hereinafter referred to as a compound [53-6])

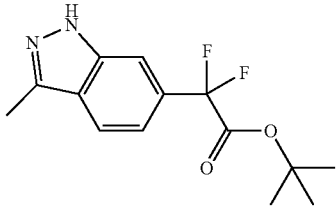 [SMILES: Cc1n[nH]c2cc(C(F)(F)C(=O)OC(C)(C)C)ccc12]

A solution of the compound [53-5] (260 mg) in tetrahydrofuran (6 mL) was cooled to 0° C., 1.0M aqueous solution of tetrabutylammonium fluoride (0.73 mL) was added to the solution, and the mixture was stirred at 0° C. for 1 hour. The reaction mixture was quenched with a satureated aqueous solution of ammonium chloride, and extracted with ethyl acetate. The obtained organic layer was dried over anhydrous sodium sulfate, filtered, and the filtrate was concentrated under reduced pressure. The obtained residue was purified by silica gel column chromatography to give the titled compound (179 mg) as a white solid.

ESI-MS found: 283 [M+H]$^+$

(7) Synthesis of tert-butyl [1-(2-bromo-6-formylbenzyl)-3-methyl-1H-indazol-6-yl]difluoroacetate [53-7] (hereinafter referred to as a compound [53-7])

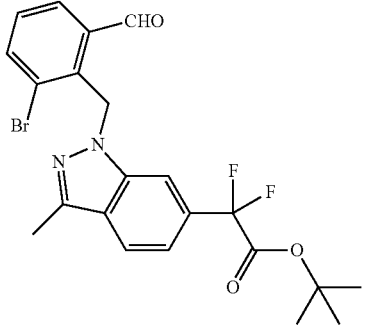 [SMILES: Cc1nn(Cc2c(Br)cccc2C=O)c2cc(C(F)(F)C(=O)OC(C)(C)C)ccc12]

The titled compound (26 mg) as a white solid was prepared from the compound [53-2] (63 mg) and the compound [53-6] (50 mg) according to the method of the process (1) in Example 1.

ESI-MS found: 479 [M+H]$^+$ (8) Synthesis of 1-(2-cyano-6-formylbenzyl)-3-methyl-1H-indazol-6-yl]difluoroacetic acid [53-8] (hereinafter referred to as a compound [53-8])

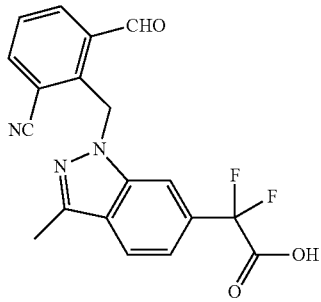 [SMILES: Cc1nn(Cc2c(C#N)cccc2C=O)c2cc(C(F)(F)C(=O)O)ccc12]

The titled compound (18 mg) as a white solid was prepared from the compound [53-7] (26 mg) according to the method of the process (5) in Example 5.

ESI-MS found: 370 [M+H]$^+$ (9) Synthesis of [1-(2-cyano-6-hydroxymethylbenzyl)-3-methyl-1H-indazol-6-yl]difluoroacetic acid [53]

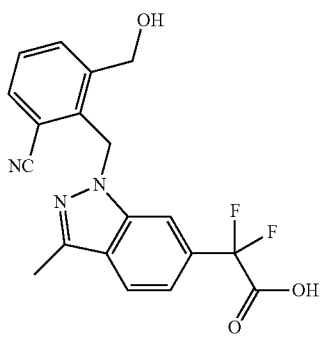 [SMILES: Cc1nn(Cc2c(C#N)cccc2CO)c2cc(C(F)(F)C(=O)O)ccc12]

To a solution of the compound [53-8] (18 mg) in methanol (2 mL) was added sodium borohydride (5 mg) at room temperature, and the mixture was stirred at room temperature for 10 minutes. The reaction mixture was quenched with a saturated aqueous solution of ammonium chloride, and extracted with chloroform. The obtained organic layer was dried over anhydrous sodium sulfate, filtered, and the filtrate was concentrated under reduced pressure to give the titled compound (15 mg) as a white solid.

$^1$H-NMR (400 MHz, CD$_3$OD) δ: 7.90 (1H, s), 7.82-7.80 (2H, m), 7.73 (1H, d, J=6.8 Hz), 7.55 (1H, t, J=7.8 Hz), 7.37 (1H, d, J=9.8 Hz), 5.80 (2H, s), 4.62 (2H, s), 2.50 (3H, s).

ESI-MS found: 372 [M+H]$^+$

Example 54

Synthesis of potassium [1-(2-cyano-6-hydroxymethylbenzyl)-3-methyl-1H-indazol-6-yl]difluoroacetate [54] (hereinafter referred to as a compound [54])

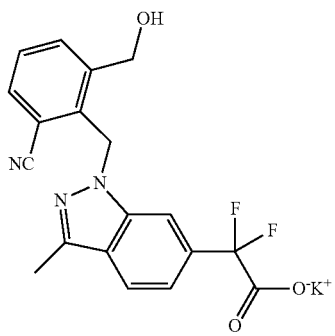

To a solution of the compound [53] (14 mg) in ethanol (2 mL) was added an aqueous solution of 1N-potassium hydroxide (37 μL) at room temperature, and the solution was concentrated under reduced pressure to give the titled compound (12 mg) as a white solid.

$^1$H-NMR (400 MHz, CD$_3$OD) δ: 7.89 (1H, s), 7.81 (1H, d, J=7.8 Hz), 7.74-7.72 (2H, m), 7.54 (1H, t, J=7.3 Hz), 7.44 (1H, d, J=9.8 Hz), 5.79 (2H, s), 4.52 (2H, s), 2.48 (3H, s).

Example 55

Synthesis of [1-(2-cyano-6-methylbenzyl)-3-cyclopropyl-1H-indazol-6-yl]difluoroacetic acid [55] (hereinafter referred to as a compound [55])

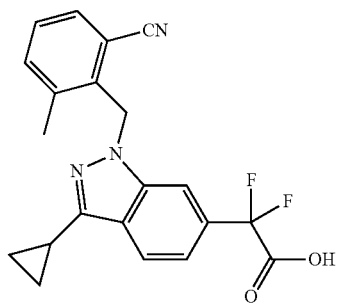 [SMILES: Cc1cccc(C#N)c1Cn1nc(C2CC2)c2ccc(C(F)(F)C(=O)O)cc21]

(1) 1-(4-bromo-2-fluorophenyl)-1-cyclopropylmethanol [55-1] (hereinafter referred to as compound [55-1])

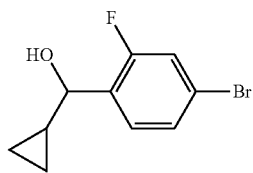 [SMILES: OC(c1ccc(Br)cc1F)C1CC1]

To a solution of 4-bromo-2-fluorobenzaldehyde (3.0 g) in diethyl ether (34 mL) was added 0.7M tetrahydrofuran solution of cyclopropylmagnesium bromide (20 mL), and the mixture was stirred at room temperature for 2 hours. The reaction mixture was quenched with a saturated aqueous solution of ammonium chloride, and extracted with ethyl acetate. The obtained organic layer was dried over anhydrous sodium sulfate, filtered, and the filtrate was concentrated under reduced pressure. The obtained residue was purified by silica gel column chromatography to give the titled compound (4.18 g) as a yellow liquid.

$^1$H-NMR (400 MHz, CDCl$_3$) δ: 7.44 (1H, t, J=7.9 Hz), 7.31 (1H, dd, J=8.1, 1.7 Hz), 7.22 (1H, dd, J=9.8, 1.7 Hz), 4.33 (1H, dd, J=8.3, 3.4 Hz), 0.64 (1H, dd, J=5.1, 2.9 Hz), 0.54-0.41 (4H, m).

(2) Synthesis of 6-bromo-3-cyclopropyl-1H-indazole [55-2] (hereinafter referred to as a compound [55-2])

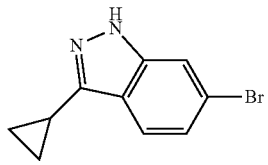 [SMILES: Brc1ccc2c(C3CC3)n[nH]c2c1]

To a solution of the compound [55-1] (3.62 g) in 1,4-dioxane (25 mL) was added manganese dioxide (6.12 g), and the mixture was stirred at 115° C. for 12 hours. The reaction mixture was filtered by Celite, and the filtrate was concentrated under reduced pressure. The obtained residue was purified by silica gel column chromatography to give a colorless oil (457 mg). To a solution of the above obtained oil in ethylene glycol (10 mL) was added hydrazine monohydrate (0.3 mL), and the mixture was stirred at 140° C. for 12 hours. Water was added to the reaction mixture, and the mixture was extracted with chloroform. The obtained organic layer was dried over anhydrous sodium sulfate, filtered, and the filtrate was concentrated under reduced pressure. The obtained residue was purified by silica gel column chromatography to give the titled compound (202 mg) as a yellow solid.

$^1$H-NMR (400 MHz, CDCl$_3$) δ: 9.57 (1H, br), 7.61 (2H, t, J=12.5 Hz), 7.27-7.23 (1H, m), 2.22-2.17 (1H, m), 1.06-1.04 (4H, m).

(3) Synthesis of 2-iodo-6-methylbenzyl chloride [55-3] (hereinafter referred to as a compound [55-3])

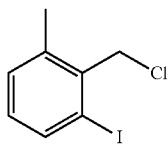

To a suspension of 2-amino-6-methylbenzoic acid (2.01 g) in water (4 mL) was added concentrated hydrochloric acid (5 mL) at 0° C. To the mixture were added a solution of sodium nitrite (1.19 g) in water (3 mL) and a solution of potassium iodide (7.18 g) in water (5 mL) at 0° C. After warmed up to room temperature, the mixture was stirred for 20 hours. Water was added to the reaction mixture, and the mixture was extracted with ethyl acetate. The obtained organic layer was dried over anhydrous sodium sulfate, filtered, and the filtrate was concentrated under reduced pressure. The obtained residue was dissolved in tetrahydrofuran (30 mL), and to the mixture was added boranedimethylsulfide complex (9.0 mL) at room temperature, and the mixture was heated at reflux for 2 hours. Methanol and water were added to the reaction mixture, and the mixture was extracted with ethyl acetate. The obtained organic layer was dried over anhydrous sodium sulfate, filtered, and the filtrate was concentrated under reduced pressure. The obtained residue was dissolved in dimethylsulfoxide (20 mL). To the mixture was added cyanuric chloride (2.70 g) at 0° C., and the mixture was stirred at 0° C. for 30 minutes. Water was added to the reaction mixture, and extracted with hexane. The obtained organic layer was dried over anhydrous sodium sulfate, filtered, and the filtrate was concentrated under reduced pressure to give the titled compound (2.28 g) as a yellow solid.

$^1$H-NMR (400 MHz, CDCl$_3$) δ: 7.73 (1H, d, J=8.1 Hz), 7.16 (1H, d, J=7.3 Hz), 6.90 (1H, t, J=7.8 Hz), 4.81 (2H, s), 2.52 (3H, s).

(4) Synthesis of [6-bromo-3-cyclopropyl-1-(2-iodo-6-methylbenzyl)-1H-indazole [55-4] (hereinafter referred to as a compound [55-4])

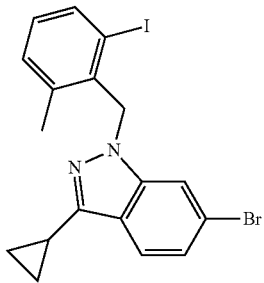 [SMILES: Cc1cccc(I)c1Cn1nc(C2CC2)c2ccc(Br)cc21]

The titled compound (360 mg) as a white solid was prepared from the compound [55-2] (202 mg) and the compound [55-3] (250 mg) according to the method of the process (1) in Example 1.

$^1$H-NMR (400 MHz, CDCl$_3$) δ: 7.80 (1H, d, J=8.3 Hz), 7.54 (1H, d, J=7.8 Hz), 7.34 (1H, d, J=1.0 Hz), 7.18-7.14 (3H, m), 5.58 (2H, s), 2.28 (3H, s), 2.14 (1H, m), 0.99 (4H, dt, J=6.2, 2.1 Hz).

(5) Synthesis of 2-(6-bromo-3-cyclopropylindazol-1-ylmethyl)-3-methylbenzonitrile[55-5] (hereinafter referred to as a compound [55-5])

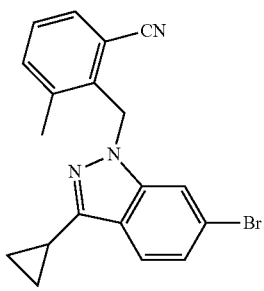 [SMILES: Cc1cccc(C#N)c1Cn1nc(C2CC2)c2ccc(Br)cc21]

To a solution of the compound [55-4] (360 mg) in N,N-dimethylformamide (5 mL) were added zinc cyanide (145 mg) and tetrakis(triphenylphosphine)palladium(0) (177 mg) and the mixture was stirred at 80° C. for 1.5 hours.

The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (147 mg) as a white solid.

ESI-MS found: 366 [M+H]+

(6) Synthesis of tert-butyl [1-(2-cyano-6-methylbenzyl)-3-cyclopropyl-1H-indazol-6-yl]acetate [55-6] (hereinafter referred to as a compound [55-6])

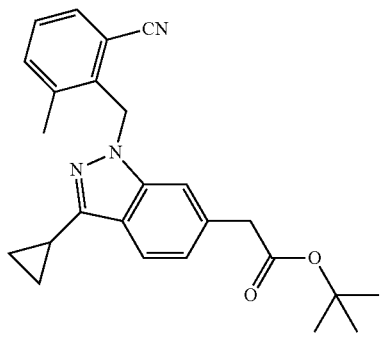 [SMILES: Cc1cccc(C#N)c1Cn1nc(C2CC2)c2ccc(CC(=O)OC(C)(C)C)cc21]

The titled compound (36 mg) as a red oil was prepared from a solution of the compound [55-5] (122 mg) in tetrahydrofuran (2 mL), bis(dibenzylideneacetone)palladium(0) (10 mg), 1,2,3,4,5-pentaphenyl-1'-(di-tert-butylphosphino)ferrocene (10 mg) and 0.5M diethyl ether solution of 2-(tert-butoxy)-2-oxoethylzinc bromide (1.3 mL) according to the method of the process (4) in Example 3.

ESI-MS found: 402 [M+H]+

(7) Synthesis of tert-butyl [1-(2-cyano-6-methylbenzyl)-3-cyclopropyl-1H-indazol-6-yl]difluoroacetate [55-7] (hereinafter referred to as a compound [55-7])

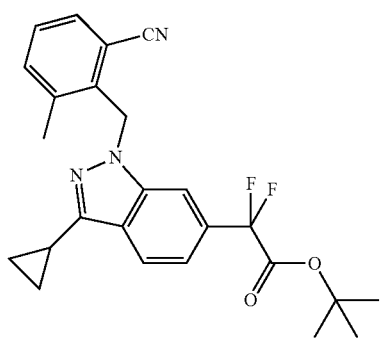 [SMILES: Cc1cccc(C#N)c1Cn1nc(C2CC2)c2ccc(C(F)(F)C(=O)OC(C)(C)C)cc21]

The titled compound (43 mg) as a yellow oil was prepared from the compound [55-6] (54 mg) according to the method of the process (5) in Example 3.

ESI-MS found: 438 [M+H]+

(8) Synthesis of [1-(2-cyano-6-methylbenzyl)-3-cyclopropyl-1H-indazol-6-yl]difluoroacetic acid [55]

The titled compound (5 mg) as a white solid was prepared from the compound [55-7] (43 mg) according to the method of the process (6) in Example 3.

1H-NMR (400 MHz, CD3OD) δ: 7.79 (2H, t, J=7.8 Hz), 7.63 (1H, t, J=6.5 Hz), 7.49 (1H, d, J=7.3 Hz), 7.40 (2H, dd, J=8.5, 7.3 Hz), 5.66 (2H, s), 2.22-2.17 (4H, m), 1.01-0.96 (4H, m).

Example 56

Synthesis of [1-(2-cyano-6-methylbenzyl)-3-isopropyl-1H-indazol-6-yl]difluoroacetic acid [56] (hereinafter referred to as a compound [56])

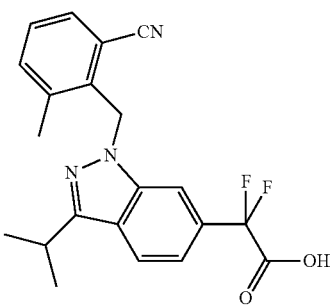 [SMILES: Cc1cccc(C#N)c1Cn1nc(C(C)C)c2ccc(C(F)(F)C(=O)O)cc21]

The titled compound (8.7 mg) as a white solid was prepared from 4-bromo-2-fluorobenzaldehyde (4.0 g) and 1.0M ether solution of isopropylmagnesium chloride (32 mL) according to the method of Example 55.

1H-NMR (400 MHz, CD3OD) δ: 7.82 (2H, t, J=5.9 Hz), 7.64 (1H, d, J=7.8 Hz), 7.50 (1H, d, J=7.1 Hz), 7.40 (2H, dd, J=16.1, 8.3 Hz), 5.73 (2H, s), 3.35 (1H, q, J=7.0 Hz), 2.24 (3H, s), 1.39 (6H, dd, 16.5, 8.4 Hz).

Example 57

Synthesis of [3-chloro-1-(2-cyano-6-methylbenzyl)-1H-indazol-6-yl]difluoroacetic acid [57] (hereinafter referred to as a compound [57])

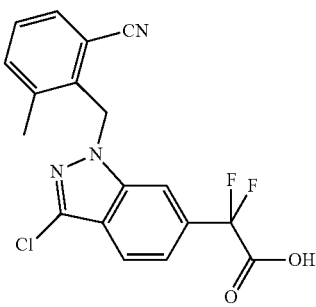 [SMILES: Cc1cccc(C#N)c1Cn1nc(Cl)c2ccc(C(F)(F)C(=O)O)cc21]

(1) Synthesis of 6-bromo-3-chloro-1-(2-iodo-6-methylbenzyl)-1H-indazole [57-1] (hereinafter referred to as a compound [57-1])

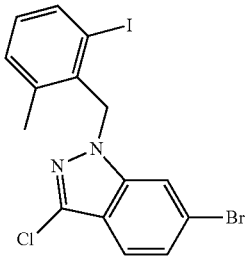 [SMILES: Cc1cccc(I)c1Cn1nc(Cl)c2ccc(Br)cc21]

The titled compound (1.26 g) as a white solid was prepared from the compound [34-1] (728 mg) and the compound [55-3] (920 mg) according to the method of the process (1) in Example 1.
ESI-MS found: 462 [M+H]$^+$ (2) Synthesis of 2-(6-bromo-3-chloroindazol-1-ylmethyl)-3-methylbenzonitrile[57-2] (hereinafter referred to as a compound [57-2])

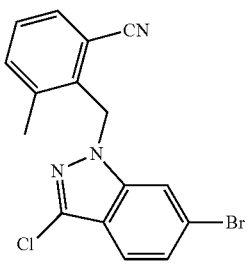 [SMILES: Cc1cccc(C#N)c1Cn1nc(Cl)c2ccc(Br)cc21]

The titled compound (384 mg) as a yellow solid was prepared from the compound [57-1] (1.26 g) according to the method of the process (5) in Example 55.
ESI-MS found: 362 [M+H]$^+$ (3) Synthesis of 2-(3-chloro-6-tributylstannylindazol-1-ylmethyl)-3-methylbenzonitrile[57-3] (hereinafter referred to as a compound [57-3])

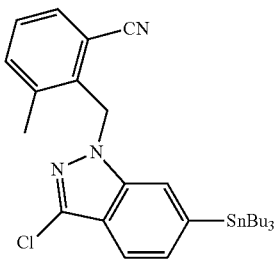

The titled compound (171 mg) as a yellow oil was prepared from the compound [57-2] (147 mg) according to the method of the process (2) in Example 1.
ESI-MS found: 572 [M+H]$^+$ (4) Synthesis of ethyl [3-chloro-1-(2-cyano-6-methylbenzyl)-1H-indazol-6-yl]oxoacetate [57-4] (hereinafter referred to as a compound [57-4])

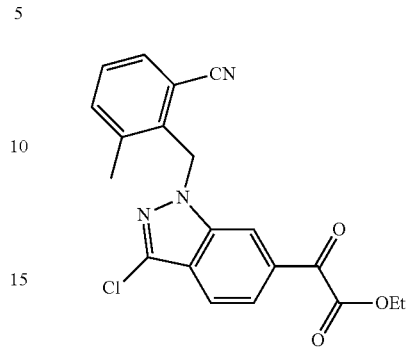

The titled compound (28 mg) as a yellow oil was prepared from the compound [57-3] (171 mg) according to the method of the process (3) in Example 1.
ESI-MS found: 382 [M+H]$^+$ (5) Synthesis of ethyl [3-chloro-1-(2-cyano-6-methylbenzyl)-1H-indazol-6-yl]difluoroacetate [57-5] (hereinafter referred to as a compound [57-6])

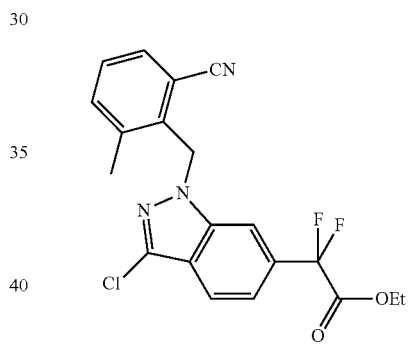

The titled compound (19 mg) as a colorless oil was prepared from the compound [57-4] (28 mg) according to the method of the process (4) in Example 1.
ESI-MS found: 404 [M+H]$^+$ (6) Synthesis of [3-chloro-1-(2-cyano-6-methylbenzyl)-1H-indazol-6-yl]difluoroacetic acid [57]

To a solution of the compound [57-5] (32 mg) in ethanol (2 mL) was added an aqueous solution of 1N-sodium hydrogen carbonate (2 mL), and the mixture was stirred at 60° C. for 1 hour. A saturated aqueous solution of ammonium chloride was added to the reaction mixture, and the mixture was extracted with chloroform. The obtained organic layer was dried over anhydrous sodium sulfate, filtered, and the filtrate was concentrated under reduced pressure to give the titled compound (10 mg) as a white solid.
$^1$H-NMR (400 MHz, CD$_3$OD) δ: 8.01 (1H, s), 7.73-7.65 (2H, m), 7.53 (2H, dd, J=8.5, 1.2 Hz), 7.44 (1H, dd, J=9.1, 6.2 Hz), 5.78 (2H, s), 2.27 (3H, s).
ESI-MS found: 376 [M+H]$^+$

Example 58

Synthesis of 2-{6-[difluoro(1H-tetrazol-5-yl)methyl]-3-methylpyrazolo[4,3-b]pyridin-1-ylmethyl}-3-methylbenzonitrile[58] (henceforth a compound [58])

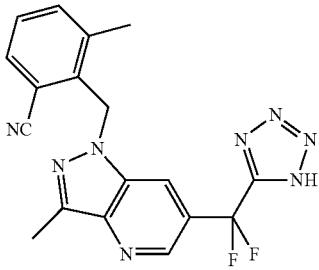 [SMILES: Cc1cccc(C#N)c1Cn1nc(C)c2ncc(C(F)(F)c3nnn[nH]3)cc21]

(1) Synthesis of 6-bromo-3-methyl-1-tosyl-1H-pyrazolo[4,3-b]pyridine [58-1] (hereinafter referred to as a compound [58-1])

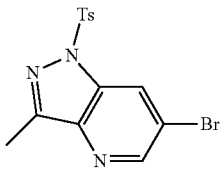 [SMILES: Cc1ccc(S(=O)(=O)n2nc(C)c3ncc(Br)cc32)cc1]

A solution of the compound [37-2] (1.03 g) in tetrahydrofuran (10 mL) was cooled to 0° C., and 1.0M tetrahydrofuran solution of potassium tertbutoxide (5.0 mL) and 4-toluenesulfonyl chloride (937 mg) were added to the mixture at 0° C., and the mixture was stirred at 0° C. for 1 hour. Water was added to the reaction mixture, and the precipitated solid was filtered to give the titled compound (1.48 g) as a yellow solid.
ESI-MS found: 366 [M+H]$^+$ (2) Synthesis of 3-methyl-1-tosyl-1H-pyrazolo[4,3-b]pyridine-6-carboaldehyde [58-2] (hereinafter referred to as a compound [58-2])

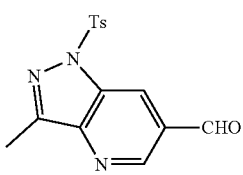

To a solution of the compound [58-1] (1.48 g) in n-propanol (10 mL) were added potassium vinyltrifluoroborate (599 mg), [1,1'-bis(diphenylphosphino)ferrocene]dichloropalladium(II) (67 mg) and triethylamine (1 mL) at room temperature, and the mixture was heated at reflux for 2 hours. The reaction mixture was quenched with water, and extracted with ethyl acetate. The obtained organic layer was dried over anhydrous sodium sulfate, filtered, and the filtrate was concentrated under reduced pressure to give a residue. The obtained residue was dissolved in tert-butanol (12 mL) and water (5 mL), a 4% aqueous osmium tetroxide solution (1 mL) and sodium periodate (2.66 g) were added to the mixture at room temperature, and the mixture was stirred at room temperature for 20 hours. The reaction mixture was quenched with a saturated aqueous solution of sodium thiosulfate, and extracted with ethyl acetate. The obtained organic layer was dried over anhydrous sodium sulfate, filtered, and the filtrate was concentrated under reduced pressure. The obtained residue was purified by silica gel column chromatography to give the titled compound (574 mg) as a yellow solid.
ESI-MS found: 316 [M+H]$^+$ (3) Synthesis of [1-(4-methoxybenzyl)-1H-tetrazol-5-yl][3-methyl-1-tosyl-1H-pyrazolo[4,3-b]pyridin-6-yl]methanone [58-3] (hereinafter referred to as a compound [58-3])

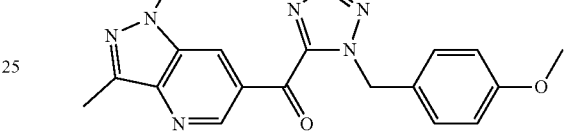

To a solution of 1-(4-methoxybenzyl)tetrazole (693 mg), which was obtained by the method described in the document (Tetrahedron Letters, 1995, Vol. 36, No. 11, pp. 1759-1762), in tetrahydrofuran (40 mL) was added N,N,N',N'-tetramethylethylenediamine (4 mL) at room temperature. The reaction mixture was cooled to −98° C., and a 1.64M n-hexane solution of n-butyllithium (2.2 mL) was added at −98° C. After addition of a solution of the compound [58-2] (574 mg) in tetrahydrofuran (15 mL) at −98° C., and the mixture was stirred at −98° C. for 30 minutes. The reaction mixture was quenched with a saturated aqueous solution of ammonium chloride, and extracted with ethyl acetate. The obtained organic layer was dried over anhydrous sodium sulfate, filtered, and the filtrate was concentrated under reduced pressure. The obtained residue was dissolved in 1,4-dioxane (15 mL), manganese dioxide (1.72 g) was added at room temperature, and the mixture was stirred at room temperature for 3 days. The reaction mixture was filtered, the filtrate was concentrated under reduced pressure to give a residue, and the obtained residue was purified by silica gel column chromatography to give the titled compound (631 mg) as a yellow solid.
ESI-MS found: 504 [M+H]$^+$ (4) Synthesis of 6-{difluoro[1-(4-methoxybenzyl)-1H-tetrazol-5-yl]methyl}-3-methyl-1-tosyl-1H-pyrazolo[4,3-b]pyridine [58-4] (hereinafter referred to as a compound [58-4])

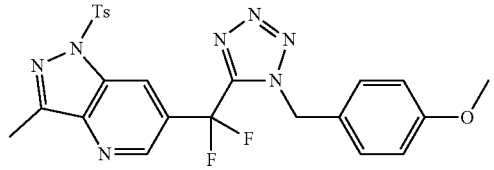

To a solution of the compound [58-3] (628 mg) in dichloromethane (5 mL) were added bis(2-methoxyethyl)aminosulfur trifluoride (1.2 mL) and ethanol (0.1 mL) at room temperature, and the mixture was stirred at room temperature for 5 days. Water and an aqueous solution of 5N-sodium hydroxide were added to the reaction mixture, and the mixture was extracted with chloroform. The obtained organic layer was dried over anhydrous sodium sulfate, filtered, and the filtrate was concentrated under reduced pressure. The obtained residue was purified by silica gel column chromatography to give the titled compound (131 mg) as a yellow solid.

ESI-MS found: 526 [M+H]+

(5) Synthesis of 6-{difluoro[1-(4-methoxybenzyl)-1H-tetrazol-5-yl]methyl}-3-methyl-1H-pyrazolo[4,3-b]pyridine [58-5] (hereinafter referred to as a compound [58-5])

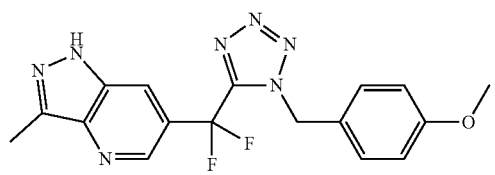

To a solution of the compound [58-4] (129 mg) in tetrahydrofuran (3 mL) was added an aqueous solution of 5N-sodium hydroxide (3 mL) at room temperature, and the mixture was heated at reflux for 1 hour. The reaction mixture was quenched with water, and extracted with chloroform. The obtained organic layer was dried over anhydrous sodium sulfate, filtered, and the filtrate was concentrated under reduced pressure. The obtained residue was purified by silica gel column chromatography to give the titled compound (84 mg) as a white solid.

ESI-MS found: 372 [M+H]+

(6) Synthesis of 6-{difluoro[1-(4-methoxybenzyl)-1H-tetrazol-5-yl]methyl}-1-(2-iodo-6-methylbenzyl)-3-methyl-1H-pyrazolo[4,3-b]pyridine [58-6] (hereinafter referred to as a compound [58-6])

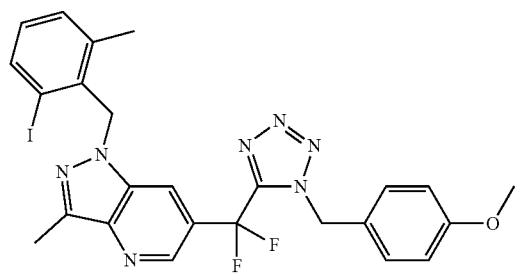 [SMILES: COc1ccc(Cn2nnnc2C(F)(F)c2cnc3c(C)nn(Cc4c(C)cccc4I)c3c2)cc1]

The titled compound (31 mg) as a yellow solid was prepared from the compound [58-5] (41 mg) and the compound [55-3] (63 mg) according to the method of the process (1) in Example 1.

ESI-MS found: 602 [M+H]+

(7) Synthesis of 2-(6-{difluoro[1-(4-methoxybenzyl)-1H-tetrazol-5-yl]methyl}-3-methyl-1H-pyrazolo[4,3-b]pyridin-1-ylmethyl)-3-methylbenzonitrile[58-7] (hereinafter referred to as a compound [58-7])

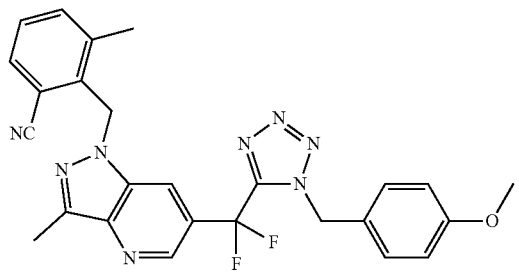 [SMILES: COc1ccc(Cn2nnnc2C(F)(F)c2cnc3c(C)nn(Cc4c(C)cccc4C#N)c3c2)cc1]

The titled compound (26 mg) as a yellow solid was prepared from the compound [58-6] (31 mg) according to the method of the process (5) in Example 5.

ESI-MS found: 501 [M+H]+

(8) Synthesis of 2-{6-[difluoro(1H-tetrazol-5-yl)methyl]-3-methylpyrazolo[4,3-b]pyridin-1-ylmethyl}-3-methylbenzonitrile[58]

Anisole (100 μL) and trifluoroacetic acid (2 mL) were added to the compound [58-7] (26 mg) at room temperature, and the mixture was stirred at room temperature for 6 hours. The reaction mixture was concentrated, and the residue was washed with hexane to give the titled compound (9 mg) as a yellow solid.

1H-NMR (400 MHz, CD3OD) δ: 8.75 (1H, d, J=2.0 Hz), 8.44 (1H, s), 7.63 (1H, d, J=7.8 Hz), 7.55 (1H, d, J=6.8 Hz), 7.44 (1H, t, J=7.8 Hz), 5.81 (2H, s), 2.58 (3H, s), 2.36 (3H, s).

ESI-MS found: 381 [M+H]+

Example 59

Synthesis of 1-(2,6-dichlorobenzyl)-6-[difluoro(1H-tetrazol-5-yl)methyl]-3-methyl-1H-pyrazolo[4,3-b]pyridine [59] (hereinafter referred to as a compound [59])

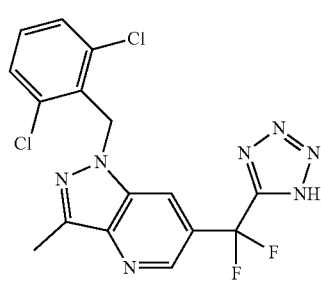 [SMILES: Cc1nn(Cc2c(Cl)cccc2Cl)c2cc(C(F)(F)c3nnn[nH]3)cnc12]

(1) Synthesis of 1-(2,6-dichlorobenzyl)-6-[difluoro(1H-tetrazol-5-yl)methyl]-3-methyl-1H-pyrazolo[4,3-b]pyridine [59-1] (hereinafter referred to as a compound [59-1])

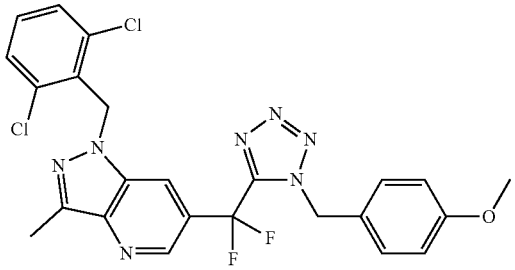 [SMILES: COc1ccc(Cn2nnnc2C(F)(F)c2cnc3c(C)nn(Cc4c(Cl)cccc4Cl)c3c2)cc1]

The titled compound (32 mg) as a white solid was prepared from the compound [58-5] (45 mg) and 2,6-dichlorobenzyl chloride (34 mg) according to the method of the process (1) in Example 1.
ESI-MS found: 530 [M+H]$^+$ (2) Synthesis of 1-(2,6-dichlorobenzyl)-6-[difluoro(1H-tetrazol-5-yl)methyl]-3-methyl-1H-pyrazolo[4,3-b]pyridine [59]

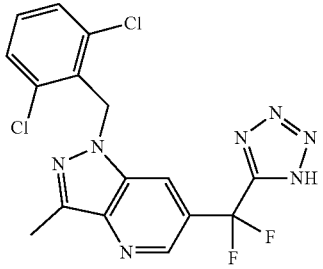 [SMILES: Cc1nn(Cc2c(Cl)cccc2Cl)c2cc(C(F)(F)c3nnn[nH]3)cnc12]

The titled compound (23 mg) as a white solid was prepared from the compound [59-1] (32 mg) according to the method of the process (8) in Example 58.
$^1$H-NMR (400 MHz, CD$_3$OD) δ: 8.72 (1H, d, J=2.0 Hz), 8.36 (1H, s), 7.45 (2H, d, J=6.8 Hz), 7.35 (1H, dd, J=8.8, 6.8 Hz), 5.87 (2H, s), 2.57 (3H, s).
ESI-MS found: 410 [M+H]$^+$ Example 60

Synthesis of 2-{6-[difluoro(1H-tetrazol-5-yl)methyl]-3-methyl-indazol-1-ylmethyl}-6-methylbenzonitrile[60] (hereinafter referred to as a compound [60])

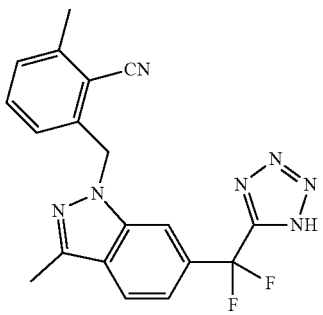 [SMILES: Cc1cccc(Cn2nc(C)c3ccc(C(F)(F)c4nnn[nH]4)cc32)c1C#N]

(1) Synthesis of 6-{difluoro[1-(4-methoxybenzyl)-1H-tetrazol-5-yl]methyl}-3-methyl-1H-indazole [60-1] (hereinafter referred to as a compound [60-1])

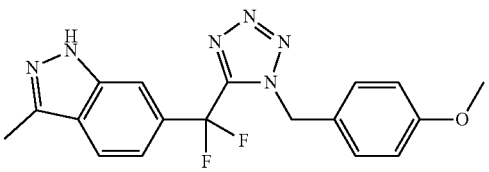

The titled compound (654 mg) as a yellow solid was prepared from 6-bromo-3-methyl-1H-indazole (1.20 g), which was obtained by the method described in the document (JP 2009-528363 W), according to the methods of the processes (1) to (5) in Example 58.
ESI-MS found: 371 [M+H]$^+$ (2) Synthesis of (2-bromo-3-methylphenyl)methanol [60-2] (hereinafter referred to as a compound [60-2])

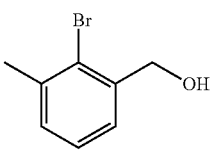

To a solution of 2-bromo-3-methylbenzoic acid (2.00 g) in tetrahydrofuran (47 mL) was added lithium aluminum hydride (706 mg) at 0° C., and the mixture was stirred at room temperature for 3 hours. A saturated aqueous solution of sodium sulfate was added to the reaction mixture, and the mixture was filtered, and the filtrate was concentrated under reduced pressure. The obtained residue was purified by silica gel column chromatography to give the titled compound (832 mg) as a white solid.
$^1$H-NMR (400 MHz, CDCl$_3$) δ: 7.32-7.29 (1H, m), 7.25-7.18 (2H, m), 4.76 (2H, d, J=5.9 Hz), 2.43 (3H, s), 2.04 (1H, t, J=6.3 Hz).

(3) Synthesis of 2-bromo-1-chloromethyl-3-methylbenzene [60-3] (hereinafter referred to as a compound [60-3])

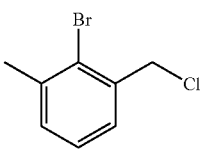

The titled compound (738 mg) as a yellow solid was prepared from the compound [60-2] (832 mg) and cyanuric chloride (840 mg) according to the method of the process (2) in Example 3.
$^1$H-NMR (400 MHz, CDCl$_3$) δ: 7.32-7.29 (1H, m), 7.23-7.20 (2H, m), 4.74 (2H, s), 2.45 (3H, s).

(4) Synthesis of 1-(2-bromo-3-methylbenzyl)-6-{difluoro[1-(4-methoxybenzyl)-1H-tetrazol-5-yl]methyl}-3-methyl-1H-indazole [60-4] (hereinafter referred to as a compound [60-4])

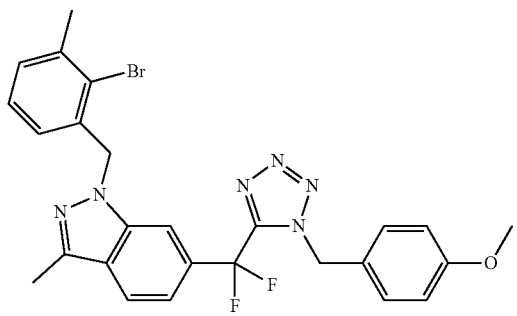 [SMILES: COc1ccc(Cn2nnnc2C(F)(F)c2ccc3c(C)nn(Cc4cccc(C)c4Br)c3c2)cc1]

The titled compound (95 mg) as a white solid was prepaed from the compound [60-1] (71 mg) and the compound [60-3] (69 mg) according to the method of the process (1) in Example 1.

ESI-MS found: 553 [M+H]$^+$ (5) Synthesis of 2-(6-{difluoro[1-(4-methoxybenzyl)-1H-tetrazol-5-yl]methyl}-3-methyl-indazol-1-ylmethyl)-6-methylbenzonitrile[60-5] (hereinafter referred to as a compound [60-5])

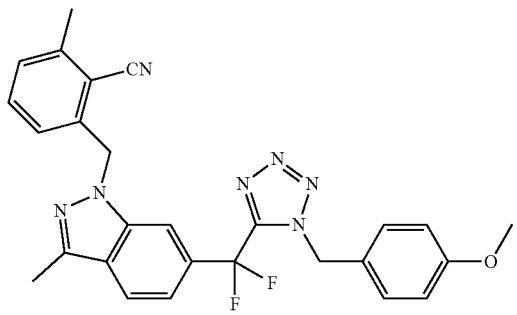 [SMILES: COc1ccc(Cn2nnnc2C(F)(F)c2ccc3c(C)nn(Cc4cccc(C)c4C#N)c3c2)cc1]

The titled compound (60 mg) as a white solid was prepared from the compound [60-4] (95 mg) according to the method of the process (5) in Example 5.

ESI-MS found: 500 [M+H]$^+$ (6) Synthesis of 2-{6-[difluoro(1H-tetrazol-5-yl)methyl]-3-methylindazol-1-ylmethyl}-6-methylbenzonitrile[60]

The titled compound (37 mg) as a white solid was prepared from the compound [60-5] (60 mg) according to the method of the process (8) in Example 58.

$^1$H-NMR (400 MHz, CD$_3$OD) δ: 7.88 (1H, d, J=8.8 Hz), 7.83 (1H, s), 7.41-7.39 (2H, m), 7.33 (1H, d, J=7.8 Hz), 6.87 (1H, d, J=7.8 Hz), 5.79 (2H, s), 2.58 (3H, s), 2.55 (3H, s).

ESI-MS found: 380 [M+H]$^+$

Example 61

Synthesis of 2-{6-[difluoro(1H-tetrazol-5-yl)methyl]-3-methylindazol-1-ylmethyl}-6-methylbenzamide [61] (hereinafter referred to as a compound [61])

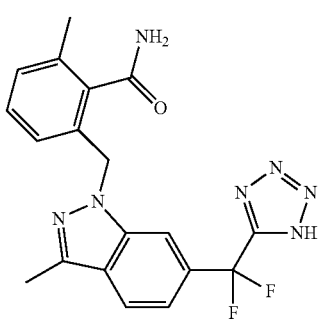 [SMILES: Cc1cccc(Cn2nc(C)c3ccc(C(F)(F)c4nnn[nH]4)cc32)c1C(N)=O]

Concentrated sulfuric acid (1 mL) was added to the compound [60] (10 mg) at room temperature, and the mixture was stirred at 80° C. for 1 hour. Water was added to the reaction mixture, and the mixture was extracted with ethyl acetate. The obtained organic layer was dried over anhydrous sodium sulfate, filtered, and the filtrate was concentrated under reduced pressure to give the titled compound (10 mg) as a yellow solid.

$^1$H-NMR (400 MHz, CD$_3$OD) δ: 7.87-7.85 (2H, m), 7.34 (1H, t, J=4.4 Hz), 7.18-7.12 (2H, m), 6.65 (1H, d, J=6.8 Hz), 5.65 (2H, s), 2.58 (3H, s), 2.39 (3H, s).

ESI-MS found: 398 [M+H]$^+$

Example 62

Synthesis of 1-(2-chloro-6-fluorobenzyl)-6-[difluoro(1H-tetrazol-5-yl)methyl]-3-methyl-1H-indazole [62] (hereinafter referred to as a compound [62])

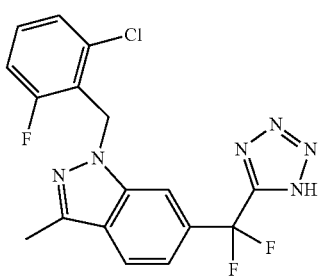 [SMILES: Cc1nn(Cc2c(F)cccc2Cl)c2cc(C(F)(F)c3nnn[nH]3)ccc12]

(1) Synthesis of 1-(2-chloro-6-fluorobenzyl)-6-{difluoro[1-(4-methoxybenzyl)-1H-tetrazol-5-yl]methyl}-3-methyl-1H-indazole [62-1] (hereinafter referred to as a compound [62-1])

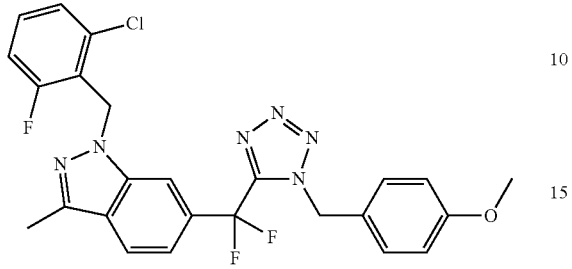

The titled compound (123 mg) as a white solid was prepared from the compound [60-1] (106 mg) and 2-chloro-6-fluorobenzyl chloride (49 µL) according to the method of the process (1) in Example 1.

ESI-MS found: 513 [M+H]$^+$ (2) Synthesis of 1-(2-chloro-6-fluorobenzyl)-6-[difluoro(1H-tetrazol-5-yl)methyl]-3-methyl-1H-indazole [62]

The titled compound (33 mg) as a white solid was prepared from the compound [62-1] (49 mg) according to the method of the process (8) in Example 58.

$^1$H-NMR (400 MHz, CD$_3$OD) δ: 7.84-7.81 (2H, m), 7.39-7.33 (2H, m), 7.28 (1H, d, J=7.8 Hz), 7.13 (1H, t, J=8.8 Hz), 5.70 (2H, s), 2.52 (3H, s).

ESI-MS found: 393 [M+H]$^+$

Example 63

Synthesis of 6-[difluoro(1H-tetrazol-5-yl)methyl]1-(2-fluoro-6-trifluoromethylbenzyl)-3-methyl-1H-indazole [63] (hereinafter referred to as a compound [63])

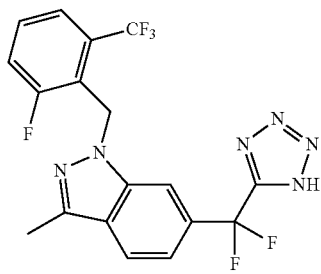 [SMILES: Cc1nn(Cc2c(F)cccc2C(F)(F)F)c2cc(C(F)(F)c3nnn[nH]3)ccc12]

The titled compound (15 mg) as a white solid was prepared from the compound [60-1] (80 mg) and 2-fluoro-6-trifluorobenzyl bromide (72 mg) according to the methods of the process (1) in Example 1 and the process (8) in Example 58.

$^1$H-NMR (400 MHz, CD$_3$OD) δ: 7.75 (1H, d, J=7.8 Hz), 7.69 (1H, s), 7.63-7.55 (2H, m), 7.42-7.38 (1H, m), 7.33 (1H, dd, J=8.5, 1.2 Hz), 5.69 (2H, s), 2.48 (3H, s).

ESI-MS found: 427 [M+H]$^+$

Example 64

Synthesis of 1-(2,3-dichlorobenzyl)-6-[difluoro(1H-tetrazol-5-yl)methyl]-3-methyl-1H-indazole [64] (hereinafter referred to as a compound [64])

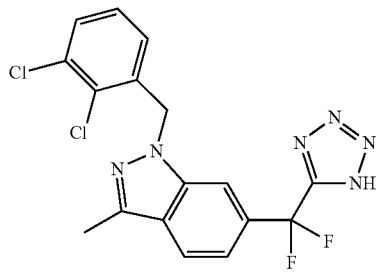 [SMILES: Cc1nn(Cc2cccc(Cl)c2Cl)c2cc(C(F)(F)c3nnn[nH]3)ccc12]

The titled compound (17 mg) as a white solid was prepared from the compound [60-1] (30 mg) and 2,3-dichlorobenzyl chloride (15 µL) according to the methods of the process (1) in Example 1 and the process (8) in Example 58.

$^1$H-NMR (400 MHz, CD$_3$OD) δ: 7.89 (1H, d, J=8.5 Hz), 7.79 (1H, s), 7.47 (1H, d, J=8.1 Hz), 7.38 (1H, d, J=8.5 Hz), 7.17 (1H, t, J=7.9 Hz), 6.70 (1H, d, J=7.8 Hz), 5.74 (2H, s), 2.59 (3H, s).

ESI-MS found: 409 [M+H]$^+$

Example 65

Synthesis of 3-chloro-2-{6-[difluoro(1H-tetrazol-5-yl)methyl]-3-methyl-1H-indazol-1-ylmethyl}benzonitrile[65] (hereinafter referred to as a compound [65])

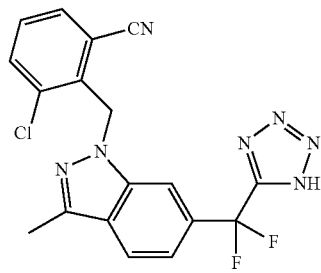 [SMILES: Cc1nn(Cc2c(Cl)cccc2C#N)c2cc(C(F)(F)c3nnn[nH]3)ccc12]

(1) Synthesis of 1-(2-bromo-6-chlorobenzyl)-6-{difluoro[1-(4-methoxybenzyl)-1H-tetrazol-5-yl]methyl}-3-methyl-1H-indazole [65-1] (hereinafter referred to as a compound [65-1])

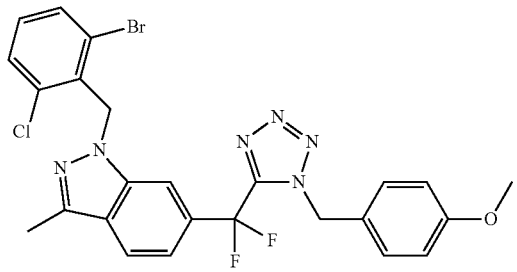 [SMILES: COc1ccc(Cn2nnnc2C(F)(F)c2ccc3c(C)nn(Cc4c(Cl)cccc4Br)c3c2)cc1]

The titled compound (143 mg) as a white solid was prepared from the compound [60-1] (104 mg) and the compound [5-2] (104 mg) according to the method of the process (1) in Example 1.

ESI-MS found: 573 [M+H]$^+$

(2) Synthesis of 3-chloro-2-(6-{difluoro[1-(4-methoxybenzyl)-1H-tetrazol-5-yl]methyl}-3-methyl-1H-indazol-1-ylmethyl)benzonitrile[65-2] (hereinafter referred to as a compound [65-2])

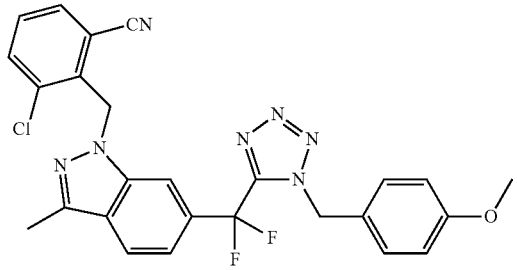 [SMILES: COc1ccc(Cn2nnnc2C(F)(F)c2ccc3c(C)nn(Cc4c(Cl)cccc4C#N)c3c2)cc1]

The titled compound (104 mg) as a white solid was prepared from the compound [65-1] (143 mg), zinc cyanide (22 mg) and tetrakis(triphenylphosphine)palladium(0) (29 mg) according to the method of the process (5) in Example 5.

ESI-MS found: 520 [M+H]$^+$

(3) Synthesis of 3-chloro-2-{6-[difluoro(1H-tetrazol-5-yl)methyl]-3-methyl-1H-indazol-1-ylmethyl}benzonitrile[65]

The titled compound (66 mg) as a white solid was prepared from the compound [65-2] (100 mg) according to the method of the process (8) in Example 58.

$^1$H-NMR (400 MHz, CD$_3$OD) δ: 7.93 (1H, s), 7.84 (1H, d, J=8.3 Hz), 7.79 (1H, dd, J=7.8, 1.2 Hz), 7.74 (1H, dd, J=8.1, 1.2 Hz), 7.53 (1H, t, J=7.9 Hz), 7.37 (1H, dd, J=8.5, 1.5 Hz), 5.82 (2H, s), 2.50 (3H, s).

ESI-MS found: 400 [M+H]$^+$

Example 66

Synthesis of 1-(2-chloro-6-methanesulfonylbenzyl)-6-[difluoro(1H-tetrazol-5-yl)methyl]-3-methyl-1H-indazole [66] (hereinafter referred to as a compound [66])

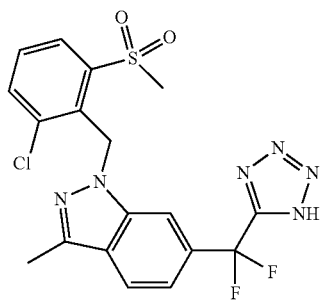 [SMILES: Cc1nn(Cc2c(Cl)cccc2S(C)(=O)=O)c2cc(C(F)(F)c3nnn[nH]3)ccc12]

(1) Synthesis of 1-(2-chloro-6-methanesulfonylbenzyl)-6-{difluoro[1-(4-methoxybenzyl)-1H-tetrazol-5-yl]methyl}-3-methyl-1H-indazole [66-1] (hereinafter referred to as a compound [66-1])

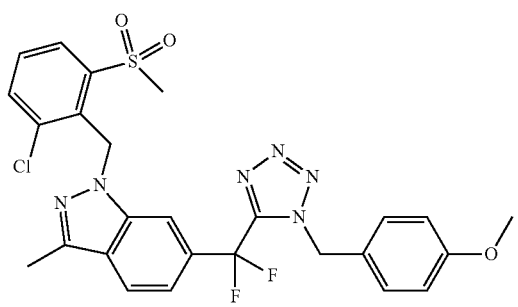 [SMILES: COc1ccc(Cn2nnnc2C(F)(F)c2ccc3c(C)nn(Cc4c(Cl)cccc4S(C)(=O)=O)c3c2)cc1]

To a solution of the compound [65-1] (29 mg) in dimethyl sulfoxide (1.0 mL) were added sodium methanesulfinate (61 mg), copper(I) iodide (9.5 mg), L-proline (12 mg) and sodium hydroxide (4.0 mg), and the mixture was stirred at 120° C. for 15 hours. The reaction mixture was quenched with water, and extracted with ethyl acetate. The obtained organic layer was washed with water and brine, dried over anhydrous sodium sulfate, filtered, and the filtrate was concentrated under reduced pressure. The obtained residue was purified by silica gel column chromatography to give the titled compound (13 mg) as a white amorphous.

ESI-MS found: 573 [M+H]$^+$

(2) Synthesis of 1-(2-chloro-6-methanesulfonylbenzyl)-6-[difluoro(1H-tetrazol-5-yl)methyl]-3-methyl-1H-indazole [66]

The titled compound (15 mg) as a white amorphous was prepared from the compound [66-1] (26 mg) according to the method of the process (8) in Example 58.

¹H-NMR (400 MHz, CD₃OD) δ: 8.15 (1H, dd, J=7.9, 1.3 Hz), 7.96 (1H, s), 7.83 (1H, dd, J=8.5, 0.7 Hz), 7.78 (1H, dd, J=8.1, 1.2 Hz), 7.63 (1H, t, J=8.1 Hz), 7.36 (1H, dd, J=8.5, 1.5 Hz), 6.17 (2H, s), 3.20 (3H, s), 2.46 (3H, s).
ESI-MS found: 453 [M+H]⁺

Example 67

Synthesis of 3-chloro-2-{6-[difluoro(1H-tetrazol-5-yl)methyl]-3-methyl-1H-indazol-1-ylmethyl}benzamide [67] (hereinafter referred to as a compound [67])

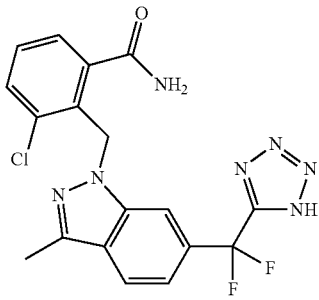 [SMILES: Cc1nn(Cc2c(Cl)cccc2C(N)=O)c2cc(C(F)(F)c3nnn[nH]3)ccc12]

(1) Synthesis of 3-chloro-2-(6-{difluoro[1-(4-methoxybenzyl)-1H-tetrazol-5-yl]methyl}-3-methyl-1H-indazol-1-ylmethyl)benzamide [67-1] (hereinafter referred to as a compound [67-1])

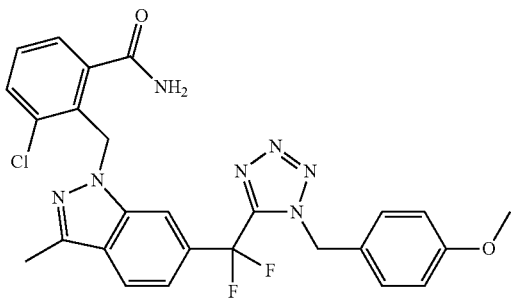 [SMILES: COc1ccc(Cn2nnnc2C(F)(F)c2ccc3c(C)nn(Cc4c(Cl)cccc4C(N)=O)c3c2)cc1]

To a solution of the compound [65-2] (40 mg) in methanol (1.5 mL) was added an aqueous solution of 3N-sodium hydroxide (1.5 mL) at room temperature, and the mixture was stirred at 80° C. for 4 hours. The reaction mixture was quenched with water, and the precipitated solid was filtered and dried under reduced pressure to give the titled compound (39 mg) as a white solid.
ESI-MS found: 538 [M+H]⁺

(2) Synthesis of 3-chloro-2-{6-[difluoro(1H-tetrazol-5-yl)methyl]-3-methyl-1H-indazol-1-ylmethyl}benzamide [67]

The titled compound (20 mg) as a white solid was prepared from the compound [67-1] (39 mg) according to the method of the process (8) in Example 58.

¹H-NMR (400 MHz, CD₃OD) δ: 7.88 (1H, s), 7.81 (1H, d, J=8.5 Hz), 7.53-7.48 (2H, m), 7.42 (1H, t, J=7.8 Hz), 7.34 (1H, dd, J=8.5, 1.2 Hz), 5.81 (2H, s), 2.50 (3H, s).
ESI-MS found: 418 [M+H]⁺

Example 68

Synthesis of potassium 5-[1-(2-carbamoyl-6-chlorobenzyl)-3-methyl-1H-indazol-6-yl]difluoromethyl-1H-tetrazol-1-ide [68] (hereinafter referred to as a compound [68])

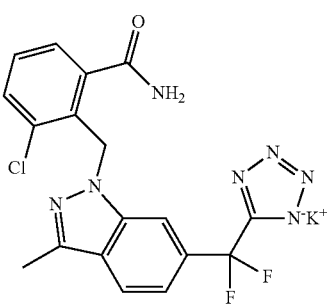

To a solution of the compound [67] (19 mg) in ethanol (2.0 mL) was added an aqueous solution of 1N-potassium hydroxide (45 μL) at room temperature, and the solution was concentrated under reduced pressure to give the titled compound (20 mg) as a white solid.
¹H-NMR (400 MHz, CD₃OD) δ: 7.77 (1H, s), 7.74 (1H, d, J=8.8 Hz), 7.52-7.48 (2H, m), 7.40 (1H, t, J=7.3 Hz), 7.31 (1H, d, J=8.8 Hz), 5.78 (2H, s), 2.48 (3H, s).
ESI-MS found: 418 [M−K+2H]⁺

Example 69

Synthesis of 3-chloro-2-{6-[difluoro(1H-tetrazol-5-yl)methyl]-3-methyl-1H-indazol-1-ylmethyl}-N-methylbenzamide [69] (hereinafter referred to as a compound [69])

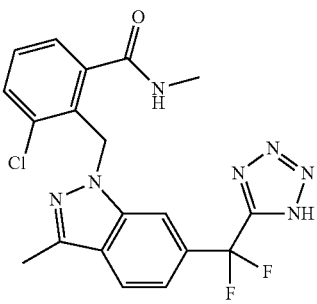 [SMILES: CNC(=O)c1cccc(Cl)c1Cn1nc(C)c2ccc(C(F)(F)c3nnn[nH]3)cc21]

(1) Synthesis of 3-chloro-2-(6-{difluoro[1-(4-methoxybenzyl)-1H-tetrazol-5-yl]methyl}-3-methyl-1H-indazol-1-ylmethyl)-N,N-(di-tert-butoxycarbonyl)benzamide[69-1] (hereinafter referred to as a compound [69-1])

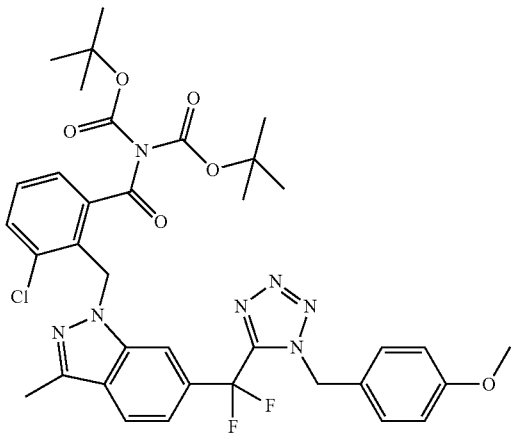 [SMILES: COc1ccc(Cn2nnnc2C(F)(F)c2ccc3c(C)nn(Cc4c(Cl)cccc4C(=O)N(C(=O)OC(C)(C)C)C(=O)OC(C)(C)C)c3c2)cc1]

The compound [67-1] (82 mg) was suspended in acetonitrile (3.0 mL), and to the suspension were added di-tert-butyldicarbonate (107 mg) and 4-dimethylaminopyridine (3.8 mg) at room temperature, and the mixture was stirred at 90° C. for 1 hour. The reaction mixture was concentrated under reduced pressure, and the obtained residue was purified by silica gel column chromatography to give the titled compound (71 mg) as a yellow amorphous.

ESI-MS found: 738 [M+H]$^+$ (2) Synthesis of 3-chloro-2-(6-{difluoro[1-(4-methoxybenzyl)-1H-tetrazol-5-yl]methyl}-3-methyl-1H-indazol-1-ylmethyl)-N-methylbenzamide [69-2] (hereinafter referred to as a compound [69-2])

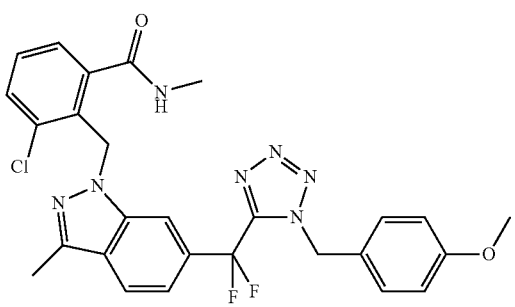 [SMILES: CNC(=O)c1cccc(Cl)c1Cn1nc(C)c2ccc(C(F)(F)c3nnnn3Cc3ccc(OC)cc3)cc21]

To a solution of the compound [69-1] (71 mg) in dichloromethane (1.0 mL) was added 2.0M tetrahydrofuran solution of methylamine (0.24 mL) at room temperature, and the mixture was stirred at room temperature for 25 minutes. The reaction mixture was concentrated under reduced pressure, and the obtained residue was purified by silica gel column chromatography to give the titled compound (45 mg) as a white amorphous.

ESI-MS found: 552 [M+H]$^+$ (3) Synthesis of 3-chloro-2-{6-[difluoro(1H-tetrazol-5-yl)methyl]-3-methyl-1H-indazol-1-ylmethyl}-N-methylbenzamide [69]

The titled compound (16 mg) as a white solid was prepared from the compound [69-2] (23 mg) according to the method of the process (8) in Example 58.

$^1$H-NMR (400 MHz, CD$_3$OD) δ: 7.74 (1H, d, J=7.8 Hz), 7.67 (1H, s), 7.52-7.50 (1H, m), 7.40-7.31 (3H, m), 5.77 (2H, s), 2.62 (3H, s), 2.49 (3H, s).

ESI-MS found: 432 [M+H]$^+$

Example 70

Synthesis of 2-{6-[difluoro(1H-tetrazol-5-yl)methyl]-3-methyl-1H-indazol-1-ylmethyl}isophthalonitrile [70] (hereinafter referred to as a compound [70])

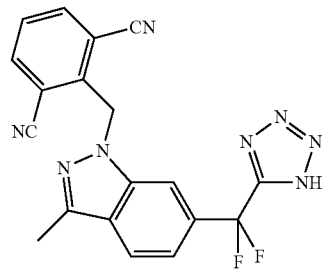 [SMILES: Cc1nn(Cc2c(C#N)cccc2C#N)c2cc(C(F)(F)c3nnn[nH]3)ccc12]

The titled compound (28 mg) as a white solid was prepared from the compound [65-1] (258 mg) according to the methods of the process (5) in Example 5 and the process (8) in Example 58.

$^1$H-NMR (400 MHz, CD$_3$OD) δ: 8.08 (2H, d, J=7.8 Hz), 8.01 (1H, s), 7.85 (1H, d, J=8.8 Hz), 7.72 (1H, t, J=7.8 Hz), 7.40 (1H, d, J=8.8 Hz), 5.89 (2H, s), 2.51 (3H, s).

ESI-MS found: 391 [M+H]$^+$

Example 71

Synthesis of 2-{6-[difluoro(1H-tetrazol-5-yl)methyl]-3-methyl-1H-indazol-1-ylmethyl}-3-methylbenzonitrile[71] (hereinafter referred to as a compound [71])

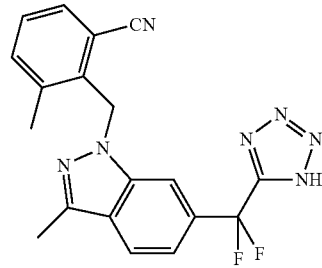 [SMILES: Cc1cccc(C#N)c1Cn1nc(C)c2ccc(C(F)(F)c3nnn[nH]3)cc21]

(1) Synthesis of 6-{difluoro[1-(4-methoxybenzyl)-1H-tetrazol-5-yl]methyl}-1-(2-iodo-6-methylbenzyl)-3-methyl-1H-indazole [71-1] (hereinafter referred to as a compound [71-1])

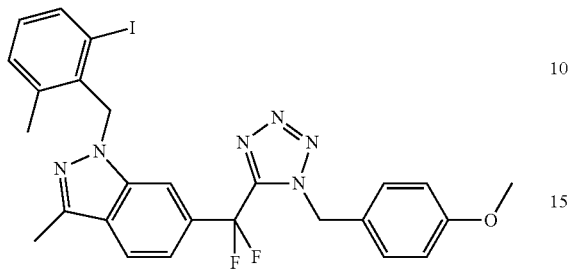

The titled compound (119 mg) as a white solid was prepared from the compound [60-1] (100 mg) and the compound [55-3] (94 mg) according to the method of the process (1) in Example 1.
ESI-MS found: 601 [M+H]$^+$ (2) Synthesis of 2-(6-{difluoro[1-(4-methoxybenzyl)-1H-tetrazol-5-yl]methyl}-3-methyl-1H-indazol-1-ylmethyl)-3-methylbenzonitrile [71-2] (hereinafter referred to as a compound [71-2])

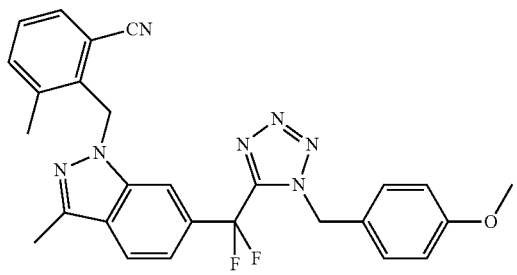 [SMILES: COc1ccc(Cn2nnnc2C(F)(F)c2ccc3c(C)nn(Cc4c(C)cccc4C#N)c3c2)cc1]

To a solution of the compound [71-1] (70 mg) in N,N-dimethylformamide (2.3 mL) were added zinc cyanide (19 mg), tris(dibenzylideneacetone)dipalladium(0) (21 mg) and 2-dicyclohexylphosphino-2',4',6'-triisopropylbiphenyl (22 mg) at room temperature, and the mixture was subjected to microwave irradiation at 130° C. for 20 minutes. After cooling to room temperature, a saturated aqueous solution of potassium carbonate was added, and the mixture was extracted with ethyl acetate. The obtained organic layer was washed sequentially with water and brine, dried over anhydrous sodium sulfate, filtered, and the filtrate was concentrated under reduced pressure. The obtained residue was purified by silica gel column chromatography to give the titled compound (47 mg) as a white solid.
ESI-MS found: 500 [M+H]$^+$ (3) Synthesis of 2-{6-[difluoro(1H-tetrazol-5-yl)methyl]-3-methyl-1H-indazol-1-ylmethyl}-3-methylbenzonitrile[71]

The titled compound (22 mg) as a white solid was prepared from the compound [71-2] (46 mg) according to the method of the process (8) in Example 58.

$^1$H-NMR (400 MHz, CD$_3$OD) δ: 7.84 (1H, d, J=7.8 Hz), 7.80 (1H, s), 7.63 (1H, d, J=7.8 Hz), 7.51 (1H, d, J=6.8 Hz), 7.42 (1H, t, J=7.8 Hz), 7.37 (1H, d, J=8.8 Hz), 5.75 (2H, s), 2.52 (3H, s), 2.24 (3H, s).
ESI-MS found: 380 [M+H]$^+$ Example 72

Synthesis of 2-{6-[difluoro(1H-tetrazol-5-yl)methyl]-3-methyl-1H-indazol-1-ylmethyl}-3-methylbenzamide [72] (hereinafter referred to as a compound [72])

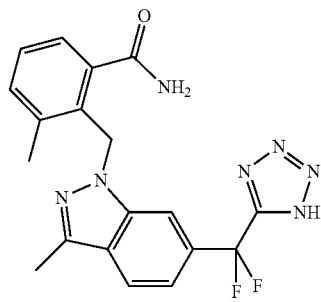 [SMILES: Cc1cccc(C(N)=O)c1Cn1nc(C)c2ccc(C(F)(F)c3nnn[nH]3)cc21]

The titled compound (29 mg) as a white solid was prepared from the compound [71-2] (311 mg) according to the methods of the process (1) in Example 67 and the process (8) in Example 58.
$^1$H-NMR (400 MHz, CD$_3$OD) δ: 7.82 (1H, dd, J=8.5, 0.7 Hz), 7.78 (1H, s), 7.38-7.26 (4H, m), 5.72 (2H, s), 2.51 (3H, s), 2.19 (3H, s).
ESI-MS found: 398 [M+H]$^+$ Example 73

Synthesis of 6-[difluoro(1H-tetrazol-5-yl)methyl]-1-(2-fluorobenzyl)-3-methyl-1H-indazole [73] (hereinafter referred to as a compound [73])

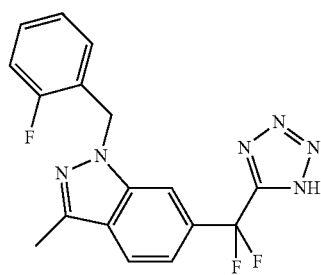 [SMILES: Cc1nn(Cc2ccccc2F)c2cc(C(F)(F)c3nnn[nH]3)ccc12]

The titled compound (10 mg) as a white solid was prepared from the compound [60-1] (30 mg) and 2-fluorobenzyl chloride (13 μL) according to the methods of the process (1) in Example 1 and the process (8) in Example 58.

¹H-NMR (400 MHz, CD₃OD) δ: 7.86-7.82 (2H, m), 7.36-7.27 (2H, m), 7.12-7.06 (3H, m), 5.64 (2H, s), 2.57 (3H, s).

ESI-MS found: 359 [M+H]⁺

Example 74

Synthesis of 8-{6-[difluoro(1H-tetrazol-5-yl)methyl]-3-methyl-1H-indazol-1-ylmethyl}quinoline [74] (hereinafter referred to as a compound [74])

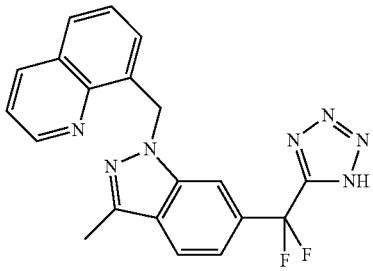 [SMILES: Cc1nn(Cc2cccc3cccnc23)c2cc(C(F)(F)c3nnn[nH]3)ccc12]

The titled compound (40 mg) as a yellow solid was prepared from the compound [60-1] (54 mg) and 8-(bromomethyl)quinoline (42 mg) according to the methods of the process (1) in Example 1 and the process (8) in Example 58.

¹H-NMR (400 MHz, CD₃OD) δ: 8.96 (1H, dd, J=4.4, 1.7 Hz), 8.42 (1H, dd, J=8.5, 1.7 Hz), 8.01 (1H, s), 7.90 (1H, dd, J=8.3, 1.2 Hz), 7.84 (1H, dd, J=8.5, 0.7 Hz), 7.61 (1H, dd, J=8.3, 4.4 Hz), 7.51 (1H, dd, J=8.2, 7.2 Hz), 7.39-7.37 (1H, m), 7.34 (1H, dd, J=8.5, 1.5 Hz), 6.25 (2H, s), 2.58 (3H, s).

ESI-MS found: 392 [M+H]⁺

Example 75

Synthesis of 3-cyclopropyl-2-{6-[difluoro(1H-tetrazol-5-yl)methyl]-3-methyl-1H-indazol-1-ylmethyl}benzonitrile[75] (hereinafter referred to as a compound [75])

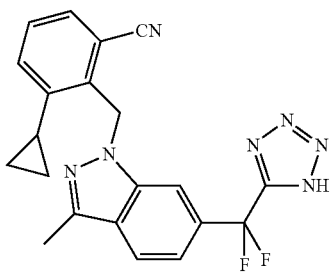 [SMILES: Cc1nn(Cc2c(C#N)cccc2C2CC2)c2cc(C(F)(F)c3nnn[nH]3)ccc12]

(1) Synthesis of 3-bromo-2-(6-{difluoro[1-(4-methoxybenzyl)-1H-tetrazol-5-yl]methyl}-3-methyl-1H-indazol-1-ylmethyl)benzonitrile[75-1] (hereinafter referred to as a compound [75-1])

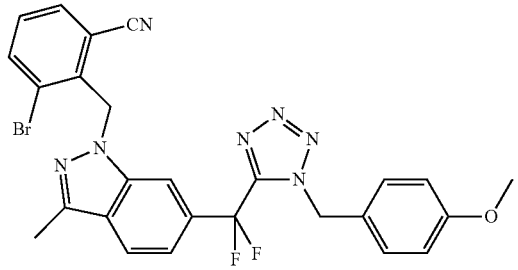

The titled compound (129 mg) as a white solid was prepared from the compound [60-1] (100 mg) and the compound [32-2] (97 mg) according to the method of the process (1) in Example 1.

ESI-MS found: 564 [M+H]⁺

(2) Synthesis of 3-cyclopropyl-2-(6-{difluoro[1-(4-methoxybenzyl)-1H-tetrazol-5-yl]methyl}-3-methyl-1H-indazol-1-ylmethyl)benzonitrile[75-2] (hereinafter referred to as a compound [75-2])

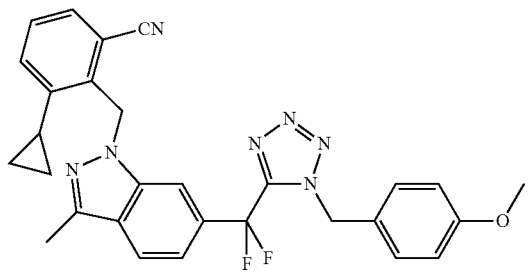 [SMILES: COc1ccc(Cn2nnnc2C(F)(F)c2ccc3c(C)nn(Cc4c(C#N)cccc4C4CC4)c3c2)cc1]

The titled compound (44 mg) as a white solid was prepared from the compound [75-1] (70 mg), cyclopropylboronic acid monohydrate (26 mg), tetrakis(triphenylphosphine)palladium(0) (7.2 mg) and cesium carbonate (121 mg) according to the method of the process (1) in Example 12.

ESI-MS found: 526 [M+H]⁺

(3) Synthesis of 3-cyclopropyl-2-{6-[difluoro(1H-tetrazol-5-yl)methyl]-3-methyl-1H-indazol-1-ylmethyl}benzonitrile[75]

The titled compound (17 mg) as a white solid was prepared from the compound [75-2] (40 mg) according to the method of the process (8) in Example 58.

¹H-NMR (400 MHz, CD₃OD) δ: 7.84 (1H, d, J=8.8 Hz), 7.76 (1H, s), 7.63 (1H, d, J=8.8 Hz), 7.44 (1H, t, J=7.8 Hz), 7.38-7.35 (2H, m), 5.92 (2H, s), 2.51 (3H, s), 1.83-1.79 (1H, m), 0.76-0.72 (2H, m), 0.58-0.54 (2H, m).

ESI-MS found: 406 [M+H]⁺

Example 76

Synthesis of 3-cyclopropyl-2-{6-[difluoro(1H-tetrazol-5-yl)methyl]-3-methyl-1H-indazol-1-ylmethyl}benzamide[76] (hereinafter referred to as a compound [76])

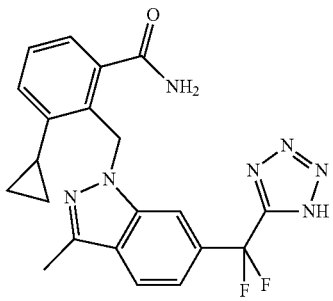 [SMILES: Cc1nn(Cc2c(C(N)=O)cccc2C2CC2)c2cc(C(F)(F)c3nnn[nH]3)ccc12]

The titled compound (13 mg) as a white solid was prepared from the compound [75-2] (35 mg) according to the methods of the process (1) in Example 67 and the process (8) in Example 58.

$^1$H-NMR (400 MHz, CD$_3$OD) δ: 7.83 (1H, d, J=7.8 Hz), 7.79 (1H, s), 7.38-7.31 (3H, m), 7.19-7.16 (1H, m), 5.90 (2H, s), 2.51 (3H, s), 1.76-1.69 (1H, m), 0.73-0.68 (2H, m), 0.54-0.50 (2H, m).

ESI-MS found: 424 [M+H]$^+$

Example 77

Synthesis of 2-{6-[difluoro(1H-tetrazol-5-yl)methyl]-3-methyl-1H-indazol-1-ylmethyl}-3-ethylbenzamide [77] (hereinafter referred to as a compound [77])

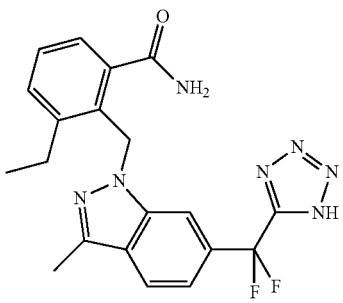 [SMILES: CCc1cccc(C(N)=O)c1Cn1nc(C)c2ccc(C(F)(F)c3nnn[nH]3)cc21]

(1) Synthesis of 2-(6-{difluoro[1-(4-methoxybenzyl)-1H-tetrazol-5-yl]methyl}-3-methyl-1H-indazol-1-ylmethyl)-3-ethylbenzonitrile [77-1] (hereinafter referred to as a compound [77-1])

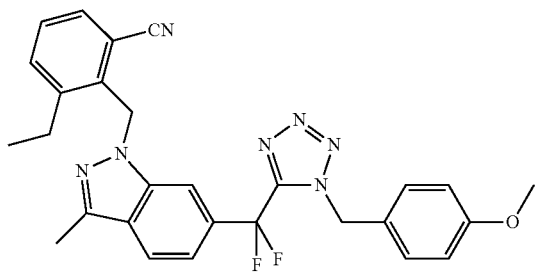

The compound [75-1] (48 mg), [1,1'-bis(diphenylphosphino)ferrocene]dichloropalladium(II) dichloromethane complex (7.0 mg) and potassium carbonate (59 mg) were dissolved in N,N-dimethylformamide (2.1 mL). To the mixture was added 1.0M toluene solution of diethylzinc (256 μL), and the mixture was subjected to microwave irradiation at 100° C. for 20 minutes. After cooling, water was added to the reaction mixture, and the mixture was extracted with ethyl acetate. The obtained organic layer was sequentially washed with water and brine, dried over anhydrous sodium sulfate, filtered, and the filtrate was concentrated under reduced pressure. The obtained residue was purified by silica gel column chromatography to give the titled compound (20 mg) as a white amorphous.

ESI-MS found: 514 [M+H]$^+$ (2) Synthesis of 2-{6-[difluoro(1H-tetrazol-5-yl)methyl]-3-methyl-1H-indazol-1-ylmethyl}-3-ethylbenzamide [77]

The titled compound (5.0 mg) as a white amorphous was prepared from the compound [75-1] (20 mg) according to the methods of the process (1) in Example 67 and the process (8) in Example 58.

$^1$H-NMR (400 MHz, CD$_3$OD) δ: 7.86-7.82 (2H, m), 7.39-7.35 (4H, m), 5.75 (2H, s), 2.66 (2H, q, J=7.5 Hz), 2.52 (3H, s), 0.91 (3H, t, J=7.5 Hz).

ESI-MS found: 412 [M+H]$^+$

Example 78

Synthesis of 2-{6-[difluoro(1H-tetrazol-5-yl)methyl]-3-methyl-1H-indazol-1-ylmethyl}benzonitrile[78] (hereinafter referred to as a compound [78])

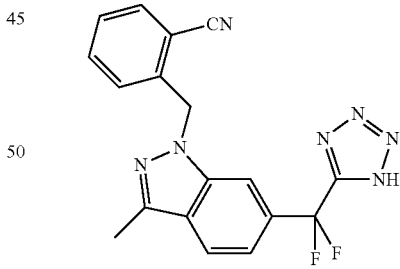

The titled compound (34 mg) as a white solid was prepared from the compound [60-1] (50 mg) and 2-bromomethylbenzonitrile (34 mg) according to the methods of the process (1) in Example 1 and the process (8) in Example 58.

$^1$H-NMR (400 MHz, CD$_3$OD) δ: 7.88 (1H, d, J=8.8 Hz), 7.85 (1H, s), 7.77 (1H, d, J=8.8 Hz), 7.56 (1H, t, J=7.8 Hz), 7.46 (1H, t, J=7.8 Hz), 7.38 (1H, d, J=8.8 Hz), 7.10 (1H, d, J=7.8 Hz), 5.81 (2H, s), 2.58 (3H, s).

ESI-MS found: 366 [M+H]$^+$

Example 79

Synthesis of potassium 5-({[1-(2-cyanobenzyl)-3-methyl-1H-indazol-6-yl]difluoromethyl}-1H-tetrazol-1-ide [79] (hereinafter referred to as a compound [79])

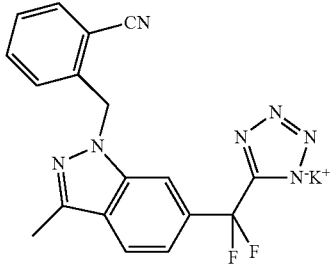

To a solution of the compound [78] (19 mg) in ethanol (2.0 mL) was added an aqueous solution of 1N-potassium hydroxide (51 µL) at room temperature, and the solution was concentrated under reduced pressure to give the titled compound (21 mg) as a white solid.

$^1$H-NMR (400 MHz, CD$_3$OD) δ: 7.82-7.75 (3H, m), 7.53 (1H, td, J=7.7, 1.5 Hz), 7.44 (1H, td, J=7.7, 1.2 Hz), 7.35 (1H, dd, J=8.4, 1.3 Hz), 6.99 (1H, d, J=7.9 Hz), 5.81 (2H, s), 2.57 (3H, s).

ESI-MS found: 366 [M−K+2H]$^+$

Example 80

Synthesis of 1-benzyl-6-[difluoro(1H-tetrazol-5-yl)methyl]-3-methyl-1H-indazole [80] (hereinafter referred to as a compound [80])

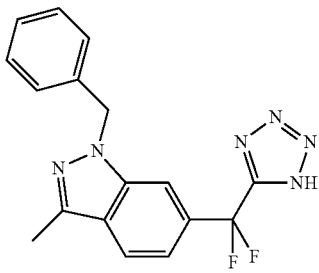 [SMILES: Cc1nn(Cc2ccccc2)c2cc(C(F)(F)c3nnn[nH]3)ccc12]

The titled compound (25 mg) as a white solid was prepared from the compound [60-1] (42 mg) and benzyl chloride (17 µL) according to the methods of the process (1) in Example 1 and the process (8) in Example 58.

$^1$H-NMR (400 MHz, CD$_3$OD) δ: 7.86 (1H, d, J=8.3 Hz), 7.77 (1H, s), 7.34-7.22 (4H, m), 7.17 (2H, d, J=6.6 Hz), 5.60 (2H, s), 2.58 (3H, s).

ESI-MS found: 341 [M+H]$^+$

Example 81

Synthesis of 2-{6-[difluoro(1H-tetrazol-5-yl)methyl]-3-methyl-1H-indazol-1-ylmethyl}-3-fluorobenzonitrile [81] (hereinafter referred to as a compound [81])

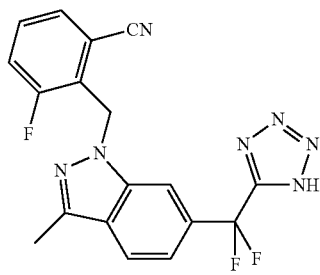

The titled compound (22 mg) as a white solid was prepared from the compound [62-1] (70 mg) according to the methods of the process (1) in Example 24 and the process (8) in Example 58.

$^1$H-NMR (400 MHz, CD$_3$OD) δ: 7.95 (1H, s), 7.83 (1H, d, J=8.3 Hz), 7.63 (1H, dd, J=7.6, 1.0 Hz), 7.55 (1H, td, J=8.1, 5.2 Hz), 7.48-7.43 (1H, m), 7.36 (1H, d, J=8.3 Hz), 5.77 (2H, s), 2.51 (3H, s).

ESI-MS found: 384 [M+H]$^+$

Example 82

Synthesis of 2-{6-[difluoro(1H-tetrazol-5-yl)methyl]-3-methyl-1H-indazol-1-ylmethyl}-3-methoxybenzonitrile [82] (hereinafter referred to as a compound [82])

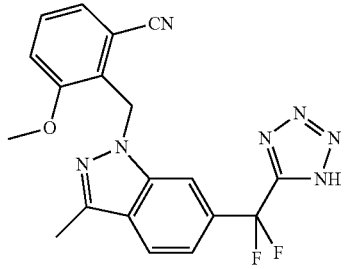 [SMILES: COc1cccc(C#N)c1Cn1nc(C)c2ccc(C(F)(F)c3nnn[nH]3)cc21]

(1) Synthesis of 1-(2-chloro-6-methoxybenzyl)-6-{difluoro[1-(4-methoxybenzyl)-1H-tetrazol-5-yl]methyl}-3-methyl-1H-indazole [82-1] (hereinafter referred to as a compound [82-1])

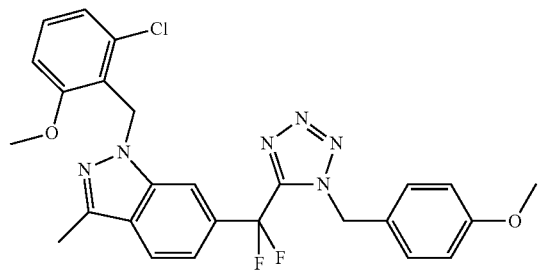

The titled compound (94 mg) as a white solid was prepared from the compound [60-1] (95 mg) and the compound [28-1] (79 mg) according to the method of the process (1) in Example 1.
ESI-MS found: 525 [M+H]$^+$ (2) Synthesis of 2-(6-{difluoro[1-(4-methoxybenzyl)-1H-tetrazol-5-yl]methyl}-3-methyl-1H-indazol-1-ylmethyl)-3-methoxybenzonitrile [82-2] (hereinafter referred to as a compound [82-2])

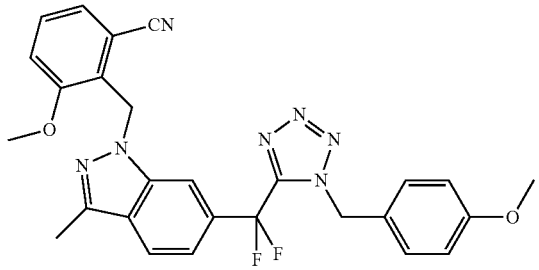

The titled compound (40 mg) as a white solid was prepared from the compound [82-1] (60 mg) according to the method of the process (1) in Example 24.
ESI-MS found: 516 [M+H]$^+$ (3) Synthesis of 2-{6-[difluoro(1H-tetrazol-5-yl)methyl]-3-methyl-1H-indazol-1-ylmethyl}-3-methoxybenzonitrile [82]

The titled compound (27 mg) as a white solid was prepared from the compound [82-2] (38 mg) according to the method of the process (8) in Example 58.
$^1$H-NMR (400 MHz, CD$_3$OD) δ: 7.93 (1H, s), 7.80 (1H, d, J=8.8 Hz), 7.47 (1H, t, J=7.8 Hz), 7.35-7.32 (2H, m), 7.26 (1H, d, J=8.8 Hz), 5.71 (2H, s), 3.71 (3H, s), 2.50 (3H, s).
ESI-MS found: 396 [M+H]$^+$ Example 83

Synthesis of 2-{6-[difluoro(1H-tetrazol-5-yl)methyl]-3-methyl-1H-indazol-1-ylmethyl}-3-methoxybenzamide [83] (hereinafter referred to as a compound [83])

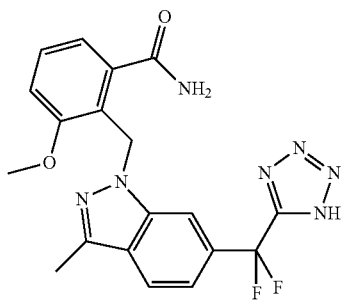 [SMILES: COc1cccc(C(N)=O)c1Cn1nc(C)c2ccc(C(F)(F)c3nnn[nH]3)cc21]

The titled compound (30 mg) as a white solid was prepared from the compound [82-2] (75 mg) according to the methods of the process (1) in Example 67 and the process (8) in Example 58.

$^1$H-NMR (400 MHz, CD$_3$OD) δ: 8.01 (1H, s), 7.80 (1H, d, J=8.8 Hz), 7.39-7.32 (2H, m), 7.16 (1H, d, J=6.8 Hz), 7.04 (1H, d, J=7.8 Hz), 5.71 (2H, s), 3.66 (3H, s), 2.50 (3H, s).
ESI-MS found: 414 [M+H]$^+$ Example 84

Synthesis of 6-[difluoro(1H-tetrazol-5-yl)methyl]-1-(2-methoxybenzyl)-3-methyl-1H-indazole [84] (hereinafter referred to as a compound [84])

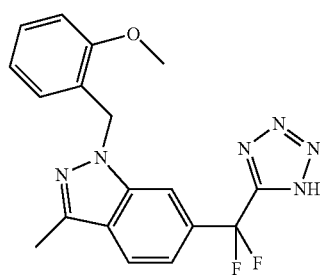 [SMILES: COc1ccccc1Cn1nc(C)c2ccc(C(F)(F)c3nnn[nH]3)cc21]

To a solution of the compound [82-1] (33 mg) in methanol (2.0 mL) was added 5% palladium-activated carbon (33 mg) at room temperature, and the mixture was stirred under a hydrogen atmosphere at room temperature for 2 days. The palladium carbon was filtered, and the filtrate was then concentrated under reduced pressure. The obtained residue was purified by reverse phase preparative liquid chromatography to give the titled compound (7.6 mg) as a white solid.
$^1$H-NMR (400 MHz, CD$_3$OD) δ: 7.83-7.81 (2H, m), 7.32 (1H, d, J=8.8 Hz), 7.25 (1H, t, J=7.8 Hz), 7.05-7.02 (1H, m), 6.95 (1H, d, J=7.8 Hz), 6.84 (1H, t, J=7.3 Hz), 5.55 (2H, s), 3.79 (3H, s), 2.56 (3H, s).
ESI-MS found: 371 [M+H]$^+$ Example 85

Synthesis of 6-[difluoro(1H-tetrazol-5-yl)methyl]-3-methyl-1-(2-trifluoromethoxybenzyl)-1H-indazole [85] (hereinafter referred to as a compound [85])

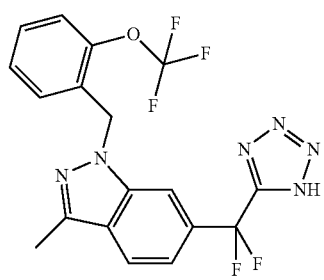 [SMILES: Cc1nn(Cc2ccccc2OC(F)(F)F)c2cc(C(F)(F)c3nnn[nH]3)ccc12]

The titled compound (37 mg) as a white solid was prepared from the compound [60-1] (57 mg) and 2-(trifluoromethoxy)benzyl bromide (51 mg) according to the methods of the process (1) in Example 1 and the process (8) in Example 58.

¹H-NMR (400 MHz, CD₃OD) δ: 7.87 (1H, d, J=8.8 Hz), 7.74 (1H, s), 7.41-7.31 (3H, m), 7.25 (1H, t, J=6.8 Hz), 7.07-7.05 (1H, m), 5.67 (2H, s), 2.58 (3H, s).
ESI-MS found: 425 [M+H]⁺

Example 86

Synthesis of 6-[difluoro(1H-tetrazol-5-yl)methyl]-3-methyl-1-(2-methylbenzyl)-1H-indazole [86] (hereinafter referred to as a compound [86])

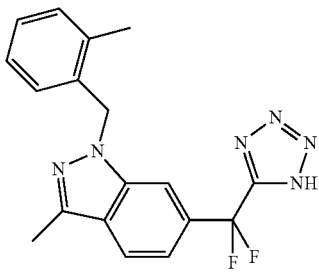 [SMILES: Cc1ccccc1Cn1nc(C)c2ccc(C(F)(F)c3nnn[nH]3)cc21]

The titled compound (33 mg) as a white solid was prepared from the compound [60-1] (50 mg) and 2-methylbenzyl chloride (25 mg) according to the methods of the process (1) in Example 1 and the process (8) in Example 58.
¹H-NMR (400 MHz, CD₃OD) δ: 7.87 (1H, d, J=8.8 Hz), 7.61 (1H, s), 7.34 (1H, d, J=8.8 Hz), 7.18-7.15 (2H, m), 7.08-7.04 (1H, m), 6.76 (1H, d, J=6.8 Hz), 5.61 (2H, s), 2.58 (3H, s), 2.29 (3H, s).
ESI-MS found: 355 [M+H]⁺

Example 87

Synthesis of 3-{6-[difluoro(1H-tetrazol-5-yl)methyl]-3-methyl-1H-indazol-1-ylmethyl}benzonitrile [87] (hereinafter referred to as a compound [87])

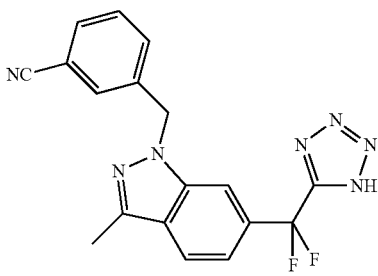 [SMILES: Cc1nn(Cc2cccc(C#N)c2)c2cc(C(F)(F)c3nnn[nH]3)ccc12]

The titled compound (35 mg) as a white solid was prepared from the compound [60-1] (56 mg) and 3-(bromomethyl)benzonitrile (39 mg) according to the methods of the process (1) in Example 1 and the process (8) in Example 58.
¹H-NMR (400 MHz, CD₃OD) δ: 7.89-7.86 (2H, m), 7.64-7.61 (1H, m), 7.57 (1H, s), 7.50-7.44 (2H, m), 7.37-7.35 (1H, m), 5.68 (2H, s), 2.59 (3H, s).
ESI-MS found: 366 [M+H]⁺

Example 88

Synthesis of 4-{6-[difluoro(1H-tetrazol-5-yl)methyl]-3-methyl-1H-indazol-1-ylmethyl}benzonitrile [88] (hereinafter referred to as a compound [88])

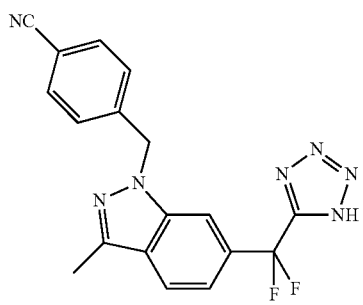 [SMILES: Cc1nn(Cc2ccc(C#N)cc2)c2cc(C(F)(F)c3nnn[nH]3)ccc12]

The titled compound (12 mg) as a white solid was prepared from the compound [60-1] (54 mg) and 4-(chloromethyl)benzonitrile (29 mg) according to the methods of the process (1) in Example 1 and the process (8) in Example 58.
¹H-NMR (400 MHz, CD₃OD) δ: 7.88 (1H, d, J=7.8 Hz), 7.83 (1H, s), 7.66 (2H, d, J=8.8 Hz), 7.36 (1H, d, J=8.8 Hz), 7.31 (2H, d, J=7.8 Hz), 5.71 (2H, s), 2.58 (3H, s).
ESI-MS found: 366 [M+H]⁺

Example 89

Synthesis of 1-(2-chloropyridin-3-ylmethyl)-6-[difluoro(1H-tetrazol-5-yl)methyl]-3-methyl-1H-indazole [89] (hereinafter referred to as a compound [89])

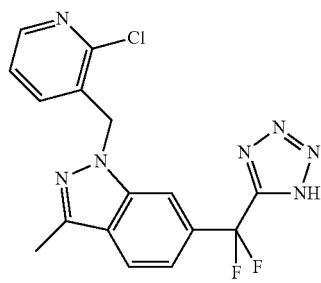 [SMILES: Cc1nn(Cc2cccnc2Cl)c2cc(C(F)(F)c3nnn[nH]3)ccc12]

(1) Synthesis of 2-chloro-3-chloromethylpyridine [89-1] (hereinafter referred to as a compound [89-1])

2-Chloro-3-pyridinemethanol (144 mg) was dissolved in dichloromethane (2.0 mL), and thionyl chloride (108 μL) was added to the solution at room temperature, and the mixture was stirred at room temperature for 1 hour. The reaction mixture was quenched with a saturated aqueous solution of sodium hydrogen carbonate, and extracted with ethyl acetate. The obtained organic layer was sequentially washed with water and brine, dried over anhydrous sodium sulfate, filtered, and the filtrate was concentrated under reduced pressure. The obtained residue was purified by silica gel column chromatography to give the titled compound (134 mg) as a colorless oil.

$^1$H-NMR (400 MHz, CDCl$_3$) δ: 8.37 (1H, d, J=3.9 Hz), 7.86 (1H, d, J=7.8 Hz), 7.31-7.26 (1H, m), 4.70 (2H, s).

(2) Synthesis of 1-(2-chloropyridin-3-ylmethyl)-6-{difluoro[1-(4-methoxybenzyl)-1H-tetrazol-5-yl]methyl-3-methyl-1H-indazole [89-2](hereinafter referred to as a compound [89-2])

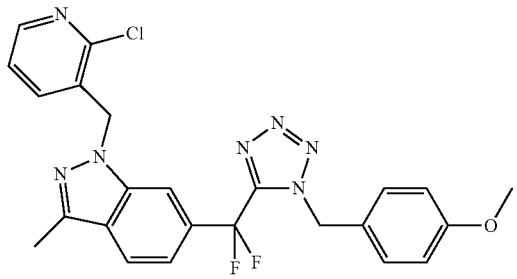 [SMILES: COc1ccc(Cn2nnnc2C(F)(F)c2ccc3c(C)nn(Cc4cccnc4Cl)c3c2)cc1]

The titled compound (76 mg) as a white solid was prepared from the compound [60-1] (80 mg) and the compound [89-1] (46 mg) according to the method of the process (1) in Example 1.
ESI-MS found: 496 [M+H]$^+$ (3) Synthesis of 1-(2-chloropyridin-3-ylmethyl)-6-[difluoro(1H-tetrazol-5-yl)methyl]-3-methyl-1H-indazole [89]

The titled compound (20 mg) as a white solid was prepared from the compound [89-2] (30 mg) according to the method of the process (8) in Example 58.
$^1$H-NMR (400 MHz, CD$_3$OD) δ: 8.29 (1H, dd, J=4.8, 2.1 Hz), 7.91-7.87 (2H, m), 7.39 (1H, dd, J=8.5, 1.5 Hz), 7.31-7.24 (2H, m), 5.73 (2H, s), 2.58 (3H, s).
ESI-MS found: 376 [M+H]$^+$ Example 90

Synthesis of 3-{6-[difluoro(1H-tetrazol-5-yl)methyl]-3-methyl-1H-indazol-1-ylmethyl}pyridine-2-carboxamide [90] (hereinafter referred to as a compound [90])

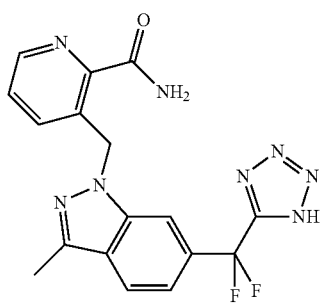 [SMILES: Cc1nn(Cc2cccnc2C(N)=O)c2cc(C(F)(F)c3nnn[nH]3)ccc12]

The titled compound (18 mg) as a white solid was prepared from the compound [89-2] (43 mg) according to the methods of the process (5) in Example 5 and the process (8) in Example 58.

$^1$H-NMR (400 MHz, CD$_3$OD) δ: 8.51-8.50 (1H, m), 7.90 (1H, d, J=8.5 Hz), 7.81 (1H, s), 7.37-7.34 (2H, m), 6.99 (1H, dd, J=8.1, 1.5 Hz), 6.17 (2H, s), 2.60 (3H, s).
ESI-MS found: 385 [M+H]$^+$ Example 91

Synthesis of 3-{6-[difluoro(1H-tetrazol-5-yl)methyl]-3-methyl-1H-indazol-1-ylmethyl}pyridine-2-carbonitrile [91] (hereinafter referred to as a compound [91])

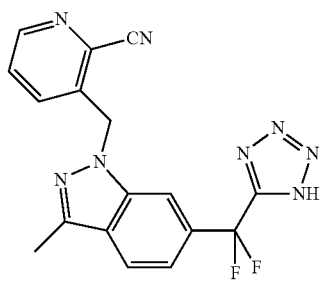 [SMILES: Cc1nn(Cc2cccnc2C#N)c2cc(C(F)(F)c3nnn[nH]3)ccc12]

The titled compound (4.8 mg) as a yellow white solid was prepared from the compound [89] (18 mg), zinc cyanide (7.9 mg), tris(dibenzylideneacetone)dipalladium(0) (8.8 mg) and 2-dicyclohexylphosphino-2',4',6'-triisopropylbiphenyl (9.1 mg) according to the method of the process (1) in Example 24.

$^1$H-NMR (400 MHz, CD$_3$OD) δ: 8.63-8.61 (1H, m), 7.96 (1H, s), 7.89 (1H, d, J=8.8 Hz), 7.59-7.54 (2H, m), 7.39 (1H, dd, J=8.8, 2.0 Hz), 5.85 (2H, s), 2.57 (3H, s).
ESI-MS found: 367 [M+H]$^+$ Example 92

Synthesis of 2-chloro-3-{6-[difluoro(1H-tetrazol-5-yl)methyl]-3-methyl-1H-indazol-1-ylmethyl}isonicotinonitrile [92] (hereinafter referred to as a compound [92])

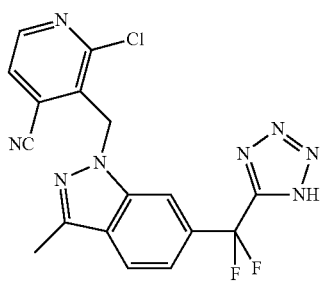 [SMILES: Cc1nn(Cc2c(C#N)ccnc2Cl)c2cc(C(F)(F)c3nnn[nH]3)ccc12]

157

(1) Synthesis of (2-chloro-4-iodopyridin-3-yl)methanol [92-1] (hereinafter referred to as a compound [92-1])

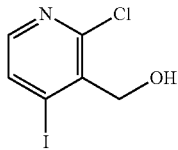

2-Chloro-4-iodopyridinecarboaldehyde (500 mg) was dissolved in methanol (19 mL), and to the solution was added sodium borohydride (74 mg) under ice cooling, and the mixture was stirred at 0° C. for 25 minutes. The reaction mixture was quenched with water, and extracted with ethyl acetate. The obtained organic layer was sequentially washed with water and brine, dried over anhydrous sodium sulfate, filtered, and the filtrate was concentrated under reduced pressure to give the titled compound (485 mg) as a white solid.
$^1$H-NMR (400 MHz, CDCl$_3$) δ: 7.92 (1H, d, J=5.1 Hz), 7.75 (1H, d, J=5.1 Hz), 4.99 (2H, d, J=7.1 Hz), 2.18 (1H, t, J=7.0 Hz).

(2) Synthesis of 2-chloro-3-chloromethyl-4-iodopyridine [92-2] (hereinafter referred to as a compound [92-2])

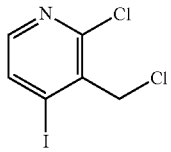

The titled compound (328 mg) as a white solid was prepared from the compound [92-1] (480 mg) and thionyl chloride (202 μL) according to the method of the process (1) in Example 89.
$^1$H-NMR (400 MHz, CDCl$_3$) δ: 7.93 (1H, d, J=5.1 Hz), 7.76 (1H, d, J=5.1 Hz), 4.90 (2H, s).

(3) Synthesis of 1-(2-chloro-4-iodopyridin-3-ylmethyl)-6-{difluoro[1-(4-methoxybenzyl)-1H-tetrazol-5-yl]methyl}-3-methyl-1H-indazole [92-3] (hereinafter referred to as a compound [92-3])

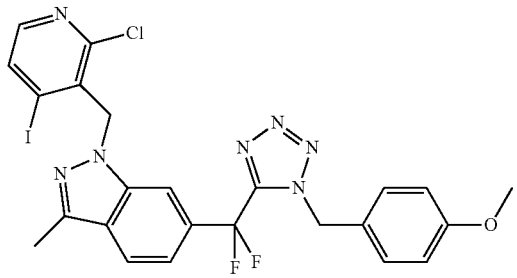

The titled compound (108 mg) as a yellow white solid was prepared from the compound [60-1] (80 mg) and the compound [92-2] (81 mg) according to the method of the process (1) in Example 1.
ESI-MS found: 622 [M+H]$^+$

158

(4) Synthesis of 2-chloro-3-(6-{difluoro[1-(4-methoxybenzyl)-1H-tetrazol-5-yl]methyl}-3-methyl-1H-indazol-1-ylmethyl)isonicotinonitrile[92-4](hereinafter referred to as a compound [92-4])

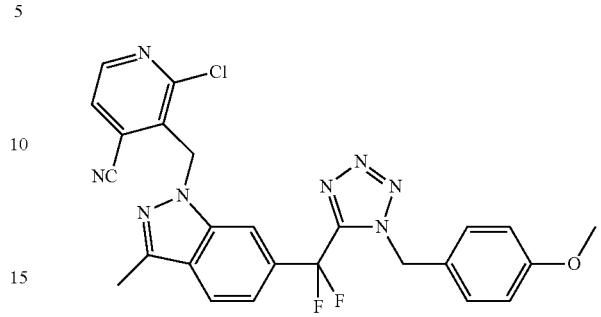

To a solution of the compound [92-3] (55 mg) in N,N-dimethylformamide (1.8 mL) were added zinc cyanide (15 mg) and tetrakis(triphenylphosphine)palladium(0) (20 mg) at room temperature, and the mixture was stirred at 80° C. for 5 hours. After cooling to room temperature, the reaction mixture was quenched with a saturated aqueous solution of potassium carbonate, and extracted with ethyl acetate. The obtained organic layer was sequentially washed with water and brine, dried over anhydrous sodium sulfate, filtered, and the filtrate was concentrated under reduced pressure. The obtained residue was purified by silica gel column chromatography to give the titled compound (32 mg) as a white solid.
ESI-MS found: 521 [M+H]$^+$ (5) Synthesis of 2-chloro-3-{6-[difluoro(1H-tetrazol-5-yl)methyl]-3-methyl-1H-indazol-1-ylmethyl}isonicotinonitrile[92]

The titled compound (15 mg) as a white solid was prepared from the compound [92-4] (30 mg) according to the method of the process (8) in Example 58.
$^1$H-NMR (400 MHz, CD$_3$OD) δ: 8.57 (1H, d, J=4.9 Hz), 8.03 (1H, s), 7.85 (1H, dd, J=8.5, 0.7 Hz), 7.79 (1H, d, J=5.1 Hz), 7.39 (1H, dd, J=8.5, 1.5 Hz), 5.82 (2H, s), 2.50 (3H, s).
ESI-MS found: 401 [M+H]$^+$ Example 93

Synthesis of 1-(2-chlorobenzyl)-6-[difluoro(1H-tetrazol-5-yl)methyl]-3-methyl-1H-indazole [93] (hereinafter referred to as a compound [93])

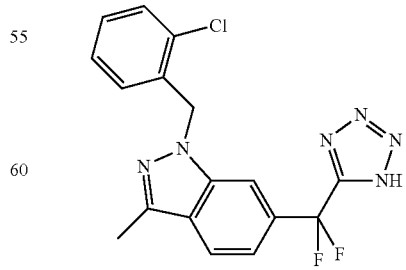

The titled compound (35 mg) as a white solid was prepared from the compound [60-1] (50 mg) and 2-chlorobenzyl chloride (28 mg) according to the methods of the process (1) in Example 1 and the process (8) in Example 58.

$^1$H-NMR (400 MHz, CD$_3$OD) δ: 7.88 (1H, d, J=8.8 Hz), 7.75 (1H, s), 7.42 (1H, d, J=7.8 Hz), 7.36 (1H, d, J=9.8 Hz), 7.27 (1H, td, J=7.8, 2.0 Hz), 7.18 (1H, t, J=8.3 Hz), 6.84 (1H, t, J=7.8 Hz), 5.70 (2H, s), 2.58 (3H, s).

ESI-MS found: 375 [M+H]$^+$

Example 94

Synthesis of 8-{6-[difluoro(1H-tetrazol-5-yl) methyl]-3-methyl-1H-indazol-1-ylmethyl}isoquinoline [94] (hereinafter referred to as a compound [94])

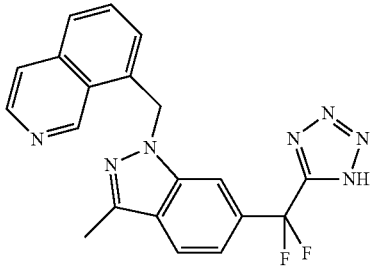 [SMILES: Cc1nn(Cc2cccc3ccncc23)c2cc(C(F)(F)c3nnn[nH]3)ccc12]

The titled compound (25 mg) as a yellow white solid was prepared from the compound [60-1] (49 mg) and 8-(bromomethyl)isoquinoline hydrogen bromide (60 mg) according to the methods of the process (1) in Example 1 and the process (8) in Example 58.

$^1$H-NMR (400 MHz, CD$_3$OD) δ: 9.92 (1H, s), 8.56 (1H, d, J=4.9 Hz), 8.28 (1H, d, J=5.9 Hz), 8.12 (1H, d, J=8.8 Hz), 7.97 (1H, t, J=7.3 Hz), 7.84-7.80 (2H, m), 7.54 (1H, d, J=6.8 Hz), 7.37 (1H, d, J=7.8 Hz), 6.27 (2H, s), 2.57 (3H, s).

ESI-MS found: 392 [M+H]$^+$

Example 95

Synthesis of 5-{6-[difluoro(1H-tetrazol-5-yl) methyl]-3-methyl-1H-indazol-1-ylmethyl}isoquinoline [95] (hereinafter referred to as a compound [95])

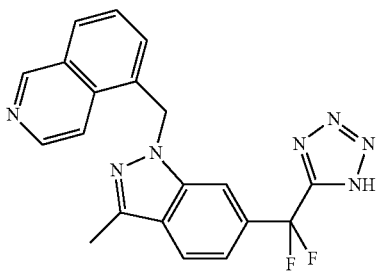 [SMILES: Cc1nn(Cc2cccc3cnccc23)c2cc(C(F)(F)c3nnn[nH]3)ccc12]

The titled compound (31 mg) as a yellow white solid was prepared from the compound [60-1] (50 mg) and 5-(bromomethyl)isoquinoline (45 mg) according to the methods of the process (1) in Example 1 and the process (8) in Example 58.

$^1$H-NMR (400 MHz, CD$_3$OD) δ: 9.56 (1H, s), 8.55 (1H, d, J=6.8 Hz), 8.49 (1H, d, J=6.8 Hz), 8.29 (1H, d, J=8.8 Hz), 7.85-7.79 (2H, m), 7.73 (1H, s), 7.68 (1H, d, J=6.8 Hz), 7.37 (1H, d, J=8.8 Hz), 6.16 (2H, s), 2.57 (3H, s).

ESI-MS found: 392 [M+H]$^+$

Example 96

Synthesis of 5-{6-[difluoro(1H-tetrazol-5-yl) methyl]-3-methyl-1H-indazol-1-ylmethyl}quinoline [96] (hereinafter referred to as a compound [96])

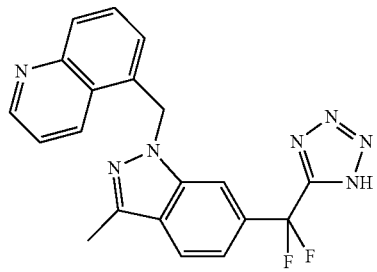 [SMILES: Cc1nn(Cc2cccc3ncccc23)c2cc(C(F)(F)c3nnn[nH]3)ccc12]

The titled compound (31 mg) as a yellow solid was prepared from the compound [60-1] (50 mg) and 5-(bromomethyl)quinoline hydrochloride (45 mg) according to the methods of the process (1) in Example 1 and the process (8) in Example 58.

$^1$H-NMR (400 MHz, CD$_3$OD) δ: 9.33 (1H, d, J=8.5 Hz), 9.11 (1H, d, J=3.9 Hz), 8.12 (1H, d, J=8.5 Hz), 7.99-7.94 (2H, m), 7.86 (1H, d, J=8.5 Hz), 7.83 (1H, s), 7.49 (1H, d, J=6.8 Hz), 7.37 (1H, dd, J=8.5, 1.2 Hz), 6.23 (2H, s), 2.57 (3H, s).

ESI-MS found: 392 [M+H]$^+$

Example 97

Synthesis of 1-{6-[difluoro(1H-tetrazol-5-yl) methyl]-3-methyl-1H-indazol-1-ylmethyl}isoquinoline [97] (hereinafter referred to as a compound [97])

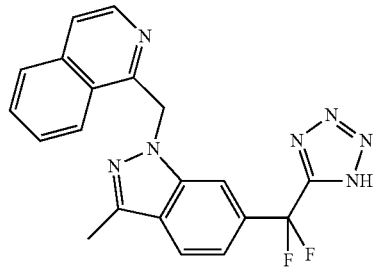 [SMILES: Cc1nn(Cc2nccc3ccccc23)c2cc(C(F)(F)c3nnn[nH]3)ccc12]

The titled compound (15 mg) as a yellow white solid was prepared from the compound [60-1] (47 mg) and 1-(bromomethyl)isoquinoline hydrogen bromide (58 mg) according to the methods of the process (1) in Example 1 and the process (8) in Example 58.

$^1$H-NMR (400 MHz, CD$_3$OD) δ: 8.49 (1H, d, J=7.8 Hz), 8.37 (1H, d, J=5.9 Hz), 8.04 (1H, d, J=8.8 Hz), 7.96 (1H, d, J=5.9 Hz), 7.90-7.82 (3H, m), 7.76 (1H, t, J=6.8 Hz), 7.36 (1H, d, J=8.8 Hz), 6.32-6.30 (2H, m), 2.55 (3H, s).

ESI-MS found: 392 [M+H]$^+$

Example 98

Synthesis of 6-[difluoro(1H-tetrazol-5-yl)methyl]-3-methyl-1-(2-trifluoromethylbenzyl)-1H-indazole [98] (hereinafter referred to as a compound [98])

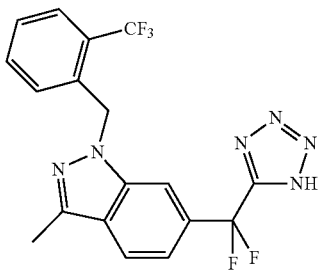

The titled compound (21 mg) as a white solid was prepared from the compound [60-1] (35 mg) and 2-(trifluoromethyl)benzyl bromide (29 mg) according to the methods of the process (1) in Example 1 and the process (8) in Example 58.

$^1$H-NMR (400 MHz, CD$_3$OD) δ: 7.91 (1H, d, J=7.8 Hz), 7.77-7.74 (1H, m), 7.64 (1H, s), 7.45-7.36 (3H, m), 6.69-6.67 (1H, m), 5.82 (2H, s), 2.61 (3H, s).

ESI-MS found: 409 [M+H]$^+$

Example 99

Synthesis of 3-{6-[difluoro(1H-tetrazol-5-yl)methyl]-3-methyl-1H-indazol-1-ylmethyl}-2-methylbenzonitrile [99] (hereinafter referred to as a compound [99])

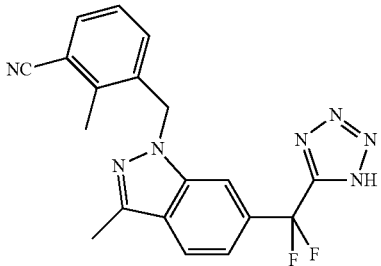 [SMILES: Cc1c(C#N)cccc1Cn1nc(C)c2ccc(C(F)(F)c3nnn[nH]3)cc21]

(1) Synthesis of (3-bromo-2-methylphenyl)methanol [99-1] (hereinafter referred to as a compound [99-1])

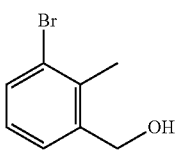

3-Bromo-2-methylbenzoic acid (1.08 g) was dissolved in tetrahydrofuran (34 mL), and to the solution was added sodium borohydride (1.15 g) under ice cooling. A solution of iodine (3.81 g) in tetrahydrofuran (16 mL) was then added to the mixture in two portions, and the mixture was stirred at room temperature for 20 hours. 4N-hydrochloric acid was added to the reaction mixture under ice cooling, and the mixture was extracted with ethyl acetate. The obtained organic layer was sequentially washed with an aqueous solution of 2N-sodium hydroxide and brine, dried over anhydrous sodium sulfate, filtered, and the filtrate was concentrated under reduced pressure. The obtained residue was purified by silica gel column chromatography to give the titled compound (934 mg) as a white solid.

$^1$H-NMR (400 MHz, CDCl$_3$) δ: 7.52-7.50 (1H, m), 7.32 (1H, d, J=7.6 Hz), 7.06 (1H, t, J=7.8 Hz), 4.73 (2H, d, J=5.9 Hz), 2.43 (3H, s), 1.58 (1H, t, J=5.9 Hz).

(2) Synthesis of 3-bromo-2-methylbenzyl chloride [99-2] (hereinafter referred to as a compound [99-2])

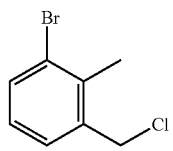

The compound [99-1] (526 mg) was dissolved in 1,4-dioxane (8.0 mL), and to the solution was added aluminum chloride (611 mg) at room temperature, and the mixture was then stirred at 70° C. for 48 hours. After cooling, the reaction mixture was quenched with water, and the extracted with ethyl acetate. The obtained organic layer was sequentially washed with water and brine, dried over anhydrous sodium sulfate, filtered, and the filtrate was concentrated under reduced pressure. The obtained residue was purified by silica gel column chromatography to give the titled compound (463 mg) as a colorless oil.

$^1$H-NMR (400 MHz, CDCl$_3$) δ: 7.54 (1H, d, J=6.8 Hz), 7.27-7.25 (1H, m), 7.04 (1H, t, J=7.8 Hz), 4.62 (2H, s), 2.51 (3H, s).

(3) Synthesis of 3-{6-[difluoro(1H-tetrazol-5-yl)methyl]-3-methyl-1H-indazol-1-ylmethyl}-2-methylbenzonitrile [99]

The titled compound (76 mg) as a white solid was prepared from the compound [60-1] (52 mg) and the compound [99-2] (40 mg) according to the methods of the process (1) in Example 1, the process (5) in Example 5 and the process (8) in Example 58.

$^1$H-NMR (400 MHz, CD$_3$OD) δ: 7.89 (1H, d, J=8.8 Hz), 7.78 (1H, s), 7.59 (1H, d, J=6.8 Hz), 7.37 (1H, d, J=8.8 Hz), 7.23 (1H, t, J=7.8 Hz), 6.96 (1H, d, J=7.8 Hz), 5.69 (2H, s), 2.58 (3H, s), 2.55 (3H, s).

ESI-MS found: 380 [M+H]$^+$

Example 100

Synthesis of 3-{6-[difluoro(1H-tetrazol-5-yl) methyl]-3-methyl-1H-indazol-1-ylmethyl}-2-methylbenzamide [100] (hereinafter referred to as a compound [100])

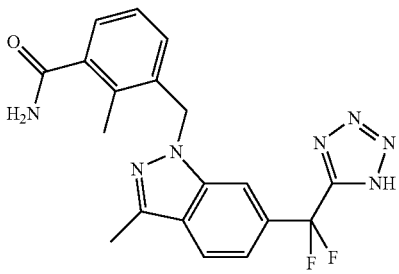 [SMILES: Cc1c(Cn2nc(C)c3ccc(C(F)(F)c4nnn[nH]4)cc32)cccc1C(N)=O]

The titled compound (9.0 mg) as a white solid was prepared from the compound [99] (13 mg) according to the method of the process (1) in Example 67.

$^1$H-NMR (400 MHz, CD$_3$OD) δ: 7.88 (1H, d, J=8.8 Hz), 7.69 (1H, s), 7.35 (1H, d, J=8.8 Hz), 7.30 (1H, d, J=7.8 Hz), 7.13 (1H, t, J=7.8 Hz), 6.79 (1H, d, J=7.8 Hz), 5.67 (2H, s), 2.59 (3H, s), 2.39 (3H, s).

ESI-MS found: 398 [M+H]$^+$

Example 101

Synthesis of 5-{[1-(2-chloro-6-fluorobenzyl)-3-methyl-1H-indazol-6-yl]difluoromethyl}-1,3,4-oxadiazol-2(3H)-one [101] (hereinafter referred to as a compound [101])

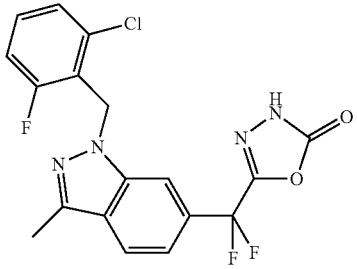 [SMILES: Cc1nn(Cc2c(F)cccc2Cl)c2cc(C(F)(F)c3n[nH]c(=O)o3)ccc12]

(1) Synthesis of tert-butyl N'-{[1-(2-chloro-6-fluorobenzyl)-3-methyl-1H-indazol-6-yl]difluoroacetyl}carbazate [101-1] (hereinafter referred to as a compound [101-1])

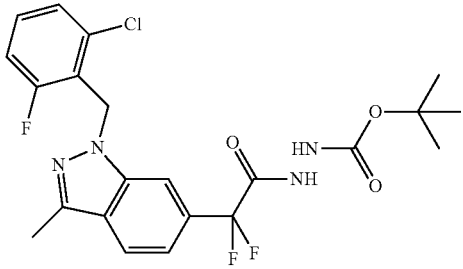

The compound [9] (100 mg) was dissolved in chloroform (1.4 mL), and to the solution were added tert-butyl carbazate (143 mg), 1-hydroxybenzotriazole monohydrate (73 mg) and 1-(3-dimethylaminopropyl)-3-ethylcarbodiimide hydrochloride (104 mg) at room temperature, and the mixture was stirred at room temperature for 3 days. The reaction mixture was quenched with a saturated aqueous solution of potassium carbonate, and extracted with ethyl acetate. The obtained organic layer was sequentially washed with water and brine, dried over anhydrous sodium sulfate, filtered, and the filtrate was concentrated under reduced pressure. The obtained residue was purified by silica gel column chromatography to give the titled compound (47 mg) as a white solid.

ESI-MS found: 483 [M+H]$^+$ (2) Synthesis of [1-(2-chloro-6-fluorobenzyl)-3-methyl-1H-indazol-6-yl]difluoroacetohydrazide [101-2] (hereinafter referred to as a compound [101-2])

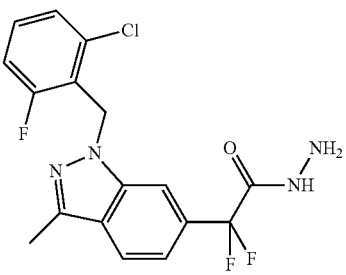 [SMILES: Cc1nn(Cc2c(F)cccc2Cl)c2cc(C(F)(F)C(=O)NN)ccc12]

The compound [101-1] (47 mg) was suspended in chloroform (2.0 mL), and to the mixture was added trifluoroacetic acid (1.0 mL) at room temperature, and the mixture was stirred at room temperature for 3 hours. The reaction mixture was concentrated under reduced pressure, and added a saturated aqueous solution of sodium hydrogen carbonate, and extracted with ethyl acetate. The obtained residue was purified by silica gel column chromatography to give the titled compound (23 mg) as a white solid.

ESI-MS found: 383 [M+H]$^+$ (3) Synthesis of 5-{[1-(2-chloro-6-fluorobenzyl)-3-methyl-1H-indazol-6-yl]difluoromethyl}-1,3,4-oxadiazol-2(3H)-one [101]

To a solution of the compound [101-2] (23 mg) in tetrahydrofuran (1.2 mL) were added N,N-diisopropylethylamine (54 µL) and 1,1'-carbonyldiimidazole (30 mg) at room temperature, and the mixture was stirred at room temperature for 14 hours. The reaction mixture was concentrated under reduced pressure, and the obtained residue was purified by reverse phase preparative liquid chromatography to give the titled compound (19 mg) as a white solid.

$^1$H-NMR (400 MHz, CDCl$_3$) δ: 9.30-8.60 (1H, br), 7.78 (1H, s), 7.74 (1H, d, J=8.8 Hz), 7.30-7.21 (3H, m), 7.06-7.02 (1H, m), 5.68 (2H, s), 2.56 (3H, s).

ESI-MS found: 409 [M+H]

Example 102

Synthesis of 1-(2,6-dichlorobenzenesulfonyl)-6-[difluoro(1H-tetrazol-5-yl)methyl]-3-methyl-1H-indazole [102] (hereinafter referred to as a compound [102])

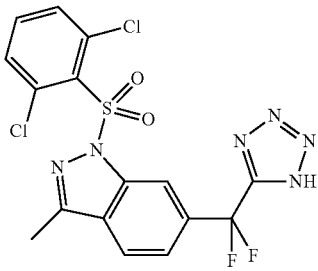 [SMILES: Cc1nn(S(=O)(=O)c2c(Cl)cccc2Cl)c2cc(C(F)(F)c3nnn[nH]3)ccc12]

(1) Synthesis of 1-(2,6-dichlorobenzenesulfonyl)-6-{difluoro[1-(4-methoxybenzyl)-1H-tetrazol-5-yl]methyl}-3-methyl-1H-indazole [102-1](hereinafter referred to as a compound [102-1])

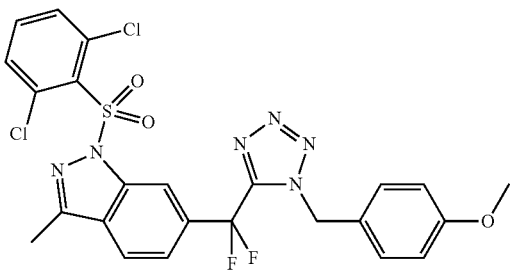 [SMILES: COc1ccc(Cn2nnnc2C(F)(F)c2ccc3c(C)nn(S(=O)(=O)c4c(Cl)cccc4Cl)c3c2)cc1]

The compound [60-1] (37 mg) was dissolved in tetrahydrofuran (2.0 mL), and to the solution was added 1.0M tetrahydrofuran solution of potassium tert-butoxide (0.15 mL) at 0° C., and the mixture was stirred at 0° C. for 5 minutes. 2,6-Dichlorobenzenesulfonyl chloride (32 mg) was then added to the mixture at 0° C., and the mixture was stirred at 0° C. for 10 minutes. The reaction mixture was quenched with water, and extracted with ethyl acetate. The obtained organic layer was sequentially washed with water and brine, dried over anhydrous sodium sulfate, filtered, and the filtrate was concentrated under reduced pressure. The obtained residue was purified by silica gel column chromatography to give the titled compound (56 mg) as a white solid.
ESI-MS found: 579 [M+H]$^+$ (2) Synthesis of 1-(2,6-dichlorobenzenesulfonyl)-6-[difluoro(1H-tetrazol-5-yl)methyl]-3-methyl-1H-indazole [102]

The titled compound (31 mg) as a white amorphous was prepared from the compound [102-1] (53 mg) according to the method of the process (8) in Example 58.
$^1$H-NMR (400 MHz, CD$_3$OD) δ: 8.36 (1H, s), 7.97 (1H, d, J=8.3 Hz), 7.67-7.54 (4H, m), 2.54 (3H, s).
ESI-MS found: 459 [M+H]$^+$

Example 103

Synthesis of 1-(2-chloro-6-methylbenzenesulfonyl)-6-[difluoro(1H-tetrazol-5-yl)methyl]-3-methyl-1H-indazole [103] (hereinafter referred to as a compound [103])

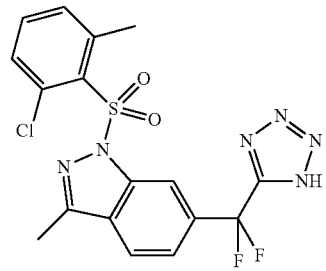 [SMILES: Cc1cccc(Cl)c1S(=O)(=O)n1nc(C)c2ccc(C(F)(F)c3nnn[nH]3)cc21]

The titled compound (24 mg) as a white amorphous was prepared from the compound [60-1] (74 mg) and 2-chloro-6-methylbenzenesulfonyl chloride (59 mg) according to the methods of the process (1) in Example 102 and the process (8) in Example 58.
$^1$H-NMR (400 MHz, CD$_3$OD) δ: 8.40 (1H, s), 7.94 (1H, dd, J=8.5, 0.7 Hz), 7.63 (1H, dd, J=8.5, 1.5 Hz), 7.49 (1H, t, J=7.7 Hz), 7.44-7.42 (1H, m), 7.39-7.37 (1H, m), 2.88 (3H, s), 2.52 (3H, s).
ESI-MS found: 439 [M+H]$^+$

Example 104

Synthesis of 2-{6-[difluoro(1H-tetrazol-5-yl)methyl]-3-methyl-1H-indazol-1-ylmethyl}-3-(hydroxymethyl)benzonitrile [104] (hereinafter referred to as a compound [104])

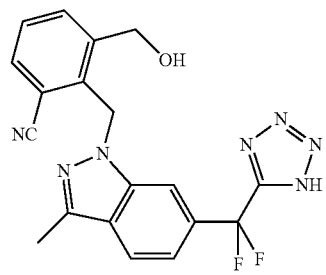 [SMILES: Cc1nn(Cc2c(C#N)cccc2CO)c2cc(C(F)(F)c3nnn[nH]3)ccc12]

(1) Synthesis of methyl 3-bromo-2-methylbenzoate [104-1] (hereinafter referred to as a compound [104-1])

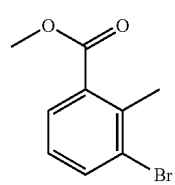

3-Bromo-2-methylbenzoic acid (1.08 g) was dissolved in methanol (16 mL), and to the solution was added concentrated sulfuric acid (1.6 mL) at room temperature, and the mixture was subjected to microwave irradiation at 110° C. for 10 minutes. The reaction mixture was cooled by ice, added an aqueous solution of 5N-sodium hydroxide, and the mixture was extracted with ethyl acetate. The obtained organic layer was sequentially washed with water and brine, dried over anhydrous sodium sulfate, filtered, and the filtrate was concentrated under reduced pressure to give the titled compound (1.10 g) as a yellow oil.

$^1$H-NMR (400 MHz, CDCl$_3$) δ: 7.74-7.68 (2H, m), 7.10 (1H, t, J=7.8 Hz), 3.91 (3H, s), 2.63 (3H, s).

(2) Synthesis of methyl 3-bromo-2-(bromomethyl)benzoate [104-2] (hereinafter referred to as a compound [104-2])

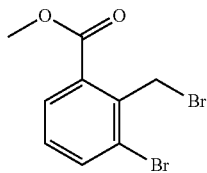

The titled compound (1.39 g) as a colorless oil was prepared from the compound [104-1] (1.10 g) according to the method of the process (2) in Example 5.

$^1$H-NMR (400 MHz, CDCl$_3$) δ: 7.89 (1H, dd, J=7.9, 1.1 Hz), 7.77 (1H, dd, J=8.1, 1.2 Hz), 7.26-7.22 (1H, m), 5.13 (2H, s), 3.96 (3H, s).

(3) Synthesis of methyl 3-bromo-2-(6-{difluoro[1-(4-methoxybenzyl)-1H-tetrazol-5-yl]methyl}-3-methyl-1H-indazol-1-ylmethyl)benzoate [104-3] (hereinafter referred to as a compound [104-3])

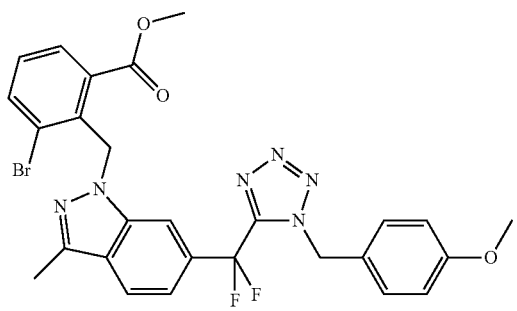 [SMILES: COC(=O)c1cccc(Br)c1Cn1nc(C)c2ccc(C(F)(F)c3nnnn3Cc3ccc(OC)cc3)cc21]

The titled compound (363 mg) as a yellow amorphous was prepared from the compound [60-1] (250 mg) and the compound [104-2] (270 mg) according to the method of the process (1) in Example 1.

ESI-MS found: 597 [M+H]$^+$ (4) Synthesis of [3-bromo-2-(6-{difluoro[1-(4-methoxybenzyl)-H-tetrazol-5-yl]ethyl}-3-methyl-1H-indazol-ylmethyl)phenyl]methanol [104-4] (hereinafter referred to as a compound [104-4])

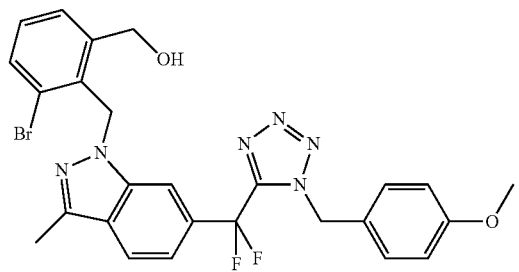 [SMILES: COc1ccc(Cn2nnnc2C(F)(F)c2ccc3c(C)nn(Cc4c(Br)cccc4CO)c3c2)cc1]

The compound [104-3] (363 mg) was dissolved in tetrahydrofuran (12 mL), and to the solution was added lithium aluminum hydride (46 mg) at 0° C., and the mixture was stirred at 0° C. for 1 hour. The reaction mixture was quenched with a saturated aqueous solution of sodium sulfate, and the mixture was stirred at room temperature for 2 hours. The white gel was filtered, and the filtrate was concentrated under reduced pressure. The obtained residue was purified by silica gel column chromatography to give the titled compound (257 mg) as a yellow white solid.

ESI-MS found: 569 [M+H]$^+$ (5) Synthesis of 2-{6-[difluoro(1H-tetrazol-5-yl)methyl]-3-methyl-1H-indazol-1-ylmethyl}-3-(hydroxymethyl)benzonitrile [104]

The titled compound (15 mg) as a white solid was prepared from the compound [104-4] (175 mg) according to the method of the process (5) in Example 5 and the process (8) in Example 58.

$^1$H-NMR (400 MHz, CD$_3$OD) δ: 7.90 (1H, s), 7.85-7.80 (2H, m), 7.71 (1H, d, J=7.8 Hz), 7.54 (1H, t, J=7.8 Hz), 7.39-7.36 (1H, m), 5.80 (2H, s), 4.64 (2H, s), 2.51 (3H, s).

ESI-MS found: 396 [M+H]$^+$

Example 105

Synthesis of potassium 5-({1-[2-cyano-6-(hydroxymethyl)benzyl]-3-methyl-1H-indazol-6-yl}difluoromethyl)-1H-tetrazol-1-ide [105] (hereinafter referred to as a compound [105])

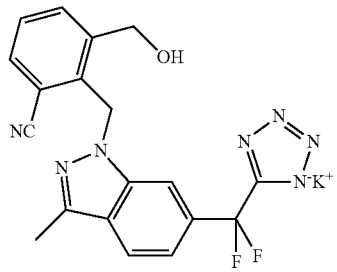

To a solution of the compound [104] (31 mg) in ethanol (1.0 mL) was added an aqueous solution of 1N-potassium hydroxide (79 µL) at room temperature, and the solution was concentrated under reduced pressure to give the titled compound (28 mg) as a white solid.

$^1$H-NMR (400 MHz, CD$_3$OD) δ: 7.80-7.70 (4H, m), 7.54 (1H, t, J=7.3 Hz), 7.34-7.32 (1H, m), 5.79 (2H, s), 4.53 (2H, s), 2.49 (3H, s).

ESI-MS found: 396 [M−K+2H]$^+$

Example 106

Synthesis of (2-{6-[difluoro(1H-tetrazol-5-yl)methyl]-3-methyl-1H-indazol-1-ylmethyl}-3-methylphenyl)methanol [106] (hereinafter referred to as a compound [106])

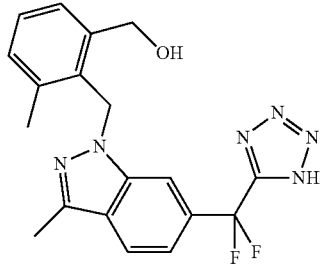 [SMILES: Cc1cccc(CC#N)c1Cn1nc(C)c2ccc(C(F)(F)c3nnn[nH]3)cc21]

(1) Synthesis of [2-(6-{difluoro[1-(4-methoxybenzyl)-1H-tetrazol-5-yl]methyl}-3-methyl-1H-indazol-1-ylmethyl)-3-methylphenyl]methanol [106-1] (hereinafter referred to as a compound [106-1])

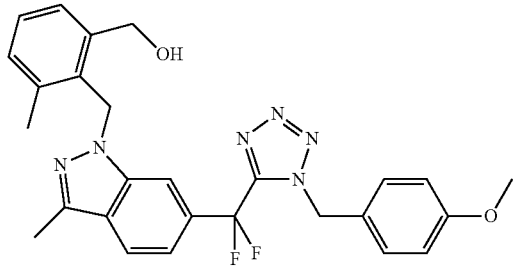 [SMILES: COc1ccc(Cn2nnnc2C(F)(F)c2ccc3c(C)nn(Cc4c(C)cccc4CC#N)c3c2)cc1]

The compound [104-4] (40 mg), methylboronic acid (8.4 mg), tetrakis(triphenylphosphine)palladium(0) (4.1 mg) and cesium carbonate (69 mg) were suspended in a mixed solvent (1.0 mL) of 1,4-dioxane/water (volume ratio 2/1), and the suspension was subjected to microwave irradiation at 160° C. for 10 minutes. After cooling, water was added to the mixture, and the mixture was extracted with ethyl acetate. The obtained organic layer was sequentially washed with water and brine, dried over anhydrous sodium sulfate, filtered, and the filtrate was concentrated under reduced pressure. The obtained residue was purified by silica gel column chromatography to give the titled compound (18 mg) as a white solid.

ESI-MS found: 505 [M+H]$^+$ (2) Synthesis of (2-{6-[difluoro(1H-tetrazol-5-yl)methyl]-3-methyl-1H-indazol-1-ylmethyl-3-methylphenyl)methanol [106]

The titled compound (10 mg) as a white solid was prepared from the compound [106-1] (16 mg) according to the method of the process (8) in Example 58.

$^1$H-NMR (400 MHz, CD$_3$OD) δ: 7.83 (1H, d, J=8.8 Hz), 7.54 (1H, s), 7.34-7.29 (2H, m), 7.24 (1H, t, J=7.8 Hz), 7.14 (1H, d, J=6.8 Hz), 5.67 (2H, s), 4.68 (2H, s), 2.52 (3H, s), 2.19 (3H, s).

ESI-MS found: 385 [M+H]$^+$

Example 107

Synthesis of (2-{6-[difluoro(1H-tetrazol-5-yl)methyl]-3-methyl-1H-indazol-1-ylmethyl}-3-methylphenyl)acetonitrile [107] (hereinafter referred to as a compound [107])

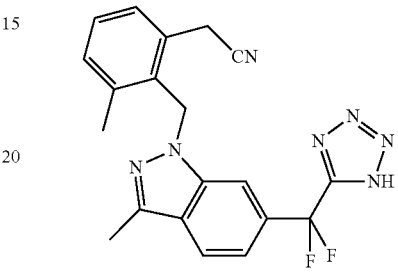

(1) Synthesis of [2-(6-{difluoro[1-(4-methoxybenzyl)-1H-tetrazol-5-yl]methyl}-3-methyl-1H-indazol-1-ylmethyl)-3-methylphenyl]acetonitrile [107-1] (hereinafter referred to as a compound [107-1])

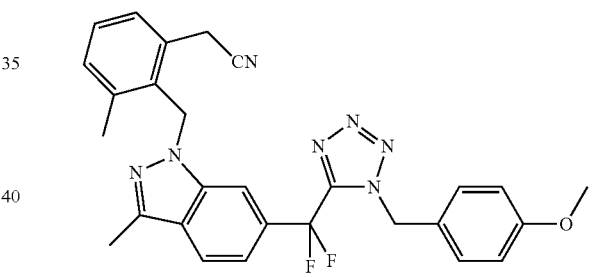

The compound [106-1] (38 mg) was dissolved in dichloromethane (2.5 mL), and to the solution was added thionyl chloride (16 μL) at room temperature, and the mixture was stirred at room temperature for 30 minutes. The reaction mixture was concentrated under reduced pressure, and the obtained residue was dissolved in acetonitrile (2.5 mL). To the mixture was added tetraethylammonium cyanide (118 mg) at room temperature, and stirred at room temperature for 1 hour. The reaction mixture was quenched with water, and extracted with ethyl acetate. The obtained organic layer was sequentially washed with water and brine, dried over anhydrous sodium sulfate, filtered, and the filtrate was concentrated under reduced pressure. The obtained residue was purified by silica gel column chromatography to give the titled compound (25 mg) as a white solid.

ESI-MS found: 514 [M+H]$^+$ (2) Synthesis of (2-{6-[difluoro(1H-tetrazol-5-yl)methyl]-3-methyl-1H-indazol-1-ylmethyl-3-methylphenyl)acetonitrile [107]

The titled compound (17 mg) as a yellow solid was prepared from the compound [107-1] (25 mg) according to the method of the process (8) in Example 58.

$^1$H-NMR (400 MHz, CD$_3$OD) δ: 7.84 (1H, d, J=7.8 Hz), 7.63 (1H, s), 7.36-7.28 (3H, m), 7.22 (1H, d, J=6.8 Hz), 5.61 (2H, s), 4.01 (2H, s), 2.52 (3H, s), 2.31 (3H, s).
ESI-MS found: 394 [M+H]$^+$ Example 108

Synthesis of 1-(2,6-dichlorobenzyl)-6-[difluoro(1H-tetrazol-5-yl)methyl]-3-methyl-1H-pyrazolo[3,4-b]pyridine [108] (hereinafter referred to as a compound [108])

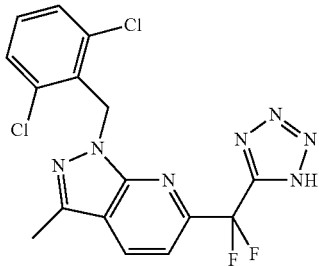 [SMILES: Cc1nn(Cc2c(Cl)cccc2Cl)c2nc(C(F)(F)c3nnn[nH]3)ccc12]

(1) Synthesis of 2,6-dichloro-N-methoxy-N-methyl-nicotinamide [108-1] (hereinafter referred to as a compound [108-1])

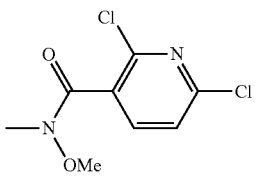

To a suspension of 2,6-dichloronicotine acid (1.92 g), N,O-dimethylhydroxylamine hydrochloride (1.46 g) and triethylamine (2.1 mL) in N,N-dimethylformamide (30 mL) was added 1-ethyl-3-(3-dimethylaminopropyl)carbodiimide hydrochloride (2.30 g) at room temperature, and the mixture was stirred at room temperature for 4 days. The reaction mixture was diluted with ethyl acetate and sequentially washed with an aqueous solution of 5% potassium hydrogen sulfate, a saturated aqueous solution of sodium hydrogen carbonate and brine. The obtained organic layer was dried over anhydrous sodium sulfate, filtered, and the filtrate was concentrated under reduced pressure. The obtained residue was purified by silica gel column chromatography to give the titled compound (1.61 g) as a white solid.
$^1$H-NMR (400 MHz, CDCl$_3$) δ: 7.65 (1H, d, J=8.0 Hz), 7.34 (1H, d, J=8.0 Hz), 3.51 (3H, s), 3.40 (3H, s).

(2) Synthesis of 1-(2,6-dichloropyridin-3-yl)ethanone [108-2] (hereinafter referred to as a compound [108-2])

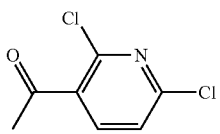

The compound [108-1] (487 mg) was dissolved in tetrahydrofuran (10 mL). To the solution was added 2.0M diethyl ether solution of methylmagnesium iodide (1.24 mL) at 0° C., and the mixture was then stirred at 70° C. for 72 hours. The reaction mixture was quenched with a saturated aqueous solution of ammonium chloride, and extracted with ethyl acetate. The obtained organic layer was sequentially washed with water and brine, dried over anhydrous sodium sulfate, filtered, and the filtrate was concentrated under reduced pressure. The obtained residue was purified by silica gel column chromatography to give the titled compound (205 mg) as a colorless oil.
$^1$H-NMR (400 MHz, CDCl$_3$) δ: 7.93 (1H, d, J=8.1 Hz), 7.37 (1H, d, J=8.1 Hz), 2.71 (3H, s).

(3) Synthesis of 6-chloro-3-methyl-1H-pyrazolo[3,4-b]pyridine [108-3] (hereinafter referred to as a compound [108-3])

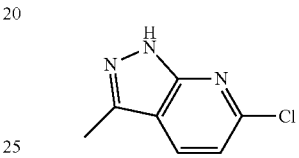

The compound [108-2] (205 mg) was dissolved in dichloromethane (2.7 mL), and to the solution was added titanium (IV) tetraisopropoxide (0.63 mL) at room temperature, and the mixture was stirred at room temperature for 15 minutes. Hydrazine monohydrate (0.11 mL) was then added to the reaction mixture at room temperature, and the mixture was stirred at room temperature for 3 hours. The reaction mixture was quenched with water, and the mixture was stirred for 30 minutes, the insoluble material was separated by filtration, and rinsed with chloroform. The filtrate was concentrated under reduced pressure to give a white solid. The obtained solid was suspended in ethanol (1.5 mL), and the suspension was subjected to microwave irradiation at 150° C. for 20 minutes. Water was added to the reaction mixture, and the mixture was extracted with ethyl acetate. The obtained organic layer was sequentially washed with water and brine, dried over anhydrous sodium sulfate, filtered, and the filtrate was concentrated under reduced pressure. The obtained residue was purified by silica gel column chromatography to give the titled compound (86 mg) as a white solid.
$^1$H-NMR (400 MHz, CDCl$_3$) δ: 10.18-10.08 (1H, br), 7.96 (1H, d, J=8.3 Hz), 7.14 (1H, d, J=8.3 Hz), 2.57 (3H, s).
ESI-MS found: 168 [M+H]$^+$ (4) Synthesis of 6-chloro-1-(2,6-dichlorobenzyl)-3-methyl-1H-pyrazolo[3,4-b]pyridine [108-4] (hereinafter referred to as a compound [108-4])

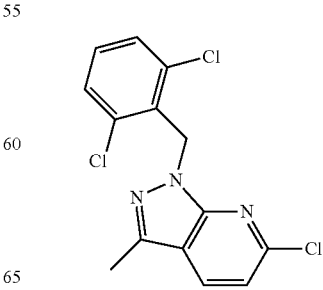

The titled compound (104 mg) as a white solid was prepared from the compound [108-3] (86 mg) and 2,6-dichlorobenzyl chloride (208 mg) according to the method of the process (1) in Example 1.

ESI-MS found: 326 [M+H]$^+$ (5) Synthesis of [1-(2,6-dichlorobenzyl)-3-methyl-1H-pyrazolo[3,4-b]pyridin-6-yl]acetonitrile [108-5] (hereinafter referred to as a compound [108-5])

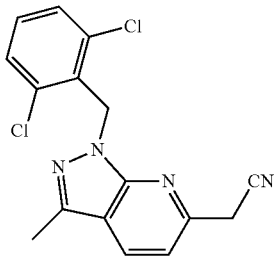 [SMILES: Cc1nn(Cc2c(Cl)cccc2Cl)c2nc(CC#N)ccc12]

The compound [108-4] (98 mg) was dissolved in toluene (4.0 mL), and to the solution was added acetonitrile (157 μL) under argon atmosphere, and the mixture was cooled to 0° C. To the mixture was added 1.0M tetrahydrofuran solution (6.0 mL) of sodium bis(trimethylsilyl)amide at 0° C., and stirred at 0° C. for 4 hours. The reaction mixture was quenched with a saturated aqueous solution of ammonium chloride, and extracted with ethyl acetate. The obtained organic layer was sequentially washed with water and brine, dried over anhydrous sodium sulfate, filtered, and the filtrate was concentrated under reduced pressure. The obtained residue was purified by silica gel column chromatography to give the titled compound (50 mg) as a yellow solid.

ESI-MS found: 331 [M+H]$^+$ (6) Synthesis of [1-(2,6-dichlorobenzyl)-3-methyl-1H-pyrazolo[3,4-b]pyridin-6-yl]difluoroacetonitrile [108-6] (hereinafter referred to as a compound [108-6])

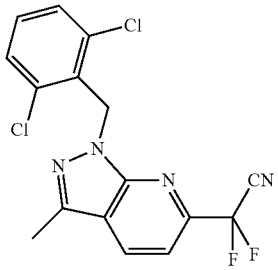 [SMILES: Cc1nn(Cc2c(Cl)cccc2Cl)c2nc(C(F)(F)C#N)ccc12]

The compound [108-5] (61 mg) was dissolved in tetrahydrofuran (3.6 mL), and cooled to −78° C. under an argon atmosphere. To the solution was added 1.0M tetrahydrofuran solution (0.4 mL) of lithium bis(trimethylsilyl)amide at −78° C., and the mixture was stirred at −78° C. for 10 minutes. N-fluorobenzenesulfonimide (127 mg) was then added at −78° C., and the mixture was stirred at −78° C. for 2 hours. The reaction mixture was quenched with a saturated aqueous solution of ammonium chloride, and extracted with ethyl acetate. The obtained organic layer was sequentially washed with water and brine, dried over anhydrous sodium sulfate, filtered, and the filtrate was concentrated under reduced pressure. The obtained residue was purified by silica gel column chromatography to give the titled compound (47 mg) as a white solid.

ESI-MS found: 367 [M+H]$^+$ (7) Synthesis of 1-(2,6-dichlorobenzyl)-6-[difluoro(1H-tetrazol-5-yl)methyl]-3-methyl-1H-pyrazolo[3,4-b]pyridine [108]

The compound [108-6] (44 mg) was dissolved in N,N-dimethylformamide (2.4 mL), and to the solution was added sodium azide (12 mg) at room temperature. The mixture was subjected to microwave irradiation at 100° C. for 10 minutes. After cooling to room temperature, 4N-hydrochloric acid was added, and the mixture was extracted with ethyl acetate. The obtained organic layer was sequentially washed with water and brine, dried over anhydrous sodium sulfate, filtered, and the filtrate was concentrated under reduced pressure. The obtained residue was purified by silica gel column chromatography to give the titled compound (15 mg) as a white solid.

$^1$H-NMR (400 MHz, CD$_3$OD) δ: 8.39 (1H, d, J=8.8 Hz), 7.72 (1H, d, J=7.8 Hz), 7.35 (2H, d, J=6.8 Hz), 7.27 (1H, dd, J=8.8, 6.8 Hz), 5.77 (2H, s), 2.52 (3H, s).

ESI-MS found: 410 [M+H]$^+$

Example 109

Synthesis of 2-{6-[difluoro(1H-tetrazol-5-yl)methyl]-3-methyl-1H-pyrazolo[3,4-b]pyridin-1-ylmethyl}-3-methylbenzonitrile [109] (hereinafter referred to as a compound [109])

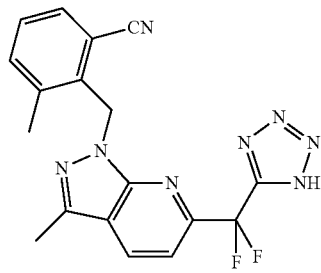 [SMILES: Cc1cccc(C#N)c1Cn1nc(C)c2ccc(C(F)(F)c3nnn[nH]3)nc21]

(1) Synthesis of difluoro[1-(2-iodo-6-methylbenzyl)-3-methyl-1H-pyrazolo[3,4-b]pyridin-6-yl]acetonitrile [109-1] (hereinafter referred to as a compound [109-1])

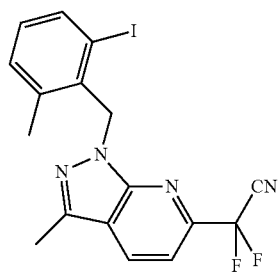 [SMILES: Cc1cccc(I)c1Cn1nc(C)c2ccc(C(F)(F)C#N)nc21]

The titled compound (114 mg) as a white solid was prepared from the compound [108-3] (335 mg) and the compound [55-3] (693 mg) according to the methods of the process (1) in Example 1 and the processes (5) and (6) in Example 108.
ESI-MS found: 439 [M+H]+

(2) Synthesis of 2-[6-(cyanodifluoromethyl)-3-methyl-1H-pyrazolo[3,4-b]pyridin-1-ylmethyl]-3-methylbenzonitrile [109-2] (hereinafter referred to as a compound [109-2])

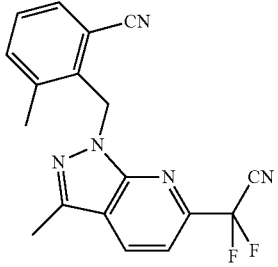 [SMILES: Cc1cccc(C#N)c1Cn1nc(C)c2ccc(C(F)(F)C#N)nc21]

The titled compound (34 mg) as a white solid was prepared from the compound [109-1] (50 mg) according to the method of the process (5) in Example 55.
ESI-MS found: 338 [M+H]+

(3) Synthesis of 2-{6-[difluoro(1H-tetrazol-5-yl)methyl]-3-methyl-1H-pyrazolo[3,4-b]pyridin-1-ylmethyl}-3-methylbenzonitrile [109]

The compound [109-2] (34 mg) was dissolved in N,N-dimethylformamide (2.0 mL), and to the solution was added sodium azide (10 mg) at room temperature, and the mixture was stirred at room temperature for 18 hours. 3N-hydrochloric acid was added to the reaction mixture, and the mixture was extracted with ethyl acetate. The obtained organic layer was sequentially washed with water and brine, dried over anhydrous sodium sulfate, filtered, and the filtrate was concentrated under reduced pressure to give the titled compound (38 mg) as a white solid.
$^1$H-NMR (400 MHz, CD$_3$OD) δ: 8.42 (1H, d, J=8.3 Hz), 7.74 (1H, d, J=8.1 Hz), 7.56-7.54 (1H, m), 7.41 (1H, d, J=6.8 Hz), 7.36 (1H, t, J=7.6 Hz), 5.70 (2H, s), 2.54 (3H, s), 2.09 (3H, s).
ESI-MS found: 381 [M+H]+

Example 110

Synthesis of 2-{6-[difluoro(1H-tetrazol-5-yl)methyl]-3-methyl-1H-pyrazolo[3,4-b]pyridin-1-ylmethyl}-3-methylbenzamide [110] (hereinafter referred to as a compound [110])

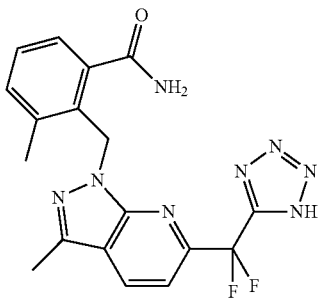 [SMILES: Cc1cccc(C(N)=O)c1Cn1nc(C)c2ccc(C(F)(F)c3nnn[nH]3)nc21]

The titled compound (32 mg) as a white solid was prepared from the compound [109] (36 mg) according to the method of the process (1) in Example 67.
$^1$H-NMR (400 MHz, CD$_3$OD) δ: 8.41 (1H, d, J=8.8 Hz), 7.72 (1H, d, J=7.8 Hz), 7.33 (1H, d, J=6.8 Hz), 7.26 (1H, t, J=7.3 Hz), 7.20 (1H, d, J=6.8 Hz), 5.71 (2H, s), 2.53 (3H, s), 2.02 (3H, s).
ESI-MS found: 399 [M+H]+

Example 111

Synthesis of potassium 5-{[1-(2-carbamoyl-6-methylbenzyl)-3-methyl-1H-pyrazolo[3,4-b]pyridin-6-yl]difluoromethyl}-1H-tetrazol-1-ide [111](hereinafter referred to as a compound [111])

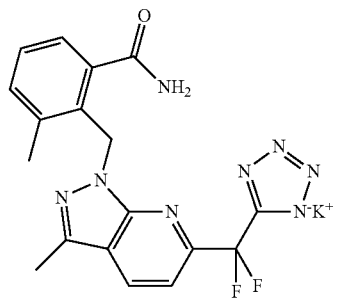

To a solution of the compound [110] (30 mg) in ethanol (1.0 mL) was added an aqueous solution of 1N-potassium hydroxide (74 μL) at room temperature, and the solution was concentrated under reduced pressure to give the titled compound (32 mg) as a white solid.
$^1$H-NMR (400 MHz, CD$_3$OD) δ: 8.37 (1H, d, J=8.3 Hz), 7.67 (1H, d, J=8.3 Hz), 7.34-7.32 (1H, m), 7.25 (1H, t, J=7.6 Hz), 7.18 (1H, d, J=7.1 Hz), 5.71 (2H, s), 2.53 (3H, s), 2.01 (3H, s).
ESI-MS found: 399 [M−K+2H]+

Example 112

Synthesis of 2-{6-[difluoro(1H-tetrazol-5-yl)methyl]-3-methyl-1H-pyrazolo[3,4-b]pyridin-1-ylmethyl}benzamide [112] (hereinafter referred to as a compound [112])

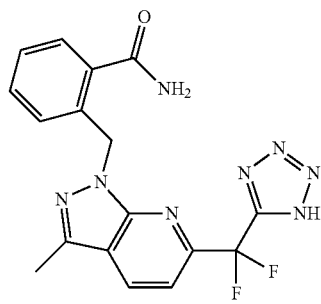 [SMILES: Cc1nn(Cc2ccccc2C(N)=O)c2nc(C(F)(F)c3nnn[nH]3)ccc12]

The titled compound (9.5 mg) as a white solid was prepared from the compound [108-3] (100 mg) and 2-bromomethylbenzonitrile (152 mg) according to the methods of the process (1) in Example 1, the processes (5) to (6) in Example 108, the process (3) in Example 109 and the process (1) in Example 67.

$^1$H-NMR (400 MHz, CD$_3$OD) δ: 8.43 (1H, d, J=8.3 Hz), 7.72 (1H, d, J=8.3 Hz), 7.53-7.51 (1H, m), 7.33-7.25 (2H, m), 6.92-6.89 (1H, m), 5.78 (2H, s), 2.58 (3H, s).

ESI-MS found: 385 [M+H]$^+$

Example 113

Synthesis of 3-chloro-2-{6-[difluoro(1H-tetrazol-5-yl)methyl]-3-methyl-1H-pyrazolo[3,4-b]pyridin-1-ylmethyl}benzonitrile [113] (hereinafter referred to as a compound [113])

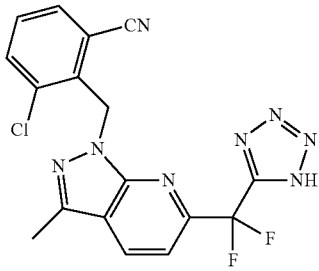 [SMILES: Cc1nn(Cc2c(Cl)cccc2C#N)c2nc(C(F)(F)c3nnn[nH]3)ccc12]

(1) Synthesis of 2-chloro-6-iodobenzyl bromide [113-1] (hereinafter referred to as a compound [113-1])

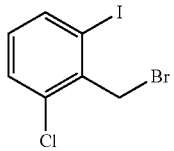

The titled compound (825 mg) as a white solid was prepared from 2-chloro-6-iodotoluene (1.26 g), N-bromosuccinimide (1.07 g) and 2,2'-azobis(isobutyronitrile) (85 mg) according to the method of the process (2) in Example 5.

$^1$H-NMR (400 MHz, CDCl$_3$) δ: 7.78 (1H, d, J=7.8 Hz), 7.39 (1H, d, J=7.8 Hz), 6.92 (1H, t, J=8.3 Hz)), 4.82 (2H, s).

(2) Synthesis of [1-(2-chloro-6-iodobenzyl)-3-methyl-1H-pyrazolo[3,4-b]pyridin-6-yl]difluoroacetonitrile [113-2] (hereinafter referred to as a compound [113-2])

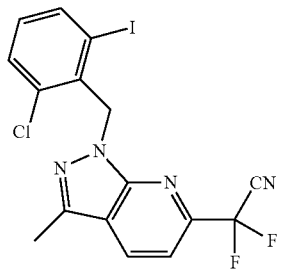 [SMILES: Cc1nn(Cc2c(Cl)cccc2I)c2nc(C(F)(F)C#N)ccc12]

The titled compound (65 mg) as a white solid was prepared from the compound [108-3] (168 mg) and the compound [113-1] (431 mg) according to the methods of the process (1) in Example 1 and the processes (5) to (6) in Example [108].

ESI-MS found: 458 [M+H]$^+$ (3) Synthesis of 1-(2-chloro-6-iodobenzyl)-6-[difluoro(1H-tetrazol-5-yl)methyl]-3-methyl-1H-pyrazolo[3,4-b]pyridine [113-3] (hereinafter referred to as a compound [113-3])

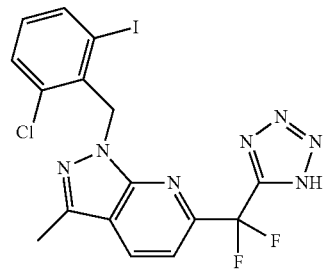 [SMILES: Cc1nn(Cc2c(Cl)cccc2I)c2nc(C(F)(F)c3nnn[nH]3)ccc12]

The titled compound (67 mg) as a white solid was prepared from the compound [113-2] (65 mg) according to the method of the process (3) in Example 109.

ESI-MS found: 501 [M+H]$^+$ (4) Synthesis of 3-chloro-2-{6-[difluoro(1H-tetrazol-5-yl)methyl]-3-methyl-1H-pyrazolo[3,4-b]pyridin-1-ylmethyl}benzonitrile [113]

To a solution of the compound [113-3] (51 mg) in N,N-dimethylformamide (3.4 mL) were added zinc cyanide (19 mg) and tetrakis(triphenylphosphine)palladium(0) (118 mg) at room temperature, and the mixture was stirred at 80° C. for 4 hours. After cooling to room temperature, 3N-hydrochloric acid was carefully added, and the mixture was stirred at room temperature for 1 hour and then extracted with ethyl acetate. The obtained organic layer was sequentially washed with water and brine, dried over anhydrous sodium sulfate, filtered, and the filtrate was concentrated under reduced pressure. The obtained residue was purified by reverse phase preparative liquid chromatography to give the titled compound (37 mg) as a white solid.

$^1$H-NMR (400 MHz, CD$_3$OD) δ: 8.42 (1H, d, J=8.3 Hz), 7.74 (1H, d, J=8.3 Hz), 7.70 (1H, dd, J=7.7, 1.3 Hz), 7.66-7.64 (1H, m), 7.48 (1H, t, J=7.9 Hz), 5.79 (2H, s), 2.54 (3H, s).

ESI-MS found: 401 [M+H]$^+$

Example 114

Synthesis of 3-chloro-2-{6-[difluoro(1H-tetrazol-5-yl)methyl]-3-methyl-1H-pyrazolo[3,4-b]pyridin-1-ylmethyl}benzamide [114] (hereinafter referred to as a compound [114])

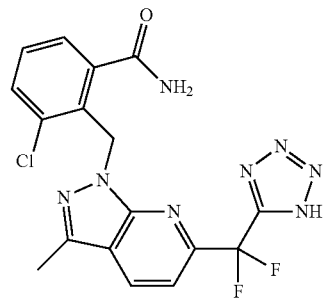 [SMILES: Cc1nn(Cc2c(Cl)cccc2C(N)=O)c2nc(C(F)(F)c3nnn[nH]3)ccc12]

The titled compound (9.3 mg) as a white solid was prepared from the compound [113] (16 mg) according to the method of the process (1) in Example 67.

¹H-NMR (400 MHz, CD₃OD) δ: 8.42 (1H, d, J=8.3 Hz), 7.74 (1H, d, J=8.3 Hz), 7.46-7.42 (2H, m), 7.37 (1H, dd, J=8.1, 7.6 Hz), 5.79 (2H, s), 2.53 (3H, s).

ESI-MS found: 419 [M+H]⁺

Example 115

Synthesis of 3-cyclopropyl-2-{6-[difluoro(1H-tetrazol-5-yl)methyl]-3-methyl-1H-pyrazolo[3,4-b]pyridin-1-ylmethyl}benzonitrile [115] (hereinafter referred to as a compound [115])

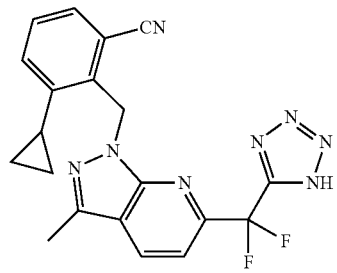 [SMILES: Cc1nn(Cc2c(C#N)cccc2C2CC2)c2nc(C(F)(F)c3nnn[nH]3)ccc12]

(1) Synthesis of ethyl 2-cyclopropylbenzoate [115-1] (hereinafter referred to as a compound [115-1])

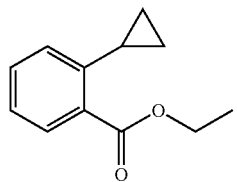

Ethyl 2-bromobenzoate (4.07 g), cyclopropylboronic acid monohydrate (2.77 g), tetrakis(triphenylphosphine)palladium(0) (1.03 g) and tripotassium phosphate (11.3 g) were suspended in a mixed solvent (60 mL) of toluene/water (volume ratio 20/1), and the suspension was stirred at 120° C. for 12 hours. After cooling, water was added to the reaction mixture, and the mixture was extracted with hexane. The obtained organic layer was sequentially washed with water and brine, dried over anhydrous sodium sulfate, filtered, and the filtrate was concentrated under reduced pressure. The obtained residue was purified by silica gel column chromatography to give the titled compound (2.13 g) as a colorless oil.

¹H-NMR (400 MHz, CDCl₃) δ: 7.78 (1H, dd, J=7.8, 1.5 Hz), 7.38 (1H, td, J=7.6, 1.3 Hz), 7.22-7.18 (1H, m), 7.01 (1H, d, J=7.3 Hz), 4.38 (2H, q, J=7.8 Hz), 2.67-2.60 (1H, m), 1.40 (3H, t, J=7.1 Hz), 1.01-0.96 (2H, m), 0.71-0.67 (2H, m).

(2) Synthesis of 2-cyclopropylbenzoic acid [115-2] (hereinafter referred to as a compound [115-2])

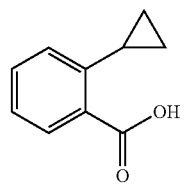 [SMILES: O=C(O)c1ccccc1C1CC1]

To the compound [115-1] (2.13 g) in ethanol (22 mL) was added an aqueous solution of 3N-sodium hydroxide (22 mL) at room temperature, and the mixture was stirred at 90° C. for 30 minutes. 3N-hydrochloric acid was added to the reaction mixture, and the mixture was extracted with ethyl acetate. The obtained organic layer was sequentially washed with water and brine, dried over anhydrous sodium sulfate, filtered, and the filtrate was concentrated under reduced pressure to give the titled compound (1.81 g) as a white solid.

¹H-NMR (400 MHz, CDCl₃) δ: 7.98 (1H, dd, J=8.1, 1.2 Hz), 7.47-7.43 (1H, m), 7.26-7.22 (1H, m), 7.05 (1H, d, J=7.8 Hz), 2.84-2.77 (1H, m), 1.07-1.02 (2H, m), 0.75-0.71 (2H, m).

(3) Synthesis of 2-cyclopropyl-6-iodobenzoic acid [115-3] (hereinafter referred to as a compound [115-3])

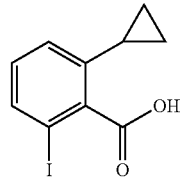 [SMILES: O=C(O)c1c(I)cccc1C1CC1]

The compound [115-2] (1.81 g), iodobenzene diacetate (3.60 g), iodine (2.84 g) and palladium(II) acetate (126 mg) were suspended in N,N-dimethylformamide (37 mL), and the suspension was stirred at 80° C. for 1 hour. After cooling, water was added to the reaction mixture, and the mixture was extracted with ethyl acetate. The obtained organic layer was sequentially washed with water and brine, dried over anhydrous sodium sulfate, filtered, and the filtrate was concentrated under reduced pressure. The obtained residue was purified by silica gel column chromatography to give the titled compound (1.32 g) as a white solid.

¹H-NMR (400 MHz, CDCl₃) δ: 7.67 (1H, dd, J=7.1, 1.7 Hz), 7.06-7.00 (2H, m), 2.10-2.03 (1H, m), 1.01-0.97 (2H, m), 0.76-0.72 (2H, m).

(4) Synthesis of 2-cyclopropyl-6-iodobenzyl chloride [115-4] (hereinafter referred to as a compound [115-4])

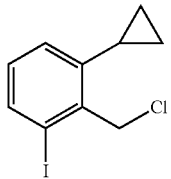

The titled compound (717 mg) as a colorless oil was prepared from the compound [115-3] (1.02 g) according to the methods of the process (1) in Example 99 and the process (1) in Example 89.

$^1$H-NMR (400 MHz, CDCl$_3$) δ: 7.73 (1H, d, J=7.8 Hz), 7.06 (1H, d, J=7.6 Hz), 6.92 (1H, t, J=7.8 Hz), 5.03 (2H, s), 2.19-2.12 (1H, m), 1.06-1.00 (2H, m), 0.74-0.70 (2H, m).

(5) Synthesis of 3-cyclopropyl-2-{6-[difluoro(1H-tetrazol-5-yl)methyl]-3-methyl-1H-pyrazolo[3,4-b]pyridin-1-ylmethyl}benzonitrile [115]

The titled compound (72 mg) as a white solid was prepared from the compound [108-3] (401 mg) and the compound [115-4] (852 mg) according to the methods of the process (1) in Example 1, the processes (5) to (6) in Example 108, the process (5) in Example 55 and the process (3) in Example 109.

$^1$H-NMR (400 MHz, CD$_3$OD) δ: 8.42 (1H, d, J=8.3 Hz), 7.74 (1H, d, J=8.3 Hz), 7.56 (1H, dd, J=7.7, 1.1 Hz), 7.38 (1H, t, J=7.8 Hz), 7.22 (1H, d, J=8.1 Hz), 5.88 (2H, s), 2.54 (3H, s), 1.75-1.68 (1H, m), 0.53-0.48 (2H, m), 0.43-0.39 (2H, m).

ESI-MS found: 407 [M+H]$^+$

Example 116

Synthesis of 3-cyclopropyl-2-{6-[difluoro(1H-tetrazol-5-yl)methyl]-3-methyl-1H-pyrazolo[3,4-b]pyridin-1-ylmethyl}benzamide [116] (hereinafter referred to as a compound [116])

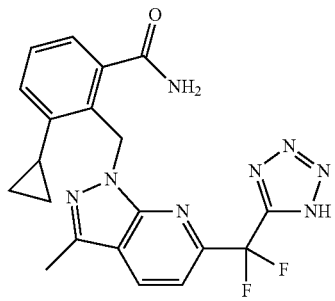 [SMILES: Cc1nn(Cc2c(C(N)=O)cccc2C2CC2)c2nc(C(F)(F)c3nnn[nH]3)ccc12]

The titled compound (27 mg) as a white solid was prepared from the compound [116] (39 mg) according to the method of the process (1) in Example 67.

$^1$H-NMR (400 MHz, CD$_3$OD) δ: 8.43 (1H, d, J=8.3 Hz), 7.73 (1H, d, J=8.1 Hz), 7.35-7.33 (1H, m), 7.28 (1H, t, J=7.6 Hz), 7.04 (1H, d, J=7.3 Hz), 5.87 (2H, s), 2.53 (3H, s), 1.65-1.57 (1H, m), 0.44-0.38 (2H, m), 0.37-0.33 (2H, m).

ESI-MS found: 425 [M+H]$^+$

Example 117

Synthesis of potassium 5-{[1-(2-carbamoyl-6-cyclopropylbenzyl)-3-methyl-1H-pyrazolo[3,4-b]pyridin-6-yl]difluoromethyl}-1H-tetrazol-1-ide [117] (hereinafter referred to as a compound [117])

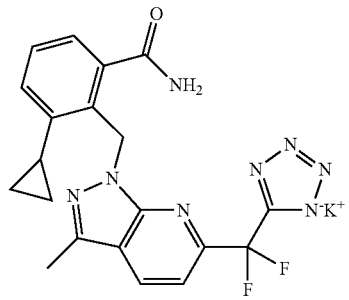

To a solution of the compound [116] (25 mg) in ethanol (1.0 mL) was added an aqueous solution of 1N-potassium hydroxide (59 μL) at room temperature, and the solution was concentrated under reduced pressure to give the titled compound (25 mg) as a white solid.

$^1$H-NMR (400 MHz, CD$_3$OD) δ: 8.33 (1H, d, J=8.3 Hz), 7.64 (1H, d, J=8.3 Hz), 7.34 (1H, dd, J=7.7, 1.3 Hz), 7.27 (1H, t, J=7.7 Hz), 7.01 (1H, d, J=7.8 Hz), 5.89 (2H, s), 2.52 (3H, s), 1.64-1.56 (1H, m), 0.43-0.38 (2H, m), 0.34-0.27 (2H, m).

ESI-MS found: 425 [M−K+2H]$^+$

Example 118

Synthesis of [1-(2-cyano-6-methylbenzyl)-3-ethyl-1H-indazol-6-yl]difluoroacetic acid [118] (hereinafter referred to as a compound [118])

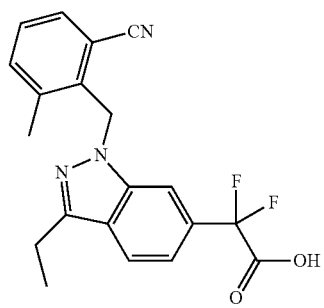 [SMILES: CCc1nn(Cc2c(C)cccc2C#N)c2cc(C(F)(F)C(=O)O)ccc12]

The titled compound (37 mg) as a white solid was prepared from 4-bromo-2-fluorobenzaldehyde (5.1 g) and 1.0M tetrahydrofuran solution of ethylmagnesium bromide (41 mL) according to the method of Example 55.

$^1$H-NMR (400 MHz, CD$_3$OD) δ: 7.86-7.82 (2H, m), 7.66 (1H, d, J=7.8 Hz), 7.52 (1H, d, J=7.1 Hz), 7.43 (1H, t, J=7.7 Hz), 7.35 (1H, d, J=7.3 Hz), 5.77 (2H, s), 2.95 (2H, q, J=7.6 Hz), 1.32 (3H, t, J=7.7 Hz).

ESI-MS found: 370 [M+H]$^+$

Example 119

Synthesis of 2-{6-[difluoro(5-oxo-4,5-dihydro-[1,3,4]oxadiazol-2-yl)methyl]-3-methyl-1H-indazol-1-ylmethyl}-3-methylbenzonitrile [119] (hereinafter referred to as a compound [119])

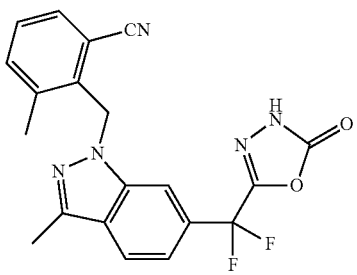 [SMILES: Cc1cccc(C#N)c1Cn1nc(C)c2ccc(C(F)(F)c3n[nH]c(=O)o3)cc21]

The titled compound (73 mg) as a white solid was prepared from the compound [24] (200 mg) according to the method of Example 101.

$^1$H-NMR (400 MHz, CD$_3$OD) δ: 7.88-7.85 (2H, m), 7.65 (1H, d, J=7.8 Hz), 7.52 (1H, d, J=7.8 Hz), 7.43 (1H, t, J=7.7 Hz), 7.36 (1H, dd, J=8.5, 1.5 Hz), 5.77 (2H, s), 2.52 (3H, s), 2.27 (3H, s).

ESI-MS found: 396 [M+H]$^+$

Example 120

Synthesis of [1-(2-cyano-6-methylbenzyl)-3-difluoromethyl-1H-indazol-6-yl]difluoroacetic acid [120] (hereinafter referred to as a compound [120])

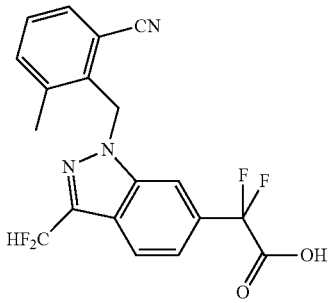

(1) Synthesis of 6-bromo-1H-indazole-3-carboaldehyde [120-1] (hereinafter referred to as a compound [120-1])

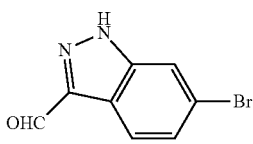 [SMILES: O=Cc1n[nH]c2cc(Br)ccc12]

To a solution of 6-bromoindole (1.0 g) in dioxane (10 mL) were added water (20 mL), sodium nitrite (3.68 g) and 6N-hydrochloric acid (10 mL) at room temperature, and the mixture was stirred at room temperature for 1 hour. The reaction mixture was quenched with water, and extracted with chloroform. The obtained organic layer was dried over anhydrous sodium sulfate, filtered, and the filtrate was concentrated under reduced pressure. The obtained residue was purified by silica gel column chromatography to give the titled compound (535 mg) as a red solid.

ESI-MS found: 226 [M+H]$^+$ (2) Synthesis of 6-bromo-1-(2-iodo-6-methylbenzyl)-1H-indazole-3-carbaldehyde [120-2] (hereinafter referred to as a compound [120-2])

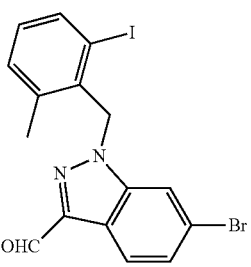 [SMILES: Cc1cccc(I)c1Cn1nc(C=O)c2ccc(Br)cc21]

The titled compound (605 mg) as a red solid was prepared from the compound [120-1] (535 mg) and the compound [55-3] (763 mg) according to the method of the process (1) in Example 1.

ESI-MS found: 456 [M+H]$^+$ (3) Synthesis of 2-(6-bromo-3-formylindazol-1-ylmethyl)-3-methylbenzonitrile [120-3] (hereinafter referred to as a compound [120-3])

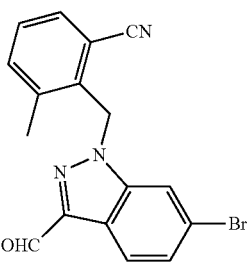 [SMILES: Cc1cccc(C#N)c1Cn1nc(C=O)c2ccc(Br)cc21]

The titled compound (188 mg) as a red solid was prepared from the compound [120-2] (605 mg) according to the method of the process (5) in Example 55.

ESI-MS found: 355 [M+H]$^+$ (4) Synthesis of 2-(3-formyl-6-tributylstannylindazol-1-ylmethyl)-3-methylbenzonitrile [120-4] (hereinafter referred to as a compound [120-4])

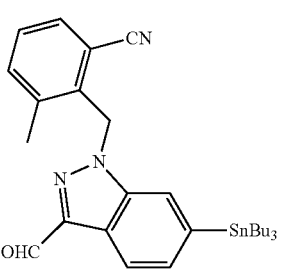

The titled compound (323 mg) as a red solid was prepared from the compound [120-3] (500 mg) according to the method of the process (2) in Example 1.
ESI-MS found: 565 [M+H]+

(5) Synthesis of ethyl [1-(2-cyano-6-methylbenzyl)-3-formyl-1H-indazol-6-yl]oxoacetate [120-5] (hereinafter referred to as a compound [120-5])

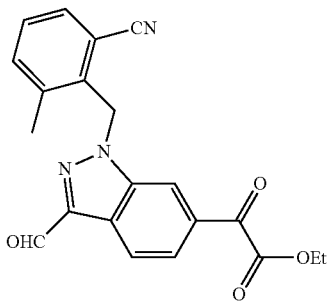 [SMILES: CCOC(=O)C(=O)c1ccc2c(C=O)nn(Cc3c(C)cccc3C#N)c2c1]

The titled compound (84 mg) as a yellow solid was prepared from the compound [120-4] (323 mg) according to the method of the process (3) in Example 1.
ESI-MS found: 376 [M+H]+

(6) Synthesis of ethyl [1-(2-cyano-6-methylbenzyl)-3-difluoromethyl-1H-indazol-6-yl]difluoroacetate [120-6] (hereinafter referred to as a compound [120-6])

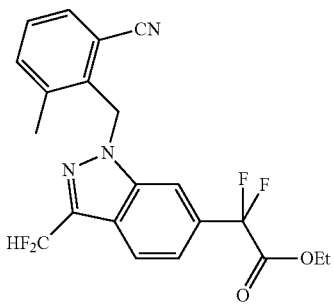

The titled compound (9 mg) as a yellow oil was prepared from the compound [120-5] (19 mg) according to the method of the process (4) in Example 1.
ESI-MS found: 420 [M+H]+

(7) Synthesis of [1-(2-cyano-6-methylbenzyl)-3-difluoromethyl-1H-indazol-6-yl]difluoroacetic acid [120]

To a solution of the compound [120-6] (9 mg) in ethanol (1 mL) was added an aqueous solution of 1N-sodium hydrogen carbonate (1 mL) at room temperature, and the mixture was stirred at 60° C. for 10 minutes. The reaction mixture was quenched with a saturated aqueous solution of ammonium chloride, and extracted with chloroform. The obtained organic layer was dried over anhydrous sodium sulfate, filtered, and the filtrate was concentrated under reduced pressure to give the titled compound (3 mg) as a white solid.

$^1$H-NMR (400 MHz, CD$_3$OD) δ: 8.01 (1H, s), 7.54 (1H, d, J=15.6 Hz), 7.26-7.25 (3H, m), 7.14 (1H, d, J=7.6 Hz), 6.71 (1H, t, J=54.0 Hz), 5.43 (2H, s), 2.27 (3H, s).

Example 121

Synthesis of [1-(2-cyano-6-methylbenzyl)-3-hydroxymethyl-1H-indazol-6-yl]difluoroacetic acid [121] (hereinafter referred to as a compound [121])

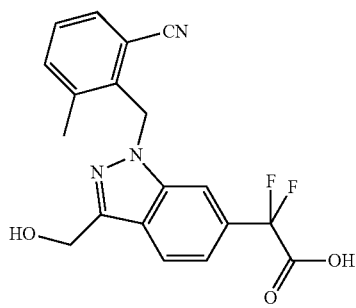 [SMILES: Cc1cccc(C#N)c1Cn1nc(CO)c2ccc(C(F)(F)C(=O)O)cc21]

(1) Synthesis of ethyl [1-(2-cyano-6-methylbenzyl)-3-dimethoxymethyl-1H-indazol-6-yl]oxoacetate [121-1] (hereinafter referred to as a compound [121-1])

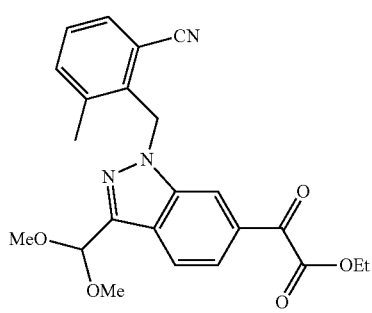 [SMILES: CCOC(=O)C(=O)c1ccc2c(C(OC)OC)nn(Cc3c(C)cccc3C#N)c2c1]

To a solution of the compound [120-5] (159 mg) in methanol (5 mL) were added trimethyl orthoformate (3 mL) and p-toluenesulfonic acid monohydrate (20 mg) at room temperature, and the mixture was stirred at room temperature for 30 minutes. The reaction mixture was quenched with a saturated aqueous solution of sodium hydrogen carbonate, and extracted with ethyl acetate. The obtained organic layer was dried over anhydrous sodium sulfate, filtered, and the filtrate was concentrated under reduced pressure to give the titled compound (185 mg) as a yellow oil.

$^1$H-NMR (400 MHz, CDCl$_3$) δ: 8.05 (2H, d, J=8.8 Hz), 7.78 (1H, dt, J=6.2, 2.8 Hz), 7.64 (1H, t, J=4.5 Hz), 7.44-7.37 (2H, m), 5.86 (2H, s), 5.75 (1H, s), 4.49 (2H, q, J=7.0 Hz), 3.45 (6H, s), 2.30 (3H, s), 1.46-1.42 (3H, m).

(2) Synthesis of ethyl [1-(2-cyano-6-methylbenzyl)-3-dimethoxymethyl-1H-indazol-6-yl]difluoroacetate [121-2] (hereinafter referred to as a compound [121-2])

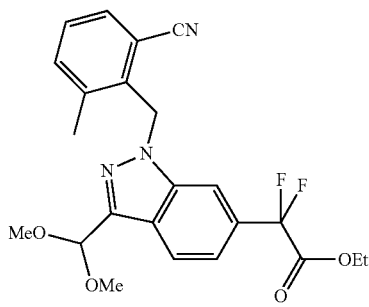 [SMILES: CCOC(=O)C(F)(F)c1ccc2c(C(OC)OC)nn(Cc3c(C)cccc3C#N)c2c1]

The titled compound (9 mg) as a yellow oil was prepared from the compound [121-1] (185 mg) according to the method of the process (4) in Example 1.

$^1$H-NMR (400 MHz, CD$_3$OD) δ: 8.03 (1H, d, J=7.8 Hz), 7.62-7.60 (2H, m), 7.43-7.36 (3H, m), 5.82 (2H, s), 5.72 (1H, s), 4.28 (2H, q, J=7.2 Hz), 3.43 (6H, s), 2.27 (3H, s), 1.31-1.25 (3H, m).

(3) Synthesis of [1-(2-cyano-6-methylbenzyl)-3-hydroxymethyl-1H-indazol-6-yl]difluoroacetic acid [121]

Trifluoroacetic acid (1 mL) and water (0.2 mL) were added to the compound [121-2] (12 mg) at room temperature, and the mixture was stirred at room temperature for 20 minutes. The reaction mixture was concentrated under reduced pressure. To a solution of the obtained residue in methanol (1 mL) was added sodium borohydride (1.9 mg) at room temperature, and the mixture was stirred at room temperature for 30 minutes. 1N-hydrochloric acid was added to the reaction mixture, and the mixture was extracted with chloroform. The obtained organic layer was dried over anhydrous sodium sulfate, filtered, and the filtrate was concentrated under reduced pressure to give the titled compound (1.2 mg) as a white solid.

$^1$H-NMR (400 MHz, CD$_3$OD) δ: 7.92 (2H, t, J=6.8 Hz), 7.66 (1H, d, J=7.6 Hz), 7.46 (3H, tt, J=12.6, 5.8 Hz), 5.77 (2H, s), 4.85 (2H, s), 2.19 (3H, s).

Example 122

Test for Uric Acid Transport Inhibition Using Human URAT1 Expression Cells

In this Example, it was evaluated whether the Example compound and the Reference example compound mentioned below has the URAT1 inhibitory activity.

Human URAT1 full-length cDNA was introduced to an expression vector pcDNA5/FRT/V5-His TOPO (registered trademark) (Invitrogen Corporation). The obtained expression plasmid was introduced to Chinese hamster ovary cell (hereinafter referred to as the CHO cell) by the liposome method using Lipofectamine LTX (Invitrogen) and cultured in a selection medium including hygromycin, whereby to repare human URAT1 stable expression cell.

The human URAT1 expression CHO cell were cultured using D-MEM/F-12 (1:1) mixed medium including 10% bovine fatal serum and hygromycin at 37° C. in the presence of 5% CO$_2$. The cells were seeded onto a 96-well plate (Corning Incorporated) at 0.8×10$^5$ cells/well, and after 24 hours, the test for uric acid transport inhibition below was performed.

The medium was removed by aspiration, and then the cells were washed once with an assay buffer including 125 mM of sodium gluconate, 4.8 mM of potassium gluconate, 1.2 mM of potassium dihydrogen phosphate, 1.2 mM of magnesium sulfate, 1.3 mM of calcium gluconate and 5.6 mM of glucose, 50 µL assay buffer including the test compound in various concentrations was added, and further 50 µL assay buffer including a radioactive ligand (uric acid labeled with $^{14}$C; 38 µM final concentration) was added, and incorporation reaction was performed at room temperature for 5 minutes. Immediately after the completion of the reaction, the reaction mixture was washed twice with 100 µL ice-cold assay buffer, and 100 µL of 0.1N sodium hydroxide was added. The reaction mixture was stirred to lyse the cells, and 4 mL of Hionic-Fluor (Packard BioScience CO.) was added, and then the radioactivity was measured with a liquid scintillation counter (Beckman Coulter, Inc. and Packard BioScience CO).

The radioactivitiy when each concentration of the test compound was added (uric acid incorporation activity, %) was calculated in which the difference of the radioactivity when the test compound was not added (DMSO added) and the radioactivity when a positive control compound, benzbromarone (a known URAT1 inhibitor) was added in 100 µM, was taken as 100%, and the concentration of the test compound when the uric acid incorporation activity was inhibited to 50% (IC$_{50}$) was obtained. The results are shown in Table 1.

TABLE 1

| Test compound | URAT1 inhibitory activity (IC$_{50}$, nM) |
|---|---|
| The compound of example 3 | 26 |
| The compound of example 9 | 40 |
| The compound of example 12 | 17 |
| The compound of example 14 | 48 |
| The compound of example 22 | 52 |
| The compound of example 24 | 26 |
| The compound of example 32 | 23 |
| The compound of example 34 | 15 |
| The compound of example 36 | 107 |
| The compound of example 38 | 34 |
| The compound of example 46 | 243 |
| The compound of example 49 | 38 |
| The compound of example 50 | 7 |
| The compound of the reference example 2 | 53 |
| The compound of the reference example 3 | 32 |
| The compound of the reference example 5 | 13 |

TABLE 1-continued

| Test compound | URAT1 inhibitory activity (IC$_{50}$, nM) |
|---|---|
| The compound of the reference example 8 | 24 |
| The compound of the reference example 9 | 78 |
| The compound of the reference example 11 | 15 |
| The compound of the reference example 12 | 16 |
| The compound of example 53 | 390 |
| The compound of example 67 | 46 |
| The compound of example 71 | 6 |
| The compound of example 88 | 34 |
| The compound of example 92 | 21 |
| The compound of example 94 | 125 |
| The compound of example 101 | 9 |
| The compound of example 102 | 142 |
| The compound of example 104 | 30 |
| The compound of example 107 | 12 |
| The compound of example 109 | 13 |
| The compound of example 110 | 44 |
| The compound of example 116 | 36 |
| The compound of example 121 | 268 |

The corresponding relationship between the compounds of Examples 1 to 121 and the formula (I) is shown below.

TABLE 1

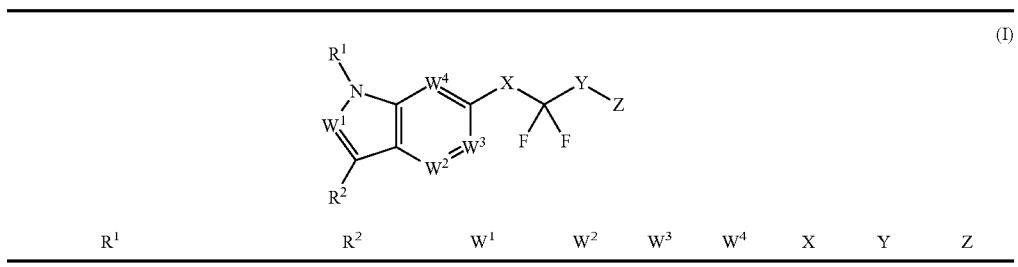

(I)

| | R$^1$ | R$^2$ | W$^1$ | W$^2$ | W$^3$ | W$^4$ | X | Y | Z |
|---|---|---|---|---|---|---|---|---|---|
| Example 1 | —Q$^1$—A$^1$<br>Q$^1$: Methylene<br>A$^1$: 2,6-Cl$_2$Ph<br>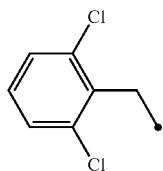 | Methyl Group | Nitrogen atom | Methine | Methine | Methine | Single Bond | Single Bond | COOH |
| Example 2 | —Q$^1$—A$^1$<br>Q$^1$: Methylene<br>A$^1$: 2,6-Cl$_2$Ph<br>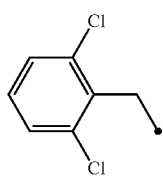 | Methyl Group | Nitrogen atom | Methine | Methine | Methine | Single Bond | Single Bond | COO$^-$K$^+$ |

TABLE 2

| | R¹ | R² | W¹ | W² | W³ | W⁴ | X | Y | Z |
|---|---|---|---|---|---|---|---|---|---|
| Example 3 | —Q¹—A¹<br>Q¹: Methylene<br>A¹:<br>2-Cl-6-Me—Ph | Methyl Group | Nitrogen atom | Methine | Methine | Methine | Single Bond | Single Bond | COOH |
| Example 4 | —Q¹—A¹<br>Q¹: Methylene<br>A¹:<br>2-Cl-6-Me—Ph | Methyl Group | Nitrogen atom | Methine | Methine | Methine | Single Bond | Single Bond | COO⁻K⁺ |
| Example 5 | —Q¹—A¹<br>Q¹: Methylene<br>A¹:<br>2-Cl-6-CN—Ph | Methyl Group | Nitrogen atom | Methine | Methine | Methine | Single Bond | Single Bond | COOH |
| Example 6 | —Q¹—A¹<br>Q¹: Methylene<br>A¹:<br>2-Cl-6-CN—Ph | Methyl Group | Nitrogen atom | Methine | Methine | Methine | Single Bond | Single Bond | COO⁻K⁺ |

TABLE 3

| | R¹ | R² | W¹ | W² | W³ | W⁴ | X | Y | Z |
|---|---|---|---|---|---|---|---|---|---|
| Example 7 | —Q¹—A¹<br>Q¹: Methylene<br>A¹: 2,6-Me₂Ph | Methyl Group | Nitrogen atom | Methine | Methine | Methine | Single Bond | Single Bond | COOH |

TABLE 3-continued

| | R¹ | R² | W¹ | W² | W³ | W⁴ | X | Y | Z |
|---|---|---|---|---|---|---|---|---|---|
| Example 8 | —Q¹—A¹<br>Q¹: Methylene<br>A¹: 2,6-Me₂Ph | Methyl Group | Nitrogen atom | Methine | Methine | Methine | Single Bond | Single Bond | COO⁻K⁺ |
| Example 9 | —Q¹—A¹<br>Q¹: Methylene<br>A¹: 2-Cl-6-F—Ph | Methyl Group | Nitrogen atom | Methine | Methine | Methine | Single Bond | Single Bond | COOH |
| Example 10 | —Q¹—A¹<br>Q¹: Methylene<br>A¹: 2-Cl-6-F—Ph | Methyl Group | Nitrogen atom | Methine | Methine | Methine | Single Bond | Single Bond | COO⁻K⁺ |

TABLE 4

| | R¹ | R² | W¹ | W² | W³ | W⁴ | X | Y | Z |
|---|---|---|---|---|---|---|---|---|---|
| Example 11 | —Q¹—A¹<br>Q¹: Methylene<br>A¹: 2-Cl-5-F—Ph | Methyl Group | Nitrogen atom | Methine | Methine | Methine | Single Bond | Single Bond | COOH |
| Example 12 | —Q¹—A¹<br>Q¹:Methylene<br>A¹:<br>2-Cl-6-ᶜPr—Ph | Methyl Group | Nitrogen atom | Methine | Methine | Methine | Single Bond | Single Bond | COOH |

TABLE 4-continued

| | R¹ | R² | W¹ | W² | W³ | W⁴ | X | Y | Z |
|---|---|---|---|---|---|---|---|---|---|
| Example 13 | —Q¹—A¹<br>Q¹: Methylene<br>A¹:<br>2-Cl-6-$^c$Pr—Ph<br>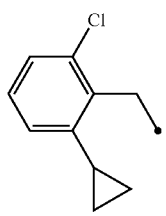 | Methyl Group | Nitrogen atom | Methine | Methine | Methine | Single Bond | Single Bond | COO⁻K⁺ |
| Example 14 | —Q¹—A¹<br>Q¹: Methylene<br>A¹: 2,3-Cl₂Ph<br>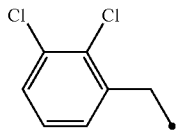 | Methyl Group | Nitrogen atom | Methine | Methine | Methine | Single Bond | Single Bond | COOH |

TABLE 5

| | R¹ | R² | W¹ | W² | W³ | W⁴ | X | Y | Z |
|---|---|---|---|---|---|---|---|---|---|
| Example 15 | —Q¹—A¹<br>Q¹: Methylene<br>A¹: 2,3-Cl₂Ph<br>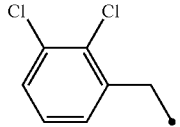 | Methyl Group | Nitrogen atom | Methine | Methine | Methine | Single Bond | Single Bond | COO⁻K⁺ |
| Example 16 | —Q¹—A¹<br>Q¹: Methylene<br>A¹: Naphtylene-1-yl<br>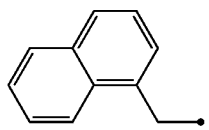 | Methyl Group | Nitrogen atom | Methine | Methine | Methine | Single Bond | Single Bond | COOH |
| Example 17 | —Q¹—A¹<br>Q¹: Methylene<br>A¹: 2,5-Me₂Ph<br>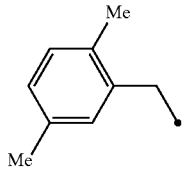 | Methyl Group | Nitrogen atom | Methine | Methine | Methine | Single Bond | Single Bond | COOH |

TABLE 5-continued

| | R¹ | R² | W¹ | W² | W³ | W⁴ | X | Y | Z |
|---|---|---|---|---|---|---|---|---|---|
| Example 18 | —Q¹—A¹<br>Q¹: Methylene<br>A¹:<br>5-Chlorobenzo[b]thiophene-3-yl | Methyl Group | Nitrogen atom | Methine | Methine | Methine | Single Bond | Single Bond | COOH |

TABLE 6

| | R¹ | R² | W¹ | W² | W³ | W⁴ | X | Y | Z |
|---|---|---|---|---|---|---|---|---|---|
| Example 19 | —Q¹—A¹<br>Q¹: Methylene<br>A¹:<br>5-Chlorobenzo[b]thiophene-3-yl | Methyl Group | Nitrogen atom | Methine | Methine | Methine | Single Bond | Single Bond | COO⁻K⁺ |
| Example 20 | —Q¹—A¹<br>Q¹: Methylene<br>A¹: 2,4,6-Me₃Ph | Methyl Group | Nitrogen atom | Methine | Methine | Methine | Single Bond | Single Bond | COOH |
| Example 21 | —Q¹—A¹<br>Q¹: Methylene<br>A¹:<br>Quinoline-8-yl | Methyl Group | Nitrogen atom | Methine | Methine | Methine | Single Bond | Single Bond | COOH |

TABLE 7

| | R¹ | R² | W¹ | W² | W³ | W⁴ | X | Y | Z |
|---|---|---|---|---|---|---|---|---|---|
| Example 22 | —Q¹—A¹<br>Q¹: Methylene<br>A¹:<br>2-F-6-CF₃-Ph<br>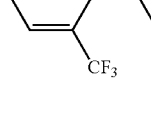 | Methyl Group | Nitrogen atom | Methine | Methine | Methine | Single Bond | Single Bond | COOH |
| Example 23 | —Q¹—A¹<br>Q¹: Methylene<br>A¹:<br>2-F-6-CF₃-Ph<br>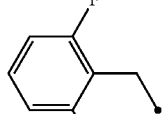 | Methyl Group | Nitrogen atom | Methine | Methine | Methine | Single Bond | Single Bond | COO⁻K⁺ |
| Example 24 | —Q¹—A¹<br>Q¹: Methylene<br>A¹:<br>2-CN-6-Me-Ph<br>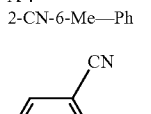 | Methyl Group | Nitrogen atom | Methine | Methine | Methine | Single Bond | Single Bond | COOH |
| Example 25 | —Q¹—A¹<br>Q¹: Methylene<br>A¹:<br>2-CN-6-Me-Ph<br>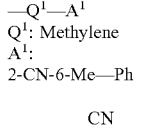 | Methyl Group | Nitrogen atom | Methine | Methine | Methine | Single Bond | Single Bond | COO⁻K⁺ |

TABLE 8

| | R¹ | R² | W¹ | W² | W³ | W⁴ | X | Y | Z |
|---|---|---|---|---|---|---|---|---|---|
| Example 26 | —Q¹—A¹<br>Q¹: Methylene<br>A¹: 2-CN-6-F—Ph | Methyl Group | Nitrogen atom | Methine | Methine | Methine | Single Bond | Single Bond | COOH |

TABLE 8-continued

| | R¹ | R² | W¹ | W² | W³ | W⁴ | X | Y | Z |
|---|---|---|---|---|---|---|---|---|---|
| Example 27 | —Q¹—A¹<br>Q¹: Methylene<br>A¹:<br>2-ᶜPr-6-F—Ph | Methyl Group | Nitrogen atom | Methine | Methine | Methine | Single Bond | Single Bond | COOH |
| Example 28 | —Q¹—A¹<br>Q¹: Methylene<br>A¹:<br>2-Cl-6-OMe—Ph | Methyl Group | Nitrogen atom | Methine | Methine | Methine | Single Bond | Single Bond | COOH |
| Example 29 | —Q¹—A¹<br>Q¹: Methylene<br>A¹:<br>2-Cl-6-OMe—Ph | Methyl Group | Nitrogen atom | Methine | Methine | Methine | Single Bond | Single Bond | COO⁻K⁺ |

TABLE 9

| | R¹ | R² | W¹ | W² | W³ | W⁴ | X | Y | Z |
|---|---|---|---|---|---|---|---|---|---|
| Example 30 | —Q¹—A¹<br>Q¹: Methylene<br>A¹:<br>2-CN-6-OMe—Ph | Methyl Group | Nitrogen atom | Methine | Methine | Methine | Single Bond | Single Bond | COOH |
| Example 31 | —Q¹—A¹<br>Q¹: Methylene<br>A¹:<br>2-CN-5-Me—Ph | Methyl Group | Nitrogen atom | Methine | Methine | Methine | Single Bond | Single Bond | COOH |

TABLE 9-continued

| | R¹ | R² | W¹ | W² | W³ | W⁴ | X | Y | Z |
|---|---|---|---|---|---|---|---|---|---|
| Example 32 | —Q¹—A¹<br>Q¹: Methylene<br>A¹:<br>2-CN-6-cPr—Ph<br>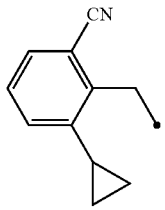 | Methyl Group | Nitrogen atom | Methine | Methine | Methine | Single Bond | Single Bond | COOH |

TABLE 10

| | R¹ | R² | W¹ | W² | W³ | W⁴ | X | Y | Z |
|---|---|---|---|---|---|---|---|---|---|
| Example 33 | —Q¹—A¹<br>Q¹: Methylene<br>A¹:<br>2-CN-6-cPr—Ph<br>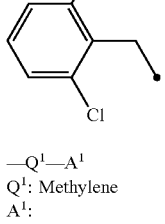 | Methyl Group | Nitrogen atom | Methine | Methine | Methine | Single Bond | Single Bond | COO⁻K⁺ |
| Example 34 | —Q¹—A¹<br>Q¹: Methylene<br>A¹: 2,6-Cl₂Ph<br>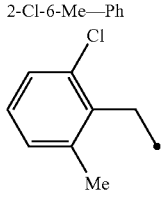 | Chlorine atom | Nitrogen atom | Methine | Methine | Methine | Single Bond | Single Bond | COOH |
| Example 35 | —Q¹—A¹<br>Q¹: Methylene<br>A¹:<br>2-Cl-6-Me—Ph<br>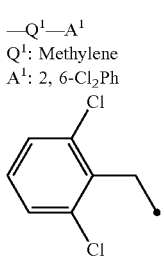 | Chlorine atom | Nitrogen atom | Methine | Methine | Methine | Single Bond | Single Bond | COOH |
| Example 36 | —Q¹—A¹<br>Q¹: Methylene<br>A¹: 2,6-Cl₂Ph | Trifluoromethyl Group | Nitrogen atom | Methine | Methine | Methine | Single Bond | Single Bond | COOH |

TABLE 11

| | R¹ | R² | W¹ | W² | W³ | W⁴ | X | Y | Z |
|---|---|---|---|---|---|---|---|---|---|
| Example 37 | —Q¹—A¹<br>Q¹: Methylene<br>A¹: 2, 6-Cl₂Ph<br>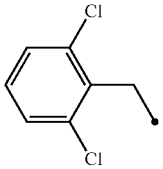 | Methyl Group | Nitrogen atom | —N= | Methine | Methine | Single Bond | Single Bond | COOH |
| Example 38 | —Q¹—A¹<br>Q¹: Methylene<br>A¹:<br>2-Cl-6-ᶜPr—Ph<br>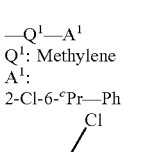 | Methyl Group | Nitrogen atom | —N= | Methine | Methine | Single Bond | Single Bond | COOH |
| Example 39 | —Q¹—A¹<br>Q¹: Methylene<br>A¹:<br>2-Cl-6-ᶜPr—Ph<br>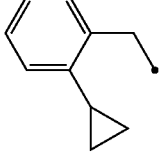 | Methyl Group | Nitrogen atom | —N= | Methine | Methine | Single Bond | Single Bond | COO⁻K⁺ |
| Example 40 | —Q¹—A¹<br>Q¹: Methylene<br>A¹:<br>2-Cl-6-Me—Ph<br>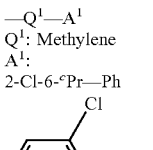 | Methyl Group | Nitrogen atom | —N= | Methine | Methine | Single Bond | Single Bond | COOH |

TABLE 12

| | R¹ | R² | W¹ | W² | W³ | W⁴ | X | Y | Z |
|---|---|---|---|---|---|---|---|---|---|
| Example 41 | —Q¹—A¹<br>Q¹: Methylene<br>A¹:<br>2-Cl-6-Me—Ph | Methyl Group | Nitrogen atom | —N= | Methine | Methine | Single Bond | Single Bond | COO⁻K⁺ |

TABLE 12-continued

| | R¹ | R² | W¹ | W² | W³ | W⁴ | X | Y | Z |
|---|---|---|---|---|---|---|---|---|---|
| Example 42 | —Q¹—A¹<br>Q¹: Methylene<br>A¹: 2-Cl-6-F—Ph<br>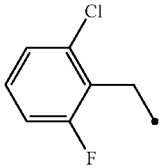 | Methyl Group | Nitrogen atom | —N= | Methine | Methine | Single Bond | Single Bond | COOH |
| Example 43 | —Q¹—A¹<br>Q¹: Methylene<br>A¹: 2, 3-Cl₂Ph<br>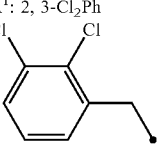 | Methyl Group | Nitrogen atom | —N= | Methine | Methine | Single Bond | Single Bond | COOH |
| Example 44 | —Q¹—A¹<br>Q¹: Methylene<br>A¹:<br>2-F-6-CF₃—Ph<br>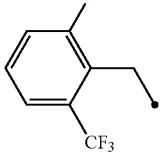 | Methyl Group | Nitrogen atom | —N= | Methine | Methine | Single Bond | Single Bond | COOH |

TABLE 13

| | R¹ | R² | W¹ | W² | W³ | W⁴ | X | Y | Z |
|---|---|---|---|---|---|---|---|---|---|
| Example 45 | —Q¹—A¹<br>Q¹: Methylene<br>A¹:<br>2-Cl-6-F—Ph<br>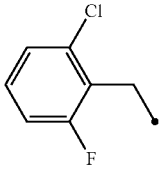 | Ethyl Group | Nitrogen atom | —N= | Methine | Methine | Single Bond | Single Bond | COOH |
| Example 46 | —Q¹—A¹<br>Q¹: Methylene<br>A¹:<br>2-ᶜPr-6-F—Ph<br>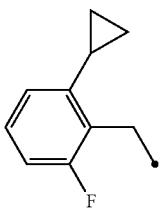 | Ethyl Group | Nitrogen atom | —N= | Methine | Methine | Single Bond | Single Bond | COOH |

TABLE 13-continued

| | R¹ | R² | W¹ | W² | W³ | W⁴ | X | Y | Z |
|---|---|---|---|---|---|---|---|---|---|
| Example 47 | —Q¹—A¹<br>Q¹: Methylene<br>A¹:<br>2-Cl-6-cPr—Ph<br>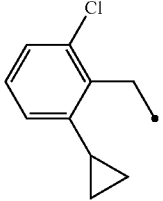 | Chlorine atom | Nitrogen atom | —N= | Methine | Methine | Single Bond | Single Bond | COOH |
| Example 48 | —Q¹—A¹<br>Q¹: Methylene<br>A¹:<br>2-Cl-6-cPr—Ph | Trifluoromethyl Group | Nitrogen atom | —N= | Methine | Methine | Single Bond | Single Bond | COOH |

TABLE 14

| | R¹ | R² | W¹ | W² | W³ | W⁴ | X | Y | Z |
|---|---|---|---|---|---|---|---|---|---|
| Example 49 | —Q¹—A¹<br>Q¹: Methylene<br>A¹: 2,6-Cl₂Ph | Methyl Group | =CH— | Methine | Methine | Methine | Single Bond | Single Bond | COOH |
| Example 50 | —Q¹—A¹<br>Q¹: Methylene<br>A¹: 2,6-Cl₂Ph | Methyl Group | Nitrogen atom | Methine | Methine | Methine | Single Bond | Single Bond | (tetrazole, H) |
| Example 51 | —Q¹—A¹<br>Q¹: Methylene<br>A¹: 2,6-Cl₂Ph | Methyl Group | Nitrogen atom | Methine | Methine | Methine | Single Bond | Single Bond | (tetrazole, K⁺) |

TABLE 15

| | R¹ | R² | W¹ | W² | W³ | W⁴ | X | Y | Z |
|---|---|---|---|---|---|---|---|---|---|
| Example 52 | —Q¹—A¹<br>Q¹: Methylene<br>A¹: 2-CN-6-Me—Ph<br>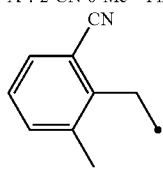 | Methyl Group | Methine | Methine | Methine | Methine | Single Bond | Single Bond | COOH |
| Example 53 | —Q¹—A¹<br>Q¹: Methylene<br>A¹: 2-CN-6-CH₂OH—Ph<br>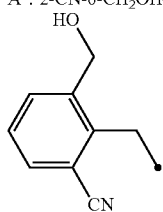 | Methyl Group | Nitrogen atom | Methine | Methine | Methine | Single Bond | Single Bond | COOH |
| Example 54 | —Q¹—A¹<br>Q¹: Methylene<br>A¹: 2-CN-6-CH₂OH—Ph<br>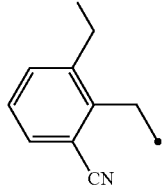 | Methyl Group | Nitrogen atom | Methine | Methine | Methine | Single Bond | Single Bond | COO⁻K⁺ |

TABLE 16

| | R¹ | R² | W¹ | W² | W³ | W⁴ | X | Y | Z |
|---|---|---|---|---|---|---|---|---|---|
| Example 55 | —Q¹—A¹<br>Q¹: Methylene<br>A¹: 2-CN-6-Me—Ph<br>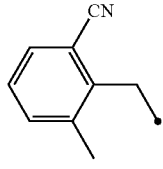 | Cyclopropyl Group | Nitrogen atom | Methine | Methine | Methine | Single Bond | Single Bond | COOH |
| Example 56 | —Q¹—A¹<br>Q¹: Methylene<br>A¹: 2-CN-6-Me—Ph<br>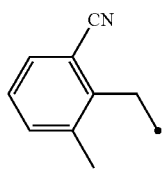 | Isopropyl Group | Nitrogen atom | Methine | Methine | Methine | Single Bond | Single Bond | COOH |

TABLE 16-continued

| | R¹ | R² | W¹ | W² | W³ | W⁴ | X | Y | Z |
|---|---|---|---|---|---|---|---|---|---|
| Example 57 | —Q¹—A¹<br>Q¹: Methylene<br>A¹: 2-CN-6-Me—Ph<br>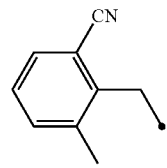 | Chlorine atom | Nitrogen atom | Methine | Methine | Methine | Single Bond | Single Bond | COOH |

TABLE 17

| | R¹ | R² | W¹ | W² | W³ | W⁴ | X | Y | Z |
|---|---|---|---|---|---|---|---|---|---|
| Example 58 | —Q¹—A¹<br>Q¹: Methylene<br>A¹: 2-CN-6-Me—Ph | Methyl Group | Nitrogen atom | Nitrogen atom | Methine | Methine | Single Bond | Single Bond | tetrazole |
| Example 59 | —Q¹—A¹<br>Q¹: Methylene<br>A¹: 2, 6-Cl₂Ph | Methyl Group | Nitrogen atom | Nitrogen atom | Methine | Methine | Single Bond | Single Bond | tetrazole |
| Example 60 | —Q¹—A¹<br>Q¹: Methylene<br>A¹: 2-CN-3-MePh | Methyl Group | Nitrogen atom | Methine | Methine | Methine | Single Bond | Single Bond | tetrazole |

TABLE 18

| | R¹ | R² | W¹ | W² | W³ | W⁴ | X | Y | Z |
|---|---|---|---|---|---|---|---|---|---|
| Example 61 | —Q¹—A¹<br>Q¹: Methylene<br>A¹: 2-CONH₂-3-Me—Ph<br>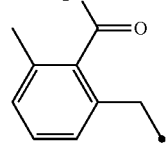 | Methyl Group | Nitrogen atom | Methine | Methine | Methine | Single Bond | Single Bond | tetrazole |

TABLE 18-continued

| | R¹ | R² | W¹ | W² | W³ | W⁴ | X | Y | Z |
|---|---|---|---|---|---|---|---|---|---|
| Example 62 | —Q¹—A¹<br>Q¹: Methylene<br>A¹: 2-Cl-6-F—Ph<br>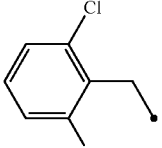 | Methyl Group | Nitrogen atom | Methine | Methine | Methine | Single Bond | Single Bond | tetrazole |
| Example 63 | —Q¹—A¹<br>Q¹: Methylene<br>A¹: 2-F-6-CF₃—Ph | Methyl Group | Nitrogen atom | Methine | Methine | Methine | Single Bond | Single Bond | tetrazole |
| Example 64 | —Q¹—A¹<br>Q¹: Methylene<br>A¹: 2, 3-Cl₂Ph | Methyl Group | Nitrogen atom | Methine | Methine | Methine | Single Bond | Single Bond | tetrazole |

TABLE 19

| | R¹ | R² | W¹ | W² | W³ | W⁴ | X | Y | Z |
|---|---|---|---|---|---|---|---|---|---|
| Example 65 | —Q¹—A¹<br>Q¹: Methylene<br>A¹: 2-Cl-6-CN—Ph | Methyl Group | Nitrogen atom | Methine | Methine | Methine | Single Bond | Single Bond | tetrazole |
| Example 66 | —Q¹—A¹<br>Q¹: Methylene<br>A¹: 2-Cl-6-SO₂Me—Ph | Methyl Group | Nitrogen atom | Methine | Methine | Methine | Single Bond | Single Bond | tetrazole |
| Example 67 | —Q¹—A¹<br>Q¹: Methylene<br>A¹: 2-CONH₂-6-Cl—Ph | Methyl Group | Nitrogen atom | Methine | Methine | Methine | Single Bond | Single Bond | tetrazole |

TABLE 20

| | R¹ | R² | W¹ | W² | W³ | W⁴ | X | Y | Z |
|---|---|---|---|---|---|---|---|---|---|
| Example 68 | —Q¹—A¹<br>Q¹: Methylene<br>A¹: 2-CONH₂-6-Cl—Ph<br>(H₂N-C(=O)-, Cl-phenyl-CH₂-) | Methyl Group | Nitrogen atom | Methine | Methine | Methine | Single Bond | Single Bond | tetrazole K⁺ salt |
| Example 69 | —Q¹—A¹<br>Q¹: Methylene<br>A¹: 2-Cl-6-CONHMe—Ph<br>(MeHN-C(=O)-, Cl-phenyl-CH₂-) | Methyl Group | Nitrogen atom | Methine | Methine | Methine | Single Bond | Single Bond | 1H-tetrazole |
| Example 70 | —Q¹—A¹<br>Q¹: Methylene<br>A¹: 2,6-(CN)₂—Ph<br>(NC-, NC-phenyl-CH₂-) | Methyl Group | Nitrogen atom | Methine | Methine | Methine | Single Bond | Single Bond | 1H-tetrazole |

TABLE 21

| | R¹ | R² | W¹ | W² | W³ | W⁴ | X | Y | Z |
|---|---|---|---|---|---|---|---|---|---|
| Example 71 | —Q¹—A¹<br>Q¹: Methylene<br>A¹: 2-CN-6-Me—Ph | Methyl Group | Nitrogen atom | Methine | Methine | Methine | Single Bond | Single Bond | 1H-tetrazole |
| Example 72 | —Q¹—A¹<br>Q¹: Methylene<br>A¹: 2-CONH₂-6-Me—Ph | Methyl Group | Nitrogen atom | Methine | Methine | Methine | Single Bond | Single Bond | 1H-tetrazole |

TABLE 21-continued

| | R¹ | R² | W¹ | W² | W³ | W⁴ | X | Y | Z |
|---|---|---|---|---|---|---|---|---|---|
| Example 73 | —Q¹—A¹<br>Q¹: Methylene<br>A¹: 2-F—Ph<br>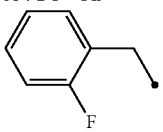 | Methyl Group | Nitrogen atom | Methine | Methine | Methine | Single Bond | Single Bond | 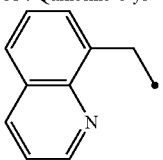 |

TABLE 22

| | R¹ | R² | W¹ | W² | W³ | W⁴ | X | Y | Z |
|---|---|---|---|---|---|---|---|---|---|
| Example 74 | —Q¹—A¹<br>Q¹: Methylene<br>A¹: Quinoline-8-yl | Methyl Group | Nitrogen atom | Methine | Methine | Methine | Single Bond | Single Bond | |
| Example 75 | —Q¹—A¹<br>Q¹: Methylene<br>A¹: 2-CN-6-ᶜPr—Ph | Methyl Group | Nitrogen atom | Methine | Methine | Methine | Single Bond | Single Bond | |
| Example 76 | —Q¹—A¹<br>Q¹: Methylene<br>A¹: 2-CONH₂-6-ᶜPr—Ph | Methyl Group | Nitrogen atom | Methine | Methine | Methine | Single Bond | Single Bond | |

TABLE 23

| | R¹ | R² | W¹ | W² | W³ | W⁴ | X | Y | Z |
|---|---|---|---|---|---|---|---|---|---|
| Example 77 | —Q¹—A¹<br>Q¹: Methylene<br>A¹: 2-CONH₂-6-Et—Ph<br>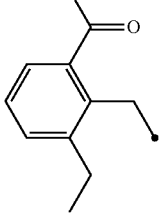 | Methyl Group | Nitrogen atom | Methine | Methine | Methine | Single Bond | Single Bond | |

TABLE 23-continued

| | R¹ | R² | W¹ | W² | W³ | W⁴ | X | Y | Z |
|---|---|---|---|---|---|---|---|---|---|
| Example 78 | —Q¹—A¹<br>Q¹: Methylene<br>A¹: 2-CN—Ph<br>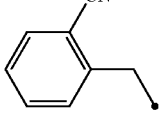 | Methyl Group | Nitrogen atom | Methine | Methine | Methine | Single Bond | Single Bond | 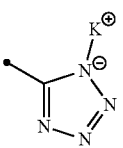 |
| Example 79 | —Q¹—A¹<br>Q¹: Methylene<br>A¹: 2-CN—Ph<br>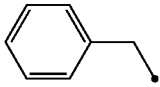 | Methyl Group | Nitrogen atom | Methine | Methine | Methine | Single Bond | Single Bond | 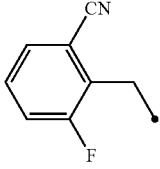 |
| Example 80 | —Q¹—A¹<br>Q¹: Methylene<br>A¹: Ph<br>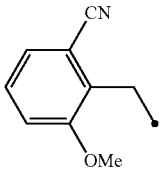 | Methyl Group | Nitrogen atom | Methine | Methine | Methine | Single Bond | Single Bond | 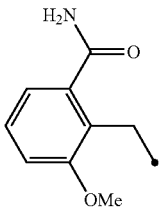 |

TABLE 24

| | R¹ | R² | W¹ | W² | W³ | W⁴ | X | Y | Z |
|---|---|---|---|---|---|---|---|---|---|
| Example 81 | —Q¹—A¹<br>Q¹: Methylene<br>A¹: 2-CN-6-F—Ph | Methyl Group | Nitrogen atom | Methine | Methine | Methine | Single Bond | Single Bond | |
| Example 82 | —Q¹—A¹<br>Q¹: Methylene<br>A¹: 2-CN-6-OMe—Ph | Methyl Group | Nitrogen atom | Methine | Methine | Methine | Single Bond | Single Bond | |
| Example 83 | —Q¹—A¹<br>Q¹: Methylene<br>A¹: 2-CONH₂-6-OMe—Ph | Methyl Group | Nitrogen atom | Methine | Methine | Methine | Single Bond | Single Bond | |

TABLE 25

| | R¹ | R² | W¹ | W² | W³ | W⁴ | X | Y | Z |
|---|---|---|---|---|---|---|---|---|---|
| Example 84 | —Q¹—A¹<br>Q¹: Methylene<br>A¹: 2-OMe—Ph<br> | Methyl Group | Nitrogen atom | Methine | Methine | Methine | Single Bond | Single Bond | 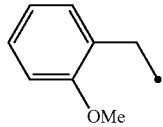 |
| Example 85 | —Q¹—A¹<br>Q¹: Methylene<br>A¹: 2-OCF₃—Ph<br> | Methyl Group | Nitrogen atom | Methine | Methine | Methine | Single Bond | Single Bond | 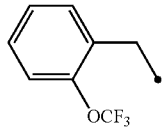 |
| Example 86 | —Q¹—A¹<br>Q¹: Methylene<br>A¹: 2-Me—Ph<br> | Methyl Group | Nitrogen atom | Methine | Methine | Methine | Single Bond | Single Bond | 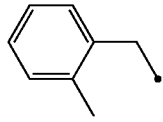 |
| Example 87 | —Q¹—A¹<br>Q¹: Methylene<br>A¹: 3-CN—Ph<br> | Methyl Group | Nitrogen atom | Methine | Methine | Methine | Single Bond | Single Bond | 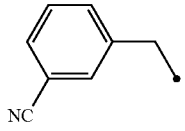 |

TABLE 26

| | R¹ | R² | W¹ | W² | W³ | W⁴ | X | Y | Z |
|---|---|---|---|---|---|---|---|---|---|
| Example 88 | —Q¹—A¹<br>Q¹: Methylene<br>A¹: 4-CN—Ph<br> | Methyl Group | Nitrogen atom | Methine | Methine | Methine | Single Bond | Single Bond | 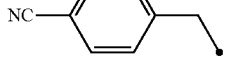 |
| Example 89 | —Q¹—A¹<br>Q¹: Methylene<br>A¹:<br>2-Cloropyridine-3-yl<br> | Methyl Group | Nitrogen atom | Methine | Methine | Methine | Single Bond | Single Bond | 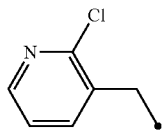 |

TABLE 26-continued

| | R¹ | R² | W¹ | W² | W³ | W⁴ | X | Y | Z |
|---|---|---|---|---|---|---|---|---|---|
| Example 90 | —Q¹—A¹<br>Q¹: Methylene<br>A¹:<br>2-Carbamoylpyridine-3-yl | Methyl Group | Nitrogen atom | Methine | Methine | Methine | Single Bond | Single Bond | tetrazole |
| Example 91 | —Q¹—A¹<br>Q¹: Methylene<br>A¹:<br>2-Cyanopyridine-3-yl | Methyl Group | Nitrogen atom | Methine | Methine | Methine | Single Bond | Single Bond | tetrazole |

TABLE 27

| | R¹ | R² | W¹ | W² | W³ | W⁴ | X | Y | Z |
|---|---|---|---|---|---|---|---|---|---|
| Example 92 | —Q¹—A¹<br>Q¹: Methylene<br>A¹:<br>2-Chloro-4-cyano-pyridine-3-yl | Methyl Group | Nitrogen atom | Methine | Methine | Methine | Single Bond | Single Bond | tetrazole |
| Example 93 | —Q¹—A¹<br>Q¹: Methylene<br>A¹: 2-Cl—Ph | Methyl Group | Nitrogen atom | Methine | Methine | Methine | Single Bond | Single Bond | tetrazole |
| Example 94 | —Q¹—A¹<br>Q¹: Methylene<br>A¹:<br>Isoquinoline-8-yl | Methyl Group | Nitrogen atom | Methine | Methine | Methine | Single Bond | Single Bond | tetrazole |

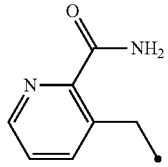

TABLE 28

| | R¹ | R² | W¹ | W² | W³ | W⁴ | X | Y | Z |
|---|---|---|---|---|---|---|---|---|---|
| Example 95 | —Q¹—A¹<br>Q¹: Methylene<br>A¹: Isoquinoline-5-yl<br>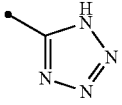 | Methyl Group | Nitrogen atom | Methine | Methine | Methine | Single Bond | Single Bond | 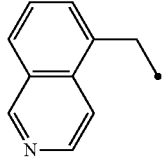 |
| Example 96 | —Q¹—A¹<br>Q¹: Methylene<br>A¹: Quinoline-5-yl<br>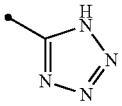 | Methyl Group | Nitrogen atom | Methine | Methine | Methine | Single Bond | Single Bond | 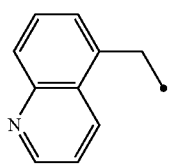 |
| Example 97 | —Q¹—A¹<br>Q¹: Methylene<br>A¹: Isoquinoline-1-yl<br>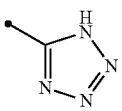 | Methyl Group | Nitrogen atom | Methine | Methine | Methine | Single Bond | Single Bond | 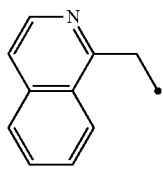 |
| Example 98 | —Q¹—A¹<br>Q¹: Methylene<br>A¹: 2-CF₃—Ph<br>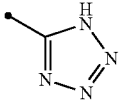 | Methyl Group | Nitrogen atom | Methine | Methine | Methine | Single Bond | Single Bond | 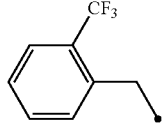 |

TABLE 29

| | R¹ | R² | W¹ | W² | W³ | W⁴ | X | Y | Z |
|---|---|---|---|---|---|---|---|---|---|
| Example 99 | —Q¹—A¹<br>Q¹: Methylene<br>A¹: 3-CN-2-Me—Ph<br>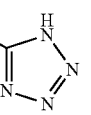 | Methyl Group | Nitrogen atom | Methine | Methine | Methine | Single Bond | Single Bond | 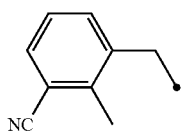 |

TABLE 29-continued

| | R¹ | R² | W¹ | W² | W³ | W⁴ | X | Y | Z |
|---|---|---|---|---|---|---|---|---|---|
| Example 100 | —Q¹—A¹<br>Q¹: Methylene<br>A¹: 3-CONH₂-2-Me—Ph<br>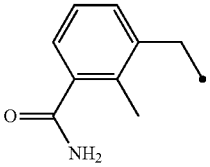 | Methyl Group | Nitrogen atom | Methine | Methine | Methine | Single Bond | Single Bond | 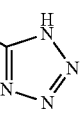 |
| Example 101 | —Q¹—A¹<br>Q¹: Methylene<br>A¹: 2-Cl-6-F—Ph<br> | Methyl Group | Nitrogen atom | Methine | Methine | Methine | Single Bond | Single Bond | 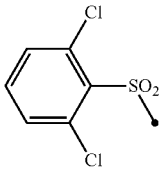 |

TABLE 30

| | R¹ | R² | W¹ | W² | W³ | W⁴ | X | Y | Z |
|---|---|---|---|---|---|---|---|---|---|
| Example 102 | —Q¹—A¹<br>Q¹: SO₂<br>A¹: 2,6-Cl₂Ph<br> | Methyl Group | Nitrogen atom | Methine | Methine | Methine | Single Bond | Single Bond | 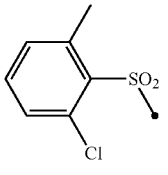 |
| Example 103 | —Q¹—A¹<br>Q¹: SO₂<br>A¹: 2-Cl-6-Me—Ph<br> | Methyl Group | Nitrogen atom | Methine | Methine | Methine | Single Bond | Single Bond | |
| Example 104 | —Q¹—A¹<br>Q¹: Methylene<br>A¹: 2-CN-6-CH₂OH—Ph<br>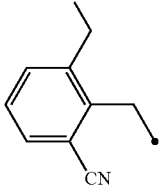 | Methyl Group | Nitrogen atom | Methine | Methine | Methine | Single Bond | Single Bond | |

TABLE 31

| | R¹ | R² | W¹ | W² | W³ | W⁴ | X | Y | Z |
|---|---|---|---|---|---|---|---|---|---|
| Example 105 | —Q¹—A¹<br>Q¹: Methylene<br>A¹: 2-CN-6-CH₂OH—Ph<br>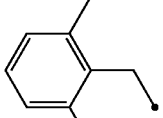 | Methyl Group | Nitrogen atom | Methine | Methine | Methine | Single Bond | Single Bond |  |
| Example 106 | —Q¹—A¹<br>Q¹: Methylene<br>A¹: 2-CH₂OH-6-Me—Ph<br>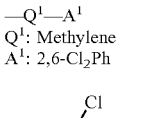 | Methyl Group | Nitrogen atom | Methine | Methine | Methine | Single Bond | Single Bond | 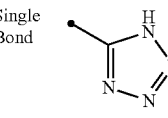 |

TABLE 32

| | R¹ | R² | W¹ | W² | W³ | W⁴ | X | Y | Z |
|---|---|---|---|---|---|---|---|---|---|
| Example 107 | —Q¹—A¹<br>Q¹: Methylene<br>A¹: 2-CH₂CN-6-Me—Ph | Methyl Group | Nitrogen atom | Methine | Methine | Methine | Single Bond | Single Bond | |
| Example 108 | —Q¹—A¹<br>Q¹: Methylene<br>A¹: 2,6-Cl₂Ph | Methyl Group | Nitrogen atom | Methine | Methine | Nitrogen atom | Single Bond | Single Bond | |

TABLE 33

| | R¹ | R² | W¹ | W² | W³ | W⁴ | X | Y | Z |
|---|---|---|---|---|---|---|---|---|---|
| Example 109 | —Q¹—A¹<br>Q¹: Methylene<br>A¹: 2-CN-6-Me—Ph | Methyl Group | Nitrogen atom | Methine | Methine | Nitrogen atom | Single Bond | Single Bond | tetrazole (H) |
| Example 110 | —Q¹—A¹<br>Q¹: Methylene<br>A¹: 2-CONH₂-6-Me—Ph | Methyl Group | Nitrogen atom | Methine | Methine | Nitrogen atom | Single Bond | Single Bond | tetrazole (H) |

TABLE 34

| | R¹ | R² | W¹ | W² | W³ | W⁴ | X | Y | Z |
|---|---|---|---|---|---|---|---|---|---|
| Example 111 | —Q¹—A¹<br>Q¹: Methylene<br>A¹: 2-CONH₂-6-Me—Ph | Methyl Group | Nitrogen atom | Methine | Methine | Nitrogen atom | Single Bond | Single Bond | tetrazole (K⁺) |
| Example 112 | —Q¹—A¹<br>Q¹: Methylene<br>A¹: 2-CONH₂—Ph | Methyl Group | Nitrogen atom | Methine | Methine | Nitrogen atom | Single Bond | Single Bond | tetrazole (H) |

TABLE 35

| | R¹ | R² | W¹ | W² | W³ | W⁴ | X | Y | Z |
|---|---|---|---|---|---|---|---|---|---|
| Example 113 | —Q¹—A¹<br>Q¹: Methylene<br>A¹: 2-Cl-6-CN—Ph<br>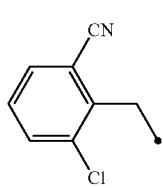 | Methyl Group | Nitrogen atom | Methine | Methine | Nitrogen atom | Single Bond | Single Bond | 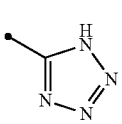 |
| Example 114 | —Q¹—A¹<br>Q¹: Methylene<br>A¹: 2-CONH₂-6-Cl—Ph<br>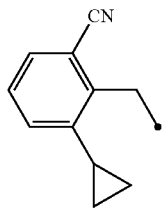 | Methyl Group | Nitrogen atom | Methine | Methine | Nitrogen atom | Single Bond | Single Bond | 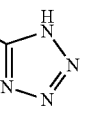 |

TABLE 36

| | R¹ | R² | W¹ | W² | W³ | W⁴ | X | Y | Z |
|---|---|---|---|---|---|---|---|---|---|
| Example 115 | —Q¹—A¹<br>Q¹: Methylene<br>A¹: 2-CN-6-ᶜPr—Ph<br>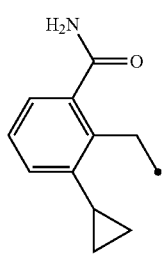 | Methyl Group | Nitrogen atom | Methine | Methine | Nitrogen atom | Single Bond | Single Bond | 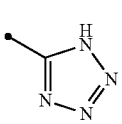 |
| Example 116 | —Q¹—A¹<br>Q¹: Methylene<br>A¹: 2-CONH₂-6-ᶜPr—Ph<br>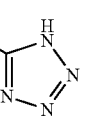 | Methyl Group | Nitrogen atom | Methine | Methine | Nitrogen atom | Single Bond | Single Bond | 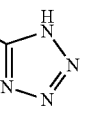 |

TABLE 37

| | R¹ | R² | W¹ | W² | W³ | W⁴ | X | Y | Z |
|---|---|---|---|---|---|---|---|---|---|
| Example 117 | —Q¹—A¹<br>Q¹: Methylene<br>A¹: 2-CONH₂-6-ᶜPr—Ph<br>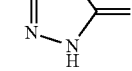 | Methyl Group | Nitrogen atom | Methine | Methine | Nitrogen atom | Single Bond | Single Bond | 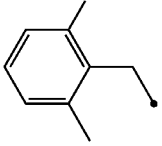 |
| Example 118 | —Q¹—A¹<br>Q¹: Methylene<br>A¹: 2-CN-6-Me—Ph<br>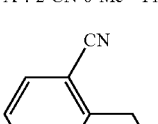 | Ethyl Group | Nitrogen atom | Methine | Methine | Methine | Single Bond | Single Bond | COOH |

TABLE 38

| | R¹ | R² | W¹ | W² | W³ | W⁴ | X | Y | Z |
|---|---|---|---|---|---|---|---|---|---|
| Example 119 | —Q¹—A¹<br>Q¹: Methylene<br>A¹: 2-CN-6-Me—Ph<br>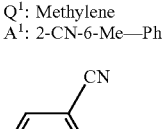 | Methyl Group | Nitrogen atom | Methine | Methine | Methine | Single Bond | Single Bond |  |
| Example 120 | —Q¹—A¹<br>Q¹: Methylene<br>A¹: 2-CN-6-Me—Ph | Difluoromethyl Group | Nitrogen atom | Methine | Methine | Methine | Single Bond | Single Bond | COOH |
| Example 121 | —Q¹—A¹<br>Q¹: Methylene<br>A¹: 2-CN-6-Me—Ph | Hydroxymethyl Group | Nitrogen atom | Methine | Methine | Methine | Single Bond | Single Bond | COOH |

Reference Example 1

Synthesis of 1-(2-chloro-6-cyclopropylbenzyl)-3-methyl-6-(1H-tetrazol-5-yl)-1H-pyrazolo[4,3-b]pyridine [1a] (hereinafter referred to as a compound [1a])

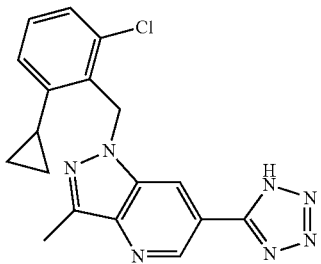 [SMILES: Cc1nn(Cc2c(Cl)cccc2C2CC2)c2cc(-c3nnn[nH]3)cnc12]

(1) Synthesis of 6-bromo-1-(2-chloro-6-cyclopropylbenzyl)-3-methyl-1H-pyrazolo[4,3-b]pyridine [1a-1] (hereinafter referred to as a compound [1a-1])

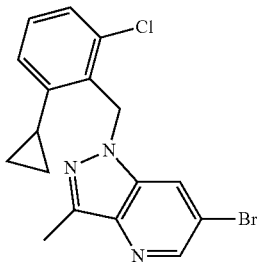 [SMILES: Cc1nn(Cc2c(Cl)cccc2C2CC2)c2cc(Br)cnc12]

The titled compound (386 mg) as a yellow solid was prepared from the compound [37-2] (281 mg) and the compound [12-2] (320 mg) according to the method of the step (1) in Example 1.

$^1$H-NMR (400 MHz, CDCl$_3$) δ: 8.49 (1H, d, J=1.5 Hz), 7.67 (1H, d, J=1.5 Hz), 7.32 (1H, d, J=7.8 Hz), 7.29-7.20 (1H, m), 7.03 (1H, d, J=7.8 Hz), 5.84 (2H, s), 2.61 (3H, s), 2.15-2.08 (1H, m), 0.94-0.89 (2H, m), 0.67-0.60 (2H, m).

(2) Synthesis of 1-(2-chloro-6-cyclopropylbenzyl)-3-methyl-1H-pyrazolo[4,3-b]pyridine-6-carbonitrile [1a-2] (hereinafter referred to as a compound [1a-2])

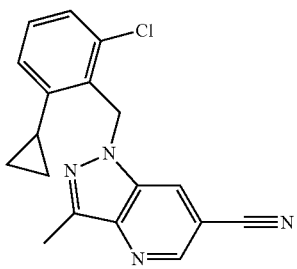 [SMILES: Cc1nn(Cc2c(Cl)cccc2C2CC2)c2cc(C#N)cnc12]

The compound [1a-1] (130 mg) was dissolved in N,N-dimethylformamide (1.3 mL). To the solution were added zinc cyanide (30 mg) and tetrakis(triphenylphosphine)palladium(0) (40 mg) at room temperature, and the mixture was subjected to microwave irradiation at 150° C. for 10 minutes. After cooling, the reaction mixture was quenched with a saturated aqueous solution of potassium carbonate, and extracted with ethyl acetate. The obtained organic layer was dried over anhydrous sodium sulfate, filtered, and the filtrate was concentrated under reduced pressure. The obtained residue was purified by silica gel column chromatography to give the titled compound (91 mg) as a white solid.

$^1$H-NMR (400 MHz, CDCl$_3$) δ: 8.66 (1H, s), 7.78 (1H, s), 7.34 (1H, d, J=7.8 Hz), 7.30-7.22 (1H, m), 7.04 (1H, d, J=7.6 Hz), 5.93 (2H, s), 2.66 (3H, s), 2.13-2.05 (1H, m), 0.96-0.88 (2H, m), 0.67-0.59 (2H, m).

(3) Synthesis of 1-(2-chloro-6-cyclopropylbenzyl)-3-methyl-6-(1H-tetrazol-5-yl)-1H-pyrazolo[4,3-b]pyridine [1a]

The compound [1a-2] (91 mg) was dissolved in N,N-dimethylformamide (2.8 mL). To the solution were added ammonium chloride (60 mg) and sodium azide (55 mg) at room temperature, and the mixture was subjected to microwave irradiation at 160° C. for 1 hour. After cooling, 3N-hydrochloric acid was added to the reaction mixture, and the mixture was extracted with ethyl acetate. The obtained organic layer was dried over anhydrous sodium sulfate, filtered, and the filtrate was concentrated under reduced pressure to give the titled compound (94 mg) as a white solid.

$^1$H-NMR (400 MHz, CD$_3$OD) δ: 9.12 (1H, d, J=1.5 Hz), 8.68 (1H, d, J=1.5 Hz), 7.27-7.26 (2H, m), 7.13 (1H, d, J=6.8 Hz), 6.00 (2H, s), 2.59 (3H, s), 2.24-2.17 (1H, m), 0.92-0.89 (2H, m), 0.70-0.68 (2H, m).

ESI-MS found: 366 [M+H]$^+$

Reference Example 2

Synthesis of 1-(2-chloro-6-cyclopropylbenzyl)-3-methyl-1H-pyrazolo[4,3-b]pyridine-6-carboxylic acid [2a] (hereinafter referred to as a compound [2a])

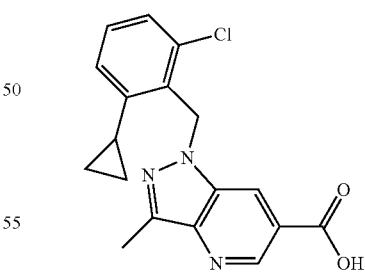

To a solution of the compound [1a-2] (44 mg) in methanol (4 mL) was added an aqueous solution of 1N-sodium hydroxide (4 mL) at room temperature, and the mixture was stirred overnight at 110° C. After cooling, 3N-hydrochloric acid was added, and the mixture was extracted with ethyl acetate. The obtained organic layer was dried over anhydrous sodium sulfate, filtered, and the filtrate was concentrated under reduced pressure to give the titled compound (39 mg) as a white solid.

¹H-NMR (400 MHz, CD₃OD) δ: 9.02 (1H, d, J=1.5 Hz), 8.54 (1H, d, J=1.5 Hz), 7.33-7.26 (2H, m), 7.11 (1H, d, J=7.6 Hz), 5.98 (2H, s), 2.58 (3H, s), 2.18-2.11 (1H, m), 0.90-0.85 (2H, m), 0.68-0.64 (2H, m).

ESI-MS found: 342 [M+H]⁺

Reference Example 3

Synthesis of 3-chloro-1-(2-chloro-6-cyclopropylbenzyl)-1H-pyrazolo[4,3-b]pyridine-6-carboxylic acid [3a] (hereinafter referred to as a compound [3a])

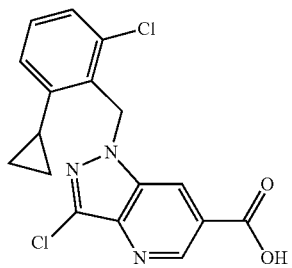 [SMILES: O=C(O)c1cnc2c(Cl)nn(Cc3c(Cl)cccc3C3CC3)c2c1]

(1) Synthesis of 3-chloro-1-(2-chloro-6-cyclopropylbenzyl)-1H-pyrazolo[4,3-b]pyridine-6-carbonitrile [3a-1] (hereinafter referred to as a compound [3a-1])

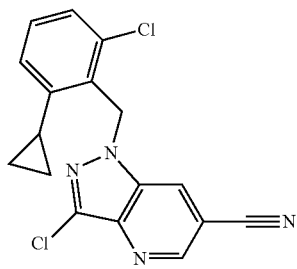 [SMILES: N#Cc1cnc2c(Cl)nn(Cc3c(Cl)cccc3C3CC3)c2c1]

The titled compound (46 mg) as a white solid was prepared from the compound [47-4] (67 mg) according to the method of the process (2) in Reference example 1.

¹H-NMR (400 MHz, CDCl₃) δ: 8.76 (1H, s), 7.91 (1H, s), 7.35-7.26 (2H, m), 7.07 (1H, d, J=7.3 Hz), 5.96 (2H, s), 2.14-2.05 (1H, m), 0.98-0.94 (2H, m), 0.68-0.64 (2H, m).

(2) Synthesis of 3-chloro-1-(2-chloro-6-cyclopropylbenzyl)-1H-pyrazolo[4,3-b]pyridine-6-carboxylic acid [3a]

The titled compound (48 mg) as a white solid was prepared from the compound [3a-1] (46 mg) according to the method of Reference example 2.

¹H-NMR (400 MHz, CD₃OD) δ: 9.10 (1H, d, J=1.5 Hz), 8.70 (1H, d, J=1.5 Hz), 7.33-7.28 (2H, m), 7.13 (1H, dd, J=7.0, 1.8 Hz), 6.03 (2H, s), 2.21-2.14 (1H, m), 0.93-0.88 (2H, m), 0.70-0.66 (2H, m).

ESI-MS found: 362 [M+H]⁺

Reference Example 4

Synthesis of 1-(2,6-dichlorobenzyl)-3-trifluoromethyl-1H-pyrazolo[4,3-b]pyridine-6-carboxylic acid [4a] (hereinafter referred to as a compound [4a])

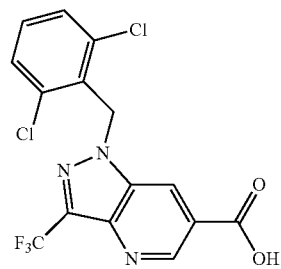 [SMILES: O=C(O)c1cnc2c(C(F)(F)F)nn(Cc3c(Cl)cccc3Cl)c2c1]

(1) 6-bromo-1-(2,6-dichlorobenzyl)-3-iodo-1H-pyrazolo[4,3-b]pyridine [4a-1] (hereinafter referred to as a compound [4a-1])

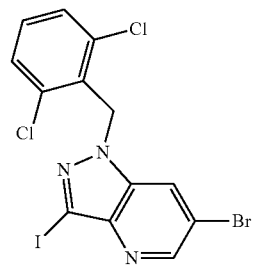 [SMILES: Clc1cccc(Cl)c1Cn1nc(I)c2ncc(Br)cc21]

The titled compound (421 mg) as a yellow solid was prepared from the compound [48-1] (510 mg) and 2,6-dichlorobenzyl chloride (369 mg) according to the method of the process (1) in Example 1.

¹H-NMR (400 MHz, CDCl₃) δ: 8.61 (1H, d, J=1.5 Hz), 7.86 (1H, d, J=1.5 Hz), 7.41 (2H, d, J=7.8 Hz), 7.31-7.29 (1H, m), 5.80 (2H, s).

(2) Synthesis of 6-bromo-1-(2,6-dichlorobenzyl)-3-trifluoromethyl-1H-pyrazolo[4,3-b]pyridine [4a-2] (hereinafter referred to as a compound [4a-2])

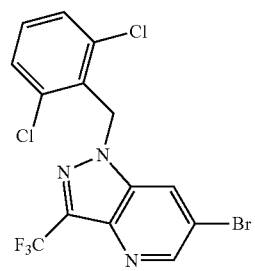 [SMILES: FC(F)(F)c1nn(Cc2c(Cl)cccc2Cl)c2cc(Br)cnc12]

The titled compound (261 mg) as a yellow solid was prepared from the compound [4a-1] (414 mg) according to the method of the process (3) in Example 36.

¹H-NMR (400 MHz, CDCl₃) δ: 8.72 (1H, d, J=1.5 Hz), 7.96 (1H, d, J=1.7 Hz), 7.42 (2H, d, J=8.1 Hz), 7.34-7.32 (1H, m), 5.84 (2H, s).

(3) Synthesis of 1-(2,6-dichlorobenzyl)-3-trifluoromethyl-1H-pyrazolo[4,3-b]pyridine-6-carboxylic acid [4a]

The titled compound (30 mg) as a white solid was prepared from the compound [4a-2] (65 mg) according to the method of the process (2) in Reference example 1 and the method of Reference example 2.
¹H-NMR (400 MHz, CD₃OD) δ: 9.23 (1H, d, J=1.5 Hz), 8.90 (1H, s), 7.50 (2H, d, J=8.1 Hz), 7.42-7.40 (1H, m), 6.06 (2H, s).
ESI-MS found: 390 [M+H]⁺

Reference Example 5

Synthesis of 1-(2-chloro-6-cyclopropylbenzyl)-3-trifluoromethyl-1H-pyrazolo[4,3-b]pyridine-6-carboxylic acid [5a] (hereinafter referred to as a compound [5a])

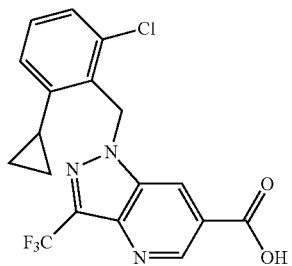 [SMILES: O=C(O)c1cnc2c(C(F)(F)F)nn(Cc3c(Cl)cccc3C3CC3)c2c1]

The titled compound (26 mg) as a white solid was prepared from the compound [48-3] (36 mg) according to the method of the process (2) in Reference example 1 and the method of Reference example 2.
¹H-NMR (400 MHz, CD₃OD) δ: 9.20 (1H, d, J=1.7 Hz), 8.77 (1H, d, J=1.7 Hz), 7.33-7.32 (2H, m), 7.14 (1H, d, J=6.3 Hz), 6.15 (2H, s), 2.20-2.14 (1H, m), 0.90-0.89 (2H, m), 0.68-0.67 (2H, m).
ESI-MS found: 396 [M+H]⁺

Reference Example 6

Synthesis of 1-(2,6-dimethylbenzyl)-3-trifluoromethyl-1H-indazole-6-carboxylic acid [6a] (hereinafter referred to as a compound [6a])

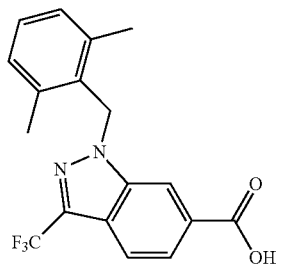 [SMILES: Cc1cccc(C)c1Cn1nc(C(F)(F)F)c2ccc(C(=O)O)cc21]

(1) 6-bromo-1-(2,6-dimethylbenzyl)-3-iodo-1H-indazole [6a-1] (hereinafter referred to as a compound [6a-1])

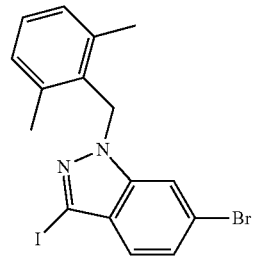 [SMILES: Cc1cccc(C)c1Cn1nc(I)c2ccc(Br)cc21]

The titled compound (467 mg) as a white solid was prepared from the compound [36-1] (482 mg) and 2,6-dimethylbenzyl chloride (276 mg) according to the method of the process (1) in Example 1.
¹H-NMR (400 MHz, CDCl₃) δ: 7.30 (1H, d, J=8.5 Hz), 7.24-7.20 (2H, m), 7.11-7.10 (3H, m), 5.56 (2H, s), 2.32 (6H, s).

(2) 6-bromo-1-(2,6-dimethylbenzyl)-3-trifluoromethyl-1H-indazole [6a-2] (hereinafter referred to as a compound [6a-2])

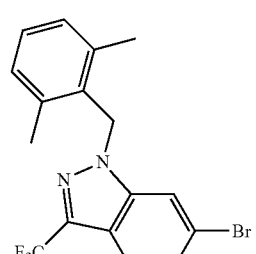

The titled compound (364 mg) as a white solid was prepared from the compound [6a-1] (465 mg) according to the method of the process (3) in Example 36.
¹H-NMR (400 MHz, CDCl₃) δ: 7.67 (1H, d, J=8.5 Hz), 7.34 (1H, d, J=8.5 Hz), 7.26-7.22 (2H, m), 7.12 (2H, d, J=7.6 Hz), 5.60 (2H, s), 2.33 (6H, s).

(3) 1-(2,6-dimethylbenzyl)-3-trifluoromethyl-1H-indazole-6-carboxylic acid [6a]

The titled compound (19 mg) as a white solid was prepared from the compound [6a-2] (130 mg) according to the method of the process (2) of Reference example 1 and the method of Reference example 2.
¹H-NMR (400 MHz, CD₃OD) δ: 8.28 (1H, s), 7.93 (1H, d, J=8.5 Hz), 7.86 (1H, d, J=8.5 Hz), 7.18-7.16 (1H, m), 7.09 (2H, d, J=7.3 Hz), 5.78 (2H, s), 2.33 (6H, s).
ESI-MS found: 349 [M+H]⁺

Reference Example 7

Synthesis of 1-(2,6-dichlorobenzyl)-3-trifluoromethyl-1H-indazole-6-carboxylic acid [7a] (hereinafter referred to as a compound [7a])

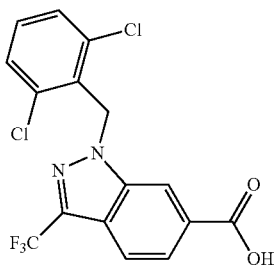 [SMILES: O=C(O)c1ccc2c(C(F)(F)F)nn(Cc3c(Cl)cccc3Cl)c2c1]

The titled compound (52 mg) as a white solid was prepared from the compound [36-3] (130 mg) according to the method of the process (2) of Reference example 1 and the method of Reference example 2.

$^1$H-NMR (400 MHz, CD$_3$OD) δ: 8.52 (1H, s), 7.96 (1H, d, J=8.1 Hz), 7.88 (1H, d, J=7.6 Hz), 7.49 (2H, d, J=8.1 Hz), 7.40-7.38 (1H, m), 6.00 (2H, s).

ESI-MS found: 389 [M+H]$^+$

Reference Example 8

Synthesis of 3-[1-(2-chloro-6-cyclopropylbenzyl)-3-methyl-1H-indazol-6-yl]propionic acid [8a] (hereinafter referred to as a compound [8a])

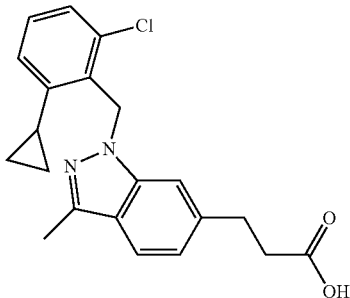 [SMILES: Cc1nn(Cc2c(Cl)cccc2C2CC2)c2cc(CCC(=O)O)ccc12]

(1) Synthesis of methyl (E)-3-(3-methyl-1H-indazol-6-yl)acrylate[8a-1] (hereinafter referred to as a compound [8a-1])

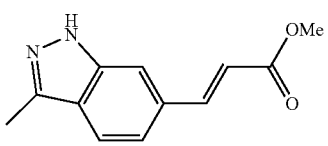 [SMILES: COC(=O)/C=C/c1ccc2c(C)n[nH]c2c1]

6-Bromo-3-methyl-1H-indazole, which was obtained by the method described in the document (JP 2009-528363 W) (2.1 g), was dissolved in N,N-dimethylformamide (10 mL). To the solution were added methyl acrylate (1.8 mL), palladium(II) acetate (225 mg), tris(2-methylphenyl)phosphine (609 mg) and triethylamine (2.8 mL) at room temperature, and the mixture was subjected to microwave irradiation at 150° C. for 10 minutes. After cooling to room temperature, water was added, and the mixture was extracted with chloroform. The obtained organic layer was washed with brine, dried over anhydrous sodium sulfate, filtered, and the filtrate was concentrated under reduced pressure. The obtained residue was purified by silica gel column chromatography to give the titled compound (1.8 g) as a yellow white solid.

$^1$H-NMR (400 MHz, CDCl$_3$) δ: 9.91 (1H, br), 7.81 (1H, d, J=15.9 Hz), 7.67 (1H, d, J=8.3 Hz), 7.54 (1H, s), 7.36 (1H, d, J=8.3 Hz), 6.52 (1H, d, J=15.9 Hz), 3.83 (3H, s), 2.57 (3H, s).

ESI-MS found: 217 [M+H]$^+$ (2) Synthesis of methyl 3-(3-methyl-1H-indazol-6-yl)propionate [8a-2] (hereinafter referred to as a compound [8a-2])

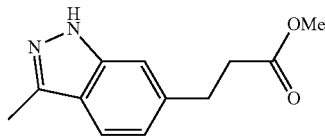 [SMILES: COC(=O)CCc1ccc2c(C)n[nH]c2c1]

The compound [8a-1] (1.8 g) was dissolved in methanol (163 mL), and to the solution was added 5% palladium-activated carbon (1.8 g) at room temperature, and the mixture was stirred under a hydrogen atmosphere at room temperature for 2 hours. The mixture was filtered, and the filtrate was concentrated under reduced pressure. The obtained residue was purified by silica gel column chromatography to give the titled compound (1.5 g) as a white solid.

$^1$H-NMR (400 MHz, CDCl$_3$) δ: 9.72 (1H, br), 7.59 (1H, d, J=8.3 Hz), 7.24 (1H, s), 7.00 (1H, d, J=8.1 Hz), 3.67 (3H, s), 3.08 (2H, t, J=7.7 Hz), 2.69 (2H, t, J=7.8 Hz), 2.56 (3H, s).

ESI-MS found: 219 [M+H]$^+$ (3) Synthesis of methyl 3-[1-(2,6-dichlorobenzyl)-3-methyl-1H-indazol-6-yl]propionate [8a-3] (hereinafter referred to as a compound [8a-3])

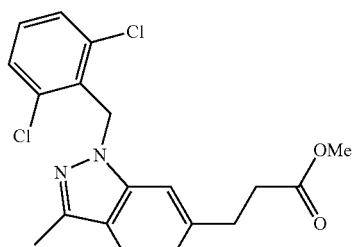

The titled compound (1.27 g) as a yellow white solid was prepared from the compound [8a-2] (871 mg) and 2,6-dichlorobenzyl chloride according to the method of the process (1) in Example 1.

$^1$H-NMR (400 MHz, CDCl$_3$) δ: 7.53 (1H, d, J=8.3 Hz), 7.37 (2H, d, J=8.1 Hz), 7.24-7.20 (1H, m), 7.18 (1H, s), 6.95

(1H, d, J=8.3 Hz), 5.69 (2H, s), 3.67 (3H, s), 3.07 (2H, t, J=7.7 Hz), 2.68 (2H, t, J=7.8 Hz), 2.50 (3H, s).
ESI-MS found: 377 [M+H]$^+$ (4) Synthesis of 3-[1-(2-chloro-6-cyclopropylbenzyl)-3-methyl-1H-indazol-6-yl]propionic acid [8a]

The titled compound (5.6 mg) as a yellow white solid was prepared from the compound [8a-3] (38 mg) according to the method of Example 27.
$^1$H-NMR (400 MHz, CD$_3$OD) δ: 7.53 (1H, d, J=8.3 Hz), 7.29 (1H, d, J=8.1 Hz), 7.19 (1H, t, J=7.9 Hz), 7.07 (1H, s), 6.99-6.94 (2H, m), 5.83 (2H, s), 3.03 (2H, t, J=7.7 Hz), 2.68 (2H, t, J=7.6 Hz), 2.51 (3H, s), 2.10-2.03 (1H, m), 0.87-0.83 (2H, m), 0.61-0.58 (2H, m).
ESI-MS found: 369 [M+H]$^+$ Reference Example 9

Synthesis of [1-(2,6-dichlorobenzyl)-3-methyl-1H-indazol-6-yl](1H-tetrazol-5-yl)methanol [9a] (hereinafter referred to as a compound [9a])

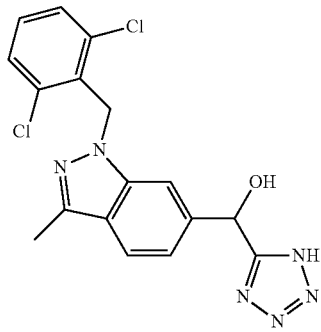 [SMILES: Cc1nn(Cc2c(Cl)cccc2Cl)c2cc(C(O)c3nnn[nH]3)ccc12]

(1) Synthesis of 1-(2,6-dichlorobenzyl)-3-methyl-6-vinyl-1H-indazole [9a-1] (hereinafter referred to as a compound [9a-1])

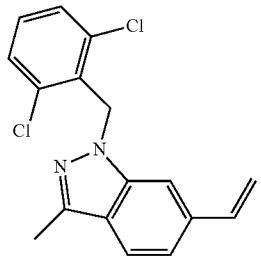 [SMILES: C=Cc1ccc2c(C)nn(Cc3c(Cl)cccc3Cl)c2c1]

To a solution of the compound [1-1] (1.1 g) in N,N-dimethylformamide (15 mL) were added tributylvinyltin (1.0 mL), lithium chloride (368 mg) and bis(triphenylphosphine)palladium(II) dichloride (102 mg) at room temperature, and the mixture was stirred at 120° C. for 40 minutes. After cooling, the reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (890 mg) as a white solid.

$^1$H-NMR (400 MHz, CDCl$_3$) δ: 7.55 (1H, d, J=8.3 Hz), 7.46-7.21 (5H, m), 6.81 (1H, dd, J=17.4, 10.9 Hz), 5.79 (1H, d, J=17.6 Hz), 5.71 (2H, s), 5.29 (1H, d, J=11.0 Hz), 2.51 (3H, s).

(2) Synthesis of 1-(2,6-dichlorobenzyl)-3-methyl-1H-indazole-6-carbaldehyde [9a-2] (hereinafter referred to as a compound [9a-2])

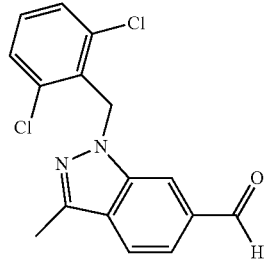 [SMILES: Cc1nn(Cc2c(Cl)cccc2Cl)c2cc(C=O)ccc12]

To a solution of the compound [9a-1] (890 mg) in mixed solution of tert-butanol (19 mL) and water (9 mL) were added sodium periodate (2.4 g) and a 4% aqueous osmium tetroxide solution (0.5 mL) at 0° C., and the mixture was stirred at 0° C. for 30 minutes, then stirred at room temperature for 2 hours. The reaction mixture was quenched with water, and extracted with chloroform. The obtained organic layer was dried over anhydrous sodium sulfate, filtered, and the filtrate was concentrated under reduced pressure. The obtained residue was purified by silica gel column chromatography to give the titled compound (560 mg) as a yellow solid.
$^1$H-NMR (400 MHz, CDCl$_3$) δ: 10.1 (1H, s), 7.92 (1H, s), 7.75 (1H, d, J=8.3 Hz), 7.64 (1H, d, J=8.3 Hz), 7.39 (2H, d, J=8.1 Hz), 7.29-7.25 (1H, m), 5.81 (2H, s), 2.56 (3H, s).

(3) Synthesis of [1-(2,6-dichlorobenzyl)-3-methyl-1H-indazol-6-yl]hydroxyacetonitrile [9a-3] (hereinafter referred to as a compound [9a-3])

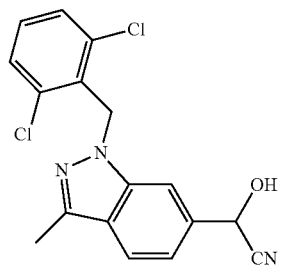 [SMILES: Cc1nn(Cc2c(Cl)cccc2Cl)c2cc(C(O)C#N)ccc12]

The compound [9a-2] (310.8 mg) was dissolved in tetrahydrofuran (5 mL), and to the solution were added trimethylsilyl cyanide (1.2 mL) and zinc iodide (31 mg) at room temperature. The mixture was stirred at room temperature for 4 hours. The reaction mixture was quenched with water, and extracted with ethyl acetate. The obtained organic layer was dried over anhydrous sodium sulfate, filtered, and the filtrate was concentrated under reduced pressure to give a brown oil. The obtained oil was dissolved in methanol (2 mL), p-toluenesulfonic acid (12 mg) was added at room temperature, and the mixture was stirred at room temperature for 3 hours. The reaction mixture was quenched with a saturated aqueous solution of sodium hydrogen carbonate, and extracted with ethyl acetate. The obtained organic layer was dried over anhydrous sodium sulfate, filtered, and the filtrate was concentrated under reduced pressure. The obtained residue was purified by silica gel column chromatography to give the titled compound (283.4 mg) as a white solid.

$^1$H-NMR (400 MHz, CDCl$_3$) δ: 7.70 (1H, d, J=8.3 Hz), 7.56 (1H, s), 7.38 (2H, d, J=8.1 Hz), 7.30-7.20 (2H, m), 5.75 (2H, s), 5.66 (1H, d, J=6.6 Hz), 2.54 (3H, s), 1.60-1.50 (1H, br).

(4) Synthesis of cyano[1-(2,6-dichlorobenzyl)-3-methyl-1H-indazol-6-yl]methyl acetate [9a-4] (hereinafter referred to as a compound [9a-4])

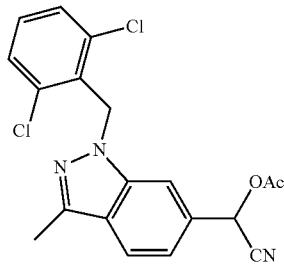 [SMILES: CC(=O)OC(C#N)c1ccc2c(C)nn(Cc3c(Cl)cccc3Cl)c2c1]

The compound [9a-3](53.0 mg) was dissolved in pyridine (0.8 mL), and to the solution was added acetic anhydride (43.4 μL) at room temperature, and the mixture was stirred at room temperature for 10 minutes. The reaction mixture was quenched with water, and extracted with chloroform. The obtained organic layer was dried over anhydrous sodium sulfate, filtered, and the filtrate was concentrated under reduced pressure. The obtained residue was purified by silica gel column chromatography to give the titled compound (60.3 mg) as a colorless oil.

$^1$H-NMR (400 MHz, CDCl$_3$) δ: 7.58 (1H, d, J=8.5 Hz), 7.45 (1H, m), 7.27 (2H, d, J=8.1 Hz), 7.15-7.10 (2H, m), 6.42 (1H, s), 5.65 (2H, s), 2.43 (3H, s), 2.07 (3H, s).

(5) Synthesis of [1-(2,6-dichlorobenzyl)-3-methyl-1H-indazol-6-yl](1H-tetrazol-5-yl)methyl acetate [9a-5] (hereinafter referred to as a compound [9a-5])

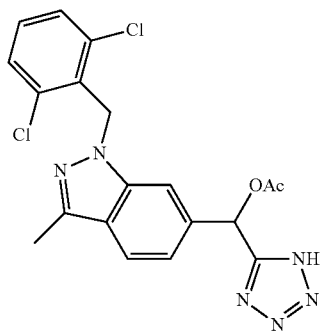

To a solution of the compound [9a-4] (60.3 mg) in N,N-dimethylformamide (1.6 mL) were added ammonium chloride (12.4 mg) and sodium azide (30.2 mg) at room temperature, and the mixture was subjected to microwave irradiation at 100° C. for 30 minutes. After cooling to room temperature, 6N-hydrochloric acid was added for acidification, and the mixture was extracted with ethyl acetate. The obtained organic layer was dried over anhydrous sodium sulfate, filtered, and the filtrate was concentrated under reduced pressure. The obtained residue was purified by reverse phase preparative liquid chromatography to give the titled compound (13.8 mg) as a white solid.

$^1$H-NMR (400 MHz, CDCl$_3$) δ: 7.59 (1H, d, J=8.5 Hz), 7.52 (1H, s), 7.31-7.25 (3H, m), 7.17-7.13 (2H, m), 5.58 (2H, s), 2.40 (3H, s), 2.16 (3H, s).

ESI-MS found: 431 [M+H]$^+$ (6) Synthesis of [1-(2,6-dichlorobenzyl)-3-methyl-1H-indazol-6-yl](1H-tetrazol-5-yl)methanol [9a]

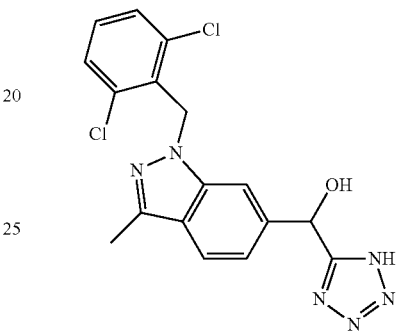

The compound [9a-5](11.0 mg) was dissolved in methanol (0.3 mL), and to the solution was added potassium carbonate (5.4 mg) at room temperature, and the mixture was stirred at room temperature for 1.5 hours. 1N-hydrochloric acid was added for acidification, and the mixture was extracted with chloroform. The obtained organic layer was dried over anhydrous sodium sulfate, filtered, and the filtrate was concentrated under reduced pressure to give the titled compound (5.2 mg) as a white solid.

$^1$H-NMR (400 MHz, CD$_3$OD) δ: 7.68 (1H, d, J=8.3 Hz), 7.61 (1H, s), 7.43 (2H, d, J=7.6 Hz), 7.33 (1H, t, J=8.0 Hz), 7.21 (1H, d, J=8.1 Hz), 6.29 (1H, s), 5.74 (2H, s), 2.46 (3H, s).

ESI-MS found: 389 [M+H]$^+$

Reference Example 10

Synthesis of [1-(2,6-dichlorobenzyl)-3-methyl-1H-indazol-6-yl](1H-tetrazol-5-yl)methanone [10a] (hereinafter referred to as a compound [10a])

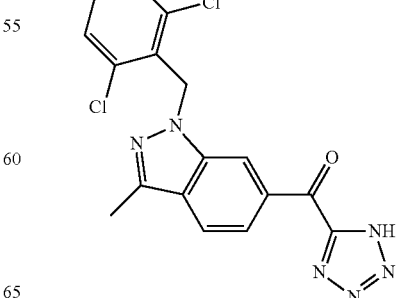

(1) Synthesis of [1-(2,6-dichlorobenzyl)-3-methyl-1H-indazol-6-yl](1-trityl-1H-tetrazol-5-yl)methanol [10a-1] (hereinafter referred to as a compound [10a-1])

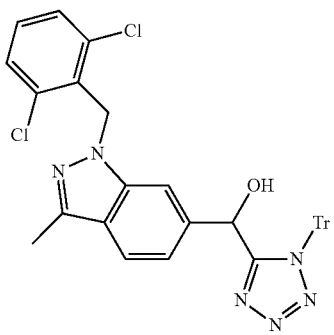

The compound [9a] (13.2 mg) and trityl chloride (11.4 mg) were dissolved in tetrahydrofuran (0.2 mL), and to the solution was added triethylamine (5.8 µL) at room temperature, and the mixture was stirred at room temperature for 1.5 hours. 1N-hydrochloric acid was added to the reaction mixture for acidification, and the mixture was extracted with chloroform. The obtained organic layer was dried over anhydrous sodium sulfate, filtered, and the filtrate was concentrated under reduced pressure to give the titled compound (5.2 mg) as a white solid.

$^1$H-NMR (400 MHz, CDCl$_3$) δ: 7.57 (1H, d, J=8.3 Hz), 7.51 (1H, s), 7.44 (1H, d, J=7.6 Hz), 7.36-7.08 (18H, m), 6.28 (1H, s), 5.65 (2H, s), 2.50 (3H, s).

(2) Synthesis of [1-(2,6-dichlorobenzyl)-3-methyl-1H-indazol-6-yl](1H-tetrazol-5-yl)methanone [10a]

The compound [10a-1] (8.4 mg) was dissolved in chloroform (0.14 mL), and to the solution was added 1,1,1-triacetoxy-1,1-dihydro-1,2-benzoiodoxol-3-(1H)-one (16.5 mg) at room temperature, and the mixture was stirred at room temperature for 2 hours. The reaction mixture was quenched with water, and extracted with chloroform. The obtained organic layer was dried over anhydrous sodium sulfate, filtered, and the filtrate was concentrated under reduced pressure. The obtained residue was purified by silica gel column chromatography. The purified compound was dissolved in 1,4-dioxane (1.3 mL), 3N-hydrochloric acid was added to the mixture at room temperature, and the mixture was stirred at 60° C. for 10 minutes. Water was added to the reaction mixture, and the mixture was extracted with chloroform. The obtained residue was purified by reverse phase preparative liquid chromatography to give the titled compound (2.2 mg) as a yellow solid.

$^1$H-NMR (400 MHz, CD$_3$OD) δ: 8.08 (1H, d, J=8.5 Hz), 7.89-7.87 (2H, m), 7.48-7.46 (2H, m), 7.36 (1H, d, J=8.1 Hz), 5.89 (2H, s), 2.55 (3H, s).

ESI-MS found: 387 [M+H]$^+$

Reference Example 11

Synthesis of [1-(2,6-dichlorobenzyl)-3-trifluoromethyl-1H-indazol-6-yl]acetic acid [11a] (hereinafter referred to as a compound [11a])

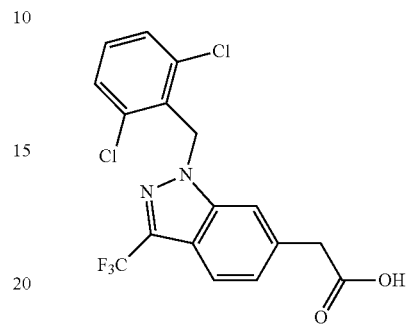

The titled compound as a white solid was prepared from the compound [36-4] according to the method of the process (6) in Example 3.

$^1$H-NMR (400 MHz, CD$_3$OD) δ: 7.74-7.72 (2H, m), 7.47 (2H, d, J=8.1 Hz), 7.38-7.36 (1H, m), 7.28 (1H, d, J=9.0 Hz), 5.90 (2H, s), 3.81 (2H, s).

ESI-MS found: 403 [M+H]$^+$

Reference Example 12

Synthesis of [3-chloro-1-(2,6-dichlorobenzyl)-1H-indazol-6-yl]acetic acid [12a] (hereinafter referred to as a compound [12a])

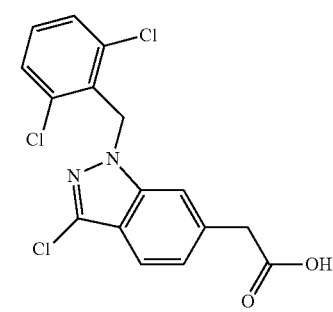 [SMILES: O=C(O)Cc1ccc2c(Cl)nn(Cc3c(Cl)cccc3Cl)c2c1]

The titled compound (3.0 mg) as a white solid was prepared from the compound [34-3] (29 mg) according to the method of the process (6) in Example 3.

$^1$H-NMR (400 MHz, CD$_3$OD) δ: 7.61 (1H, s), 7.57 (1H, d, J=8.5 Hz), 7.45 (2H, d, J=7.6 Hz), 7.35 (1H, dd, J=8.8, 7.3 Hz), 7.19 (1H, d, J=8.3 Hz), 5.77 (2H, s), 3.77 (2H, s).

ESI-MS found: 369 [M+H]$^+$

Reference Example 13

Synthesis of [1-(2-chloro-6-methoxybenzyl)-3-methyl-1H-indazol-6-yl]acetic acid [13a] (hereinafter referred to as a compound [13a])

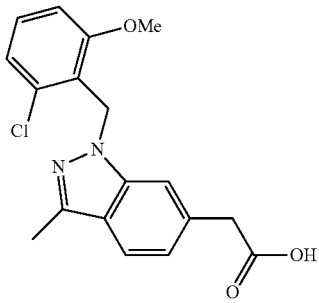 [SMILES: COc1cccc(Cl)c1Cn1nc(C)c2ccc(CC(=O)O)cc21]

The titled compound (20 mg) as a white solid was prepared from the compound [28-3] (25 mg) according to the method of the process (6) in Example 3.

$^1$H-NMR (400 MHz, CD$_3$OD) δ: 7.58 (1H, d, J=8.3 Hz), 7.46 (1H, s), 7.28 (1H, t, J=8.3 Hz), 7.05-7.02 (2H, m), 6.95 (1H, d, J=8.5 Hz), 5.62 (2H, s), 3.76 (3H, s), 3.72 (2H, s), 2.46 (3H, s).

ESI-MS found: 345 [M+H]$^+$

Reference Example 14

Synthesis of [1-(2-cyano-6-methylbenzyl)-3-methyl-1H-indazol-6-yl]acetic acid [14a] (hereinafter referred to as a compound [14a])

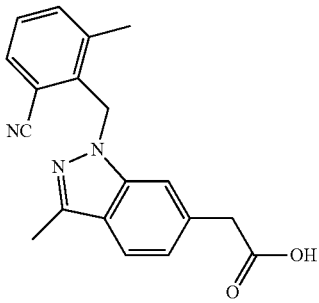 [SMILES: Cc1cccc(C#N)c1Cn1nc(C)c2ccc(CC(=O)O)cc21]

The titled compound (123.4 mg) as a yellow solid was prepared from the compound [24-1] (155.6 mg) according to the method of the process (6) in Example 3.

$^1$H-NMR (400 MHz, CD$_3$OD) δ: 7.66-7.63 (2H, m), 7.50 (1H, d, J=7.8 Hz), 7.46 (1H, s), 7.42 (1H, t, J=7.7 Hz), 7.10 (1H, dd, J=8.3, 1.5 Hz), 5.68 (2H, s), 3.74 (2H, s), 2.47 (3H, s), 2.20 (3H, s).

ESI-MS found: 320 [M+H]$^+$

Reference Example 15

Synthesis of [1-(2-cyano-6-methoxybenzyl)-3-methyl-1H-indazol-6-yl]acetic acid [15a] (hereinafter referred to as a compound [15a])

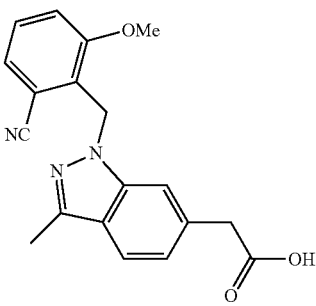 [SMILES: COc1cccc(C#N)c1Cn1nc(C)c2ccc(CC(=O)O)cc21]

The titled compound (32 mg) as a white solid was prepared from the compound [28-3] (130 mg) according to the method of the process (1) in Example 24.

$^1$H-NMR (400 MHz, CD$_3$OD) δ: 7.59 (1H, dd, J=8.3, 1.2 Hz), 7.54 (1H, s), 7.46 (1H, t, J=8.1 Hz), 7.33 (1H, dd, J=7.8, 1.0 Hz), 7.25 (1H, d, J=8.5 Hz), 7.06 (1H, dd, J=8.3, 1.2 Hz), 5.63 (2H, s), 3.76 (2H, s), 3.71 (3H, s), 2.45 (3H, s).

ESI-MS found: 336 [M+H]$^+$

Reference Example 16

Synthesis of [1-(2,6-dichlorobenzyl)-3-methyl-1H-indazol-6-yl]fluoroacetic acid [16a] (hereinafter referred to as a compound [16a])

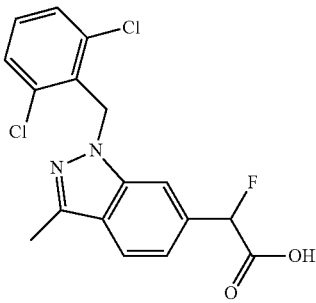 [SMILES: Cc1nn(Cc2c(Cl)cccc2Cl)c2cc(C(F)C(=O)O)ccc12]

(1) Synthesis of [1-(2,6-dichlorobenzyl)-3-methyl-1H-indazol-6-yl]fluoroacetonitrile [16a-1] (hereinafter referred to as a compound [16a-1])

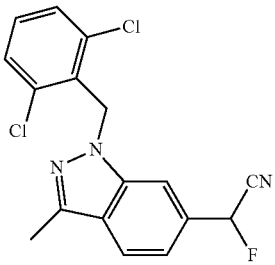 [SMILES: Cc1nn(Cc2c(Cl)cccc2Cl)c2cc(C(F)C#N)ccc12]

The compound [9a-3] (34 mg) was dissolved in methylene chloride (1 mL), and to the solution was added N,N-diethylaminosulfur trifluoride (20 μL) at 0° C., and the mixture was stirred at room temperature for 3 days. The reaction mixture was quenched with a saturated a coqueous solution of sodium hydrogen carbonate, and extracted with ethyl acetate. The obtained organic layer was dried over anhydrous sodium sulfate, filtered, and the filtrate was concentrated under reduced pressure. The obtained residue was purified by silica gel column chromatography to give the titled compound (26 mg) as a brown solid.

$^1$H-NMR (400 MHz, CDCl$_3$) δ: 7.74 (1H, d, J=8.1 Hz), 7.57 (1H, s), 7.39 (2H, d, J=8.1 Hz), 7.30-7.22 (2H, m), 6.17 (1H, d, J=47.1 Hz), 5.77 (2H, s), 2.59 (3H, s).

(2) Synthesis of [1-(2,6-dichlorobenzyl)-3-methyl-1H-indazol-6-yl]fluoroacetic acid [16a]

The compound [16a-1] (26 mg) was dissolved in acetic acid (1 mL), and to the solution was added concentrated hydrochloric acid (1 mL), and the mixture was stirred at 100° C. for 1 hour. After cooling, water was added to the reaction mixture, and the mixture was extracted with ethyl acetate. The obtained organic layer was dried over anhydrous sodium sulfate, filtered, and the filtrate was concentrated under reduced pressure. The obtained residue was purified by reverse phase preparative liquid chromatography to give the titled compound (16 mg) as a brown solid.

H-NMR (400 MHz, CD$_3$OD) δ: 7.73 (1H, d, J=8.5 Hz), 7.69 (1H, s), 7.45 (2H, d, J=7.8 Hz), 7.34 (1H, dd, J=8.5, 7.3 Hz), 7.23 (1H, d, J=8.4 Hz), 5.97 (1H, d, J=48.4 Hz), 5.77 (2H, s), 2.48 (3H, s).

ESI-MS found: 367 [M+H]$^+$

INDUSTRIAL APPLICABILITY

The compound represented by the formula (I) and the pharmaceutically acceptable salt and ester of the compound of the present invention have an excellent URAT1 inhibitory action and thus can reduce a blood uric acid level, and thus are useful as therapeutic drugs or prophylactic drug for a pathological condition associated with blood uric acid such as hyperuricemia, gouty node, acute gout arthritis, chronic gout arthritis, gouty kidney, urolithiasis, renal function disorder, coronary artery diseases or ischemic cardiac diseases.

The invention claimed is:
1. A compound represented by the formula (I) or a pharmaceutically acceptable salt or ester of the compound: the formula (I):

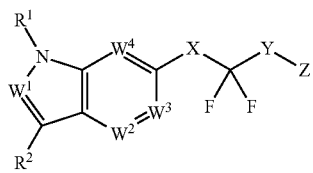

wherein
R$^1$ represents a group represented by the general formula: -Q$^1$-A$^1$,
Q$^1$ represents a single bond or a lower alkylene group (wherein the entirety of each of the 1 or 2 or more methylene group(s) that constitute(s) the lower alkylene group may be independently replaced with a carbonyl group, a sulfinyl group or a sulfonyl group, and/or the hydrogen(s) that constitute(s) the methylene group(s) may be substituted by lower alkyl group(s)),
A$^1$ represents an aryl group or a heteroaryl group optionally substituted by 1 to 3 substituent(s) selected from the following <Substituent group L> (wherein the adjacent optional two substituents on the aryl group or heteroaryl group may be together to form a lower alkylenedioxy group)(wherein when said substituent selected from the following <Substituent group L> is a chlorine atom, the number of chlorine atom present in A$^1$ is one);
R$^2$ represents a hydrogen atom, a substituent selected from the following <Substituent group M> or a group represented by the general formula: -Q$^2$-A$^2$,
Q$^2$ represents a single bond, a lower alkylene group or lower alkenylene group (wherein the entirety of each of the 1 or 2 or more methylene group(s) that constitute(s) the lower alkylene group may be independently replaced with an oxygen atom, a nitrogen atom or a carbonyl group, and/or the hydrogen(s) that constitute(s) the methylene group(s) may be substituted by a halogen atom, a cyano group, a hydroxyl group or a lower alkyl group),
A$^2$ represents a cycloalkyl group, an aliphatic heterocycle group, an aryl group or a heteroaryl group optionally substituted by 1 to 3 substituent(s) selected from <Substituent group L> (wherein the adjacent optional two substituents on the aryl group or heteroaryl group may be together to form a lower alkylenedioxy group);
W$^1$ is a methine group or a nitrogen atom, W$^2$, W$^3$ and W$^4$ are each independently a methine group, and said methine group of W$^1$, W$^2$, W$^3$ and W$^4$ is a methine group optionally having substituent(s) selected from the group consisting of a halogen atom, a hydroxyl group, a cyano group, a lower alkyl group, a cycloalkyl group, a halo lower alkyl group, a lower alkoxy group and a halo lower alkoxy group;
X and Y are each independently a single bond, a lower alkylene group, a lower alkenylene group or a lower alkynylene group, wherein the entirety of each of the 1 or 2 or more methylene group(s) that constitute(s) the lower alkylene group may be independently replaced with an oxygen atom, a sulfur atom, a sulfinyl group, a sulfonyl group, a carbonyl group or a group represented by the general formula: —N(R$^N$)—, and/or the hydrogen(s) that constitute(s) the methylene group(s) may be substituted by a halogen atom, a cyano group, a hydroxyl group or a lower alkyl group,
R$^N$ represents a hydrogen atom, a lower alkyl group, a halo lower alkyl group or a lower alkanoyl group;
Z represents a hydroxyl group, COOR$^3$, CONR$^4$R$^5$, SO$_3$R$^3$, SO$_3$NR$^4$R$^5$, a 5-tetrazolyl group, a 5-oxo-1,2,4-oxadiazolyl group, a 2-oxo-1,3,4-oxadiazolyl group, a 5-imino-4,5-dihydro-1,3,4-oxadiazolyl group, a 2-thioxo-1,3,4-oxadiazolyl group or a 5-oxo-1,2,4-thiaziazolyl group,
wherein R$^3$, R$^4$ and R$^5$ each independently represents a hydrogen atom or a lower alkyl group; and <Substituent group L> and <Substituent group M> are defined as follows:
<Substituent group L>:
a halogen atom, a hydroxyl group, a nitro group, a cyano group, a formyl group, an amino group, a carboxyl group, a lower alkyl group, a halo lower alkyl group, a cycloalkyl group, a lower alkoxy group, a halo lower alkoxy group, a hydroxy lower alkyl group, a lower alkoxy lower alkyl group, a lower alkoxy carbonyl group, a lower alkanoyl group, a lower alkylthio group, a lower alkyl sulfonyl group, a lower alkylamino group, a di-lower alkylamino group, a carbamoyl group, a mono-lower alkyl carbamoyl group, a di-lower alkyl carbamoyl group, a lower alkanoyl amino group, a lower alkyl sulfonylamino group, a lower alkoxy carbonylamino group, a lower alkenyl group, and a cyano lower alkyl group;

<Substituent group M>:
a halogen atom, a hydroxyl group, a nitro group, a cyano group, a formyl group, an amino group, a carboxyl group, a lower alkyl group, a halo lower alkyl group, a cycloalkyl group, a lower alkoxy group, a halo lower alkoxy group, a hydroxy lower alkyl group, a lower alkoxy lower alkyl group, a lower alkoxy carbonyl group, a lower alkanoyl group, a lower alkylthio group, a lower alkyl sulfonyl group, a lower alkylamino group, a di-lower alkylamino group, a carbamoyl group, a mono-lower alkyl carbamoyl group, a di-lower alkyl carbamoyl group, a lower alkanoyl amino group, a lower alkyl sulfonylamino group, and a lower alkoxycarbonylamino group.

2. The compound or a pharmaceutically acceptable salt or ester of the compound according to claim 1, wherein $Q^1$ is a methylene group.

3. The compound or a pharmaceutically acceptable salt or ester of the compound according to claim 1, wherein $R^2$ is a halogen atom, a cyano group, a lower alkyl group, a halo lower alkyl group, a cycloalkyl group or a hydroxy lower alkyl group.

4. The compound or a pharmaceutically acceptable salt or ester of the compound according to claim 1, wherein X and Y are each a single bond.

5. The compound or a pharmaceutically acceptable salt or ester of the compound according to claim 1, wherein $A^1$ is an optionally substituted phenyl group, an optionally substituted naphthyl group, an optionally substituted quinolyl group, an optionally substituted isoquinolyl group, an optionally substituted isoindolyl group, an optionally substituted benzothienyl group or an optionally substituted pyridyl group.

6. The compound or a pharmaceutically acceptable salt or ester of the compound according to claim 1, wherein $R^2$ is a methyl group, an ethyl group, a trifluoromethyl group, a hydroxymethyl group or a chlorine atom.

7. The compound or a pharmaceutically acceptable salt or ester of the compound according to claim 1, wherein $W^1$ is a nitrogen atom.

8. The compound or a pharmaceutically acceptable salt or ester of the compound according to claim 1, wherein Z is COOH, a 5-tetrazolyl group or a 2-oxo-1,3,4-oxadiazolyl group.

9. The compound or a pharmaceutically acceptable salt or ester of the compound according to claim 1, wherein $W^2$, $W^3$ and $W^4$ are each a group represented by the general formula: =CH—.

10. The compound or a pharmaceutically acceptable salt or ester of the compound according to claim 1, wherein $Q^1$ is a sulfonyl group.

11. The compound or a pharmaceutically acceptable salt or ester of the compound according to claim 1, which is [1-(2-chloro-6-fluorobenzyl)-3-methyl-1H-indazol-6-yl]difluoroacetic acid.

12. A compound or a pharmaceutically acceptable salt or ester of the compound, which is [1-(2,3-dichlorobenzyl)-3-methyl-1H-indazol-6-yl]difluoroacetic acid.

13. The compound or a pharmaceutically acceptable salt or ester of the compound according to claim 1, which is difluoro[1-(2-fluoro-6-trifluoromethylbenzyl)-3-methyl-1H-indazol-6-yl]acetic acid.

14. The compound or a pharmaceutically acceptable salt or ester of the compound according to claim 1, which is [1-(2-cyano-6-methylbenzyl)-3-methyl-1H-indazol-6-yl]difluoroacetic acid.

15. The compound or a pharmaceutically acceptable salt or ester of the compound according to claim 1, which is [1-(2-cyano-6-cyclopropylbenzyl)-3-methyl-1H-indazol-6-yl]difluoroacetic acid.

16. The compound or a pharmaceutically acceptable salt or ester of the compound according to claim 1, which is [1-(2-cyano-6-hydroxymethylbenzyl)-3-methyl-1H-indazol-6-yl]difluoroacetic acid.

17. The compound or a pharmaceutically acceptable salt of the compound according to claim 1, which is 3-chloro-2-{6-[difluoro(1H-tetrazol-5-yl)methyl]-3-methyl-1H-indazol-1-ylmethyl}benzamide.

18. The compound or a pharmaceutically acceptable salt of the compound according to claim 1, which is 2-{6-[difluoro(1H-tetrazol-5-yl)methyl]-3-methyl-1H-indazol-1-ylmethyl}-3-hydroxymethyl)benzonitrile.

19. A compound or a pharmaceutically acceptable salt of the compound, which is 2-{6-[difluoro(1H-tetrazol-5-yl)methyl]-3-methyl-1H-pyrazolo[3,4-b]pyridin-1-ylmethyl}-3-methylbenzamide.

20. A compound or a pharmaceutically acceptable salt of the compound, which is 3-cyclopropyl-2-{6-[difluoro(1H-tetrazol-5-yl)methyl]-3-methyl-1H-pyrazolo[3,4-b]pyridin-1-ylmethyl}benzamide.

21. The compound or a pharmaceutically acceptable salt or ester of the compound according to claim 1, which is [1-(2-cyano-6-methylbenzyl)-3-hydroxymethyl-1H-indazol-6-yl]difluoroacetic acid.

22. An URAT1 inhibitor comprising the compound or a pharmaceutically acceptable salt or ester of the compound according to claim 1.

23. A blood uric acid level-reducing agent comprising the compound or a pharmaceutically acceptable salt or ester of the compound according to claim 1.

24. A pharmaceutical composition for treating or preventing a pathological condition associated with blood uric acid, comprising the compound or a pharmaceutically acceptable salt or ester of the compound according to claim 1 and a pharmaceutically acceptable carrier.

25. The pharmaceutical composition according to claim 24, wherein the pathological condition associated with blood uric acid is selected from the group consisting of hyperuricemia, gouty node, acute gout arthritis, chronic gout arthritis, gouty kidney, urolithiasis, renal function disorder, coronary artery diseases and ischemic cardiac diseases.

26. The pharmaceutical composition according to claim 24, wherein the pathological condition associated with blood uric acid is hyperuricemia.

27. The compound or a pharmaceutically acceptable salt or ester of the compound according to claim 1, wherein $Q^1$ is a methylene group or a sulfonyl group.

28. The compound or a pharmaceutically acceptable salt or ester of the compound according to claim 27, wherein X and Y are each a single bond.

29. The compound or a pharmaceutically acceptable salt or ester of the compound according to claim 28, wherein $R^2$ represents a hydrogen atom, or a substituent selected from the <Substituent group M>.

30. The compound or a pharmaceutically acceptable salt or ester of the compound according to claim 29, wherein $R^2$ is a halogen atom, a lower alkyl group, a halo lower alkyl group, a cycloalkyl group or a hydroxy lower alkyl group.

31. The compound or a pharmaceutically acceptable salt or ester of the compound according to claim 30, wherein Z is COOH, a 5-tetrazolyl group or a 2-oxo-1,3,4-oxadiazolyl group.

32. A compound or a pharmaceutically acceptable salt or ester of the compound, which is [3-chloro-1-(2,6-dichlorobenzyl)-1H-indazol -6-yl]difluoroacetic acid.

33. A compound or a pharmaceutically acceptable salt or ester of the compound, which is 1-(2,6-dichlorobenzyl)-6-[difluoro(1H-tetrazol-5-yl)methyl]-3-methyl-1H-indazole.

34. A compound or a pharmaceutically acceptable salt or ester of the compound, which is 1-(2,3-dichlorobenzyl)-6-[difluoro(1H -tetrazol-5-yl)methyl]-3-methyl-1H-indazole.

35. An URAT1 inhibitor comprising the compound or a pharmaceutically acceptable salt or ester of the compound according to claim 32.

36. An URAT1 inhibitor comprising the compound or a pharmaceutically acceptable salt or ester of the compound according to claim 33.

37. An URAT1 inhibitor comprising the compound or a pharmaceutically acceptable salt or ester of the compound according to claim 34.

38. A blood uric acid level-reducing agent comprising the compound or a pharmaceutically acceptable salt or ester of the compound according to claim 32.

39. A blood uric acid level-reducing agent comprising the compound or a pharmaceutically acceptable salt or ester of the compound according to claim 33.

40. A blood uric acid level-reducing agent comprising the compound or a pharmaceutically acceptable salt or ester of the compound according to claim 34.

* * * * *